US012761552B2

(12) United States Patent
Fukushima et al.

(10) Patent No.: US 12,761,552 B2
(45) Date of Patent: Oct. 13, 2026

(54) AMINE COMPOUND, CHEMICALLY AMPLIFIED RESIST COMPOSITION, AND PATTERNING PROCESS

(71) Applicant: Shin-Etsu Chemical Co., Ltd., Tokyo (JP)

(72) Inventors: Masahiro Fukushima, Joetsu (JP); Masaki Ohashi, Joetsu (JP); Kazuhiro Katayama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 890 days.

(21) Appl. No.: 17/948,509

(22) Filed: Sep. 20, 2022

(65) Prior Publication Data

US 2023/0134822 A1 May 4, 2023

(30) Foreign Application Priority Data

Sep. 24, 2021 (JP) ................................ 2021-155395

(51) Int. Cl.

| | |
|---|---|
| ***G03F 7/004*** | (2006.01) |
| ***C07D 209/56*** | (2006.01) |
| ***C07D 275/06*** | (2006.01) |
| ***C07D 307/33*** | (2006.01) |
| ***C07D 307/93*** | (2006.01) |
| ***C07D 327/04*** | (2006.01) |
| ***C08F 220/18*** | (2006.01) |
| ***C08F 220/38*** | (2006.01) |
| ***G03F 7/038*** | (2006.01) |
| ***G03F 7/039*** | (2006.01) |

(52) U.S. Cl.

CPC ......... *G03F 7/0045* (2013.01); *C07D 209/56* (2013.01); *C07D 275/06* (2013.01); *C07D 307/33* (2013.01); *C07D 307/93* (2013.01); *C07D 327/04* (2013.01); *C08F 220/1806* (2020.02); *C08F 220/1808* (2020.02); *C08F 220/1809* (2020.02); *C08F 220/1818* (2020.02); *C08F 220/382* (2020.02); *G03F 7/004* (2013.01); *G03F 7/0382* (2013.01); *G03F 7/0392* (2013.01)

(58) Field of Classification Search

None

See application file for complete search history.

(56) References Cited

U.S. PATENT DOCUMENTS

| | | | | |
|---|---|---|---|---|
| 2005/0234041 | A1 | 10/2005 | Tomazic et al. | |
| 2016/0299431 | A1* | 10/2016 | Adachi | G03F 7/039 |
| 2016/0327864 | A1* | 11/2016 | Funatsu | G03F 7/11 |

FOREIGN PATENT DOCUMENTS

| | | | | |
|---|---|---|---|---|
| JP | 2001-194776 | A | | 7/2001 |
| JP | 2002-226470 | A | | 8/2002 |
| JP | 2004-536079 | A | | 12/2004 |
| JP | 3790649 | B2 | | 6/2006 |
| JP | 4044741 | B2 | * | 2/2008 |
| JP | 2012-8550 | A | | 1/2012 |
| JP | 2012008551 | A | * | 1/2012 |
| JP | 5617799 | B2 | | 11/2014 |
| WO | 2008/066011 | A1 | | 6/2008 |
| WO | 2020/210630 | A1 | | 10/2020 |

OTHER PUBLICATIONS

JP2012008551 English Translation (Year: 2025).*

JP4044741 English Translation (Year: 2025).*

Jiguo Ma,et.al., Enantioselective Synthesis of Pyroglutamic Acid Esters from Glycinate via Carbonyl Catalysis, Angewandte Chemie International Edition, 2021, vol. 60, No. 19 , pp. 10588-10592. (5 pages); cited in JP Office Action dated Sep. 17, 2024.

Markus Obkircher.et.al , Photochemical Synthesis of N-Substituted 3-Hydroxy-2-pyrrolidinones, SYNLETT, No. 7, 2005, pp. 1182-118. (3 pages); cited in JP Office Action dated Sep. 17, 2024.

Office Action dated Sep. 17, 2024, issued in counterpart JP Application No. 2021-155395, with English translation. (13 pages).

Office Action dated Jun. 7, 2024, issued in counterpart KR Application No. 10-2022-0118838, with English translation. (8 pages).

Moss T et al., Catalytic Asymmetric Alkylation Reactions for Construction of Protected Ethylene-Amino and Propylene-Amino Motifs Attached to Quaternary Stereocentres, A European Journal, Chemistry, vol. 19, p. 3071-3081, 2013. ( 11 pages); cited in KR Office Action dated Jun. 7, 2024.

* cited by examiner

*Primary Examiner* — Mark F. Huff

(74) *Attorney, Agent, or Firm* — WHDA, LLP

(57) ABSTRACT

A resist composition comprising a quencher in the form of an amine compound having a highly polar lactone or sultone ring and an acid labile group in a common molecule is provided. The resist composition has a high sensitivity and forms a pattern with improved LWR or CDU, independent of whether it is of positive or negative tone.

16 Claims, 5 Drawing Sheets

AMINE COMPOUND, CHEMICALLY AMPLIFIED RESIST COMPOSITION, AND PATTERNING PROCESS

CROSS-REFERENCE TO RELATED APPLICATION

This non-provisional application claims priority under 35 U.S.C. § 119(a) on Patent Application No. 2021-155395 filed in Japan on Sep. 24, 2021, the entire contents of which are hereby incorporated by reference.

TECHNICAL FIELD

This invention relates to an amine compound, a chemically amplified resist composition, and a pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is EUV lithography.

With the progress of miniaturization in logic devices, the flash memory now takes the form of devices having stacked layers of gate, known as 3D-NAND. The capacity is increased by increasing the number of stacked layers. As the number of stacked layers increases, the hard mask used in processing of layers becomes thicker and the photoresist film also becomes thicker. While the resist film for logic devices becomes thinner, the resist film for 3D-NAND becomes thicker.

As the pattern feature size is reduced, approaching to the diffraction limit of light, light contrast lowers. In the case of positive resist film, a lowering of light contrast leads to reductions of resolution and focus margin of hole and trench patterns. The trend of the resist toward thicker films suggests that the thickness of resist film for previous generation devices is resumed. As more critical dimension uniformity (CDU) is required, the previous photoresist film cannot accommodate the requirements. For preventing a reduction of resolution of resist pattern due to a lowering of light contrast as a result of size reduction, or for improving CDU in the trend toward thicker resist film, an attempt is made to enhance the dissolution contrast of resist film.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein polarity switch or crosslinking reaction takes place under the action of acid. Quenchers (or acid diffusion controlling agents) are often added to these resist compositions for the purpose of controlling the diffusion of the acid to unexposed region to improve the contrast.

The addition of quenchers is fully effective to this purpose. A number of amine quenchers were proposed as disclosed in Patent Documents 1 and 2.

With respect to the acid labile group used in (meth) acrylate polymers for the ArF lithography resist material, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher. Patent Document 3 discloses a resist composition comprising a sulfonium or iodonium salt capable of generating carboxylic acid as a quencher.

Sulfonium and iodonium salt type quenchers are photo-decomposable like photoacid generators. That is, the amount of quencher in the exposed region is reduced. Since acid is generated in the exposed region, the reduced amount of quencher leads to a relatively increased concentration of acid and hence, an improved contrast. However, the acid diffusion in the exposed region is not suppressed, indicating the difficulty of acid diffusion control.

Since a sulfonium or iodonium salt type quencher absorbs ArF radiation of wavelength 193 nm, a resist film in which the quencher is combined with a sulfonium or iodonium salt type acid generator has a reduced transmittance to that radiation. As a result, in the case of a resist film having a thickness of at least 100 nm, the cross-sectional profile of a pattern as developed becomes tapered. For resist films having a thickness of at least 100 nm, especially at least 150 nm, a highly transparent quencher is necessary.

Lowering the post-exposure bake (PEB) temperature is effective for suppressing acid diffusion. Since dissolution contrast is reduced in this case, resolution and edge roughness (LWR) can be degraded. A resist composition of new concept which exhibits a high contrast while suppressing acid diffusion is desired.

There are known amine quenchers for inviting a polarity switch under the action of acid catalyst. Patent Documents 4 and 5 propose an amine quencher having an acid labile group. This amine compound generates a carboxylic acid via the acid-aided deprotection reaction of a tertiary ester having a carbonyl group positioned on the nitrogen atom side whereby alkaline solubility increases. In this case, however, since the molecular weight on the nitrogen atom side cannot be increased, the acid diffusion controlling ability is low, and the contrast improving effect is faint. Patent Document 6 describes a quencher adapted to generate an amino group through acid-catalyzed deprotection reaction of a tert-butoxycarbonyl group. This mechanism is adapted to generate a quencher upon light exposure, achieving a reverse effect to contrast enhancement. The contrast is enhanced by the mechanism that the quencher disappears or loses its quenching ability upon light exposure or under the action of acid. Patent Document 7 discloses a quencher in the form of an amine compound which cyclizes under the action of acid to form a lactam structure. The conversion of the strong base amine compound to the weak base lactam compound causes the acid to change its activity whereby the contrast is unproved. The application of these amine quenchers is confirmed to achieve a certain extent of performance improvement, but is still insufficient for precise control of acid diffusion. It is desired to have a quencher having a higher acid diffusion controlling ability.

CITATION LIST

Patent Document 1: JP-A 2001-194776
Patent Document 2: JP-A 2002-226470
Patent Document 3: WO 2008/066011
Patent Document 4: JP 4044741
Patent Document 5: JP-A 2012-008550
Patent Document 6: JP 3790649
Patent Document 7: JP 5617799

DISCLOSURE OF INVENTION

For the acid-catalyzed chemically amplified resist material, it is desired to develop a quencher capable of reducing the LWR of line patterns or improving the CDU of hole patterns and increasing sensitivity. To this end, it is necessary to significantly reduce the distance of acid diffusion and to increase the contrast at the same time, that is, to improve two contradictory factors.

An object of the invention is to provide a chemically amplified resist composition which exhibits a high sensitivity and a reduced LWR or improved CDU, independent of whether it is of positive tone or negative tone; and a pattern forming process using the same.

The inventors have found that using an amine compound having a highly polar ring structure and an acid labile group in a common molecule as a quencher, a chemically amplified resist composition having a reduced LWR, improved CDU, high contrast, high resolution, and wide process margin is obtained.

In one aspect, the invention provides an amine compound having the formula (1).

(1)

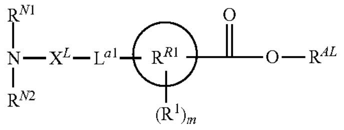

Herein m is an integer of 0 to 10, $R^{N1}$ and $R^{N2}$ are each independently hydrogen or a $C_1$-$C_{20}$ hydrocarbyl group in which some or all of the hydrogen atoms may be substituted by halogen and any constituent —$CH_2$— may be replaced by —O— or —C(═O)—, $R^{N1}$ and $R^{N2}$ may bond together to form a ring with the nitrogen atom to which they are attached, the ring optionally containing —O— or —S—, with the proviso that $R^{N1}$ and $R^{N2}$ are not hydrogen at the same time, $X^L$ is a $C_1$-$C_{40}$ hydrocarbylene group which may contain a heteroatom, $L^{a1}$ is a single bond, ether bond, ester bond, sulfonic ester bond, carbonate bond or carbamate bond, the ring $R^{R1}$ is a $C_2$-$C_{20}$ (m+2)-valent heterocyclic group having a lactone, lactam, sultone or sultan structure, $R^1$ is a $C_1$-$C_{20}$ hydrocarbyl group which may contain a heteroatom, and when m is 2 or more, a plurality of $R^1$ may be the same or different, a plurality of $R^1$ may bond together to form a ring with the atoms on $R^{R1}$ to which they are attached, and $R^{AL}$ is an acid labile group.

The preferred amine compound has the formula (1A).

(1A)

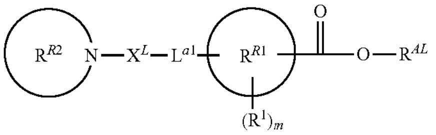

Herein m, $X^L$, $L^{R1}$, $R^{R1}$, $R^1$, and $R^{AL}$ are as defined above; a $C_3$-$C_{20}$ alicyclic hydrocarbon group forms the ring $R^{R2}$ with the nitrogen atom, any constituent —$CH_2$— in the ring may be replaced by —O— or —S—.

The amine compound having the formula (1B) is more preferred.

(1B)

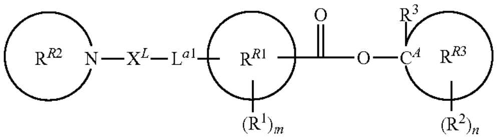

Herein m, $X^L$, $L^{a1}$, $R^{R1}$, $R^{R2}$, and $R^1$ are as defined above; n is an integer of 0 to 20; a $C_3$-$C_{20}$ alicyclic hydrocarbon group forms the ring $R^{R3}$ with the carbon atom $C^A$, any constituent —$CH_2$— in the ring may be replaced by a heteroatom-containing moiety; $R^2$ is a $C_1$-$C_{20}$ hydrocarbyl group which may contain a heteroatom, and when n is 2 or more, a plurality of $R^2$ may be the same or different, a plurality of $R^2$ may bond together to form a ring structure; and $R^3$ is a $C_1$-$C_{20}$ hydrocarbyl group which may contain a heteroatom.

In another aspect, the invention provides a chemically amplified resist composition comprising (A) a quencher in the form of the amine compound defined above.

Typically, the resist composition further comprises (B) a base polymer comprising repeat units having the formula (a1) or (a2).

(a1)

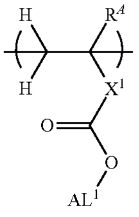

-continued (a2)

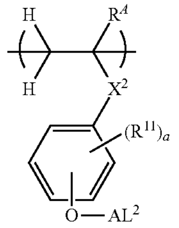

Herein $R^A$ is each independently hydrogen, fluorine, methyl or trifluoromethyl; $X^1$ is a single bond, phenylene, naphthylene, or *—C(═O)—O—$X^{11}$—, $X^{11}$ is a $C_1$-$C_{10}$ alkanediyl group which may contain a hydroxy moiety, ether bond, ester bond or lactone ring, or phenylene group or naphthylene group; $X^2$ is a single bond or *—C(═O)—O—, the asterisk (*) designates a point of attachment to the carbon atom in the backbone; $AL^1$ and $AL^2$ are each independently an acid labile group; $R^{11}$ is a $C_1$-$C_{20}$ hydrocarbyl group which may contain a heteroatom; and a is an integer of 0 to 4.

In a preferred embodiment, the base polymer further comprises repeat units having the formula (b1) or (b2).

(b1)

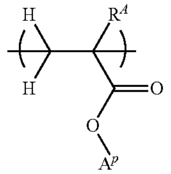

(b2)

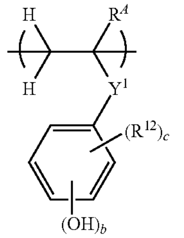

Herein $R^A$ is each independently hydrogen, fluorine, methyl or trifluoromethyl; $A^p$ is hydrogen, or a polar group containing at least one structure selected from a hydroxy moiety, cyano moiety, carbonyl moiety, carboxy moiety, ether bond, ester bond, sulfonic ester bond, carbonate bond, lactone ring, sultone ring, and carboxylic anhydride (—C(═O)—O—C(═O)—); $Y^1$ is a single bond or *—C(═O)—O—, the asterisk (*) designates a point of attachment to the carbon atom in the backbone; $R^{12}$ is halogen, cyano group, or a $C_1$-$C_{20}$ hydrocarbyl group which may contain a heteroatom, $C_1$-$C_{20}$ hydrocarbyloxy group which may contain a heteroatom, or $C_2$-$C_{20}$ hydrocarbylcarbonyl group which may contain a heteroatom; b is an integer of 1 to 4, c is an integer of 0 to 4, and $1 \leq b+c \leq 5$.

In a preferred embodiment, the base polymer further comprises repeat units of at least one type selected from the formulae (c1) to (c3).

(c1)

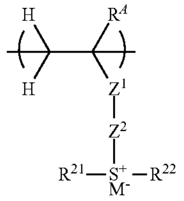

(c2)

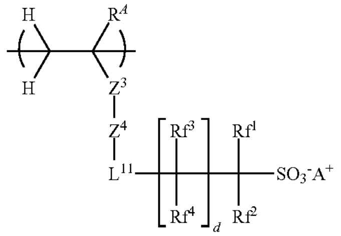

(c3)

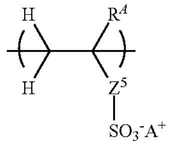

Herein $R^A$ is each independently hydrogen, fluorine, methyl or trifluoromethyl. V is a single bond or phenylene group. $Z^2$ is *—C(═O)—NH—$Z^{21}$— or *—O—$Z^{21}$—, $Z^{21}$ is a $C_1$-$C_6$ aliphatic hydrocarbylene group, phenylene group or a divalent group obtained by combining the foregoing, which may contain a carbonyl moiety, ester bond, ether bond or hydroxy moiety. $Z^3$ is a single bond, phenylene group, naphthylene group or *—C(═O)—O—$Z^{31}$—, $Z^{31}$ is a $C_1$-$C_{10}$ aliphatic hydrocarbylene group which may contain a hydroxy moiety, ether bond, ester bond or lactone ring, or phenylene group or naphthylene group. $Z^4$ is a single bond or *—$Z^{41}$—C(═O)—O—, $Z^{41}$ is a $C_1$-$C_{20}$ hydrocarbylene group which may contain a heteroatom. $Z^5$ is a single bond, methylene group, ethylene group, phenylene group, fluorinated phenylene group, trifluoromethyl-substituted phenylene group, *—C(═O)—O—$Z^{51}$—, *—C(═O)—NH—$Z^{51}$— or —O—$Z^{51}$—, $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety, the asterisk (*) designates a point of attachment to the carbon atom in the backbone. $R^{21}$ and $R^{22}$ are each independently a $C_1$-$C_{20}$ hydrocarbyl group which may contain a heteroatom, $R^{21}$ and $R^{22}$ and may bond together to form a ring with the sulfur atom to which they are attached. $L^{11}$ is a single bond, ether bond, ester bond, carbonyl group, sulfonic ester bond, carbonate bond or carbamate bond. $Rf^1$ and $Rf^2$ are each independently fluorine or a $C_1$-$C_6$ fluorinated alkyl group. $Rf^3$ and $Rf^4$ are each independently hydrogen, fluorine or a $C_1$-$C_6$ fluorinated alkyl group. $M^-$ is a non-nucleophilic counter ion. $A^-$ is an onium cation, and d is an integer of 0 to 3.

The resist composition may further comprise (C) an organic solvent, (D) a photoacid generator, (E) a quencher other than the amine compound having formula (1), and/or (F) a surfactant.

In a further aspect, the invention provides a pattern forming process comprising the steps of applying the chemically amplified resist composition defined herein onto a substrate to form a resist film thereon, exposing a selected region of the resist film to KrF excimer laser radiation, ArF excimer laser radiation, EB or EUV, and developing the exposed resist film in a developer.

In a preferred embodiment, the developing step uses an aqueous alkaline solution as the developer to form a positive tone pattern wherein the exposed region of resist film is dissolved away and the unexposed region of resist film is not dissolved.

In another preferred embodiment, the developing step uses an organic solvent as the developer to form a negative tone pattern wherein the unexposed region of resist film is dissolved away and the exposed region of resist film is not dissolved.

In a preferred embodiment, the exposing step is carried out by the immersion lithography while a liquid having a refractive index of at least 1.0 is held between the resist film and a projection lens. Preferably, the process further comprises the step of forming a protective film on the resist film prior to the exposure step, wherein the immersion lithography is carried out while the liquid is held between the protective film and the projection lens.

Advantageous Effects of Invention

The amine compound having a highly polar lactone or sultone ring and an acid labile group in a common molecule serves as a quencher when used in a chemically amplified resist composition. Since the amine compound has an acid labile group, the exposed region of resist film is decomposed with acid to bring a polarity switch whereby the contrast is improved. Since the amine compound has a highly polar lactone or sultone ring in its molecule, it has proton affinity. Since the amine compound itself has a high boiling point and is thus least volatile in the heating step, it is retained in the resist film and kept effective for trapping the generated acid. By virtue of the synergistic effect of these factors, a chemically amplified resist composition having a satisfactory sensitivity, low LWR and improved CDU can be designed.

DESCRIPTION OF EMBODIMENTS

Figure 1:
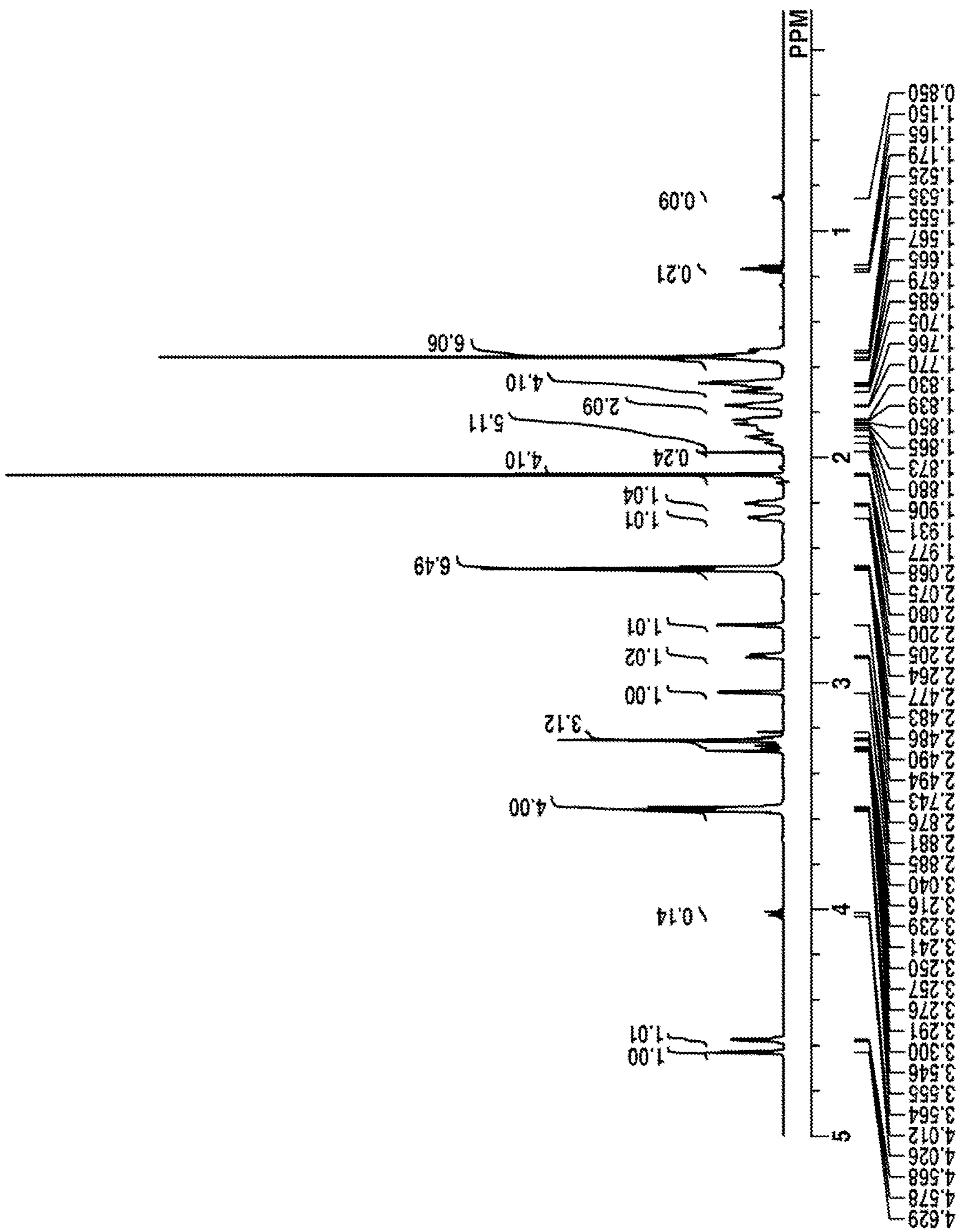
FIG. 1 is a $^{1}$H-NMR spectrum of Compound AQ-1 synthesized in Example 1-1.

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation ($C_n$-$C_m$) means a group containing from n to m carbon atoms per group. The term "group" and "moiety" are interchangeable. In chemical formulae, the broken line (---), asterisk (*) and double asterisks (**) each designate a point of attachment, namely valence bond. Me stands for methyl and Ac for acetyl.

The abbreviations and acronyms have the following meaning.

EB: electron beam

EUV: extreme ultraviolet

Mw: weight average molecular weight

Mn: number average molecular weight

Mw/Mn: molecular weight dispersity

GPC: gel permeation chromatography

PEB: post-exposure bake

PAG: photoacid generator

LWR: line width roughness

CDU: critical dimension uniformity

Amine Compound

One embodiment of the invention is an amine compound having the formula (1).

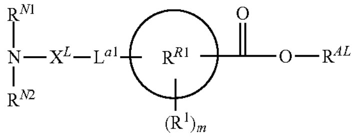

(1)

In formula (1), m is an integer of 0 to 10.

$R^{N1}$ and $R^{N2}$ are each independently hydrogen or a $C_1$-$C_{20}$ hydrocarbyl group. In the hydrocarbyl group, some or all of the hydrogen atoms may be substituted by halogen and any constituent —$CH_2$— may be replaced by —O— or —C(═O)—. $R^{N1}$ and $R^{N2}$ may bond together to form a ring with the nitrogen atom to which they are attached, the ring optionally containing —O— or —S—. It is noted that $R^{N1}$ and $R^{N2}$ are not hydrogen at the same time.

The hydrocarbyl groups $R^{N1}$ and $R^{N2}$ may be saturated or unsaturated and straight, branched or cyclic. Examples thereof include $C_1$-$C_{20}$ alkyl groups such as methyl, ethyl, n-propyl, isopropyl, n-butyl, tert-butyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl; $C_2$-$C_{20}$ alkenyl groups such as vinyl, allyl, propenyl, butenyl, and hexenyl; $C_3$-$C_{20}$ cyclic unsaturated hydrocarbyl groups such as cyclohexenyl; $C_6$-$C_{20}$ aryl groups such as phenyl and naphthyl; $C_7$-$C_{20}$ aralkyl groups such as benzyl, 1-phenylethyl and 2-phenylethyl; and combinations thereof.

The ring that $R^{N1}$ and $R^{N2}$, taken together, form with the nitrogen atom to which they are attached, is preferably alicyclic. Examples of the ring include aziridine, azetidine, pyrrolidine, and piperidine rings, but are not limited thereto. Any constituent —$CH_2$— in the nitrogen-containing heterocycle may be replaced by —O— or —S—.

In formula (1), $X^L$ is a $C_1$-$C_{40}$ hydrocarbylene group which may contain a heteroatom. Examples thereof are shown below, but not limited thereto. In the formulae, the asterisks (*) designate points of attachment to $L^{a1}$ and the nitrogen atom, respectively.

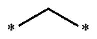

$X^L$-0

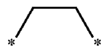

$X^L$-1

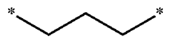

$X^L$-2

-continued
$X^L$-3
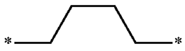
$X^L$-4
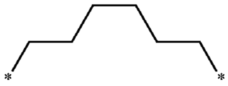
$X^L$-5
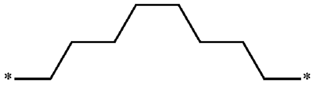
$X^L$-6
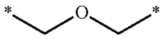
$X^L$-7
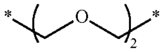
$X^L$-8
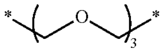
$X^L$-9
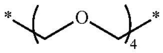
$X^L$-10
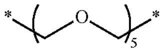
$X^L$-11
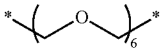
$X^L$-12
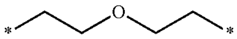
$X^L$-13
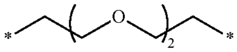
$X^L$-14
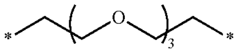
$X^L$-15
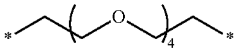
$X^L$-16
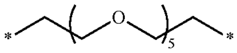
$X^L$-17
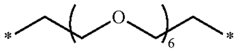
$X^L$-18
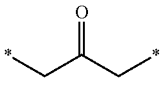
$X^L$-19
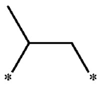
$X^L$-20
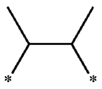
$X^L$-21
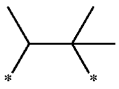
-continued
$X^L$-22
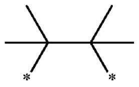
$X^L$-23
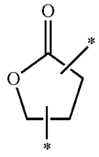
$X^L$-24
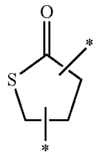
$X^L$-25
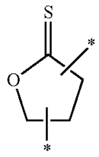
$X^L$-26
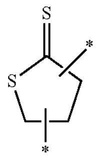
$X^L$-27
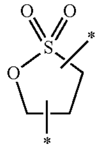
$X^L$-28
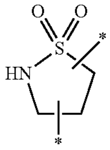
$X^L$-29
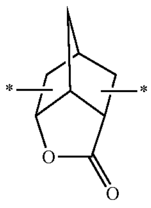
$X^L$-30
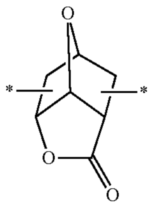

-continued $X^L$-31

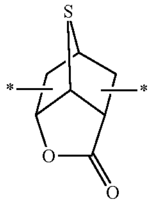

$X^L$-32

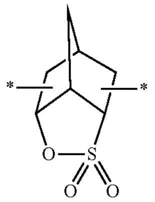

$X^L$-33

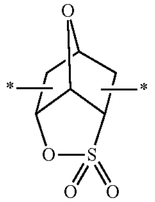

$X^L$-34

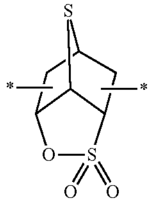

$X^L$-35

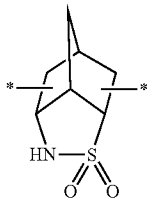

$X^L$-36

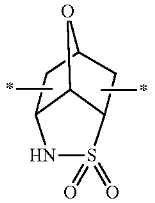

$X^L$-37

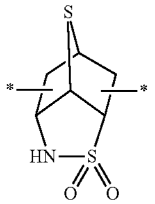

$X^L$-38

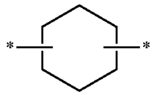

-continued $X^L$-39

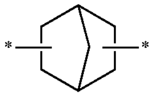

$X^L$-40

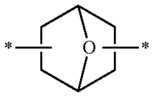

$X^L$-41

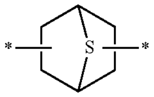

$X^L$-42

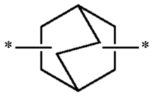

$X^L$-43

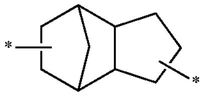

$X^L$-44

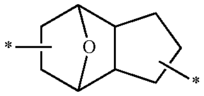

$X^L$-45

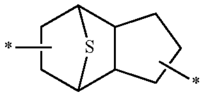

$X^L$-46

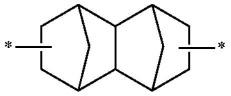

$X^L$-47

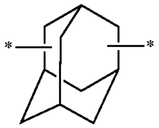

$X^L$-48

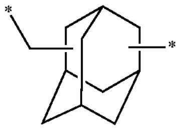

$X^L$-49

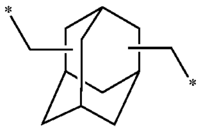

Of these, $X^L$-0 to $X^L$-22 and $X^L$-47 to $X^L$-49 are preferred, with $X^L$-0 to $X^L$-17 being more preferred.

In formula (1), $L^{a1}$ is a single bond, ether bond, ester bond, sulfonic ester bond, carbonate bond or carbamate bond. Inter alia, a single bond, ether bond and ester bond are preferred, with the ether bond and ester bond being more preferred.

In formula (1), the ring is a $C_2$-$C_{20}$ (m+2)-valent heterocyclic group having a lactone, lactam, sultone or sultam structure. The heterocyclic group may be either monocyclic or fused ring although the fused ring is preferred from the standpoints of available reactants and the compound having a high boiling point.
Examples of the heterocyclic group wherein m=0 are shown below, but not limited thereto. In the formulae, the asterisks (*) designate points of attachment to $L^{a1}$ and the carbon atom in —C(═O)—O—, respectively.
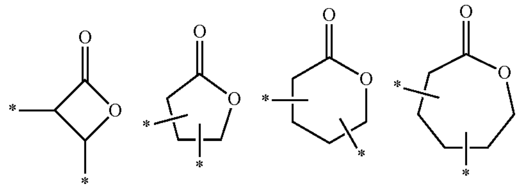
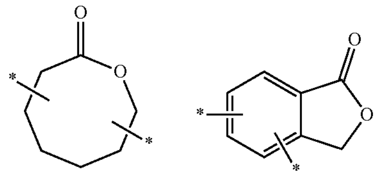
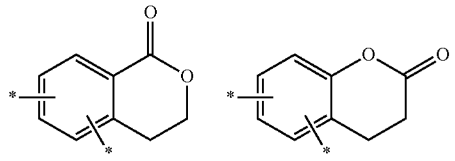
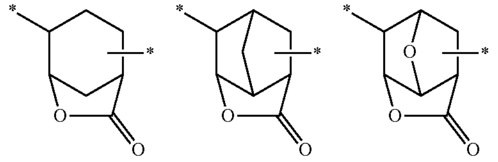
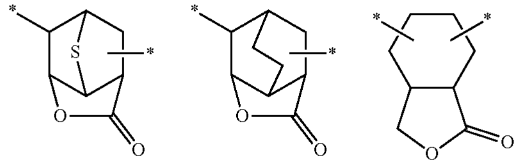
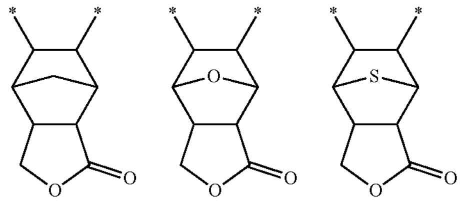
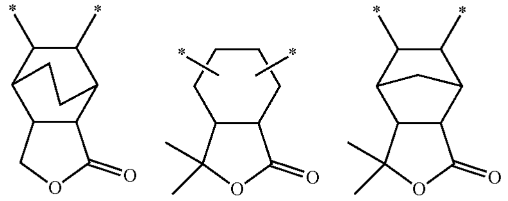
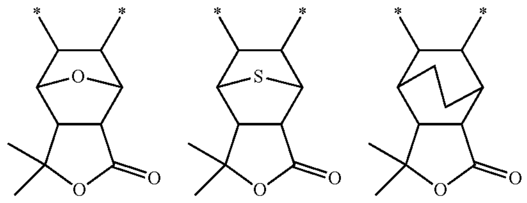
-continued
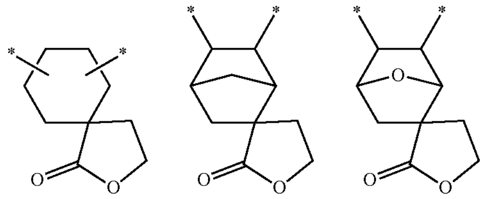
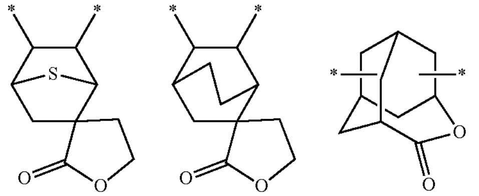
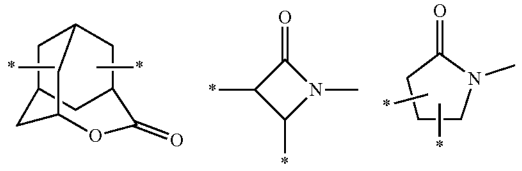
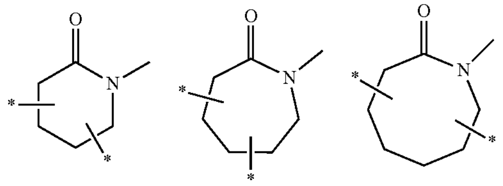
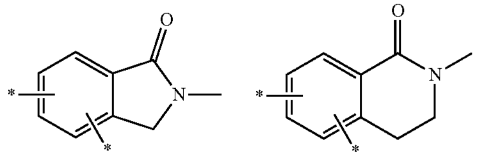
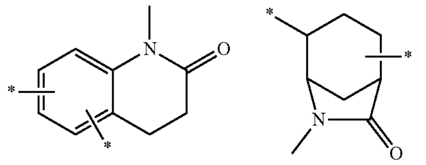
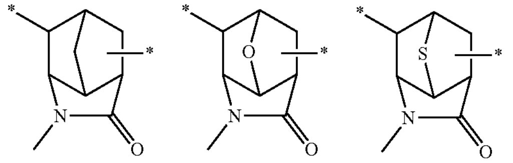
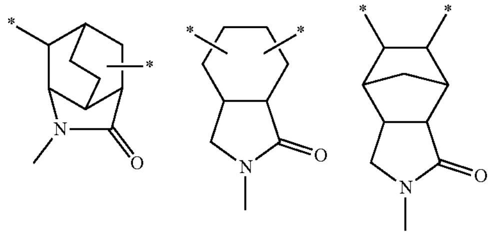
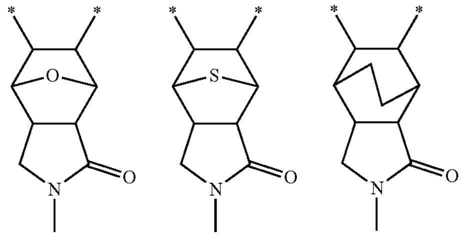

-continued
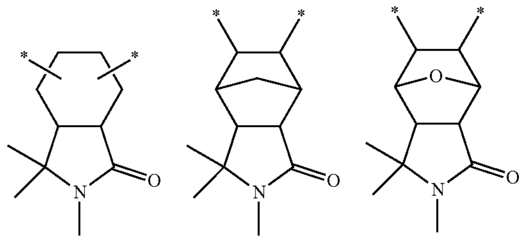
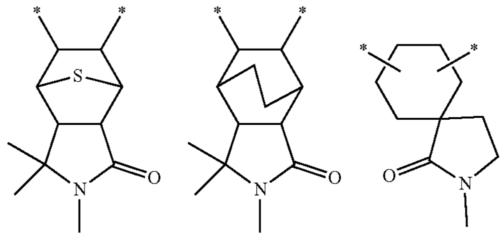
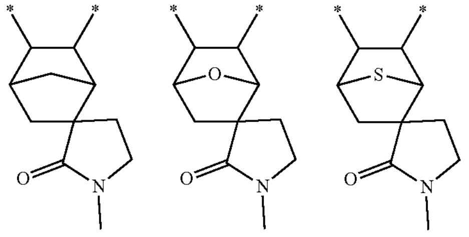
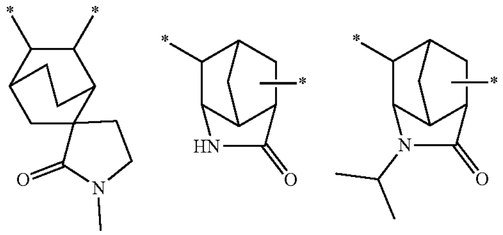
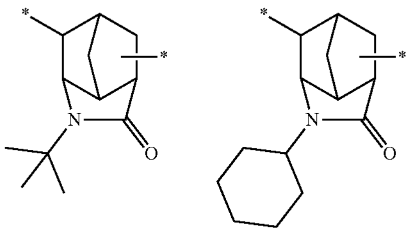
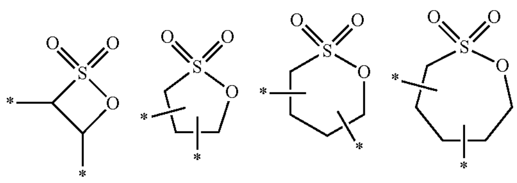
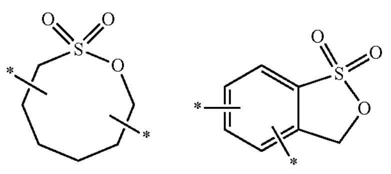
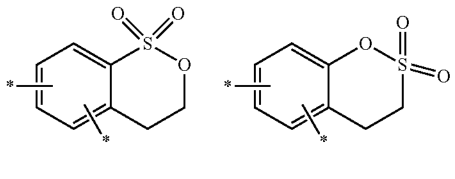
-continued
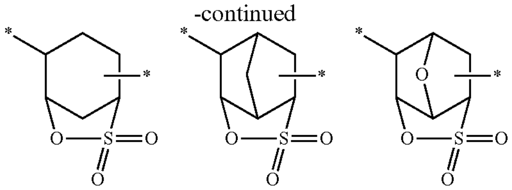
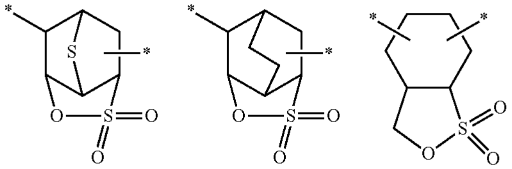
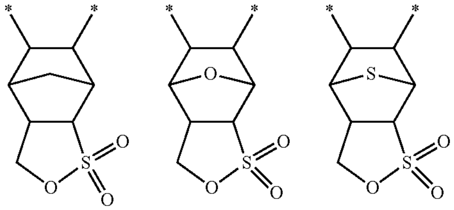
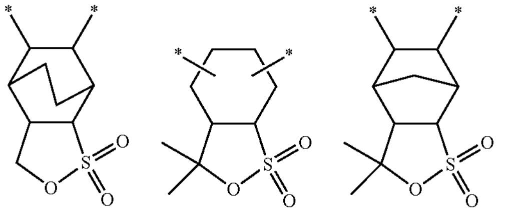
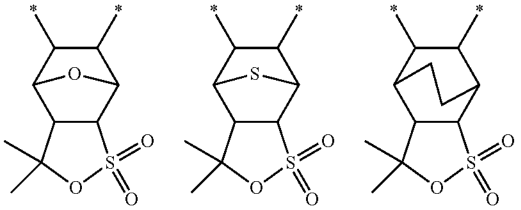
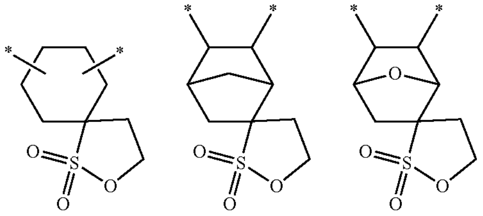
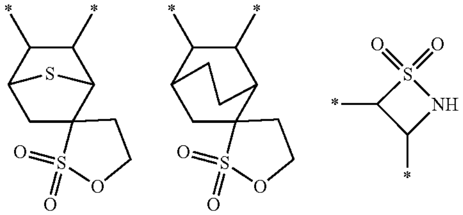
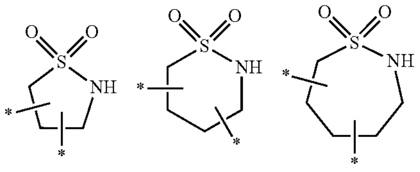
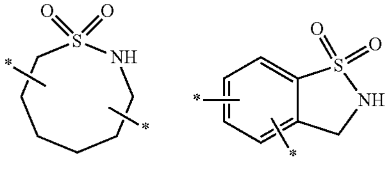

-continued

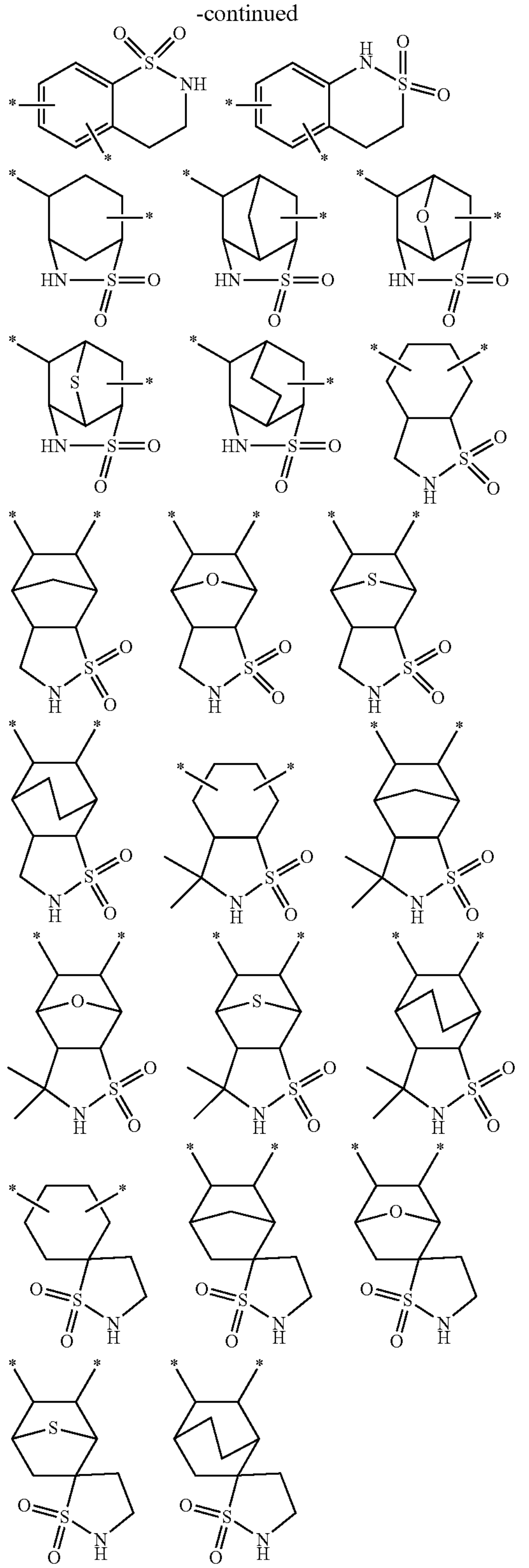

In formula (1), $R^1$ is a $C_1$-$C_{20}$ hydrocarbyl group which may contain a heteroatom. The hydrocarbyl group may be saturated or unsaturated and straight, branched or cyclic. Examples thereof include $C_1$-$C_{20}$ alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, and n-decyl; $C_3$-$C_{20}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo $[5.2.1.0^{2,6}]$decanyl, adamantyl, and adamantyhnethyl; $C_6$-$C_{20}$ aryl groups such as phenyl, naphthyl, and anthracenyl; and combinations thereof. In the hydrocarbyl group, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain a hydroxy moiety, fluorine, chlorine, bromine, iodine, cyano moiety, carbonyl moiety, ether bond, ester bond, sulfonic ester bond, carbonate bond, carbamate bond, amide bond, imide bond, lactone ring, sultone ring, thiolactone ring, lactam ring, sultam ring, carboxylic anhydride (—C(=O)—O—C(=O)—) or haloalkyl moiety.

When m is 2 or more, a plurality of IV may be the same or different, a plurality of $R^1$ may bond together to form a ring with the atoms on $R^{R1}$ to which they are attached. Examples of the ring thus formed include cyclopropane, cyclobutane, cyclopentane, cyclohexane, norbornane, and adamantane rings. Two IV bonded to a common atom in the ring $R^{R1}$ may bond together to form a ring, i.e., spiro ring.

In formula (1), $R^{AL}$ is an acid labile group. The acid labile group is preferably selected from tertiary hydrocarbyl groups and groups which form an acetal structure with the adjacent oxygen atom, with the tertiary hydrocarbyl groups being especially preferred.

The tertiary hydrocarbyl groups are preferably of 4 to 20 carbon atoms, more preferably of 4 to 15 carbon atoms. Examples thereof are shown below, but not limited thereto. The asterisk (*) designates a point of attachment to the oxygen atom.

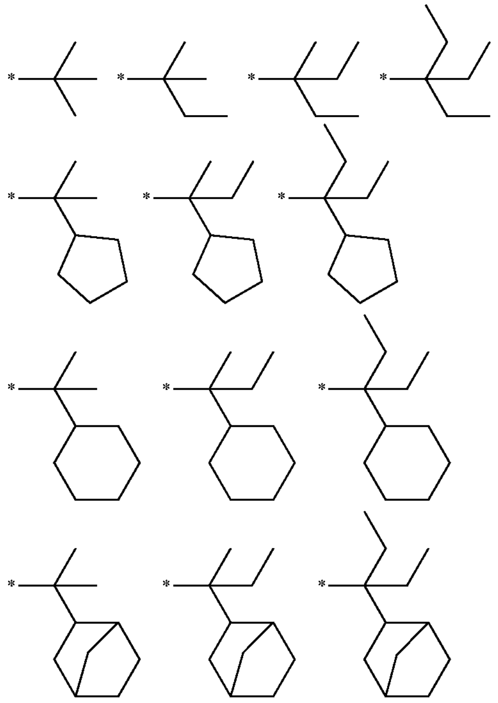

-continued
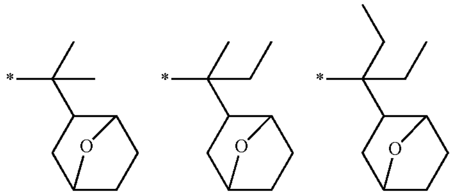
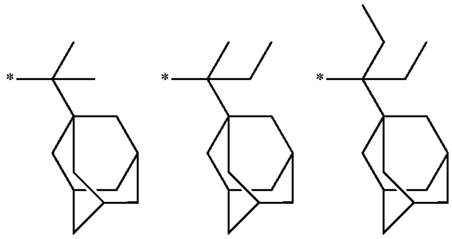
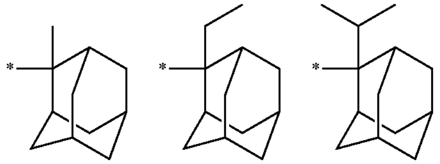
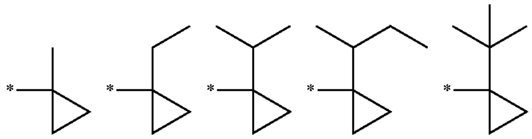
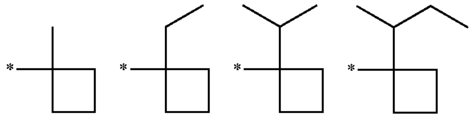
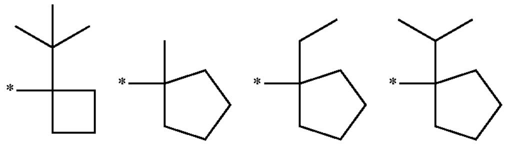
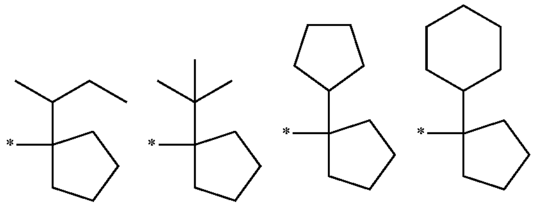
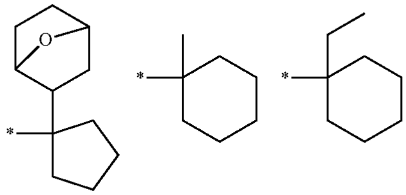
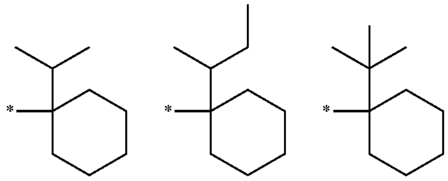
-continued
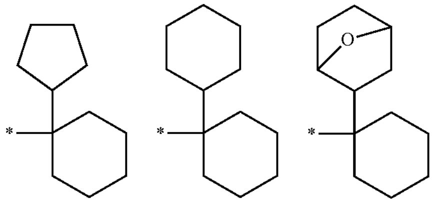
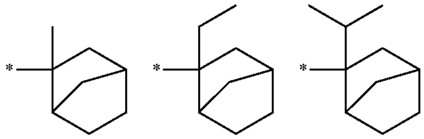
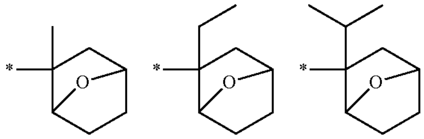
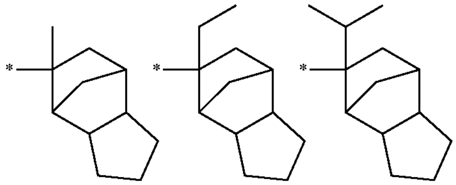
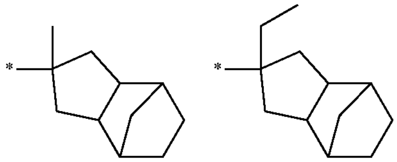
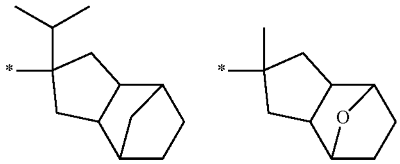
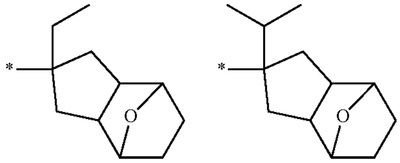
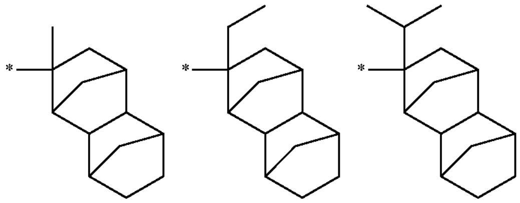
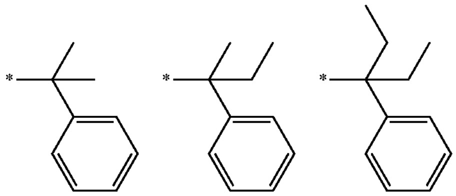

-continued
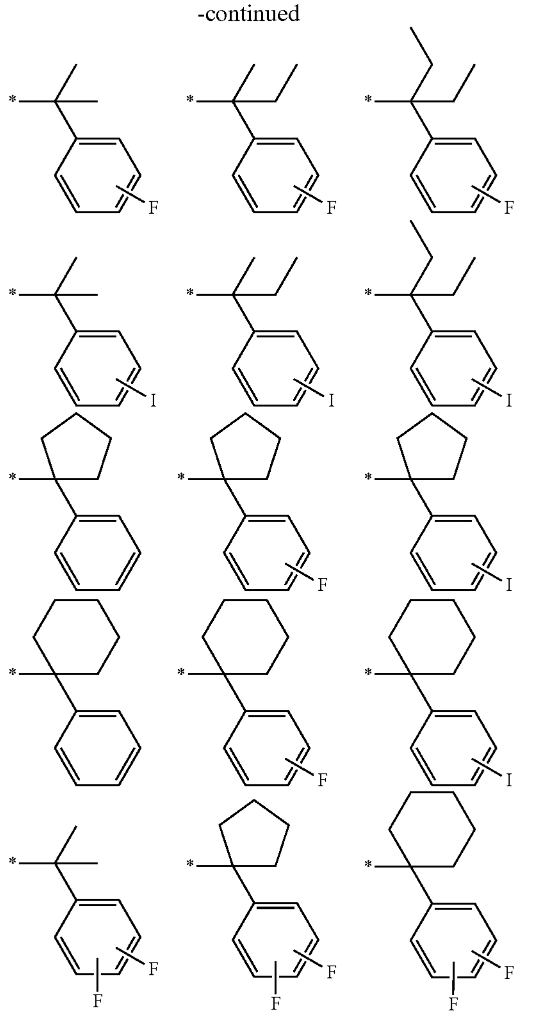
The acetal structure-forming group is typically selected from groups having the formula (L1). Examples of the acetal structure-forming group are shown below, but not limited thereto. The asterisk (*) designates a point of attachment to the oxygen atom.
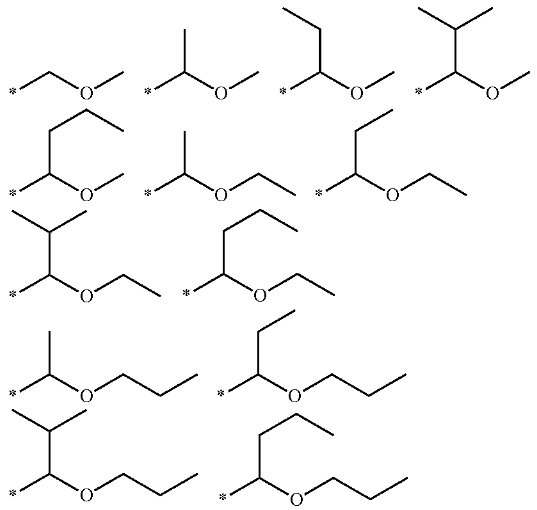
-continued
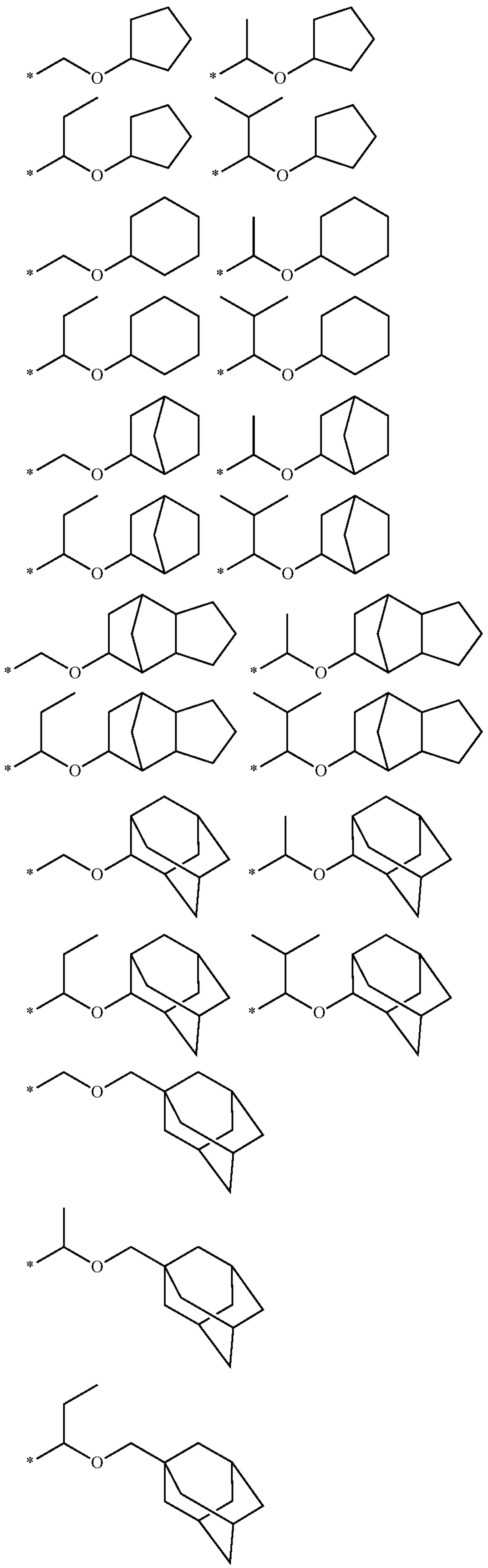

-continued

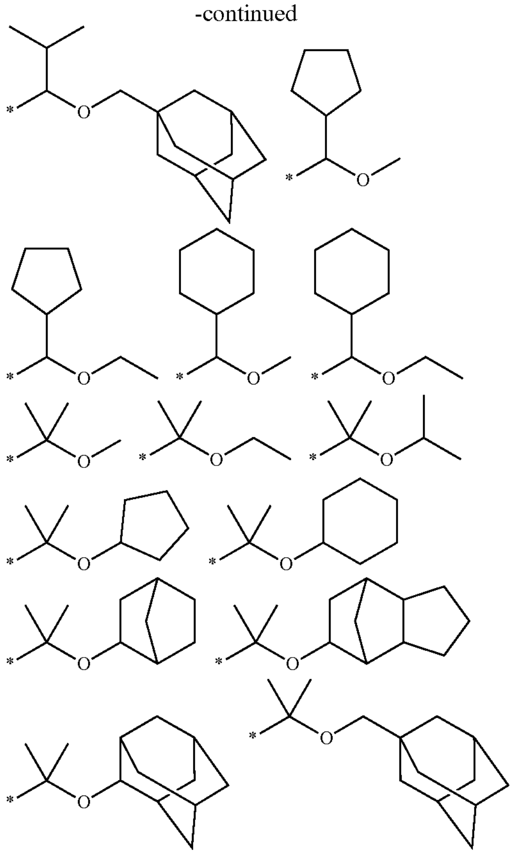

Of the amine compounds having formula (1), those having the formula (1A) are preferred.

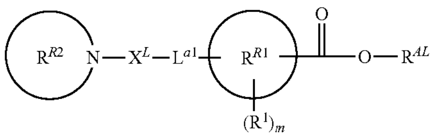

(1A)

Herein in, $X^L$, $L^{a1}$, $R^{R1}$, $R^{R2}$, $R^1$, and $R^{AL}$ are as defined above.

In formula (1A), a $C_3$-$C_{20}$ alicyclic hydrocarbon group forms the ring $R^{R2}$ with the nitrogen atom, and any constituent —$CH_2$— in the ring may be replaced by —O— or —S—. Preferred as the ring $R^{R2}$ are $C_3$-$C_{20}$ alicyclic hydrocarbon groups in which —$CH_2$— is replaced by —O— or —S—.

Of the amine compounds having formula (1A), those having the formula (1B) are more preferred.

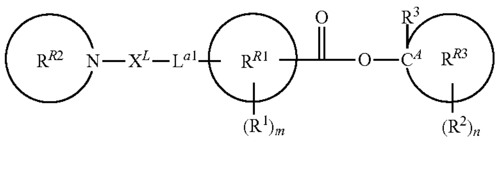

(1B)

Herein m, $X^L$, $L^{a1}$, $R^{R1}$, $R^{R2}$, and $R^1$ are as defined above.

In formula (1B), n is an integer of 0 to 20. A $C_3$-$C_{20}$ alicyclic hydrocarbon group forms the ring $R^{R3}$ with the carbon atom $C^A$. Any constituent —$CH_2$— in the ring may be replaced by a heteroatom-containing moiety. $R^2$ is a $C_1$-$C_{20}$ hydrocarbyl group which may contain a heteroatom. When n is 2 or more, a plurality of $R^2$ may be the same or different, and a plurality of $R^2$ may bond together to form a ring structure. $R^3$ is a $C_1$-$C_{20}$ hydrocarbyl group which may contain a heteroatom.

Preferred examples of the alicyclic hydrocarbon group forming the ring $R^{R3}$ include cyclopentane, cyclohexane, and adamantane rings.

Examples of the amine compound having formula (1) are shown below, but not limited thereto.

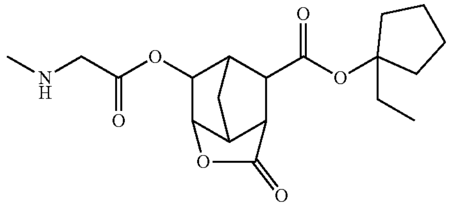

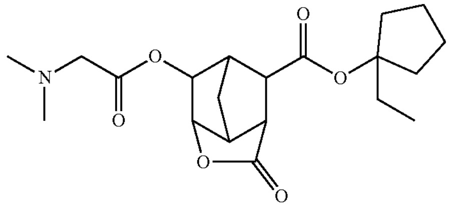

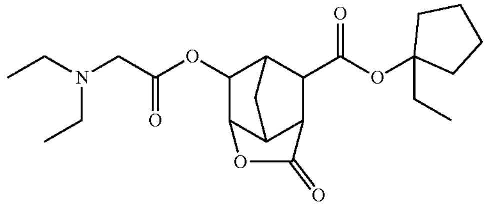

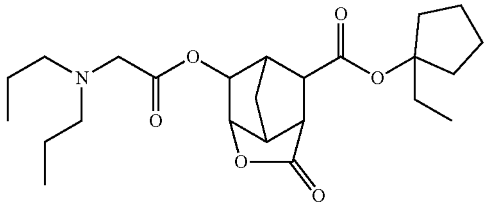

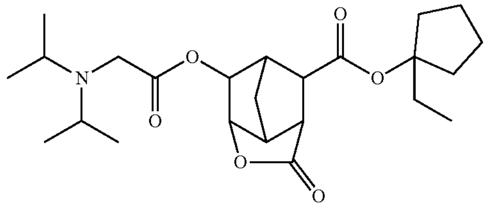

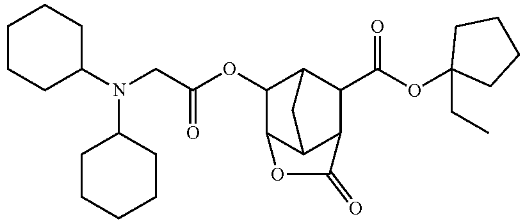

-continued
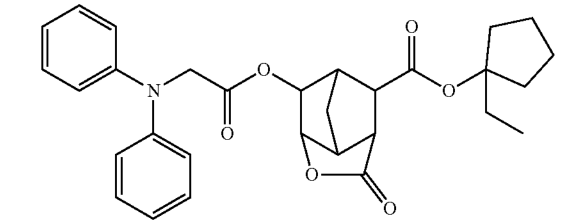
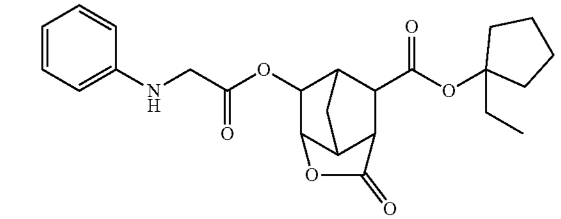
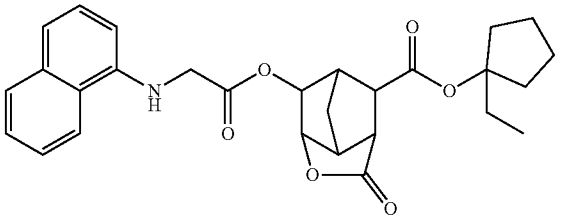
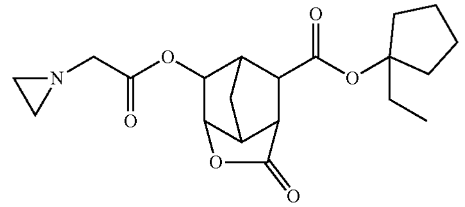
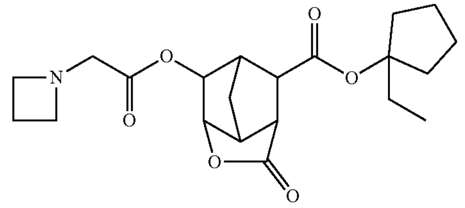
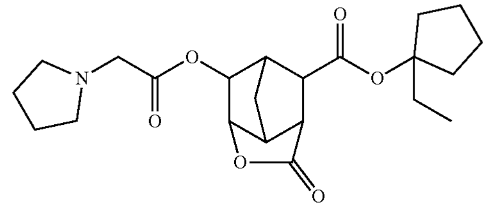
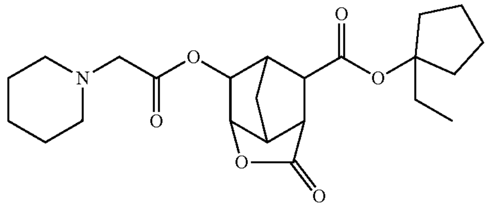
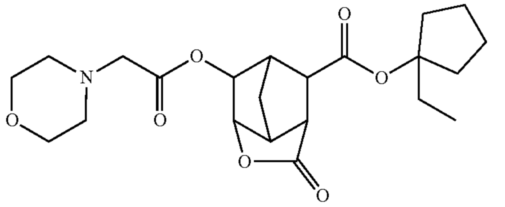
-continued
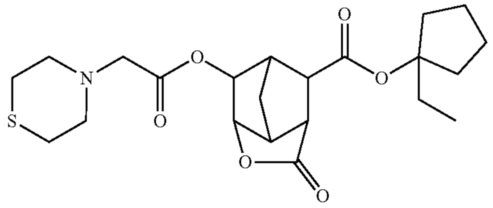
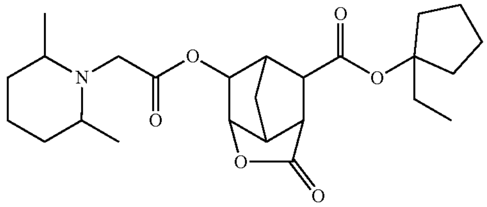
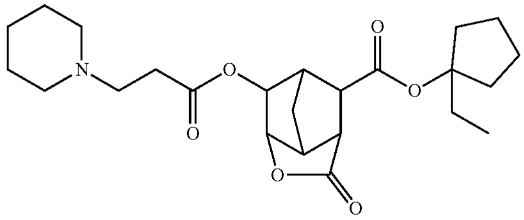
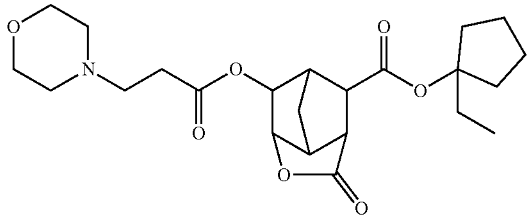
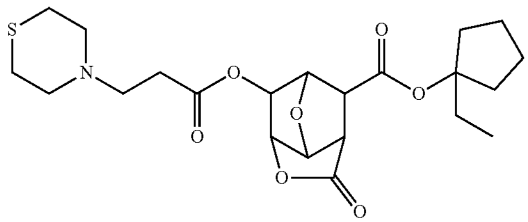
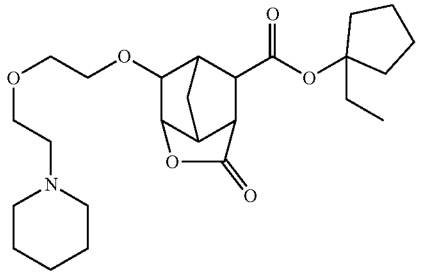
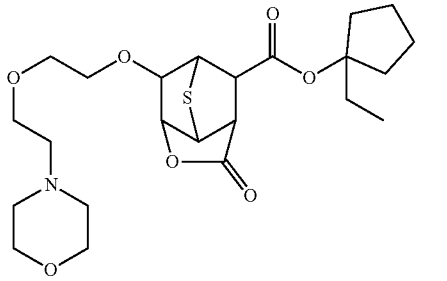

-continued
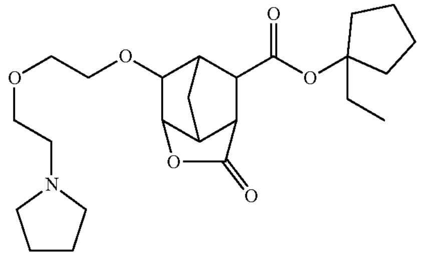
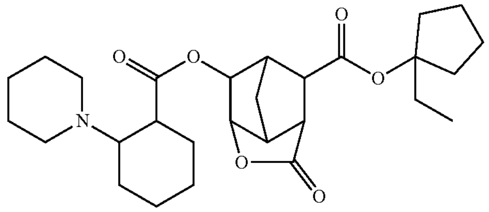
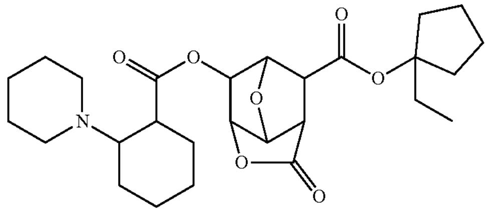
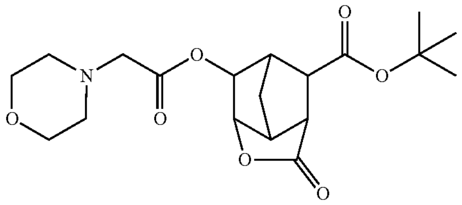
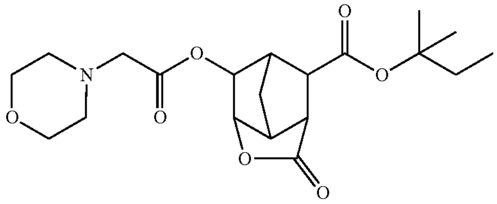
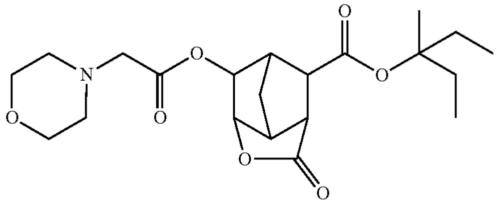
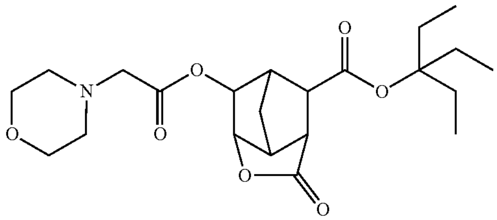
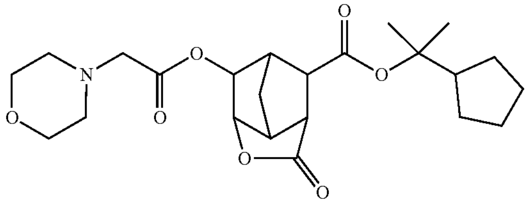
-continued
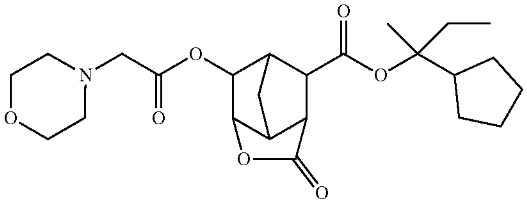
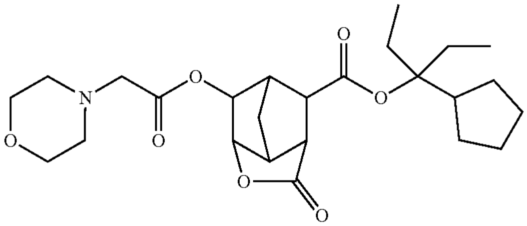
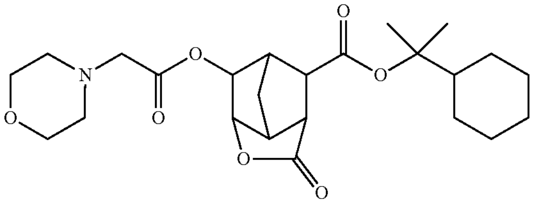
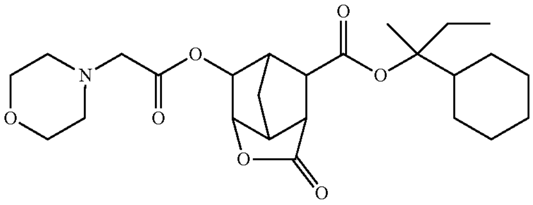
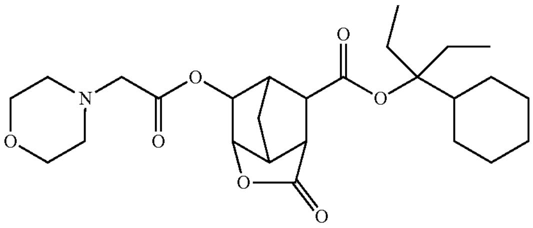
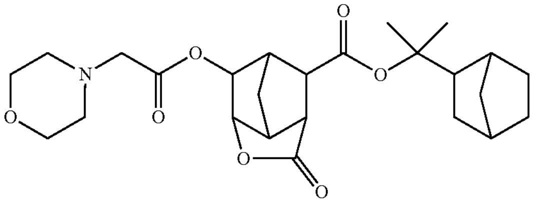
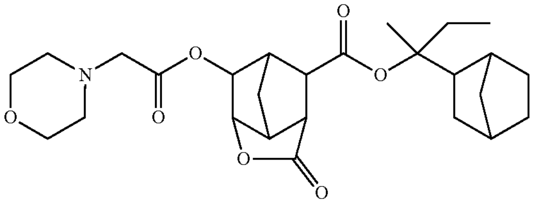
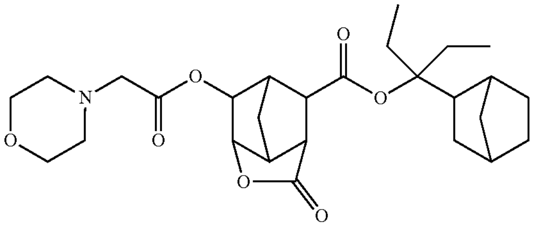

-continued
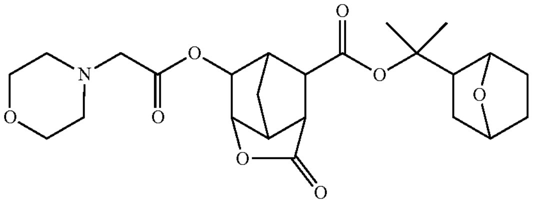
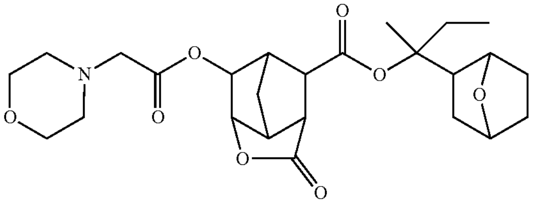
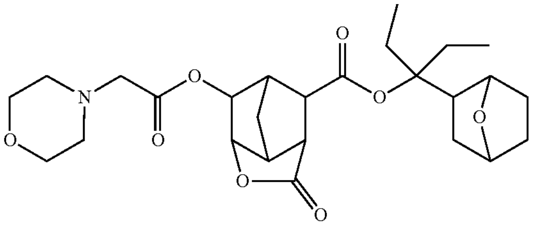
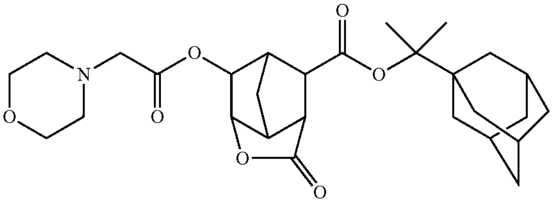
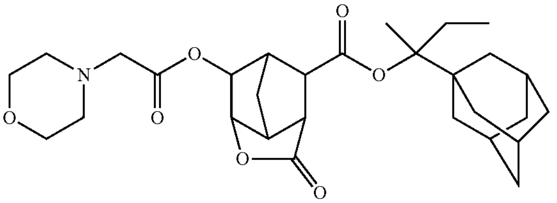
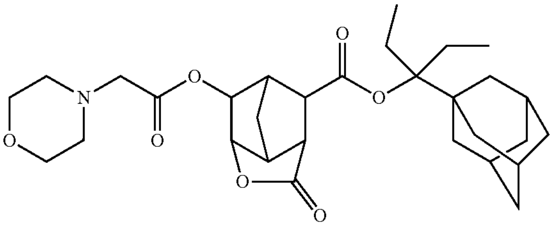
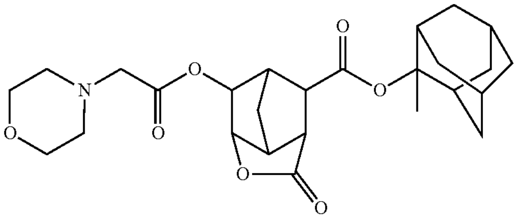
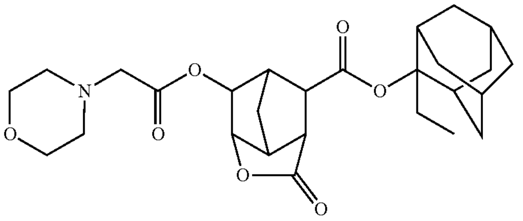
-continued
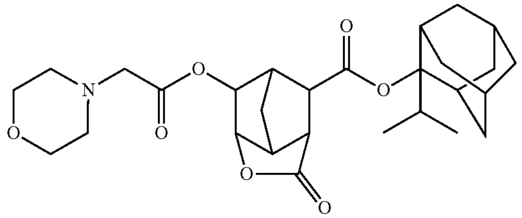
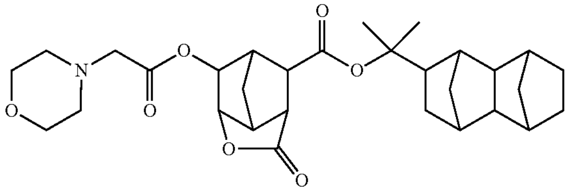
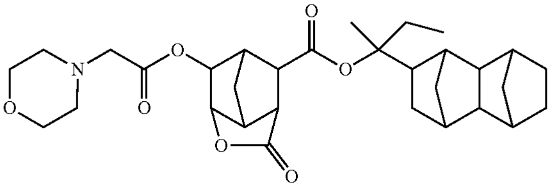
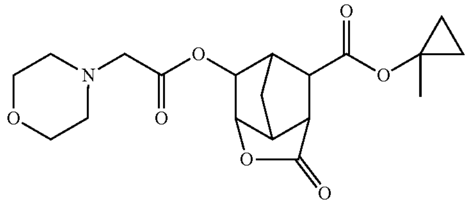
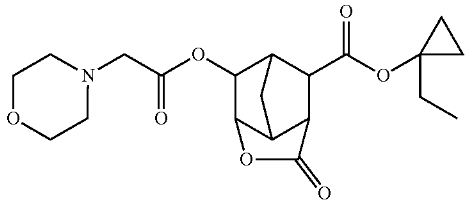
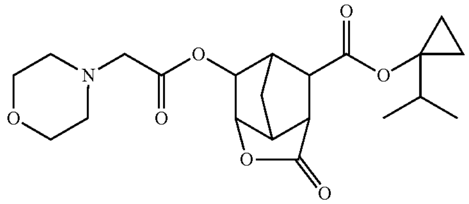
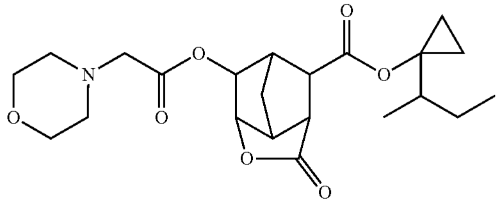
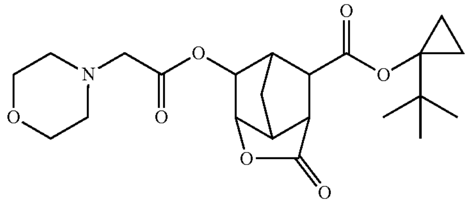

-continued
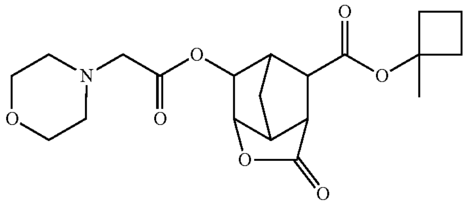
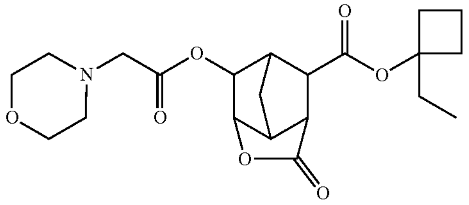
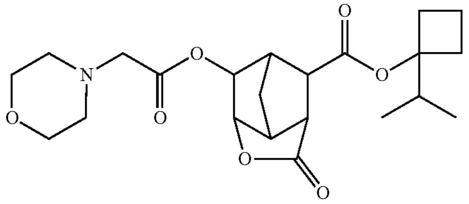
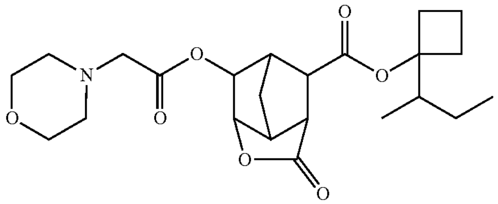
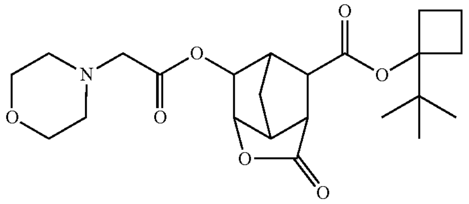
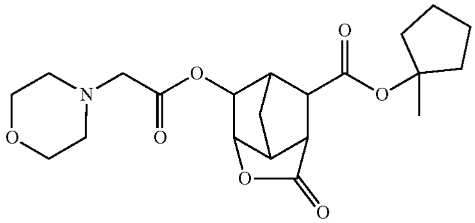
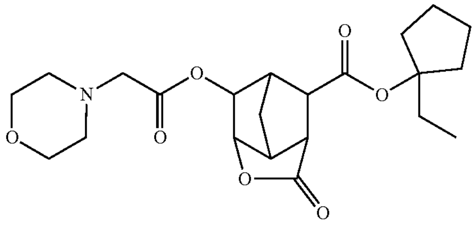
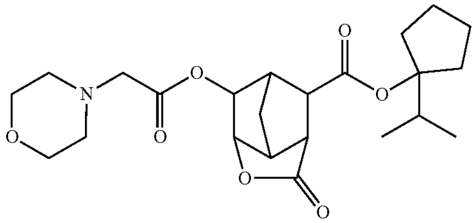
-continued
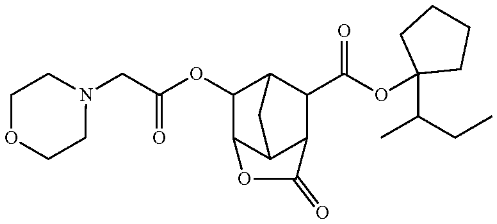
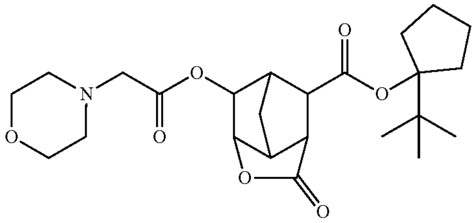
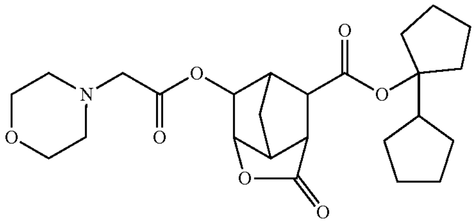
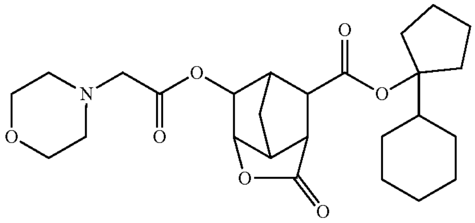
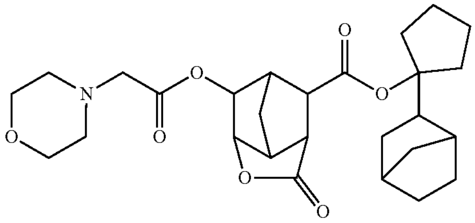
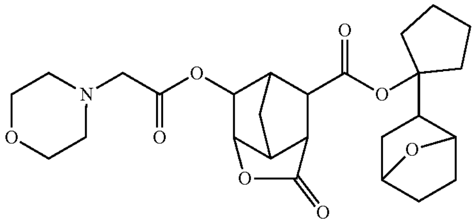
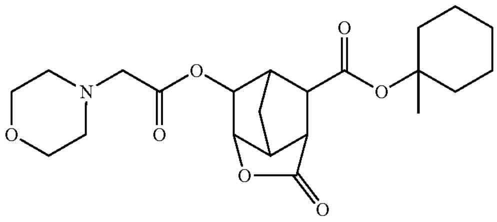

-continued
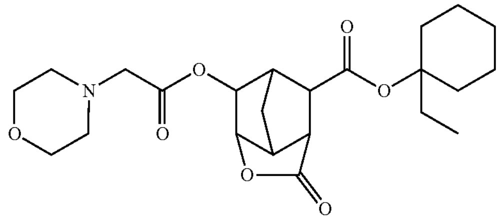
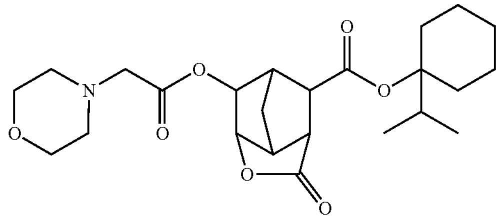
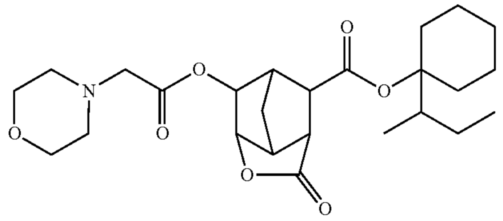
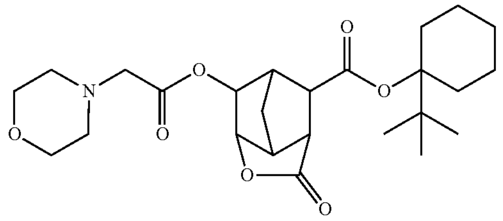
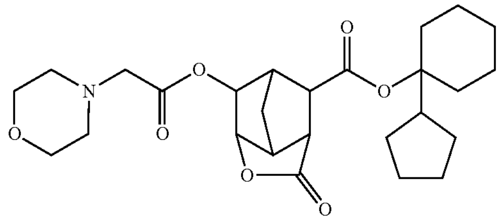
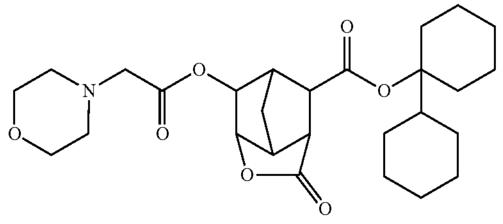
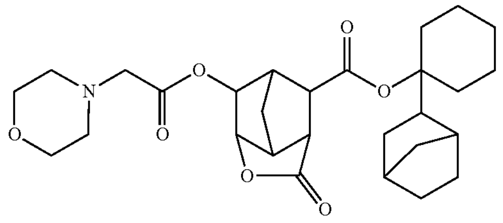
-continued
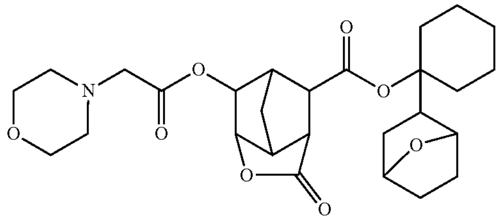
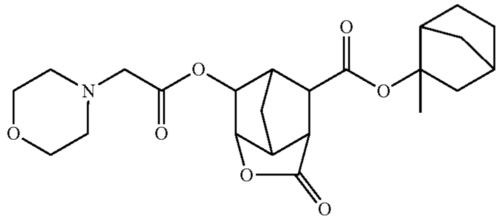
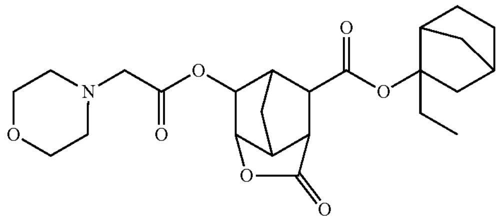
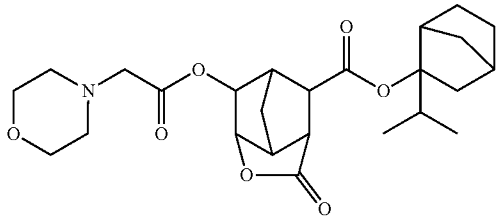
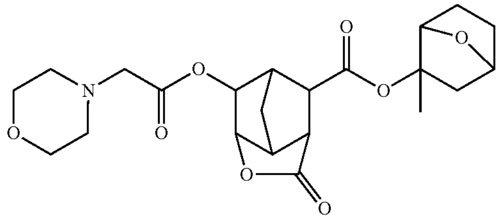
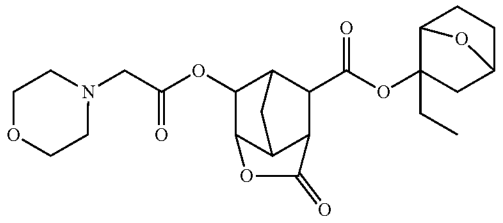
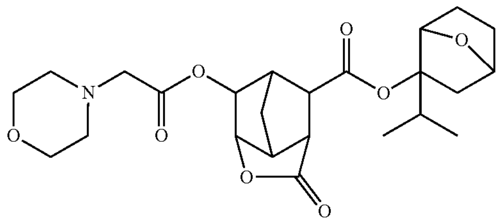

-continued
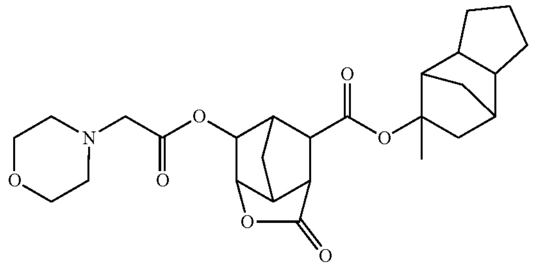
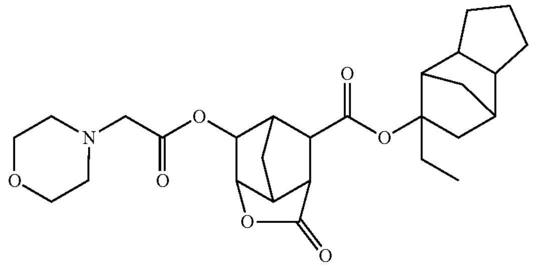
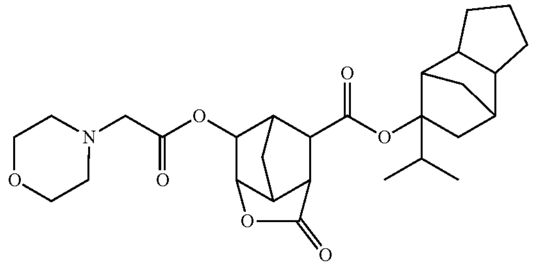
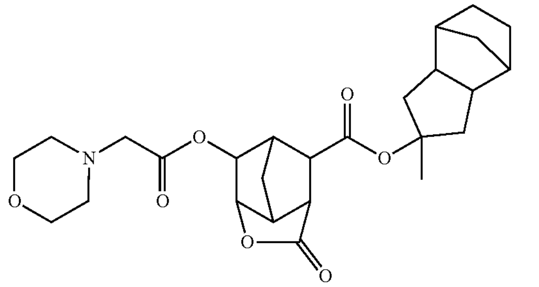
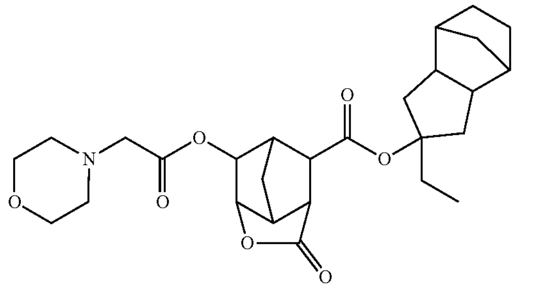
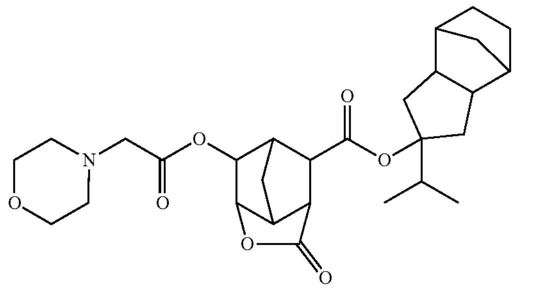
-continued
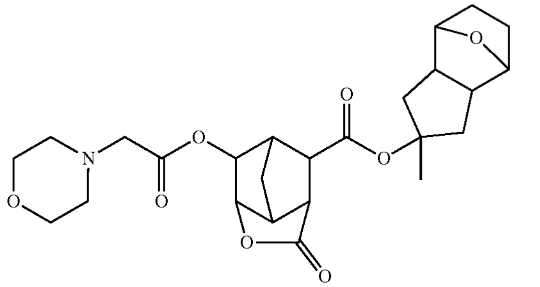
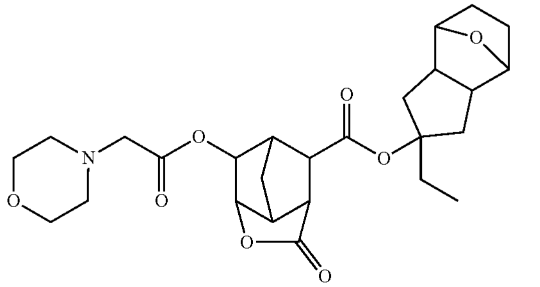
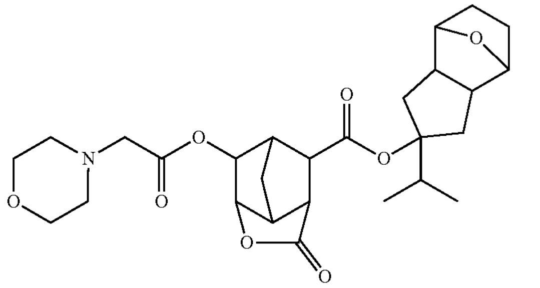
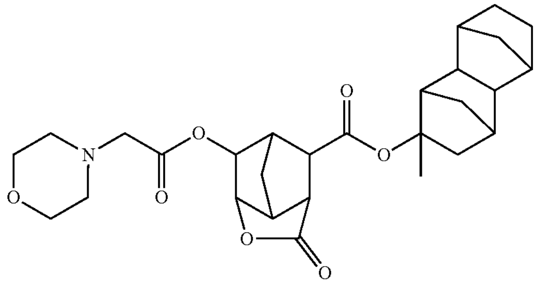
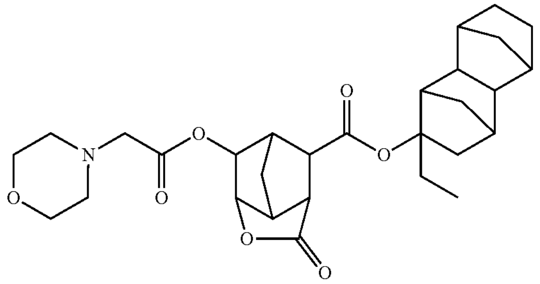
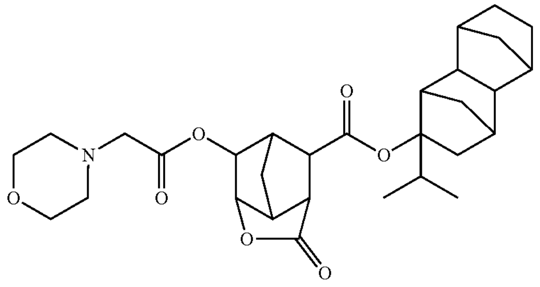

-continued
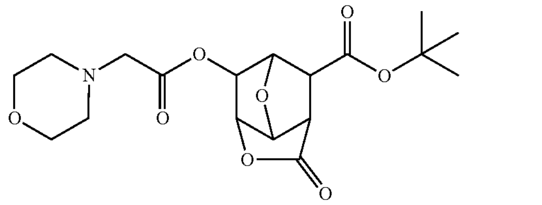
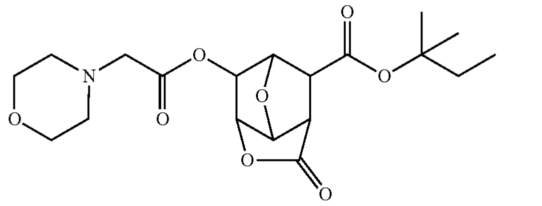
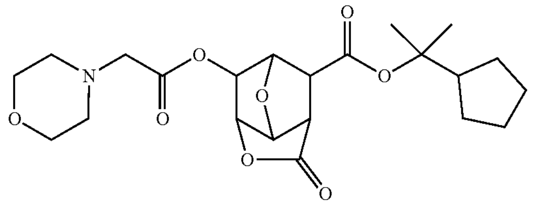
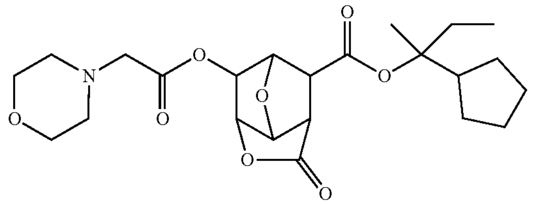
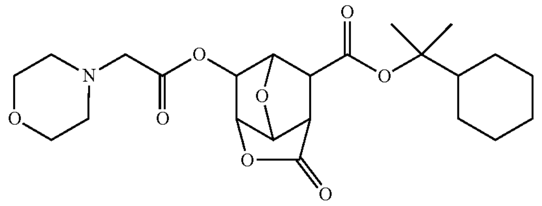
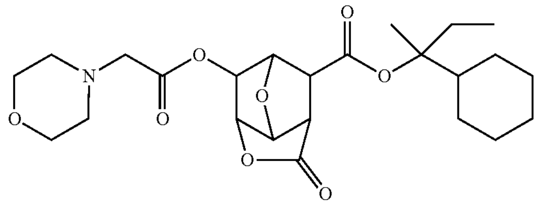
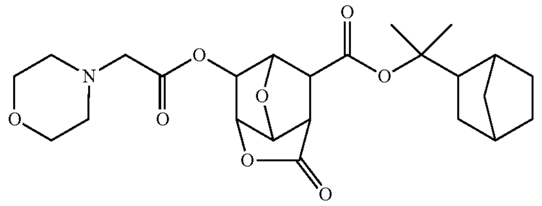
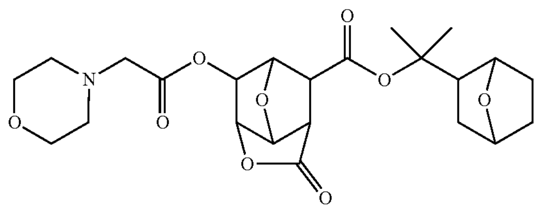
-continued
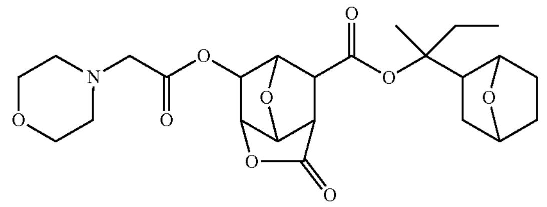
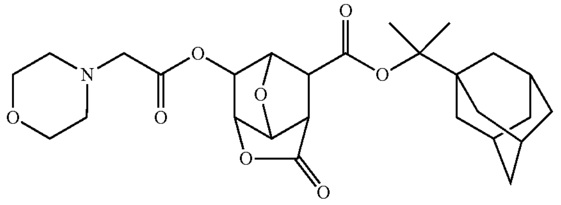
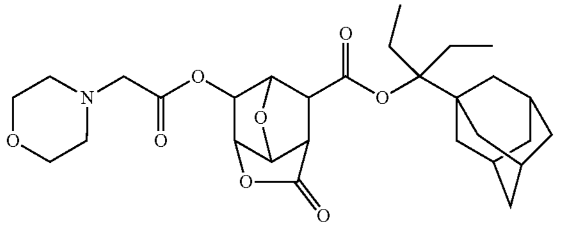
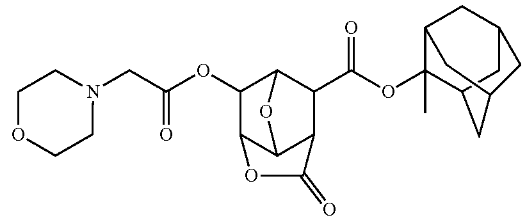
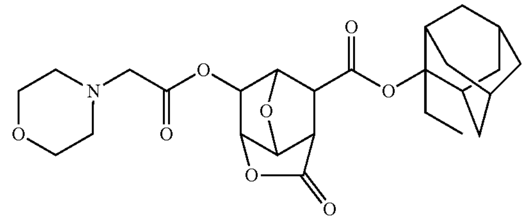
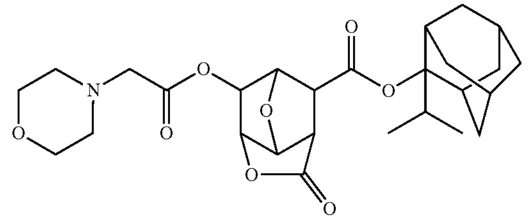
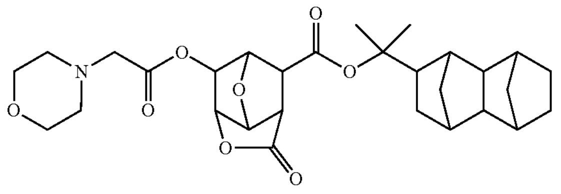
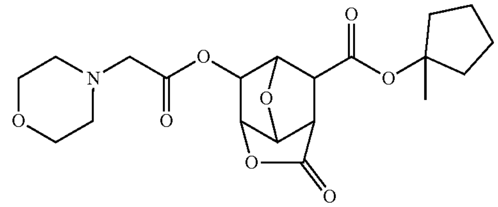

-continued
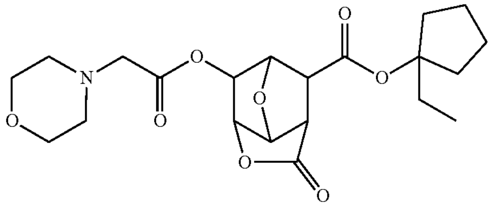
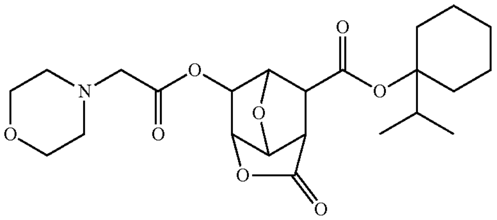
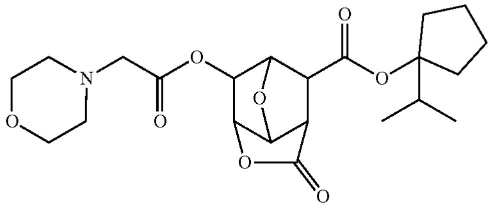
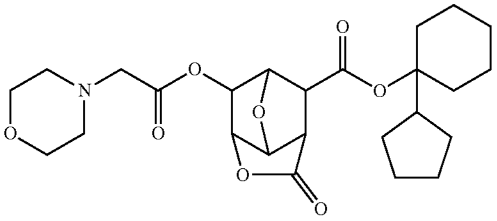
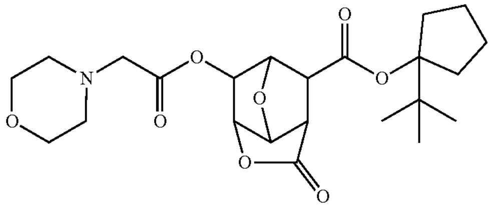
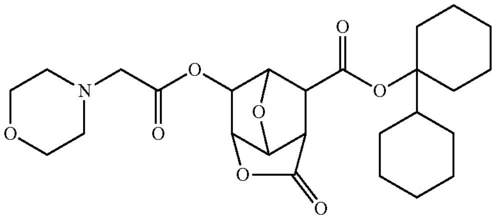
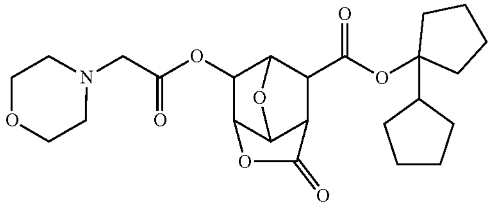
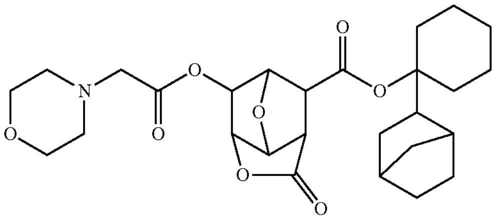
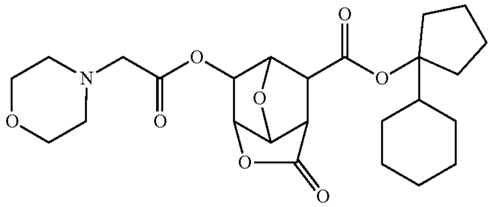
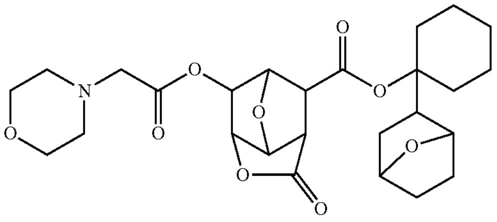
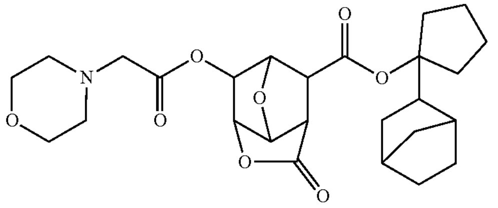
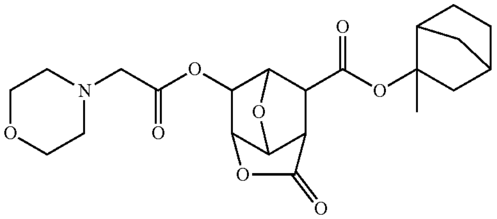
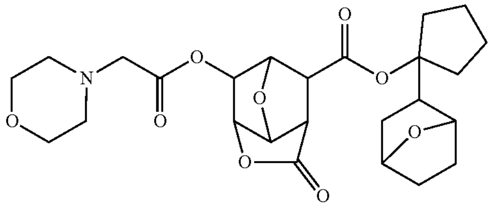
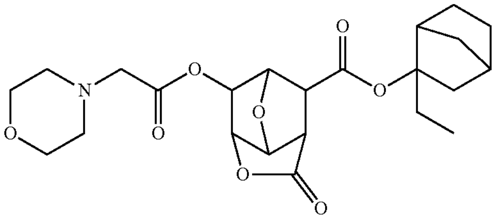
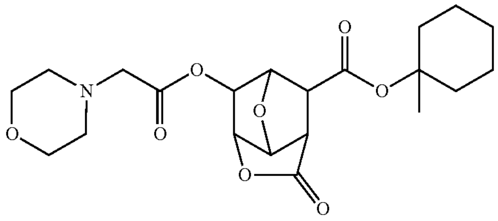

-continued
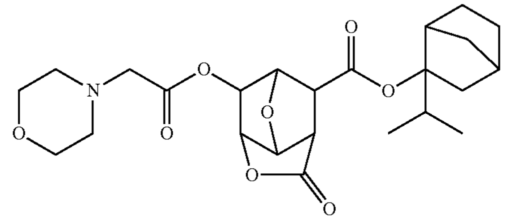
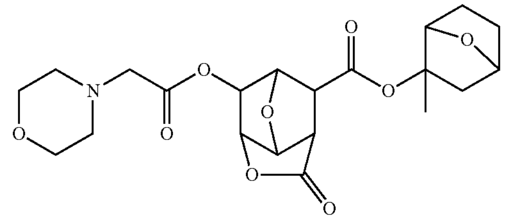
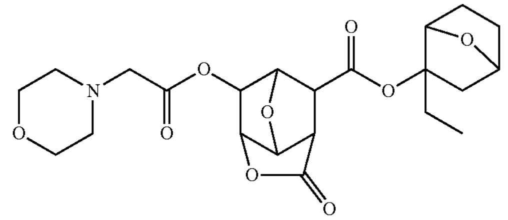
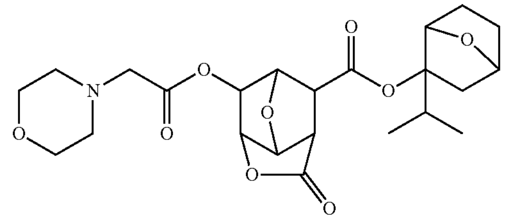
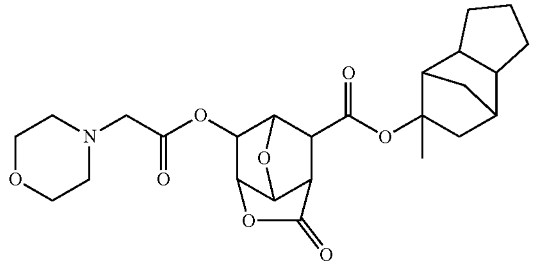
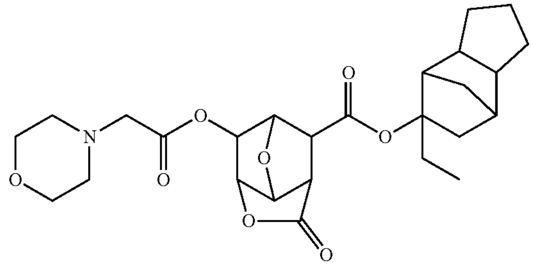
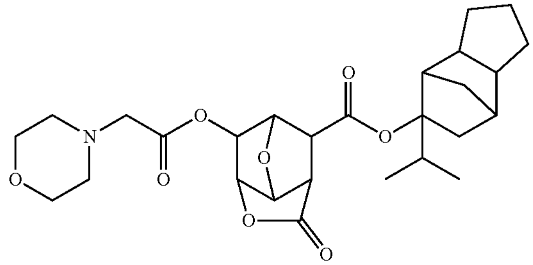
-continued
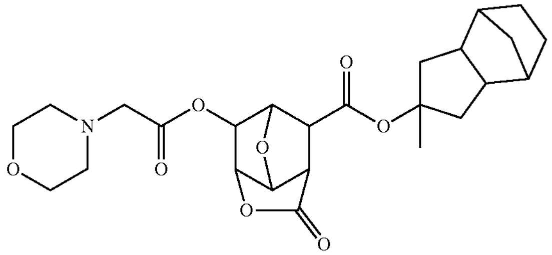
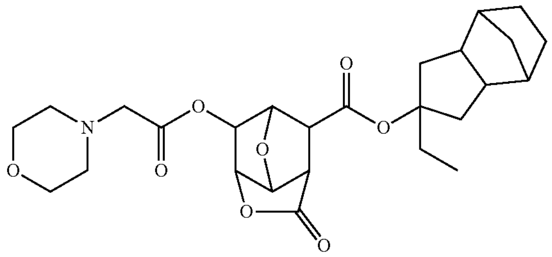
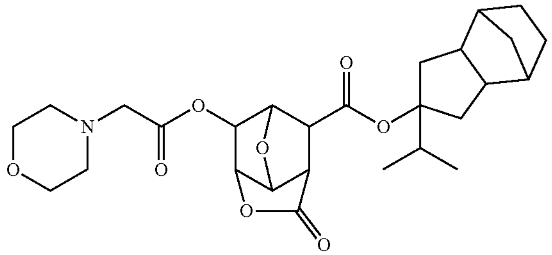
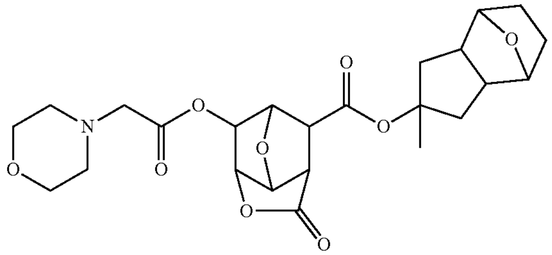
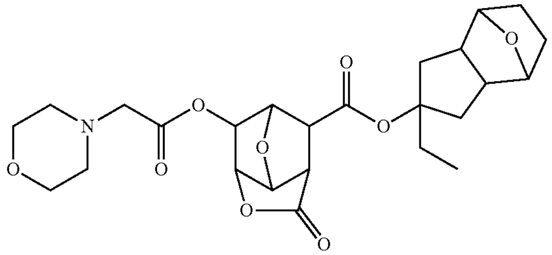
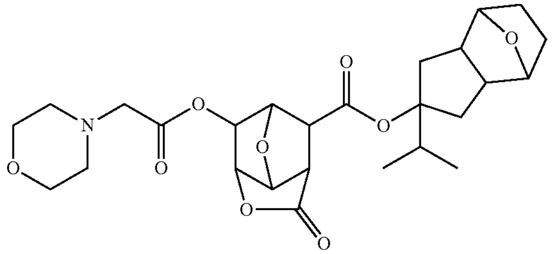

-continued
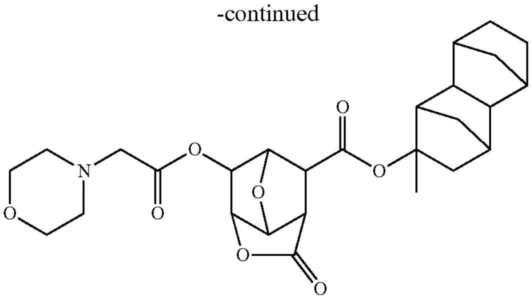
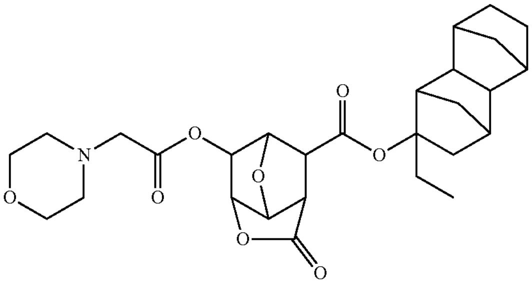
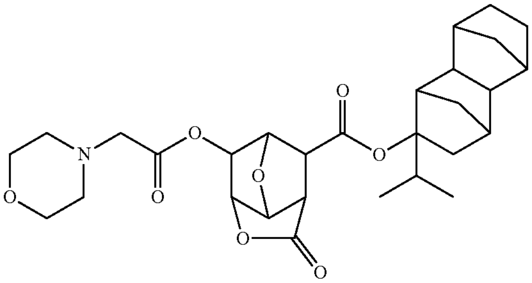
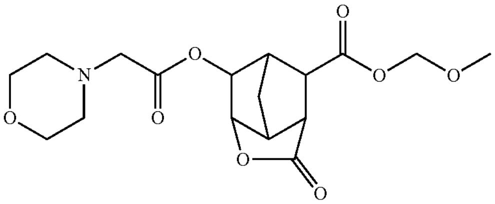
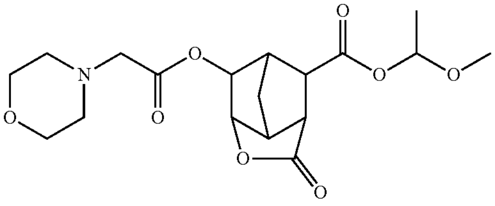
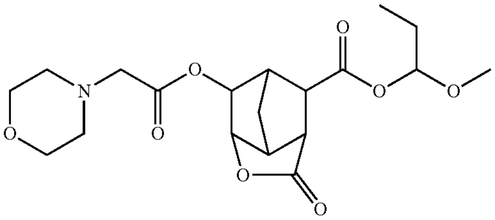
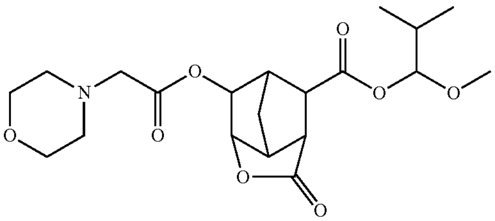
-continued
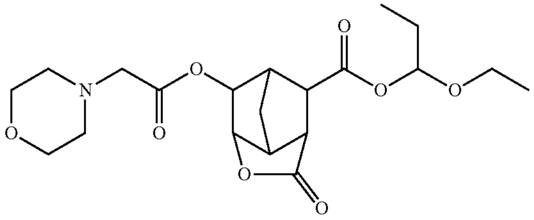
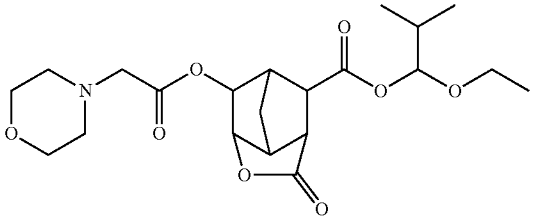
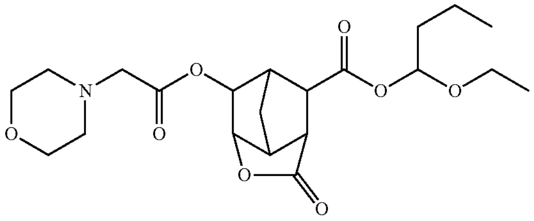
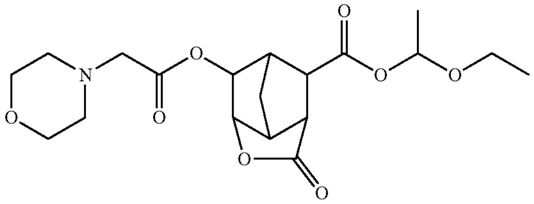
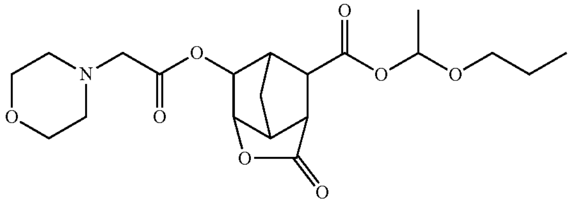
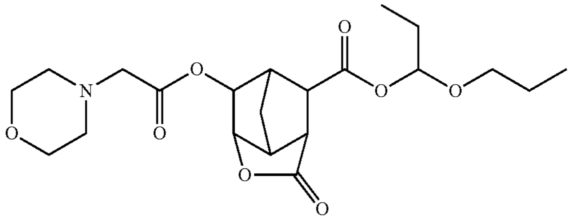
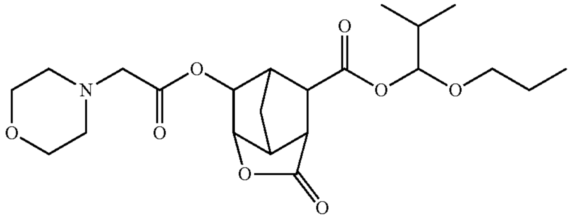
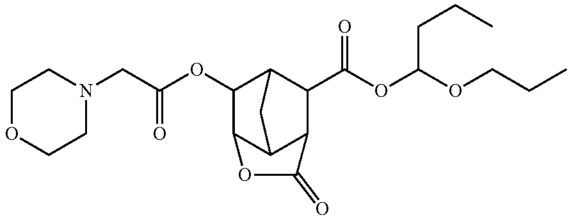

-continued
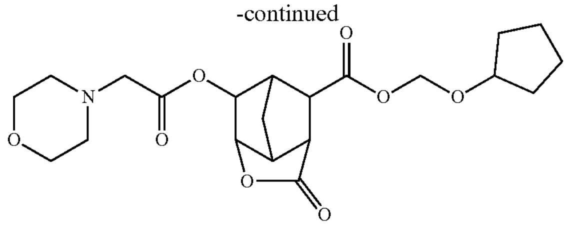
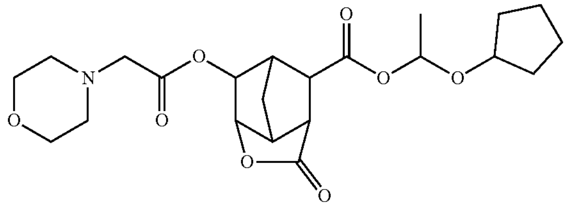
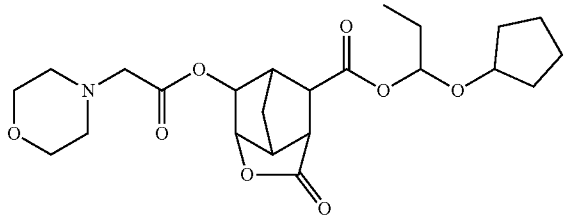
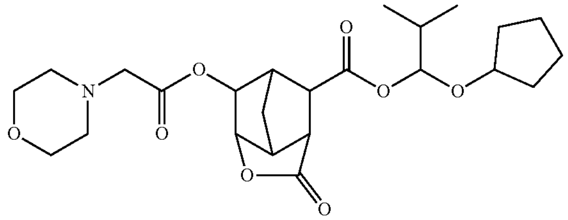
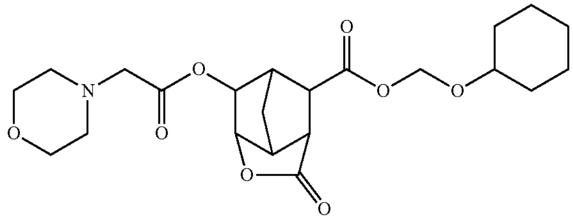
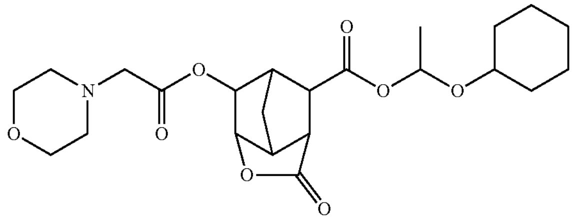
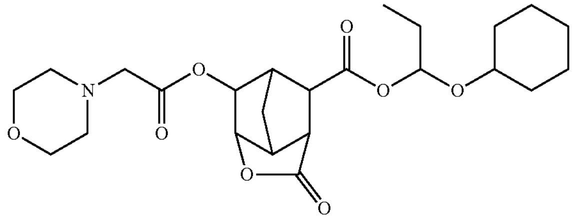
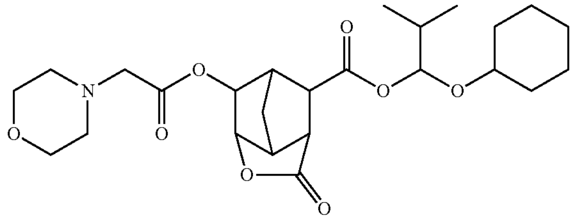
-continued
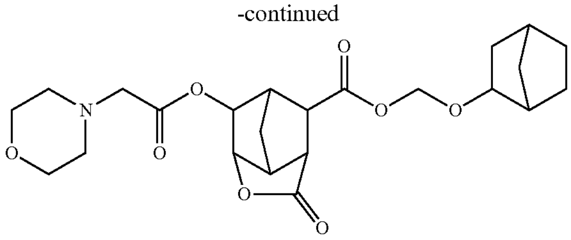
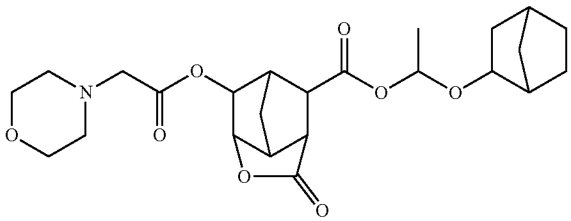
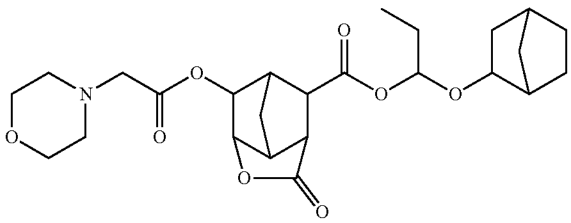
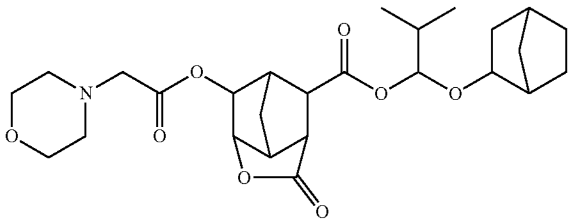
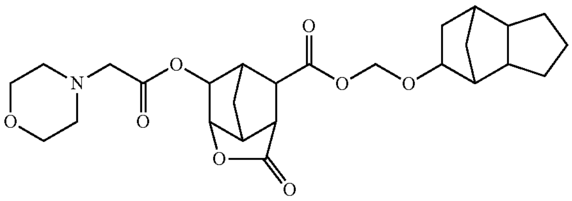
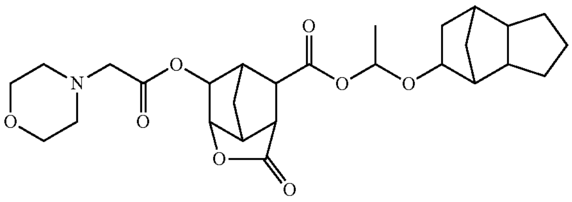
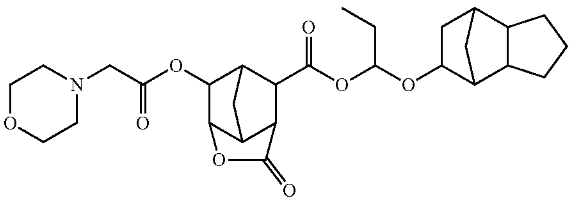
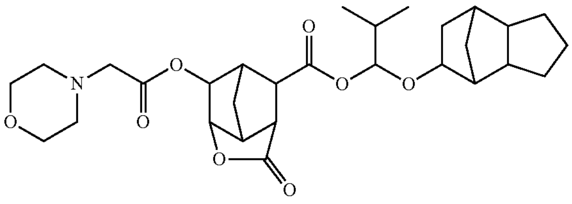

-continued
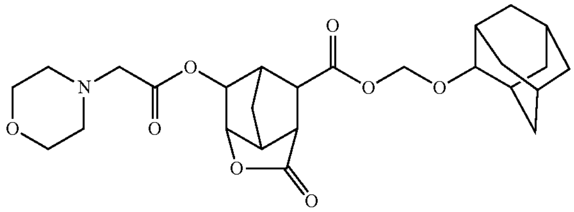
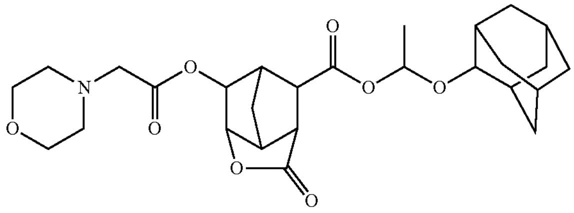
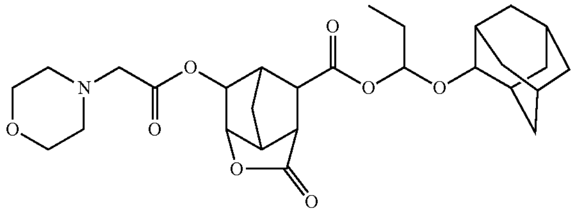
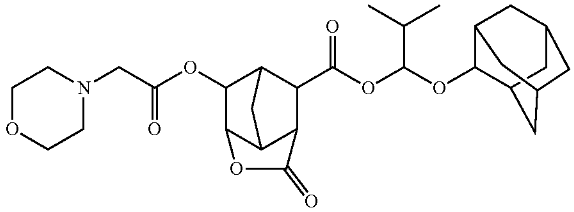
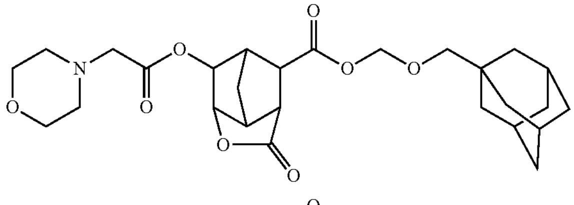
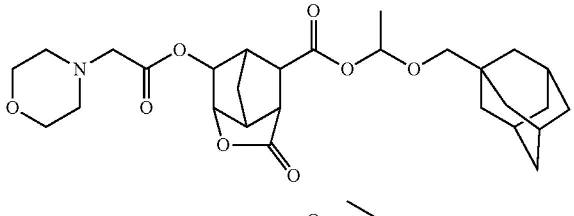
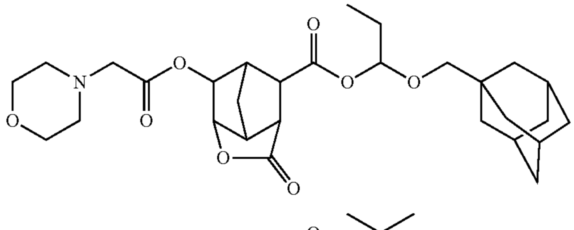
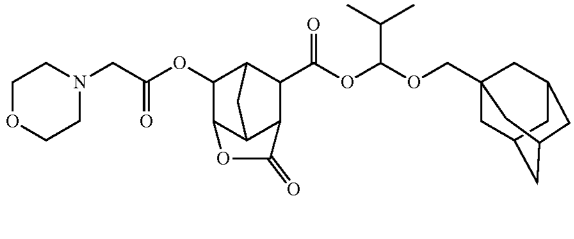
-continued
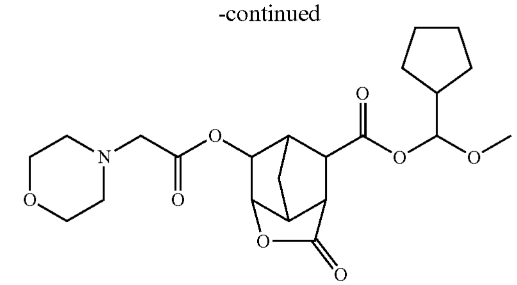
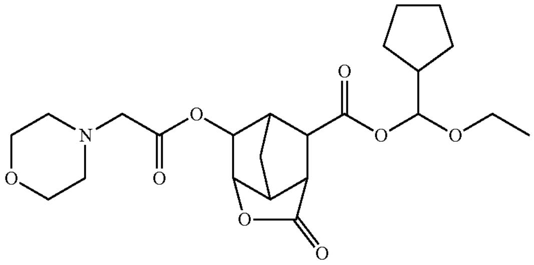
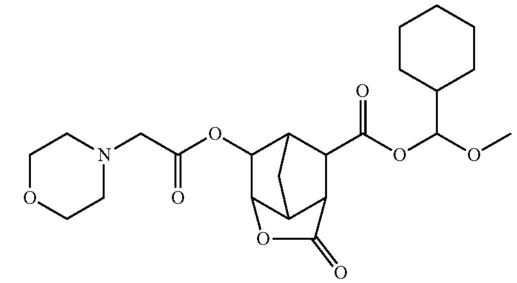
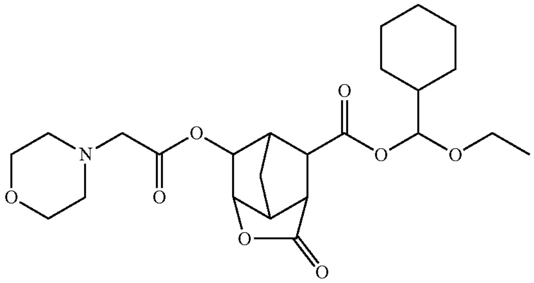
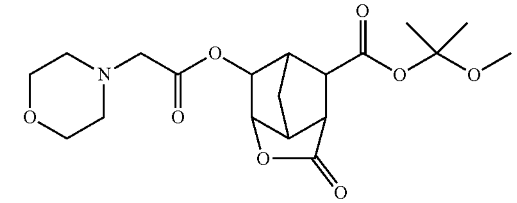
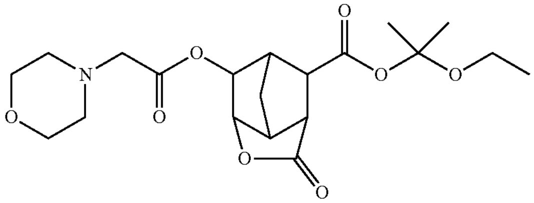
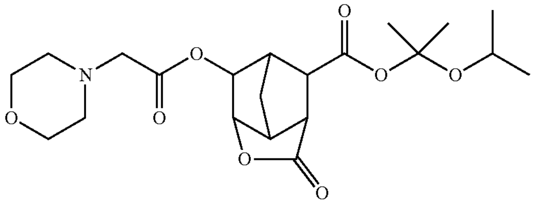

-continued
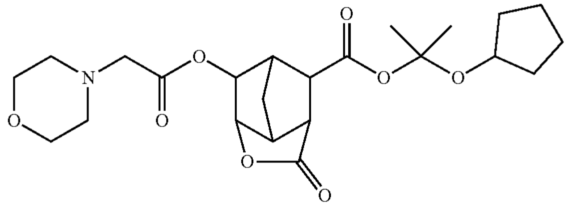
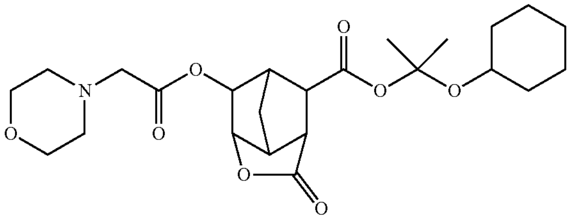
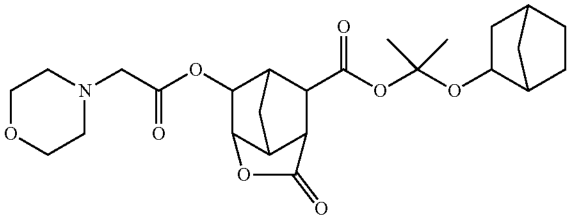
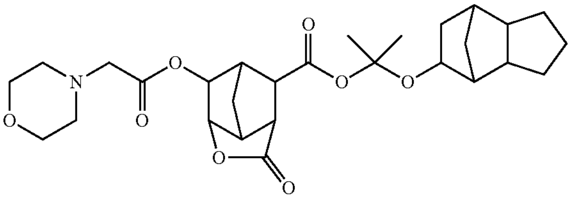
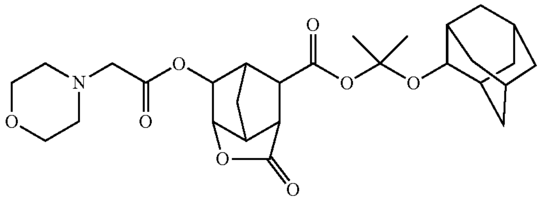
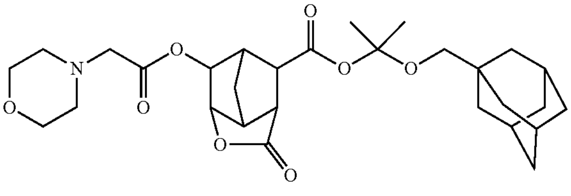
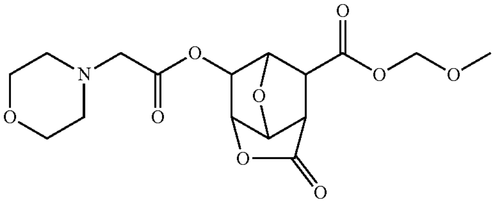
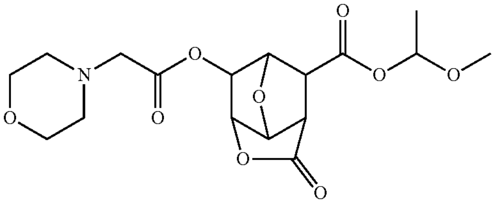
-continued
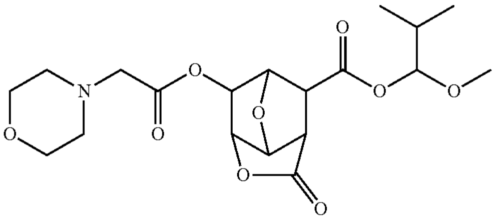
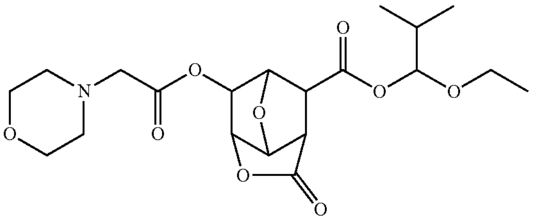
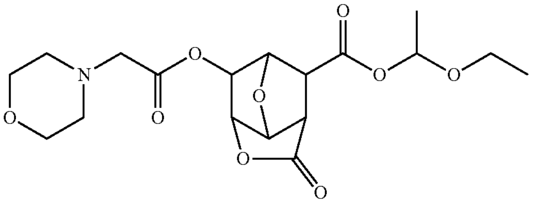
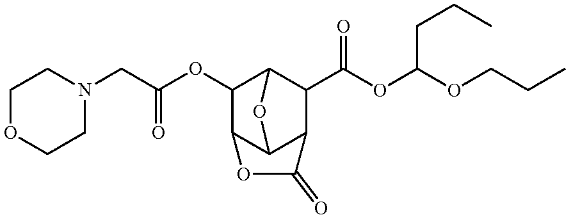
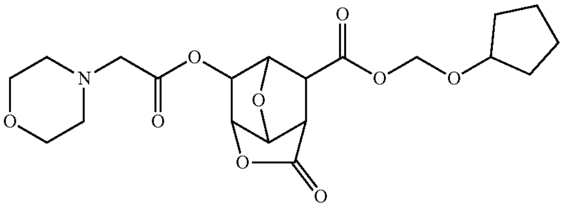
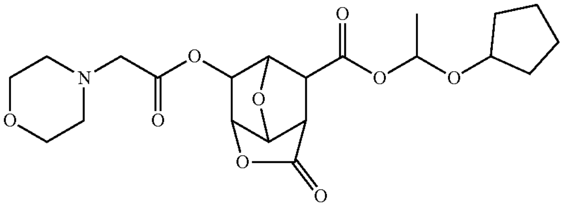
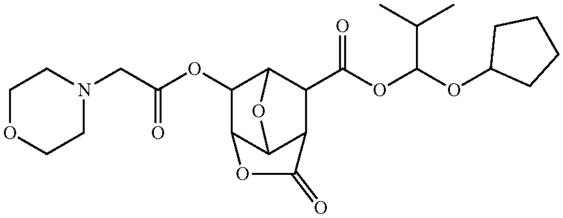
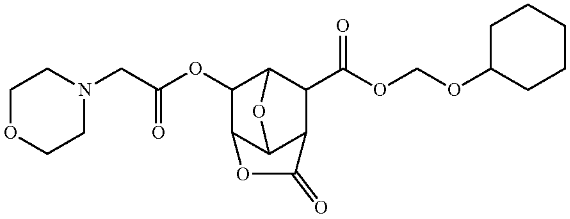

-continued
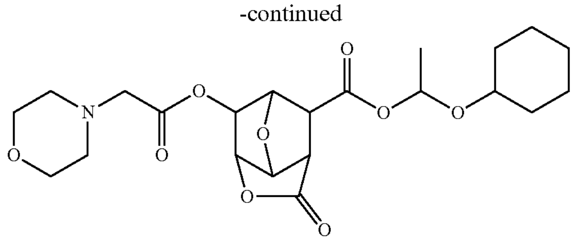
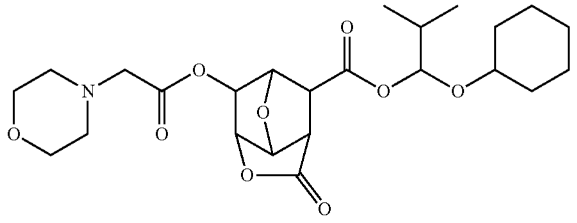
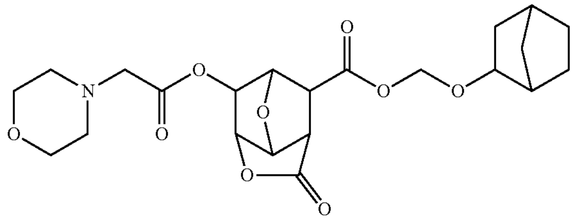
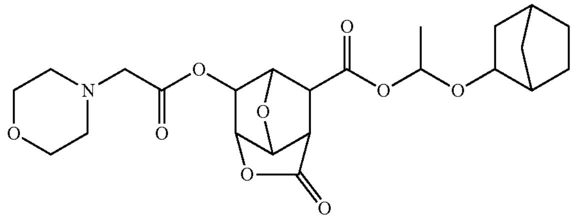
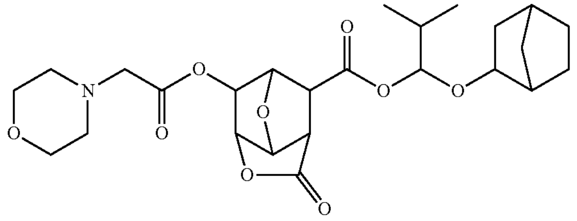
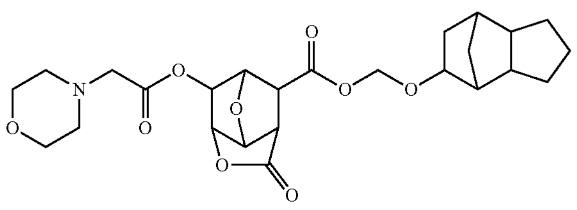
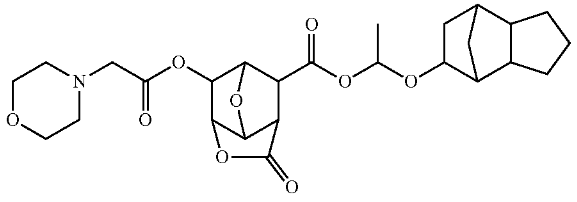
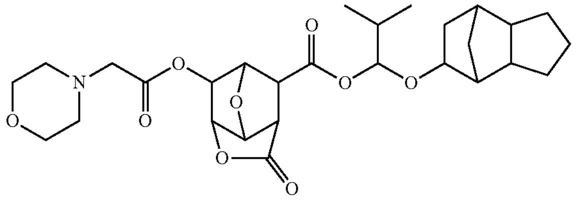
-continued
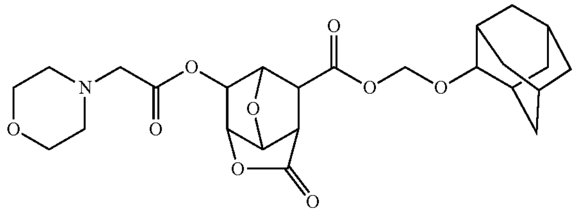
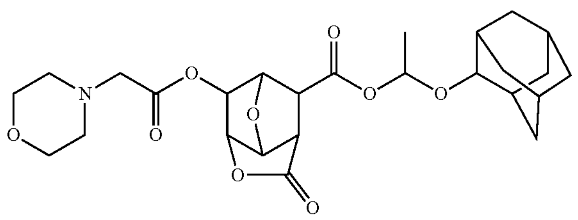
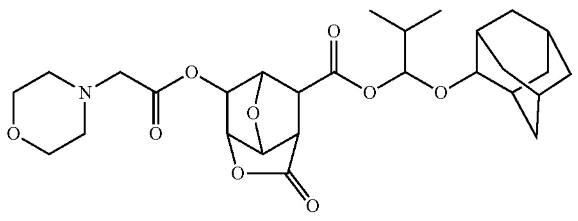
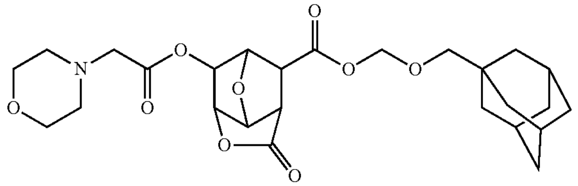
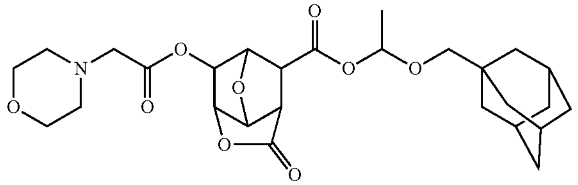
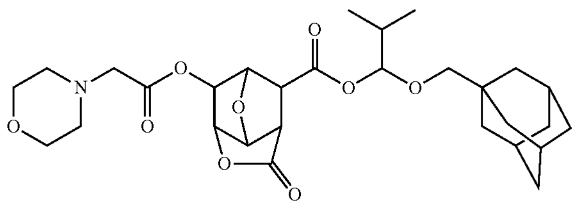
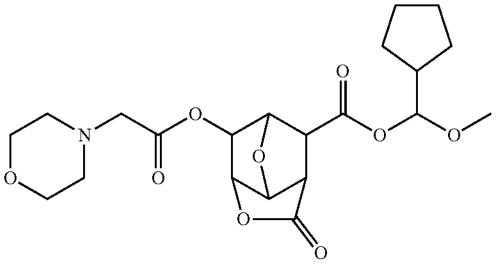

-continued
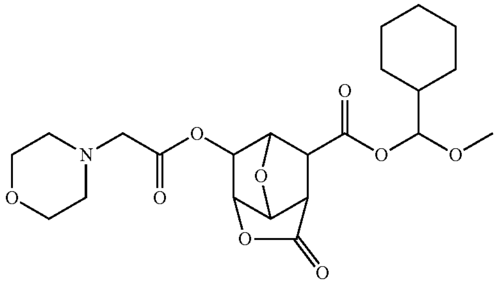
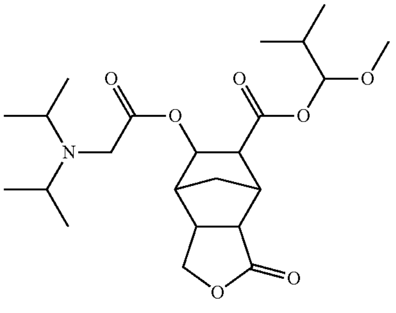
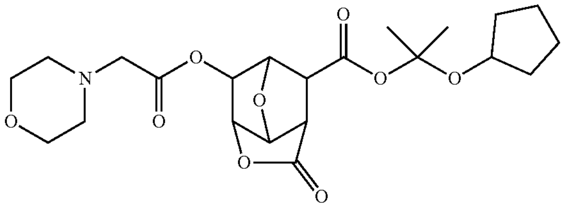
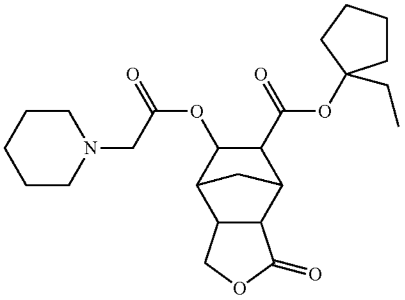
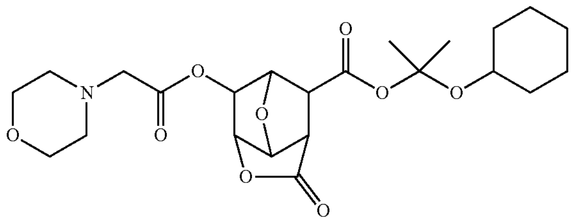
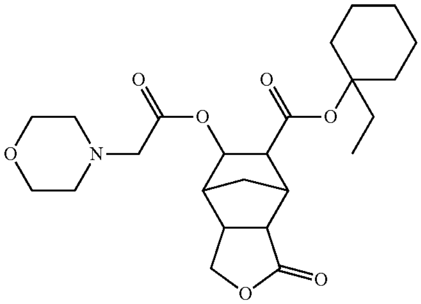
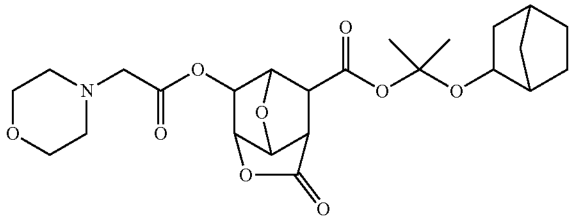
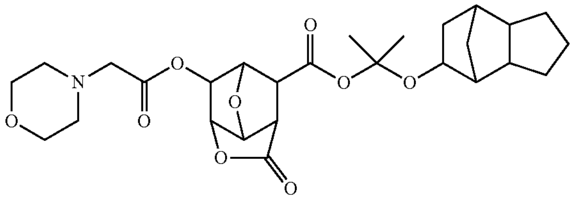
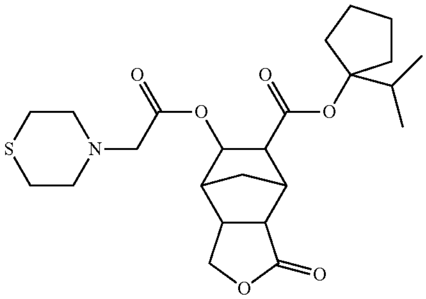
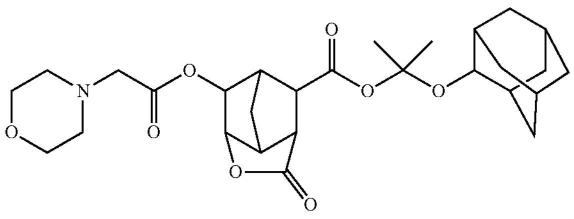
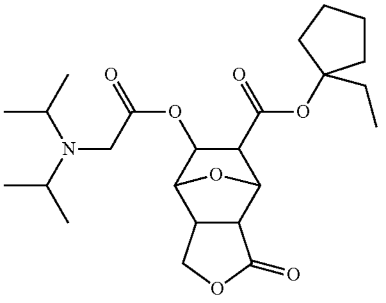
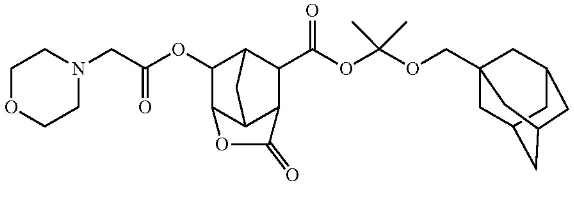

-continued
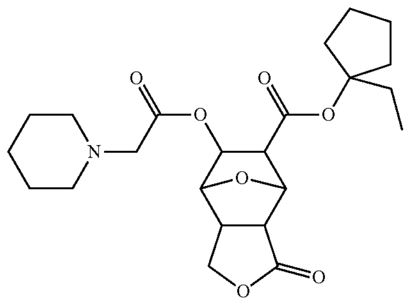
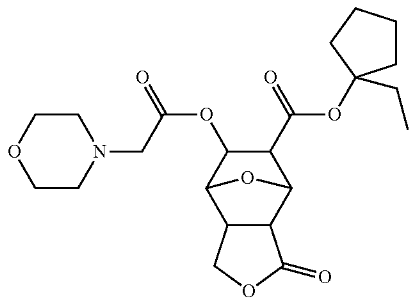
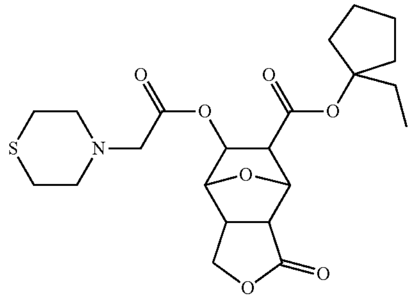
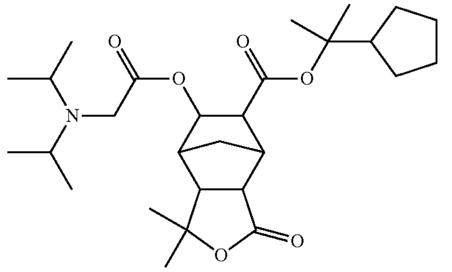
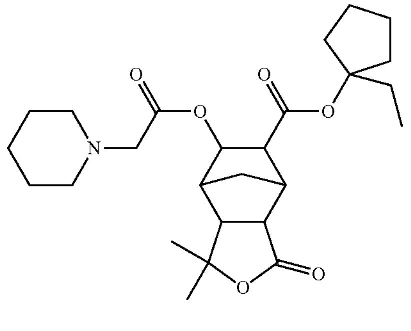
-continued
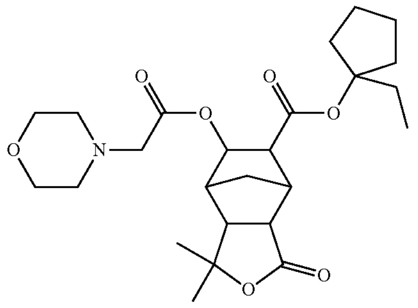
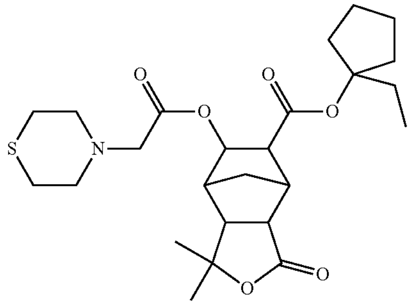
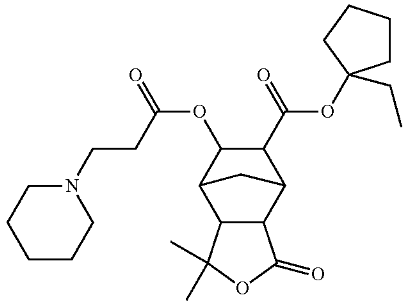 [SMILES: CCC1(OC(=O)C2C3CC(C2OC(=O)CCN2CCCCC2)C2C3C(=O)OC2(C)C)CCCC1]
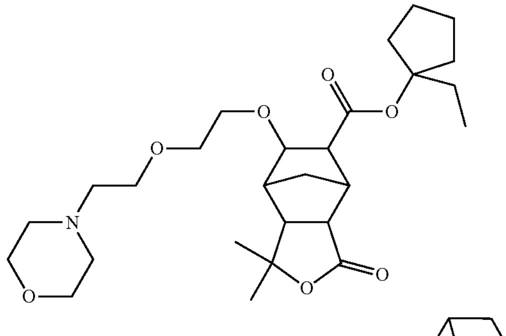
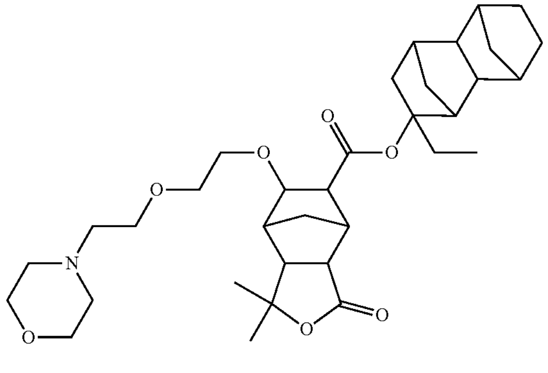

-continued
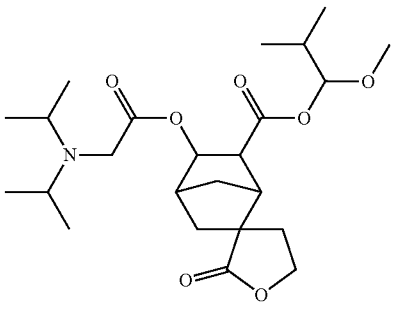
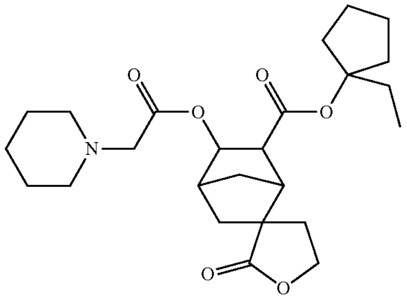
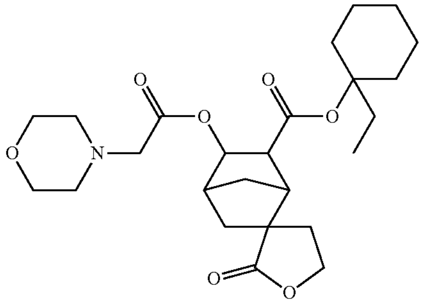
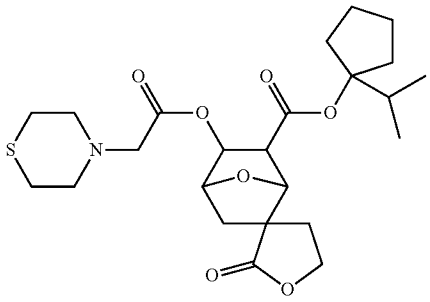
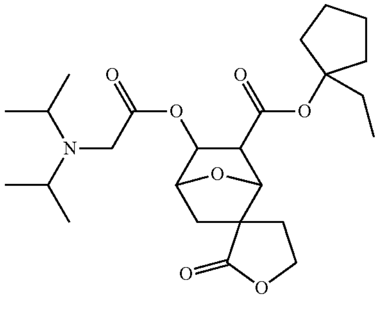
-continued
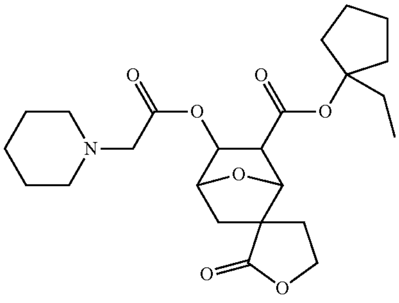
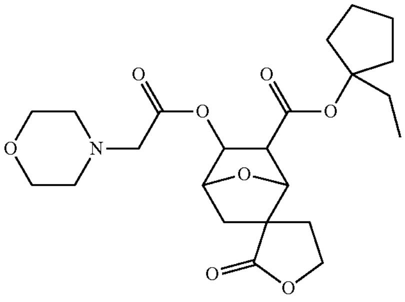
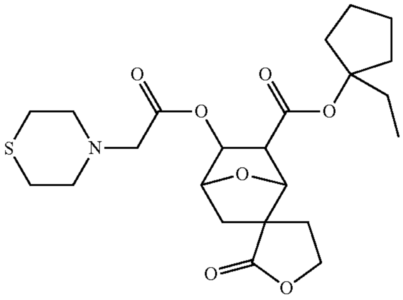
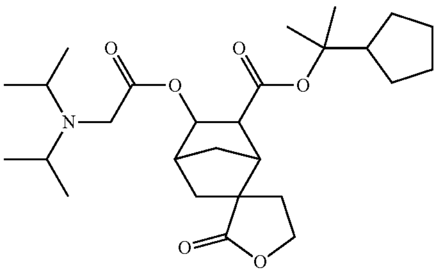
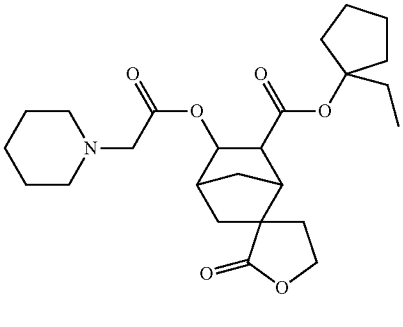

-continued
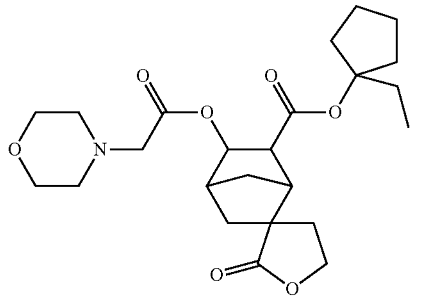
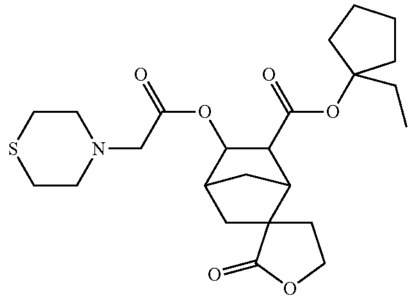
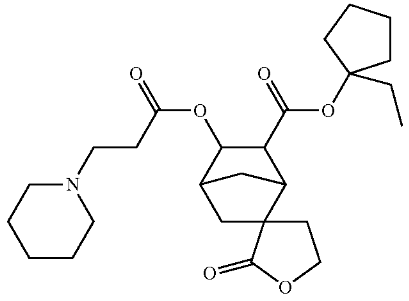
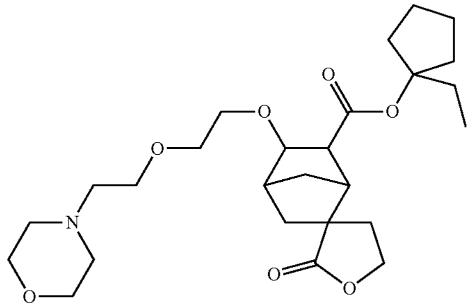
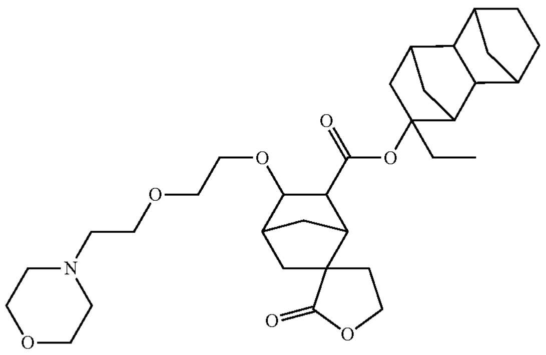
-continued
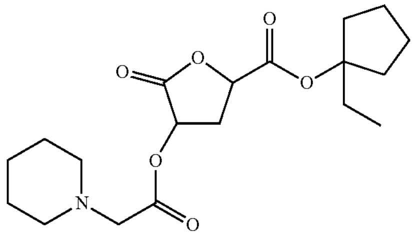
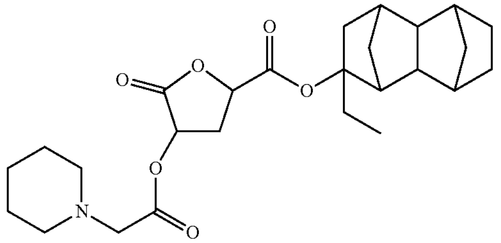
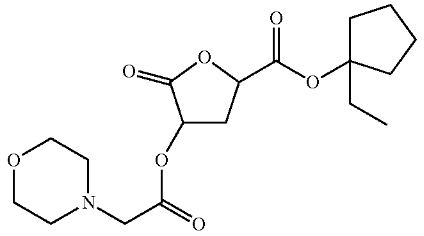
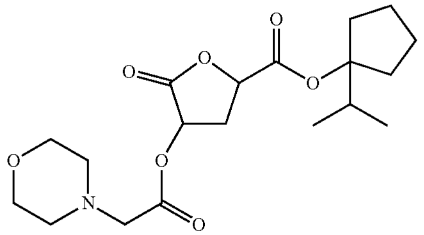
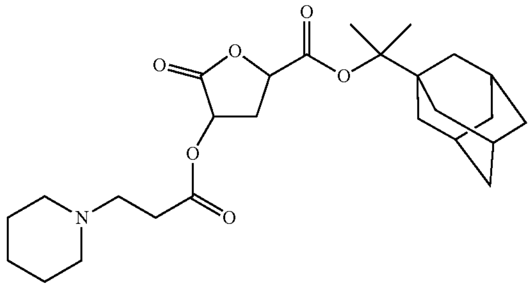
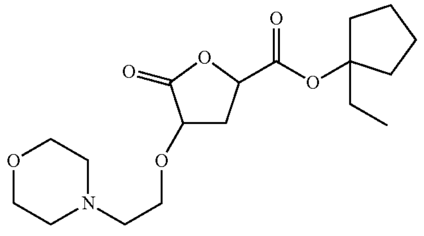
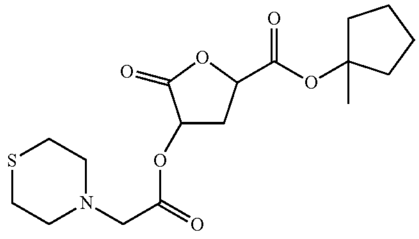

-continued
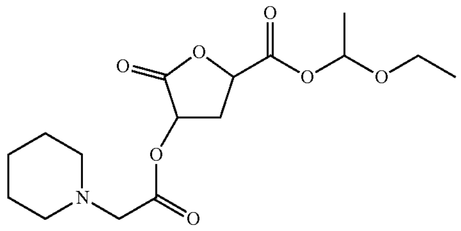
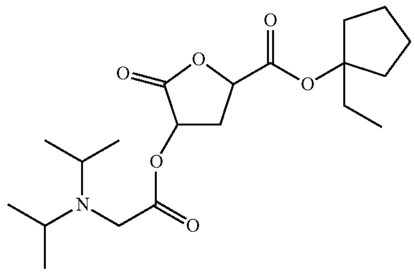
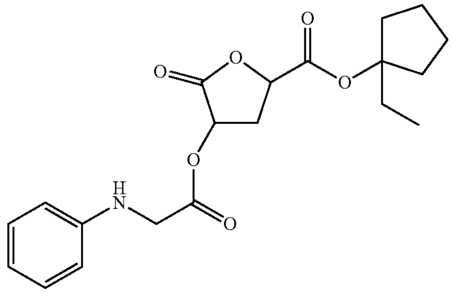
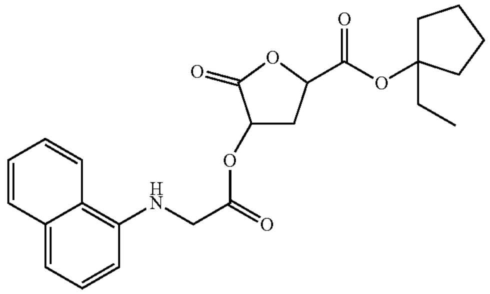
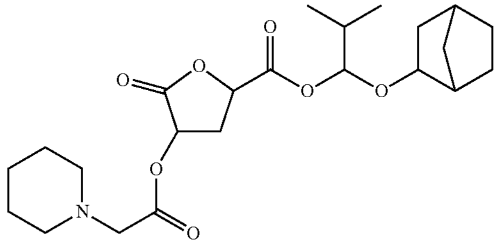
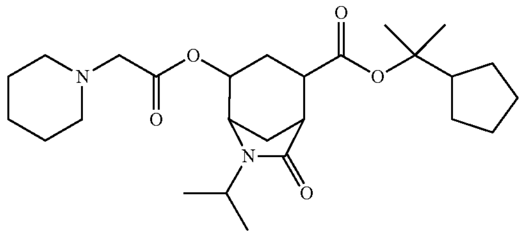
-continued
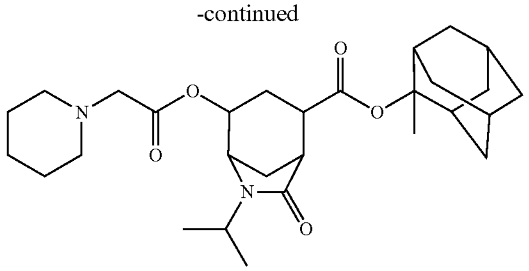
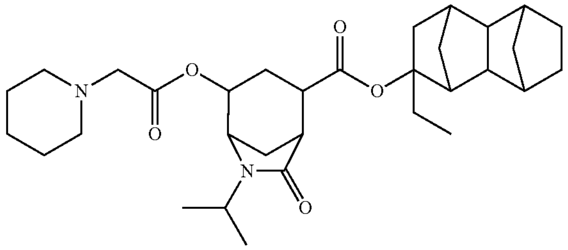
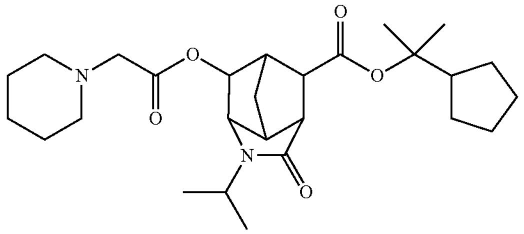
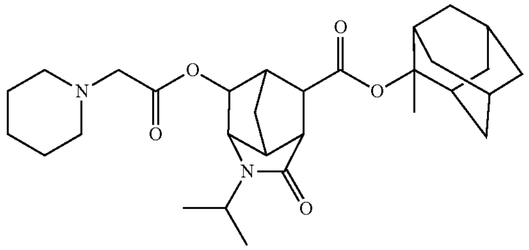
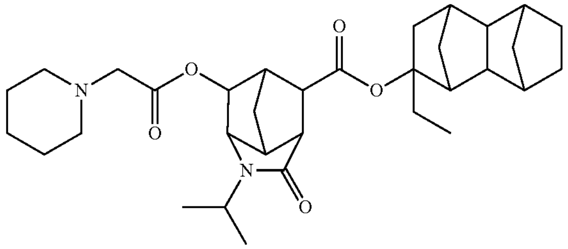
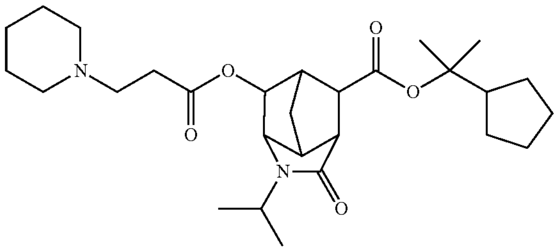
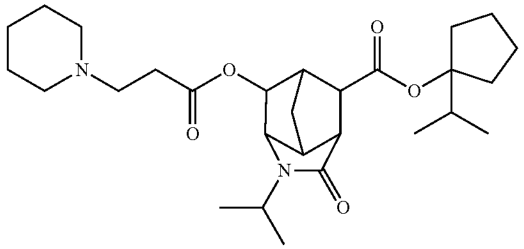

-continued
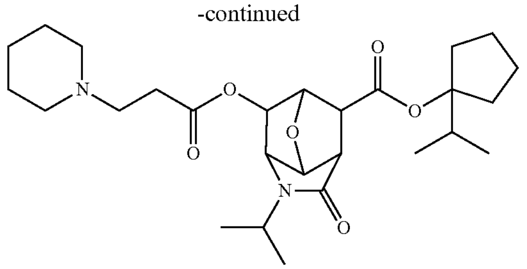
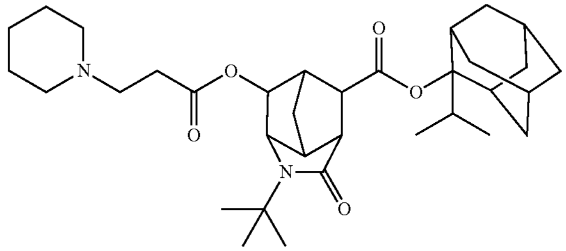
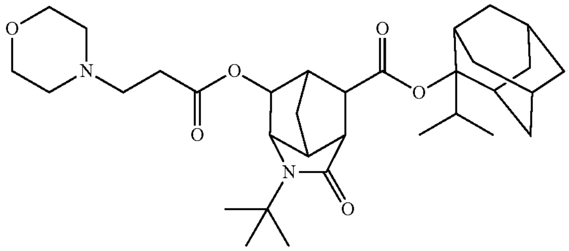
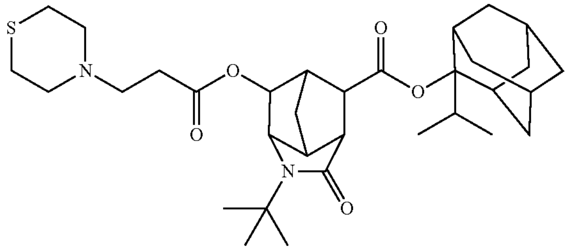
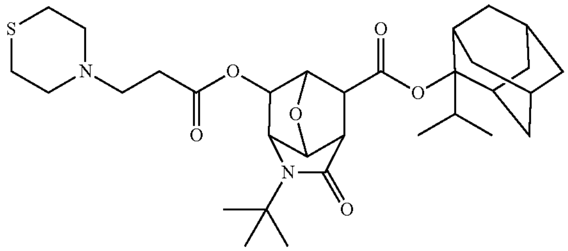
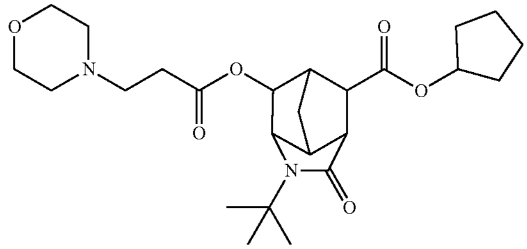
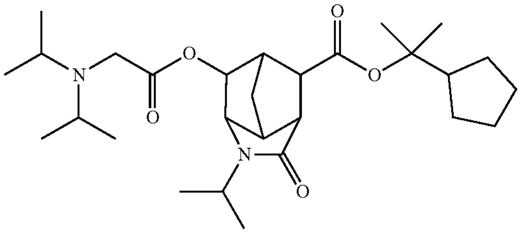
-continued
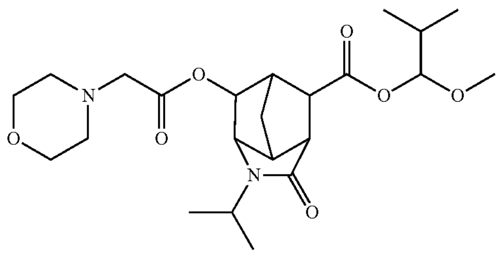
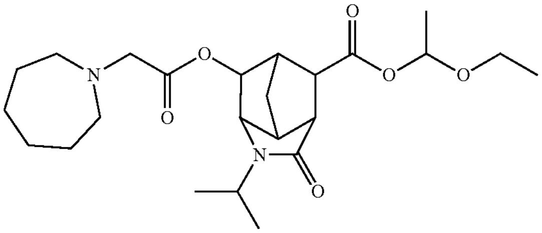
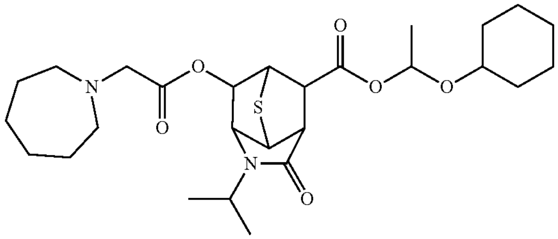
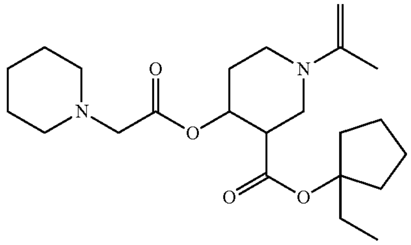
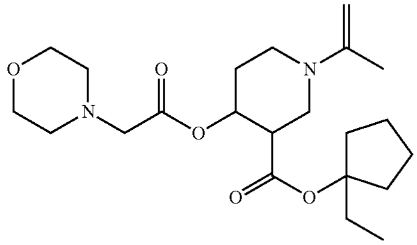
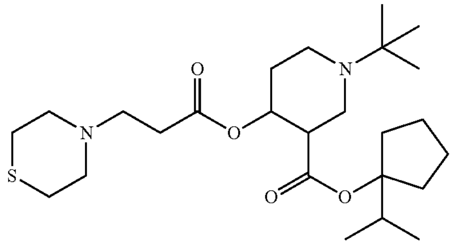

-continued
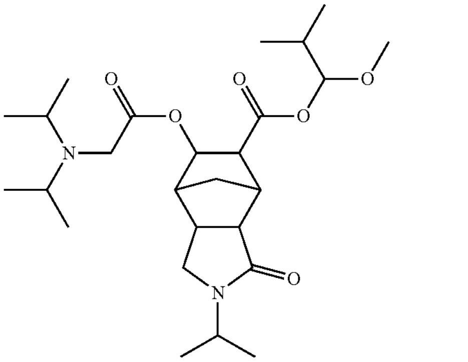
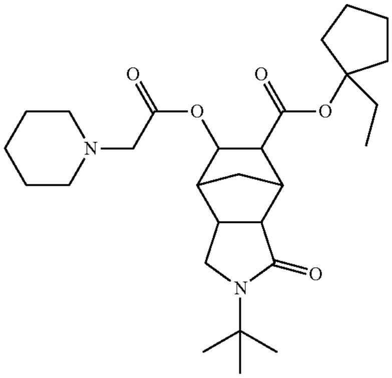
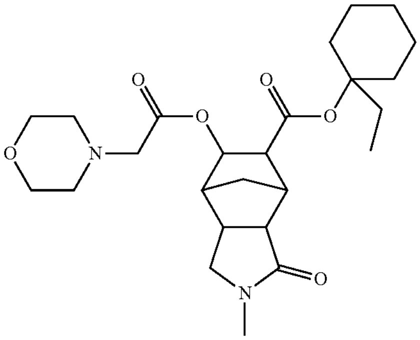
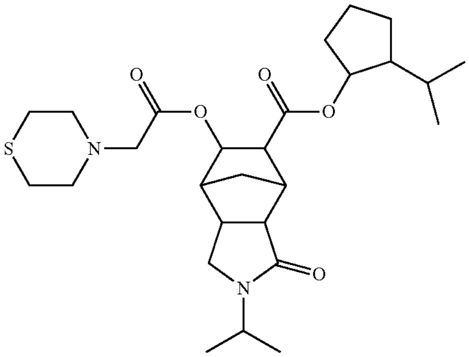
-continued
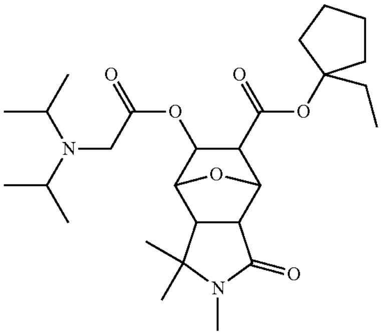
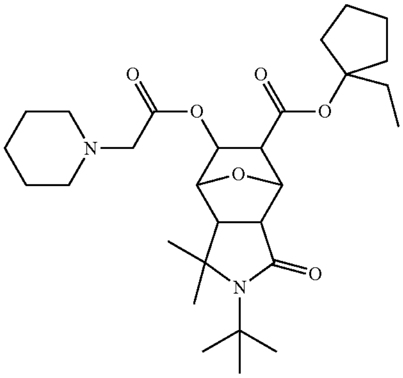
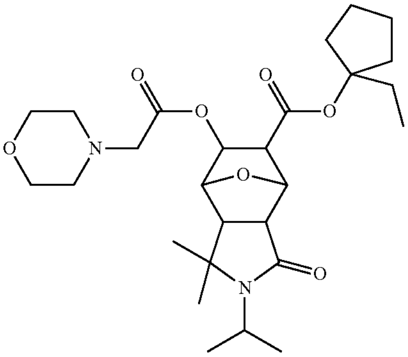
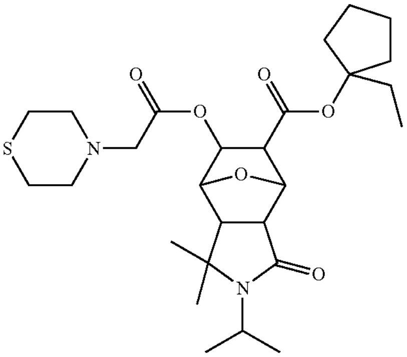

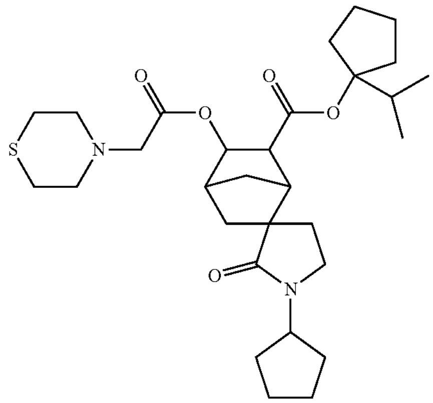
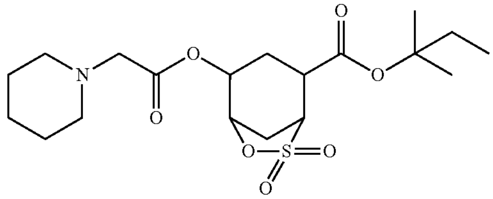
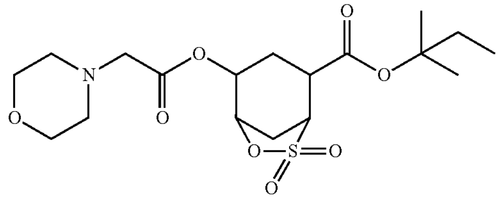
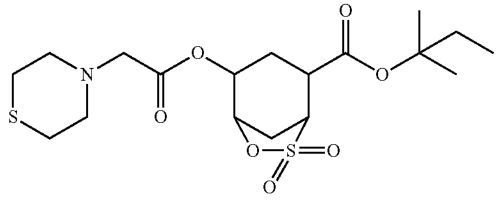
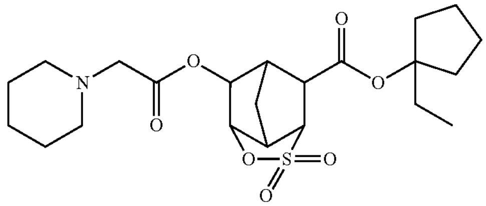
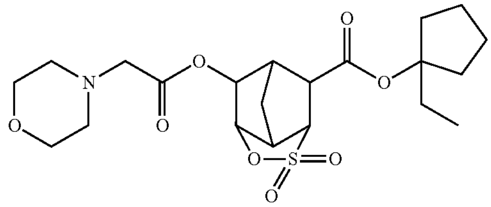
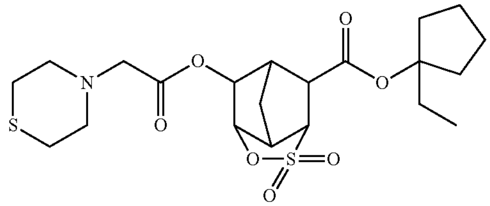
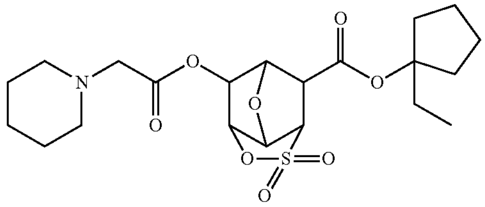
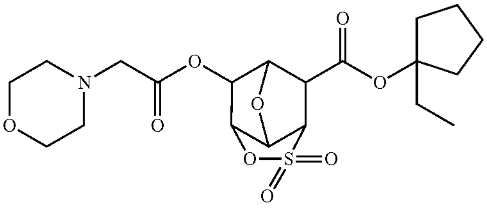
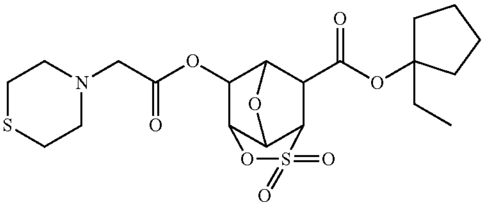
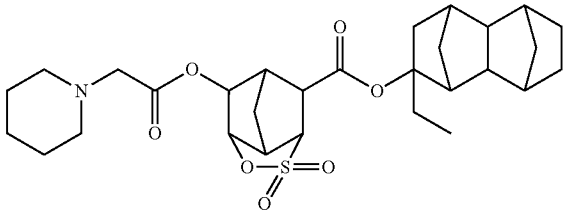
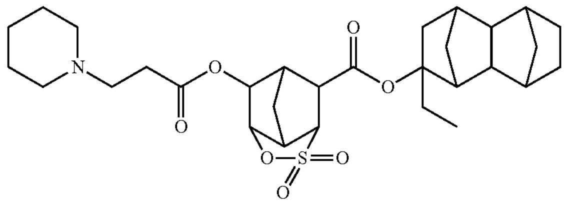
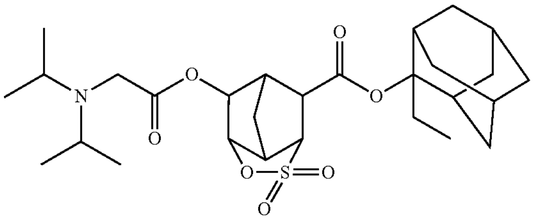
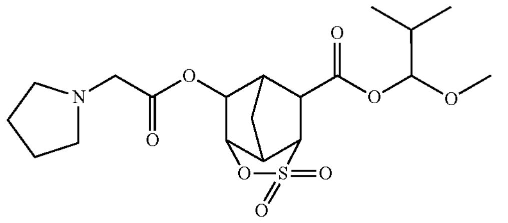
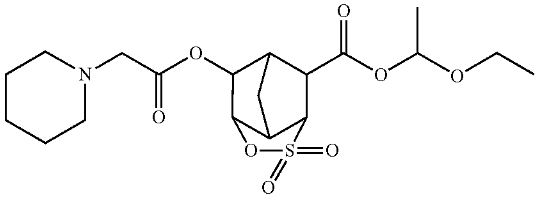

-continued
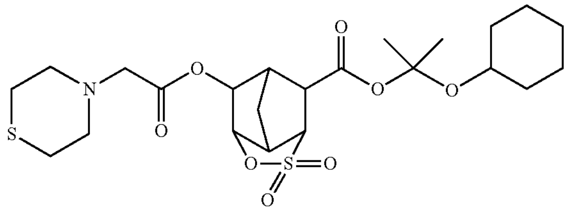
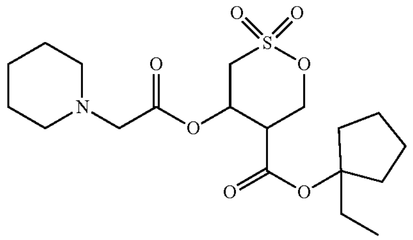
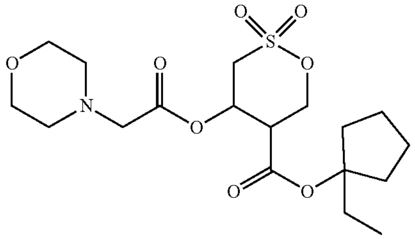
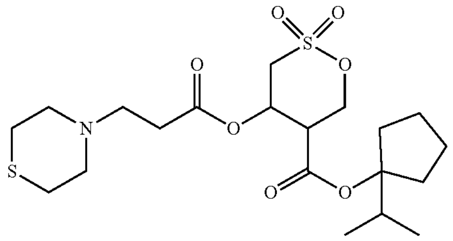
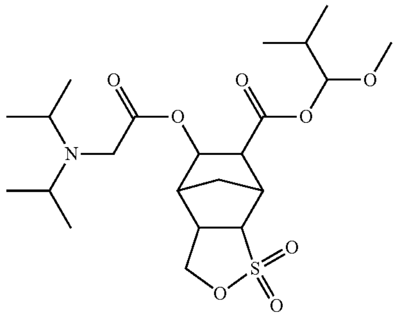
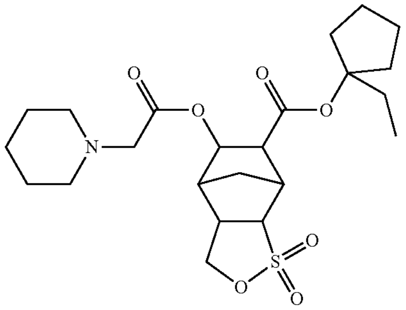
-continued
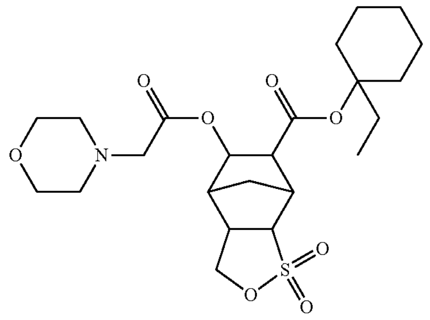
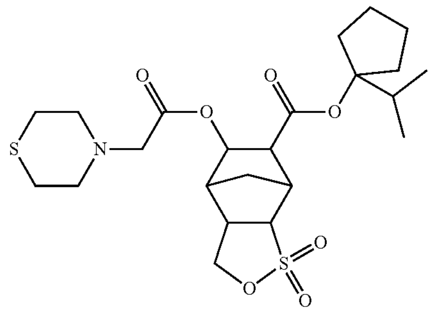
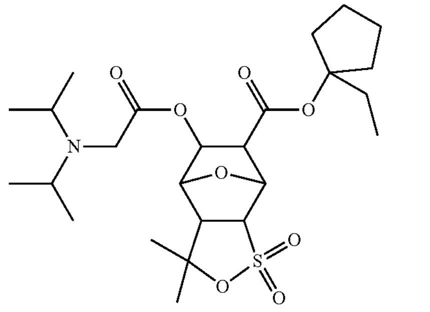
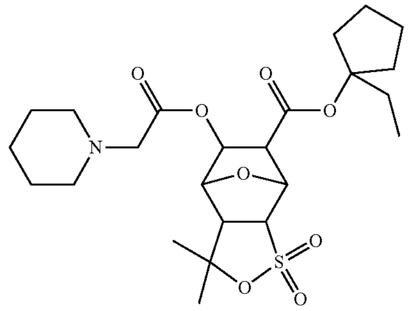
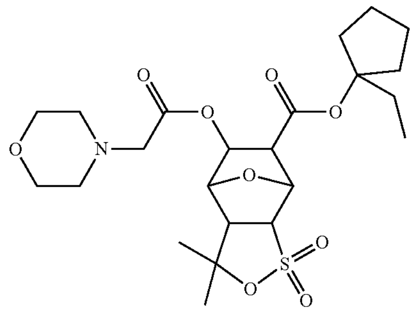

-continued
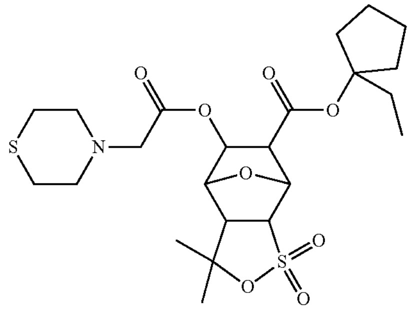
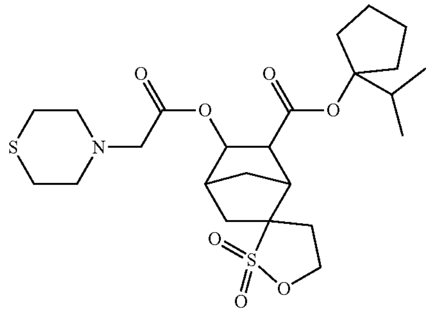
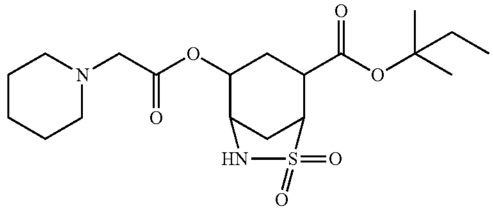
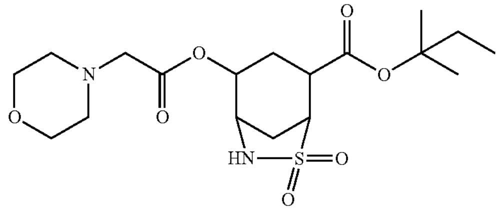
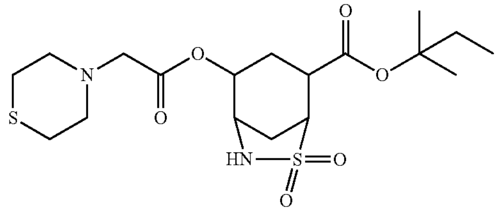
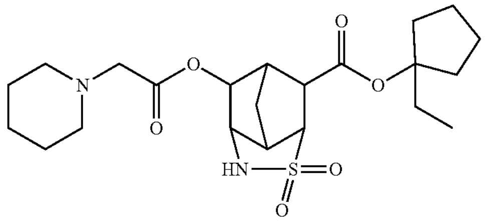
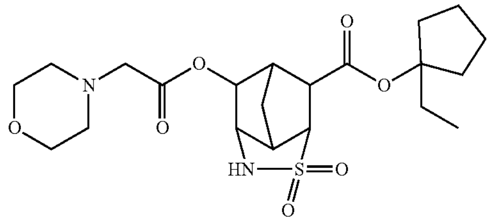
-continued
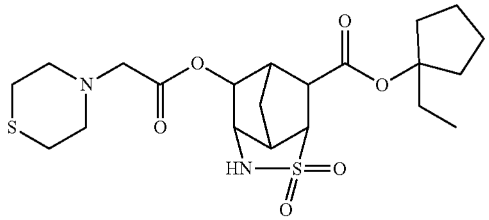
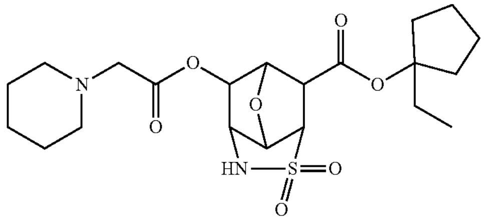
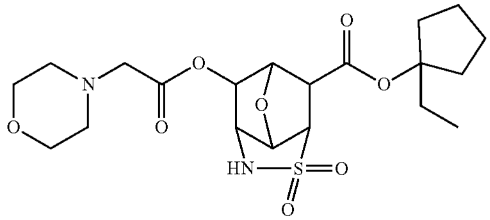
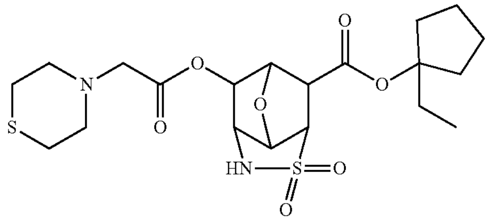
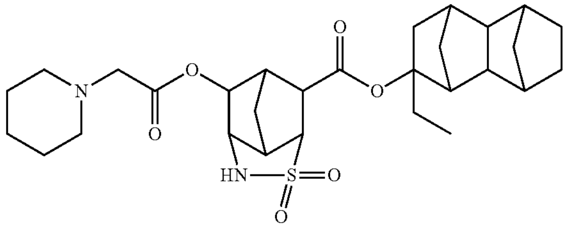
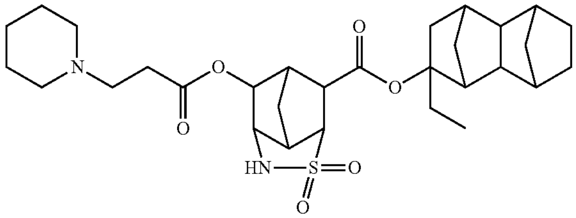
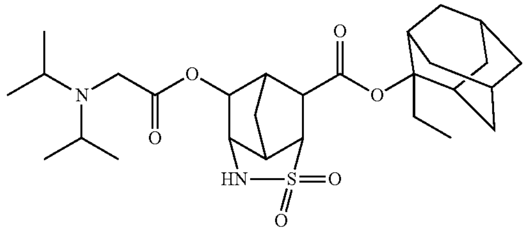

-continued
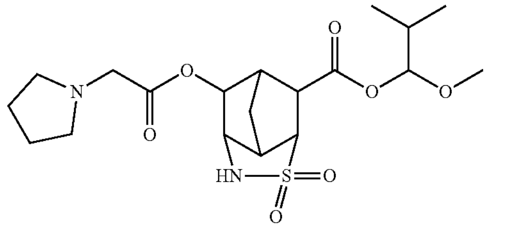
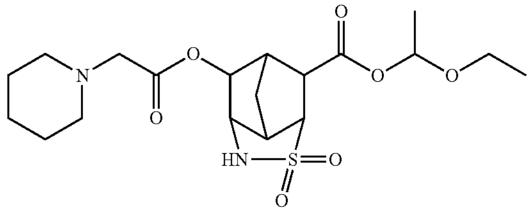
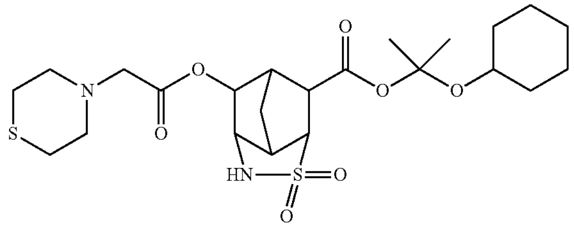
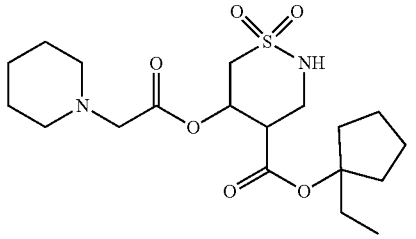
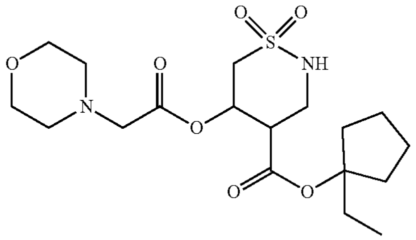
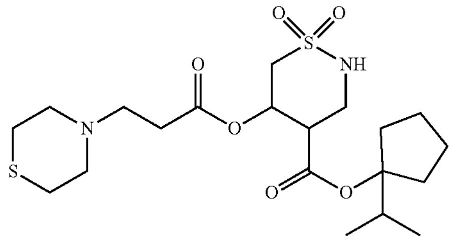
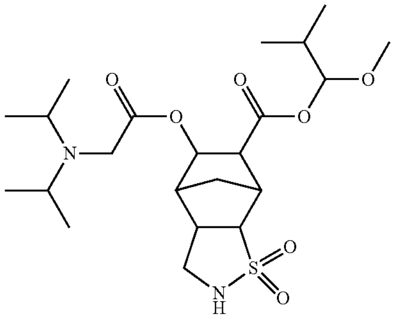
-continued
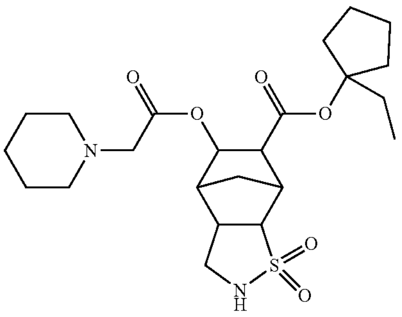
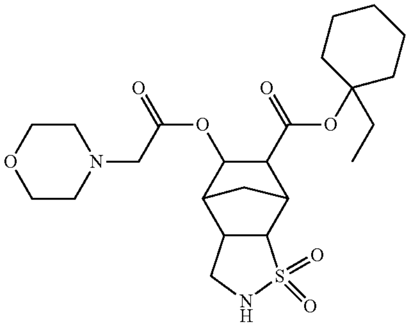
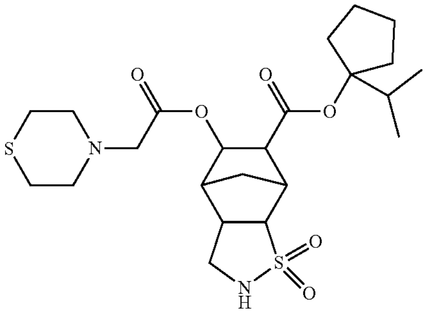
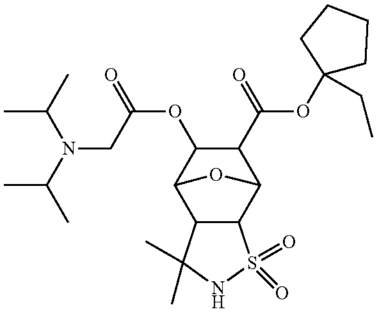
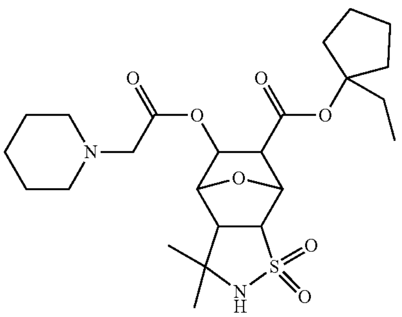

-continued
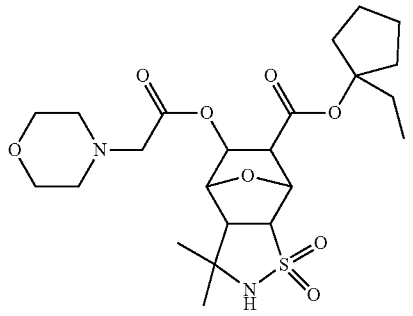
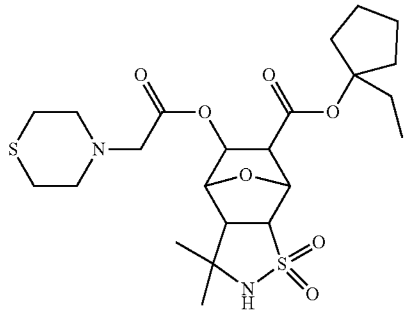
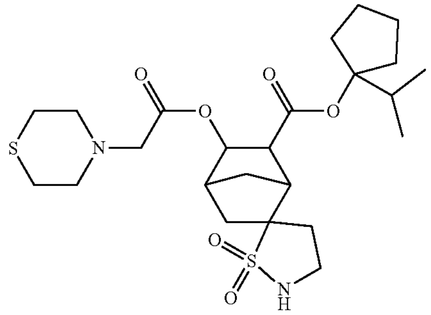
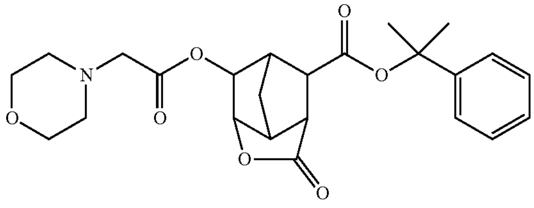
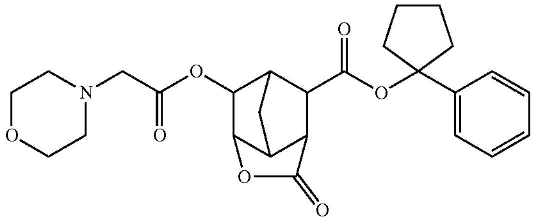
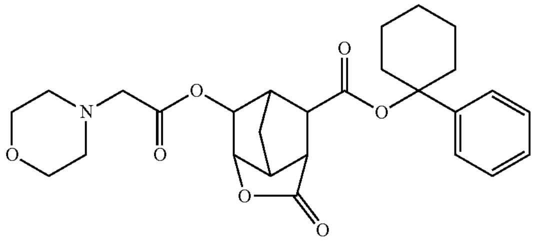
-continued
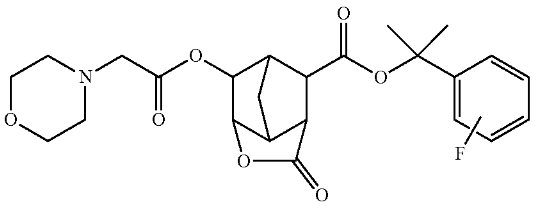
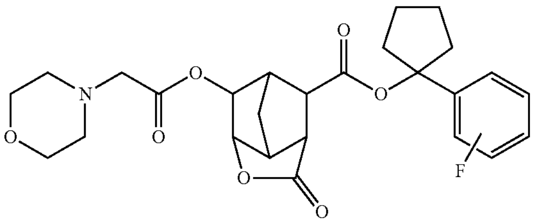
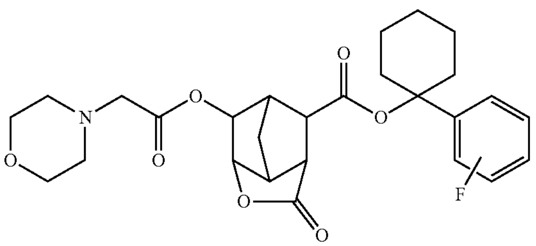
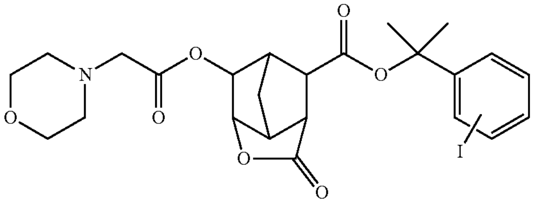
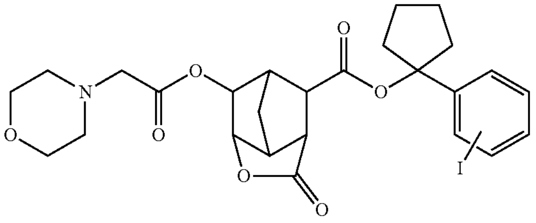
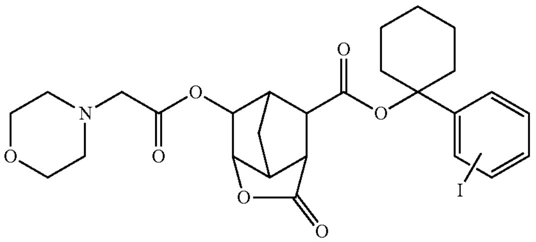
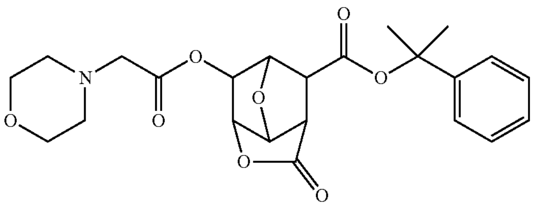

-continued
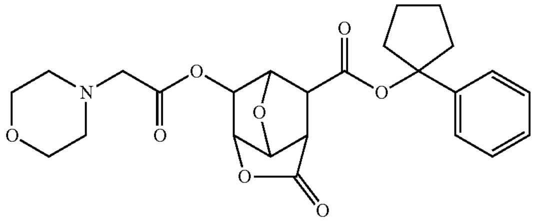
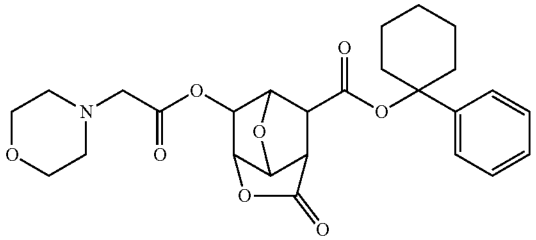
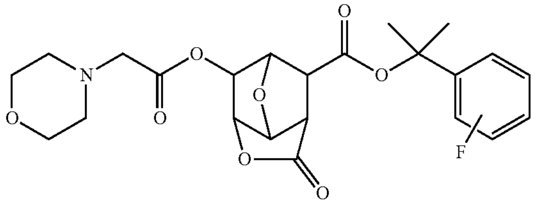
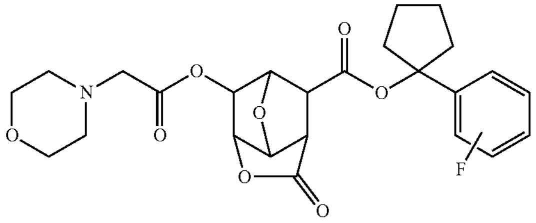
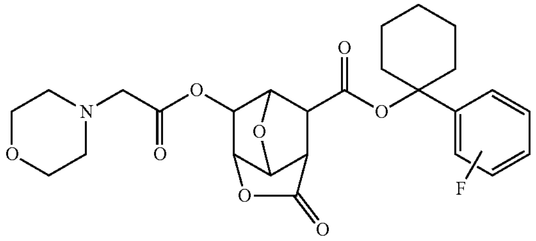
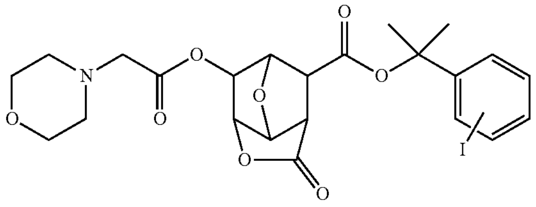
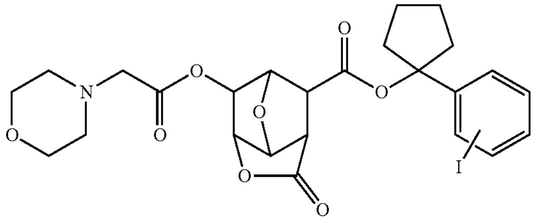
-continued
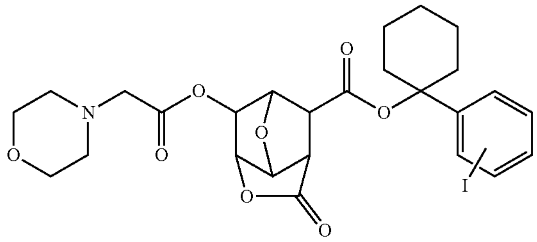
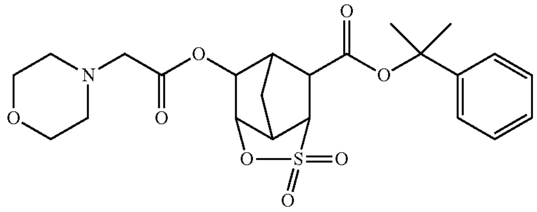
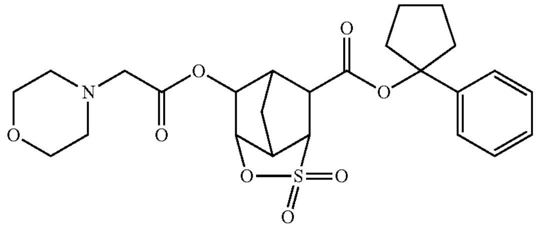
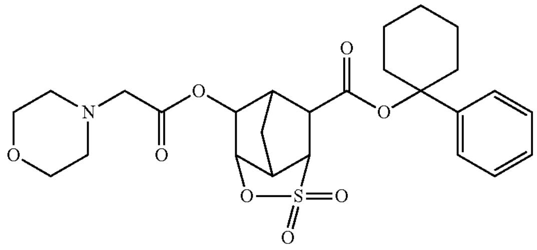
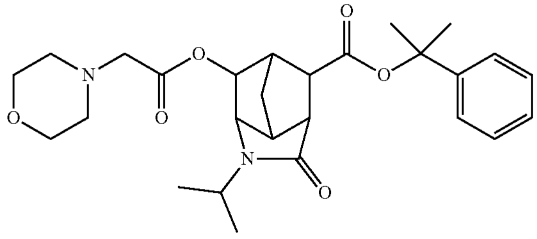
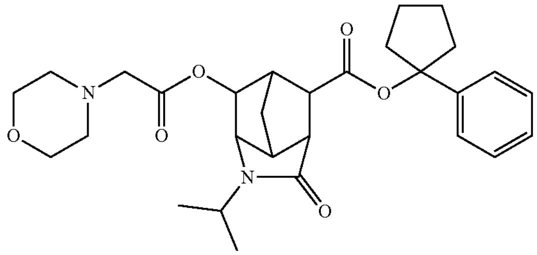
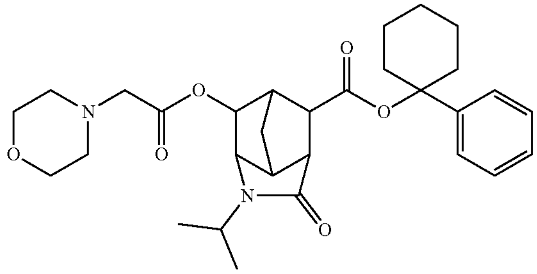

-continued

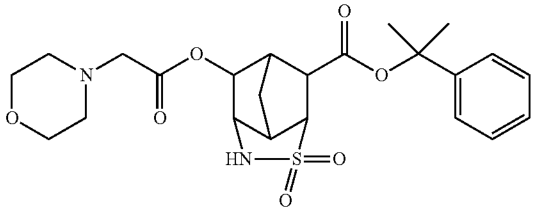

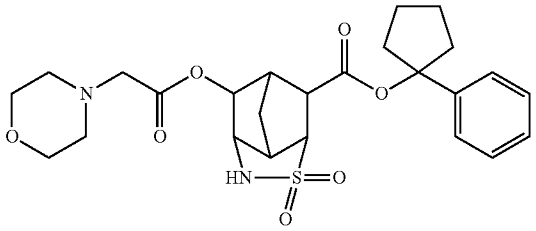

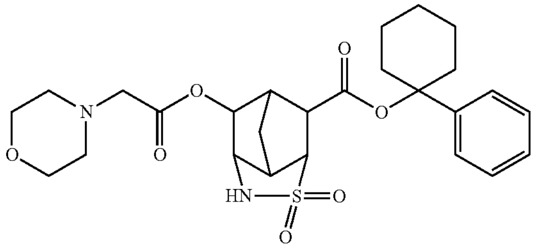

The amine compound may be prepared, for example, according to the following scheme.

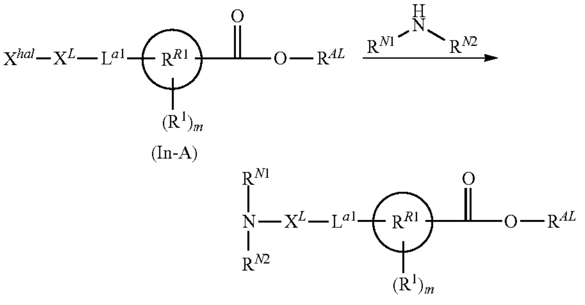

(In-A)

(1)

Herein $R^{N1}$, $R^{N2}$, m, $X^L$, $L^{a1}$, $R^{R1}$, $R^1$, and $R^{AL}$ are as defined above, and $X^{hal}$ is chlorine, bromine or iodine.

That is, the amine compound having formula (1) may be synthesized by substitution reaction of an intermediate In-A, which can be synthesized by any well-known method, with a primary or secondary amine.

The synthesis can be carried out by any well-known organic synthesis methods. Specifically, reaction is carried out by dissolving intermediate In-A in a polar aprotic solvent such as acetone, acetonitrile, dimethylformamide or dimethyl sulfoxide, and adding a primary or secondary amine to the solution. In the case of intermediate In-A wherein $X^{hal}$ is chlorine or bromine, the reaction may be accelerated by adding a catalytic amount of an alkali metal or quaternary ammonium iodide. Suitable alkali metal iodides include sodium iodide and potassium iodide. Suitable quaternary ammonium iodides include tetraethylammonium iodide and benzyltrimethylammonium iodide. The reaction temperature is preferably from room temperature to nearly the boiling point of the solvent used. While it is desirable to monitor the reaction by gas chromatography (GC) or silica gel thin layer chromatography (TLC) until the reaction is complete, the reaction time is typically 30 minutes to 20 hours. The amine compound having formula (1) may be collected from the reaction mixture by standard aqueous work-up. If necessary, the amine compound is purified by a standard technique such as chromatography or recrystallization.

The above preparation method is merely exemplary and the method of preparing the inventive amine compound is not limited thereto.

Chemically Amplified Resist Composition

Another embodiment of the invention is a chemically amplified resist composition comprising (A) a quencher in the form of the amine compound having formula (1) as an essential component. As used herein, the "quencher" refers to a compound capable of trapping an acid generated from a photoacid generator in the resist composition to prevent the acid from diffusing to the unexposed region for thereby forming the desired pattern.

The inventive amine compound is characterized by the structure possessing a heterocycle having a highly polar lactone, lactam, sultone or sultam structure and an acid labile group in a common molecule. The highly polar heterocyclic structure serves to elevate the boiling point of the molecule, which suppresses the amine compound from volatilization during the step of heating the resist composition after coating. That is, the amine compound is dispersed within the resist film. Prior to exposure, the amine compound having a lipophilic acid labile group bonded thereto remains highly soluble in solvents, whereas post exposure, deprotection reaction of the acid labile group takes place to create a hydrophilic carboxylic acid. This improves the dissolution contrast between exposed and unexposed regions. In the case of positive resist composition, the exposed region of resist film has high affinity to alkaline developer whereby a pattern with less development defects is formed. In the case of negative resist composition, the exposed region of resist film has a low solubility in organic solvent developer, indicating excellent film retention properties. By virtue of their synergistic effect, the amine compound effectively quenches the acid generated from the acid generator and exhibits improved development properties. Thus a pattern having a high sensitivity and improved LWR or CDU can be formed.

In the chemically amplified resist composition, the amount of the quencher (A) in the form of the amine compound having formula (1) blended is preferably 0.1 to 20 parts by weight, more preferably 0.5 to 15 parts by weight per 80 parts by weight of the base polymer (B) described just below. With the amount of quencher (A) in the range, sensitivity and resolution are good, and there is no risk of raising the problem of foreign particles after development or stripping of the resist film. The quencher (A) may be used alone or in admixture of two or more.

(B) Base Polymer

The chemically amplified resist composition may further comprise (B) a base polymer. The base polymer preferably contains repeat units having the formula (a1) or repeat units having the formula (a2). These units are simply referred to as repeat units (a1) and (a2).

(a1)

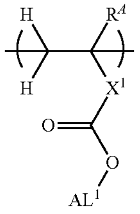

(a2)

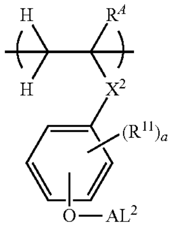

In formulae (a1) and (a2), $R^A$ is each independently hydrogen, fluorine, methyl or trifluoromethyl. $X^1$ is a single bond, phenylene, naphthylene, or *—C(O)—O—$X^{11}$—, wherein $X^{11}$ is a $C_1$-$C_{10}$ alkanediyl group which may contain a hydroxy moiety, ether bond, ester bond or lactone ring, or a phenylene group or naphthylene group. $X^2$ is a single bond or *—C(═O)—O—. The asterisk (*) designates a point of attachment to the carbon atom in the backbone. $AL^1$ and $AL^2$ are each independently an acid labile group.

In formula (a2), $R^{11}$ is a $C_1$-$C_{20}$ hydrocarbyl group which may contain a heteroatom. The hydrocarbyl group may be saturated or unsaturated and straight, branched or cyclic, and examples thereof are as exemplified above for the $C_1$-$C_{20}$ hydrocarbyl group $R^1$ in formula (1). The subscript "a" is au integer of 0 to 4, preferably 0 or 1.

Examples of the structure of formula (a1) wherein $X^1$ is a variant are illustrated below, but not limited thereto. Herein $R^A$ and $AL^1$ are as defined above.

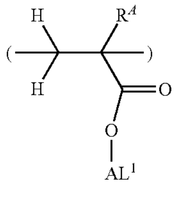

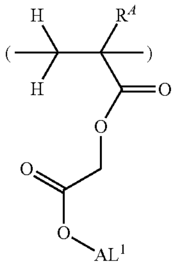

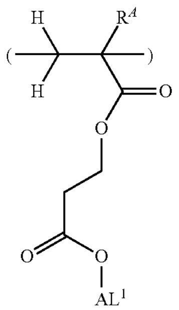

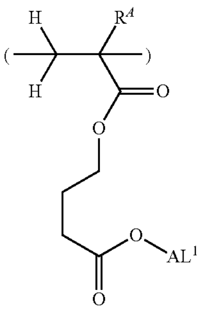

-continued

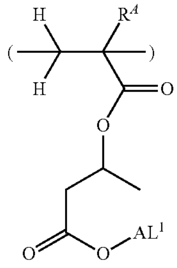

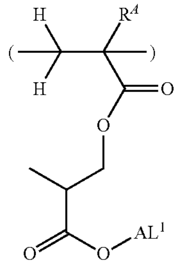

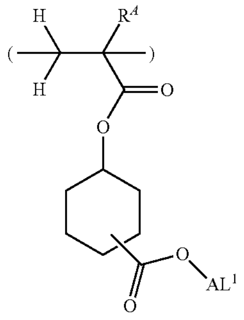

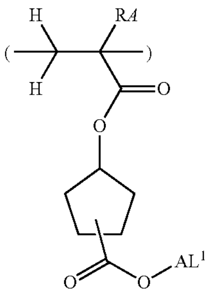

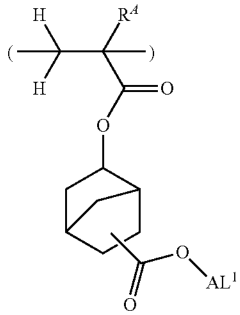

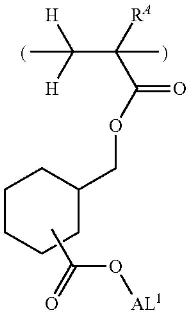

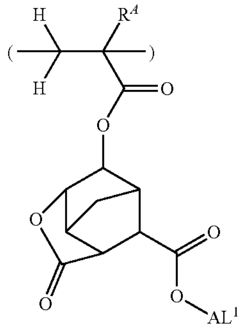

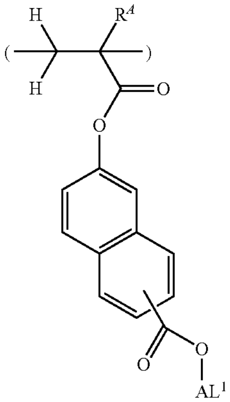

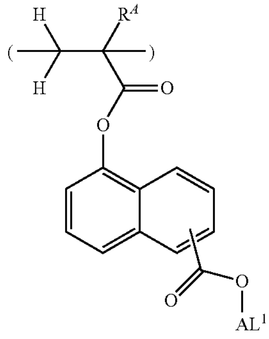

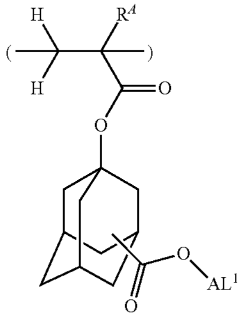

-continued

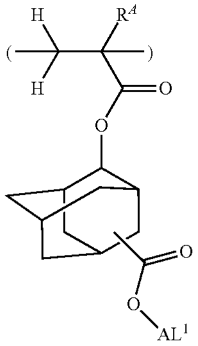

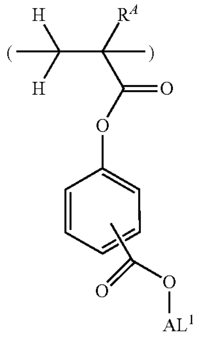

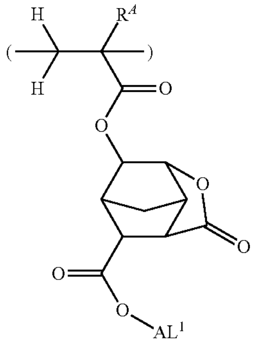

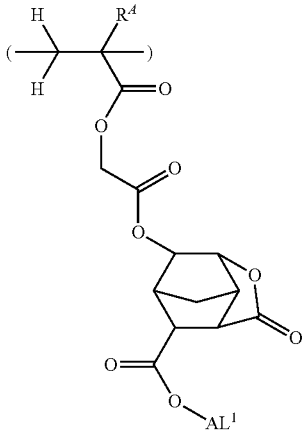

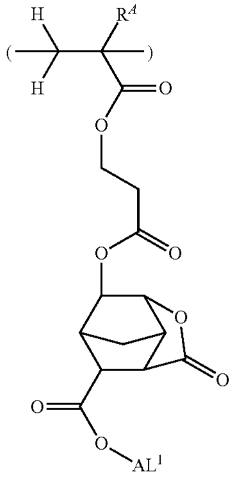

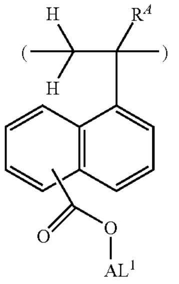

-continued

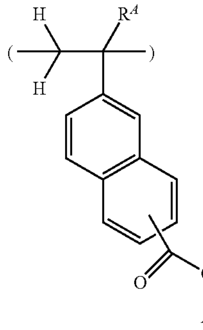

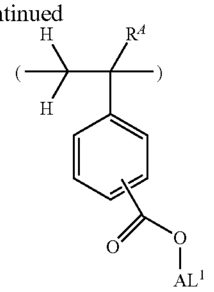

A polymer comprising repeat units (a1) turns alkali soluble through the mechanism that it is decomposed under the action of acid to generate a carboxy group.

The acid labile groups represented by $AL^1$ and $AL^2$ may be selected from a variety of such groups. Preferred examples of the acid labile group are groups of the following formulae (L1) to (L4), $C_4$-$C_{20}$, preferably $C_4$-$C_{15}$ tertiary hydrocarbyl groups, trialkylsilyl groups in which each alkyl moiety has 1 to 6 carbon atoms, and $C_4$-$C_{20}$ saturated hydrocarbyl groups containing a carbonyl moiety, ether bond or ester bond.

(L1)

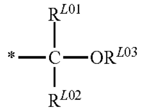

(L2)

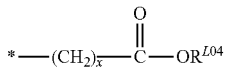

(L3)

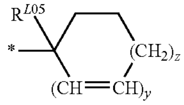

(L4)

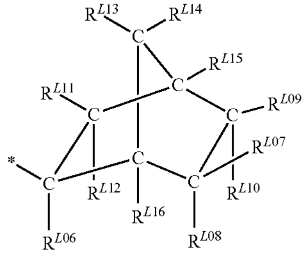

In formula (L1), $R^{L01}$ and $R^{L02}$ are each independently hydrogen or a $C_1$-$C_{18}$ saturated hydrocarbyl group. The saturated hydrocarbyl group may be straight, branched or cyclic and examples thereof include alkyl groups such as methyl, ethyl, propyl, isopropyl, n-butyl, sec-butyl, tert-butyl, n-octyl, and 2-ethylhexyl, and cyclic saturated hydrocarbyl groups such as cyclopentyl, cyclohexyl, norbornyl, tricyclodecanyl, tetracyclododecanyl, and adamantyl. Of the saturated hydrocarbyl groups, those of 1 to 10 carbon atoms are preferred.

$R^{L03}$ is a $C_1$-$C_{18}$, preferably $C_1$-$C_{10}$ hydrocarbyl group which may contain a moiety containing a heteroatom. The hydrocarbyl group may be saturated or unsaturated and straight, branched or cyclic. Saturated hydrocarbyl groups are preferred. In the saturated hydrocarbyl group, some or all of the hydrogen atoms may be substituted by hydroxy, saturated hydrocarbyloxy, oxo, amino, saturated hydrocarbylamino or the like, or any constituent $—CH_2—$ may be replaced by a moiety containing a heteroatom, typically oxygen. Suitable saturated hydrocarbyl groups are as exemplified above for the saturated hydrocarbyl groups $R^{L01}$ and $R^{L02}$. Examples of the substituted saturated hydrocarbyl group are shown below.

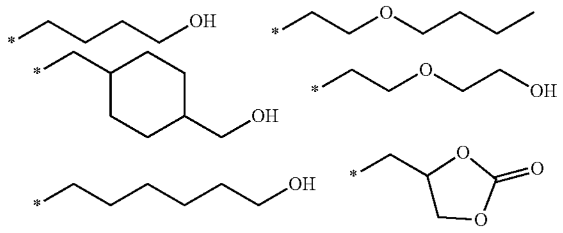

Any two of $R^{L01}$, $R^{L02}$, and $R^{L03}$ may bond together to form a ring with the carbon atom or the carbon and oxygen atoms to which they are attached. When any two of $R^{L01}$, $R^{L02}$ and $R^{L03}$ form a ring, each is a $C_1$-$C_{18}$, preferably $C_1$-$C_{10}$ alkanediyl group.

In formula (L2), $R^{L04}$ is a $C_4$-$C_{20}$, preferably $C_4$-$C_{15}$ tertiary hydrocarbyl group, a trialkylsilyl group in which each alkyl moiety has 1 to 6 carbon atoms, a $C_4$-$C_{20}$ saturated hydrocarbyl group containing a carbonyl moiety, ether bond or ester bond, or a group of formula (L1). The subscript x is an integer of 0 to 6.

Of the groups $R^{L04}$, the tertiary hydrocarbyl group may be branched or cyclic, and examples thereof include tert-butyl, tert-pentyl, 1, 1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups include trimethylsilyl, triethylsilyl, and dimethyl-tert-butylsilyl. Exemplary saturated hydrocarbyl groups containing a carbonyl, ether bond or ester bond include 3-oxocyclohexyl, 4-methyl-2-oxooxan-4-yl, and 5-methyl-2-oxooxolan-5-yl.

In formula (L3), $R^{L05}$ is an optionally substituted $C_1$-$C_8$ saturated hydrocarbyl group or an optionally substituted $C_6$-$C_{20}$ aryl group. The optionally substituted saturated hydrocarbyl group may be straight, branched or cyclic and examples thereof include alkyl groups such as methyl, ethyl, propyl, isopropyl, n-butyl, sec-butyl, tert-butyl, tert-pentyl, n-pentyl, n-hexyl, cyclic saturated hydrocarbyl groups such as cyclopentyl and cyclohexyl, and substituted forms of the foregoing in which some or all of the hydrogen atoms are substituted by hydroxy, $C_1$-$C_6$ saturated hydrocarbyloxy, carboxy, $C_1$-$C_6$ saturated hydrocarbylcarbonyl, oxo, amino, $C_1$-$C_6$ saturated hydrocarbylamino, cyano, mercapto, $C_1$-$C_6$ saturated hydrocarbylthio, sulfo or the like. Examples of the optionally substituted aryl group include phenyl, methylphenyl, naphthyl, anthryl, phenanthryl, and pyrenyl, and substituted forms of the foregoing in which some or all of the hydrogen atoms are substituted by hydroxy, $C_1$-$C_{10}$ saturated hydrocarbyloxy, carboxy, $C_1$-$C_{10}$ saturated hydrocarbylcarbonyl, oxo, amino, $C_1$-$C_{10}$ saturated hydrocarbylamino, cyano, mercapto, $C_1$-$C_{10}$ saturated hydrocarbylthio, sulfo or the like.

In formula (L3), y is equal to 0 or 1, z is an integer of 0 to 3, and 2y+z is equal to 2 or 3.

In formula (L4), $R^{L06}$ is an optionally substituted $C_1$-$C_8$ saturated hydrocarbyl group or an optionally substituted $C_6$-$C_{20}$ aryl group. Examples of the optionally substituted saturated hydrocarbyl and optionally substituted aryl groups are the same as exemplified above for $R^{L05}$.

$R^{L07}$ to $R^{L16}$ are each independently hydrogen or an optionally substituted $C_1$-$C_{15}$ hydrocarbyl group. The hydrocarbyl group may be saturated or unsaturated and straight, branched or cyclic, with saturated hydrocarbyl groups being preferred. Examples of the hydrocarbyl group include alkyl groups such as methyl, ethyl, propyl, isopropyl, n-butyl, sec-butyl, tert-butyl, tert-pentyl, n-pentyl, n-hexyl, n-octyl, n-nonyl, n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl and cyclohexylbutyl; and substituted forms of the foregoing in which some or all of the hydrogen atoms are substituted by hydroxy, $C_1$-$C_{10}$ saturated hydrocarbyloxy, carboxy, $C_1$-$C_{10}$ saturated hydrocarbyloxycarbonyl, oxo, amino, $C_1$-$C_{10}$ saturated hydrocarbylamino, cyano, mercapto, $C_1$-$C_{10}$ saturated hydrocarbylthio, sulfo or the like. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of ring-forming $R^{L07}$ to $R^{L16}$ represents a $C_1$-$C_{15}$ hydrocarbylene group, examples of which are the ones exemplified above for the hydrocarbyl groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, $R^{L14}$ and $R^{L15}$, or a similar pair).

Of the acid labile groups having formula (L1), the straight and branched ones are exemplified by the following groups, but not limited thereto.

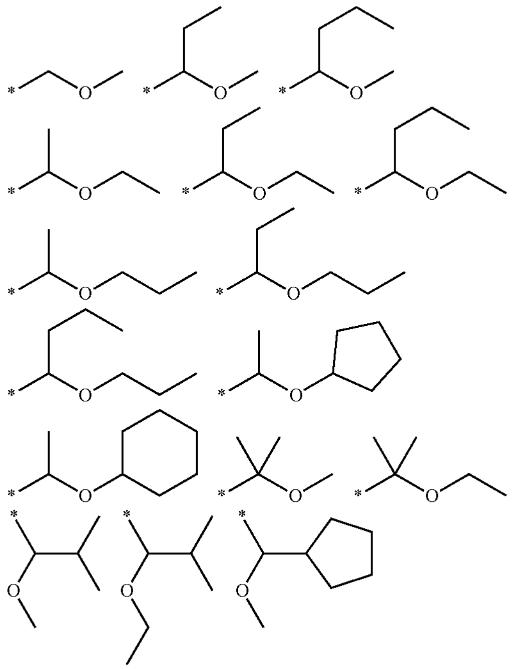

-continued

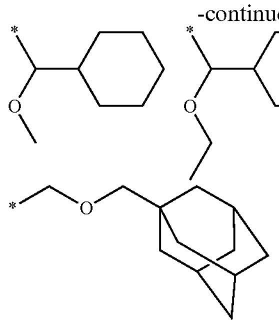

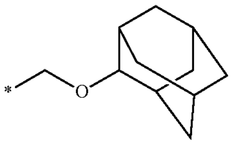

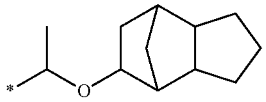

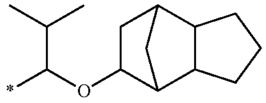

Of the acid labile groups having formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile group having formula (L2) include tert-butoxycarbouyl, tert-butoxycarbonyhnethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile group having formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulae (L4-1) to (L4-4) are preferred.

(L4-1)

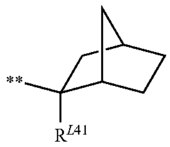

(L4-2)

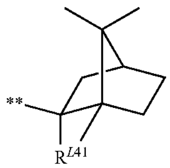

(L4-3)

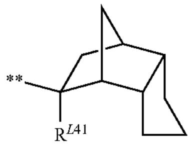

-continued (L4-4)

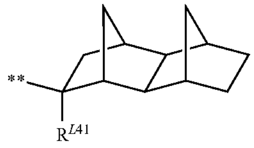

In formulae (L4-1) to (L4-4), the double asterisks (**) denotes a bonding site and direction. $R^{L41}$ is each independently a $C_1$-$C_{10}$ hydrocarbyl group. The hydrocarbyl group may be saturated or unsaturated and straight, branched or cyclic, and examples thereof include alkyl groups such as methyl, ethyl, propyl, isopropyl, n-butyl, sec-butyl, tert-butyl, tert-pentyl, n-pentyl, n-hexyl, and cyclic saturated hydrocarbyl groups such as cyclopentyl and cyclohexyl.

For formulae (L4-1) to (L4-4), there can exist stereoisomers (enantiomers or diastereomers). Each of formulae (L4-1) to (L4-4) collectively represents all such stereoisomers. When the acid labile group is of formula (L4), there may be contained a plurality of stereoisomers.

For example, the formula (L4-3) represents one or a mixture of two selected from groups having the following formulae (L4-3-1) and (L4-3-2).

(L4-3-1)

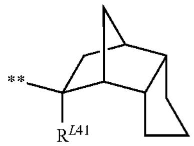

(L4-3-2)

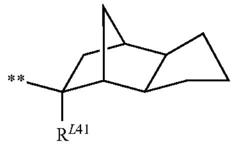

Herein $R^{L41}$ and double asterisks (**) are as defined above.

Similarly, the formula (L4-4) represents one or a mixture of two or more selected from groups having the following formulae (L4-4-1) to (L4-4-4).

(L4-4-1)

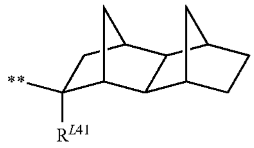

(L4-4-2)

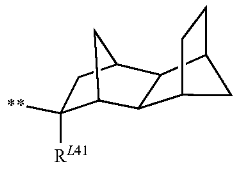

-continued (L4-4-3)

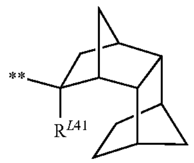

(L4-4-4)

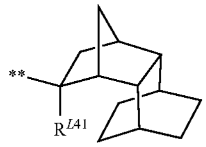

Herein $R^{L41}$ and double asterisks (**) are as defined above.

Each of formulae (L4-1) to (L4-4), (L4-3-1), (L4-3-2), and (L4-4-1) to (L4-4-4) collectively represents an enantiomer thereof and a mixture of enantiomers.

It is noted that in the above formulae (L4-1) to (L4-4), (L4-3-1), (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-saturated hydrocarbyl group of bicyclo[2.2.1]heptane skeleton as a substituent group, there may be contained monomers substituted with an endo-alkyl group as represented by the following formulae (L4-1-endo) to (L4-4-endo). For good reactivity, an exo proportion of at least 50 mol % is preferred, with an exo proportion of at least 80 mol % being more preferred.

(L4-1-endo)

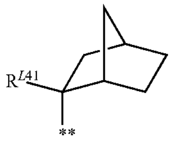

(L4-2-endo)

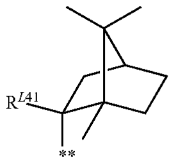

(L4-3-endo)

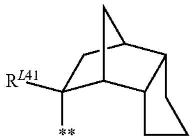

(L4-4-endo)

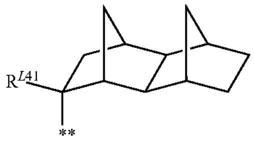

Herein $R^{L41}$ and double asterisks (**) are as defined above.

Illustrative examples of the acid labile group having formula (L4) are given below, but not limited thereto.

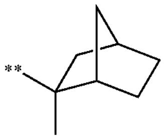
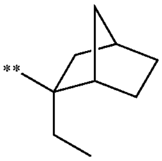
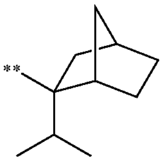

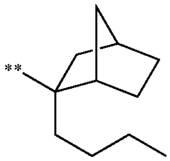
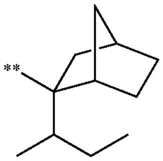

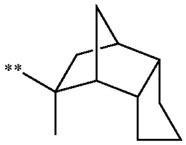
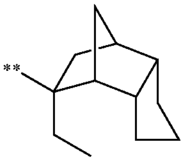

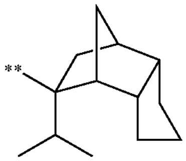
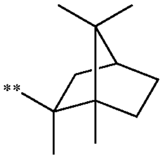

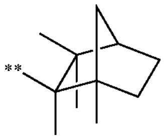
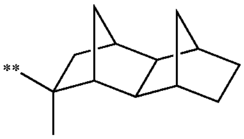

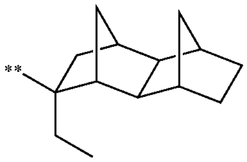
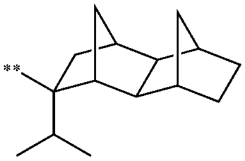

Of the acid labile groups represented by $AL^1$ and $AL^2$, examples of the $C_4$-$C_{20}$ tertiary hydrocarbyl groups, trialkylsilyl groups in which each alkyl moiety has 1 to 6 carbon atoms, and $C_4$-$C_{20}$ saturated hydrocarbyl groups containing carbonyl, ether bond or ester bond are as exemplified above for $R^{L04}$.

Illustrative examples of the repeat units (a1) are given below, but not limited thereto. Herein $R^A$ is as defined above.

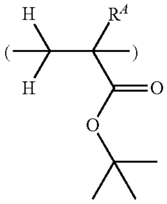
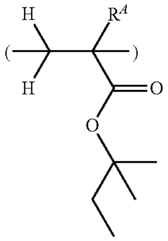

-continued
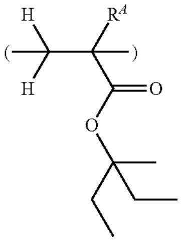
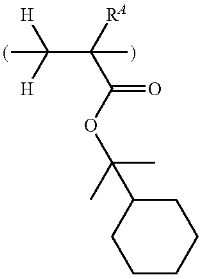
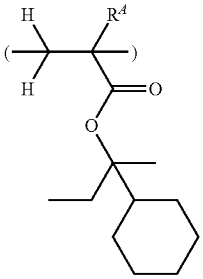
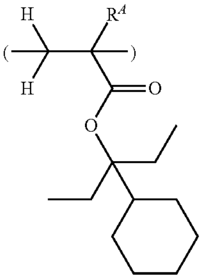
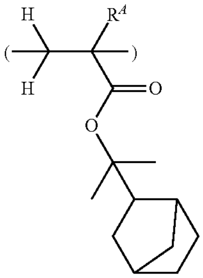
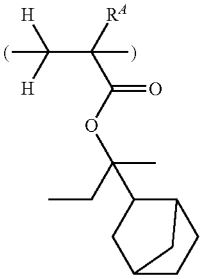
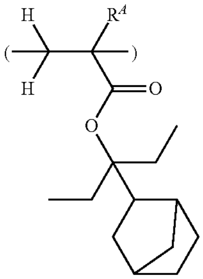
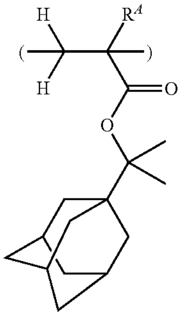
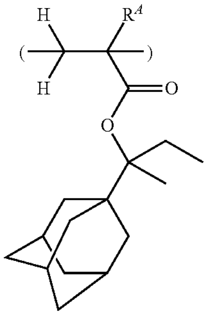
-continued
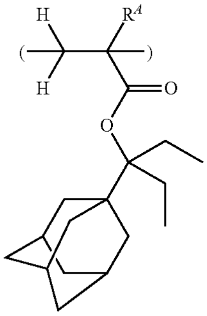
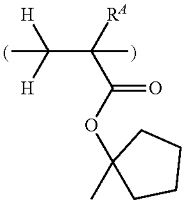
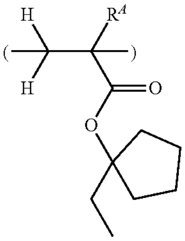
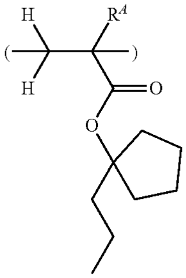
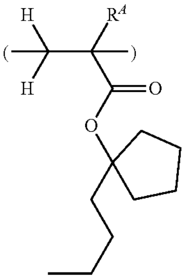
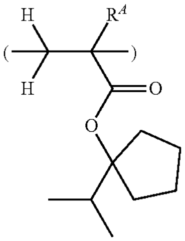
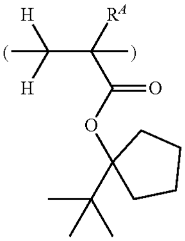
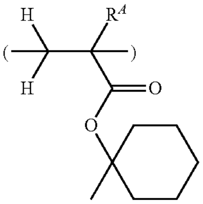
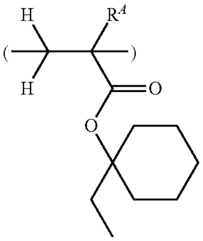
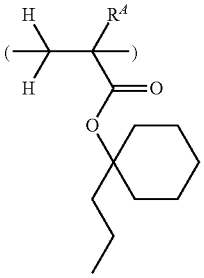
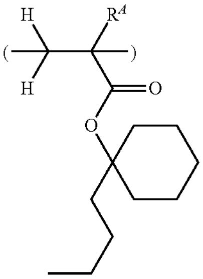
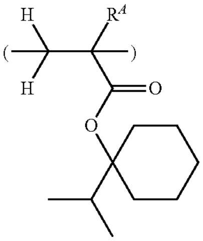

-continued
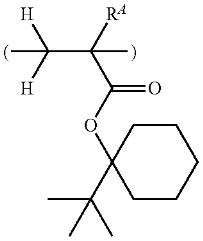
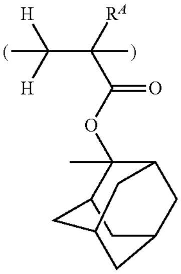
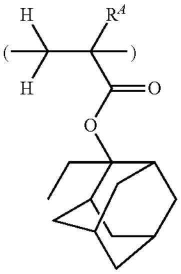
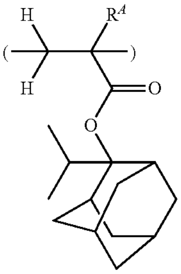
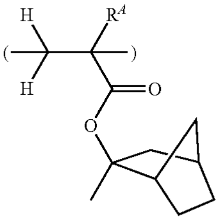
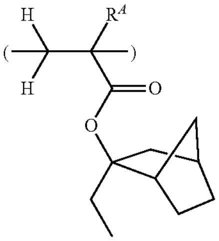
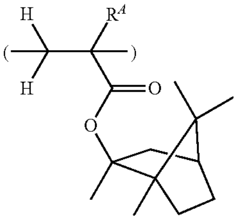
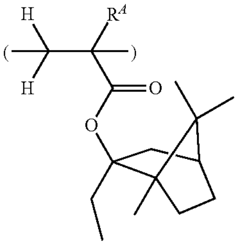
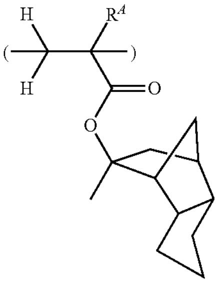
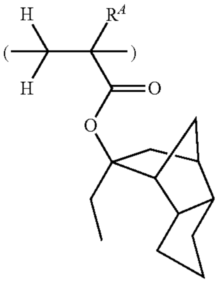
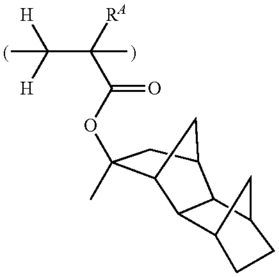
-continued
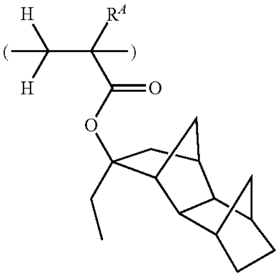
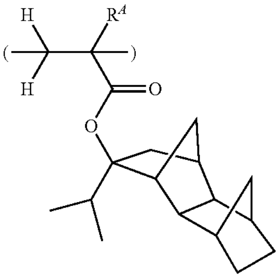
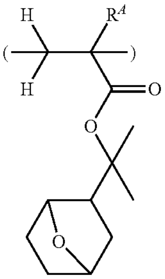
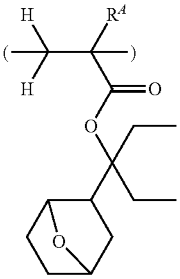
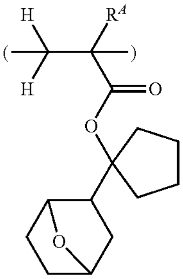
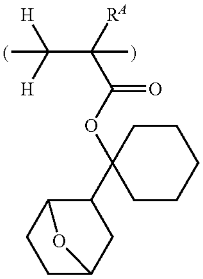
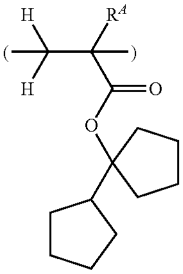
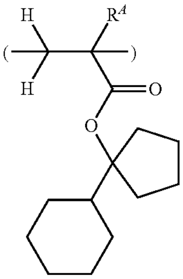
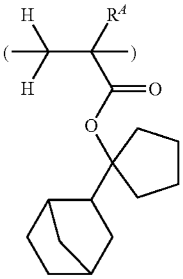
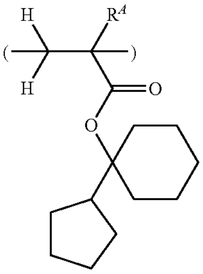
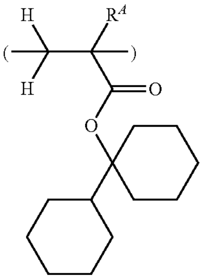

-continued
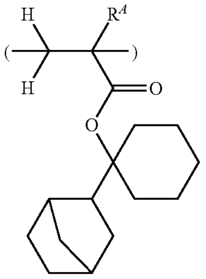
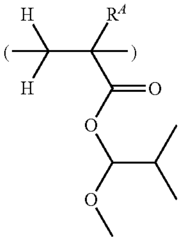
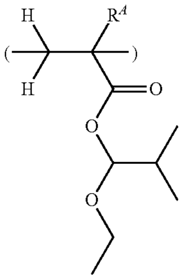
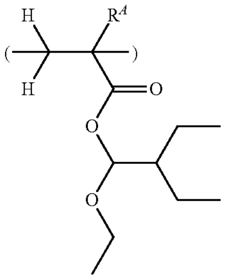
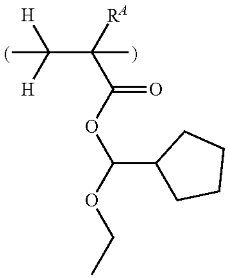
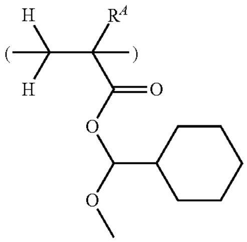
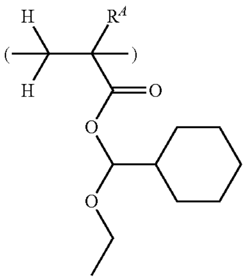
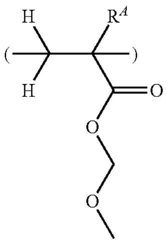
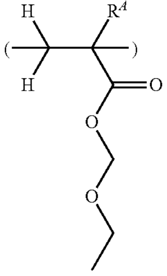
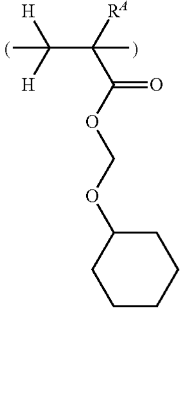
-continued
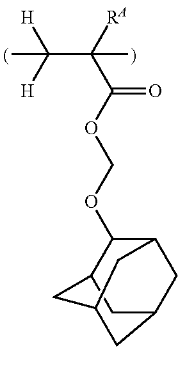
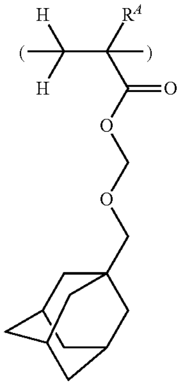
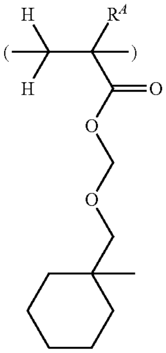
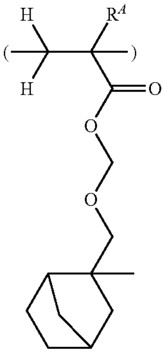
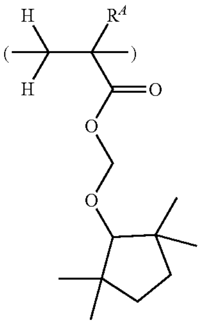
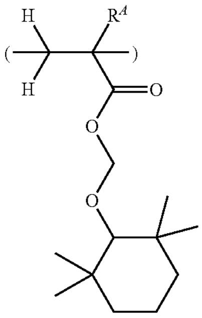
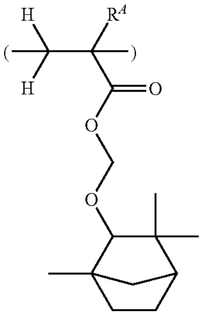
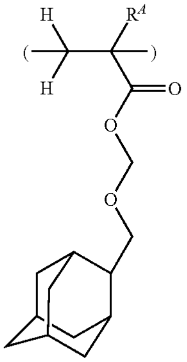
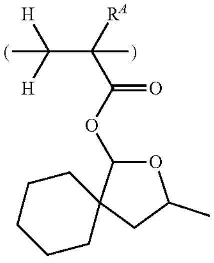
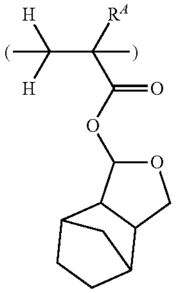

-continued

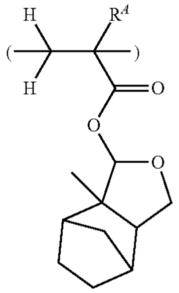

The above examples correspond to those units (a1) wherein $X^1$ is a single bond. Where $X^1$ is other than a single bond, a combination with a similar acid labile group is possible. Thus examples of the repeat units (a1) wherein $X^1$ is other than a single bond are as illustrated above.

Like the repeat units (a1), a polymer comprising repeat units (a2) turns alkali soluble through the mechanism that it is decomposed under the action of acid to generate a hydroxy group. Illustrative examples of the repeat units (a2) are given below, but not limited thereto. Herein $R^A$ is as defined above.

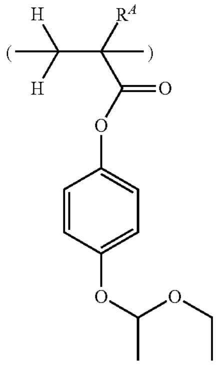

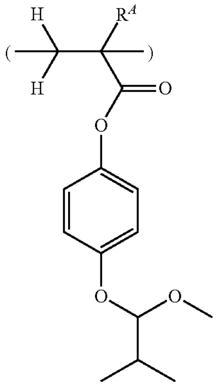

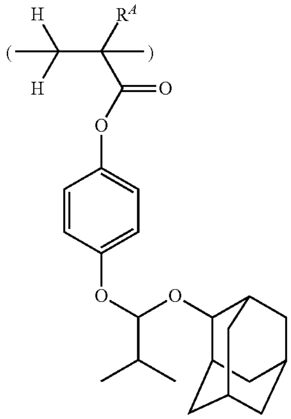

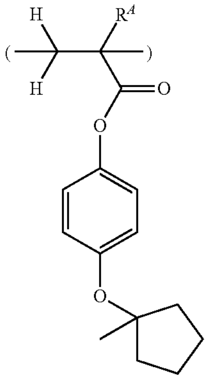

-continued

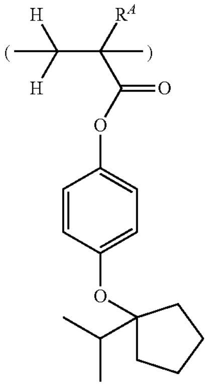

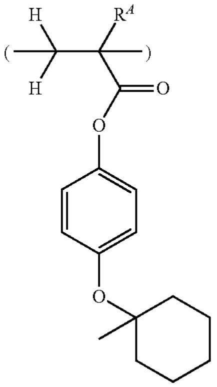

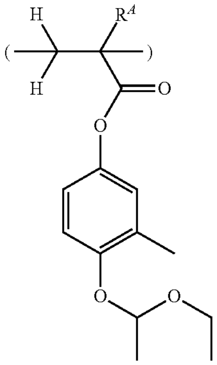

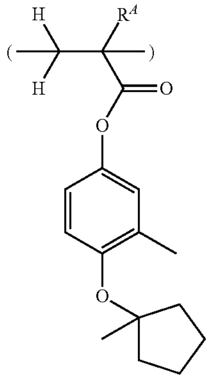

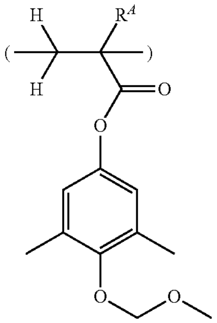

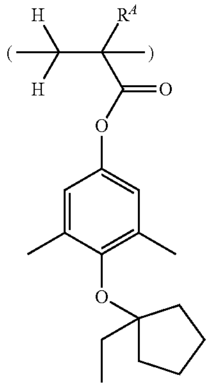

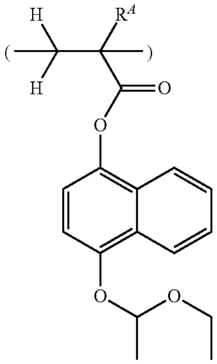

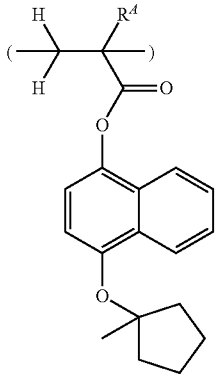

-continued
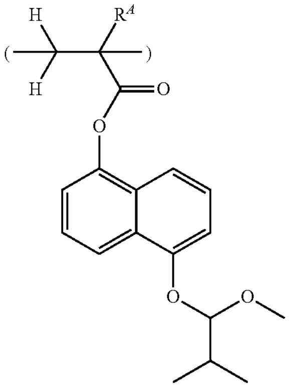
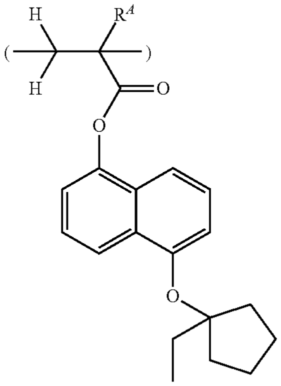
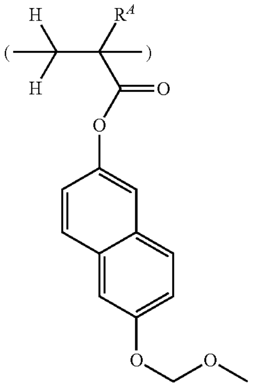
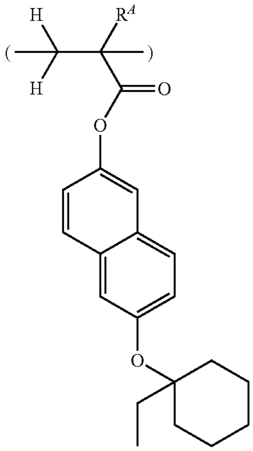
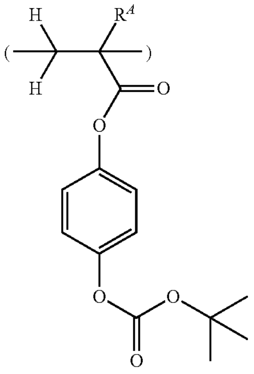
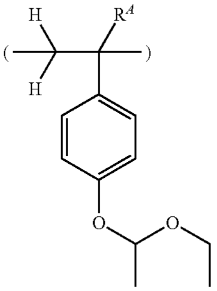
-continued
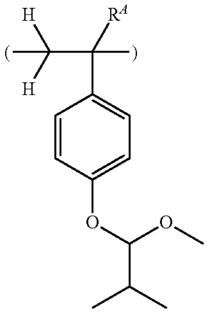
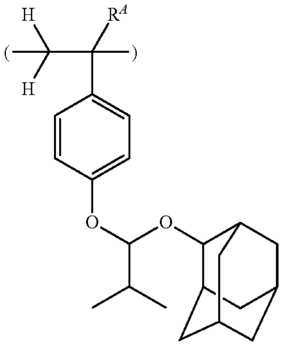
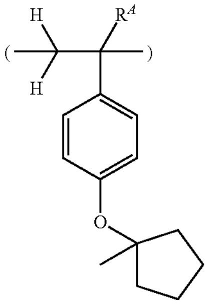
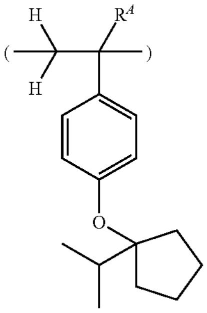
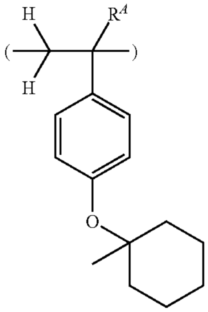
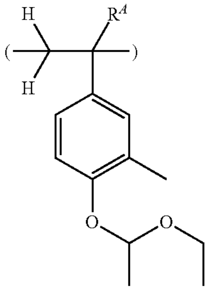
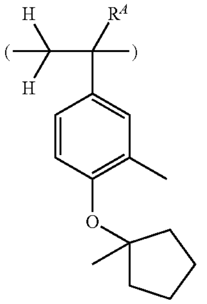
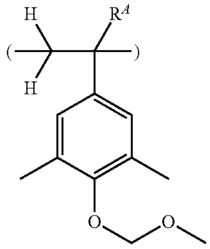
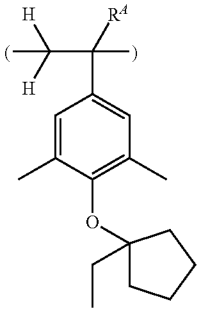
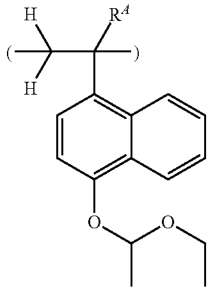

-continued

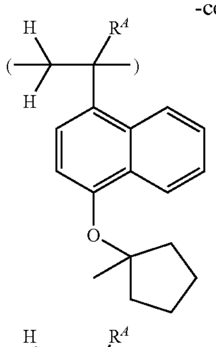

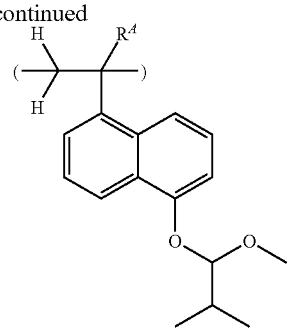

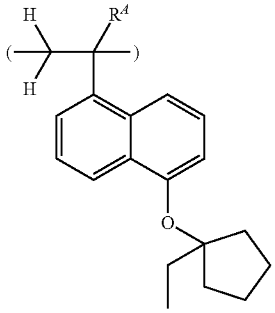

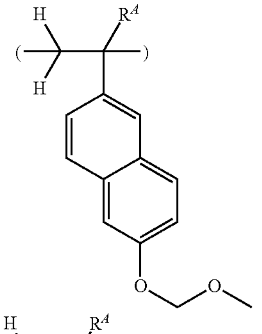

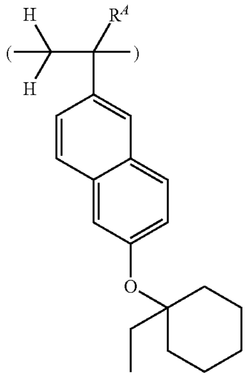

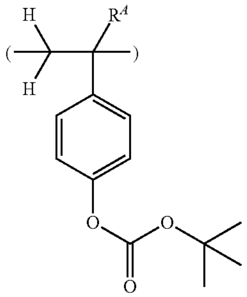

In a preferred embodiment, the base polymer further comprises repeat units having the formula (b1) or repeat units having the formula (b2), which are simply referred to as repeat units (b1) or (b2).

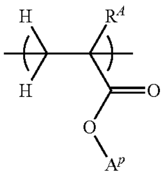

(b1)

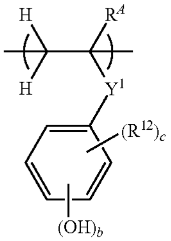

(b2)

In formulae (b1) and (b2), $R^A$ is each independently hydrogen, fluorine, methyl or trifluoromethyl. $A^P$ is hydrogen or a polar group containing at least one structure selected from among hydroxy, cyano, carbonyl, carboxy, ether bond, ester bond, sulfonic ester bond, carbonate bond, lactone ring, sultone ring and carboxylic anhydride (—C(═O)—O—C(═O)—). $Y^3$ is a single bond or *—C(═O)—O—. The asterisk (*) designates a point of attachment to the carbon atom in the backbone. $R^{12}$ is halogen, cyano, a $C_1$-$C_{20}$ hydrocarbyl group which may contain a heteroatom, $C_1$-$C_{20}$ hydrocarbyloxy group which may contain a heteroatom, or $C_2$-$C_{20}$ hydrocarbylcarbonyl group which may contain a heteroatom. The subscript b is an integer of 1 to 4, c is an integer of 0 to 4, and the sum of b and c is from 1 to 5.

Examples of the repeat unit (b1) are shown below, but not limited thereto. Herein, $R^A$ is as defined above.

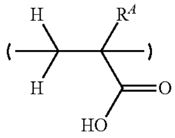

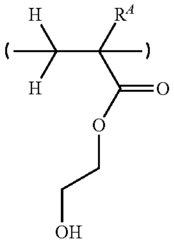

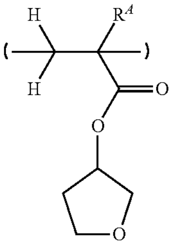

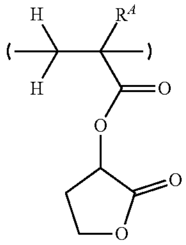

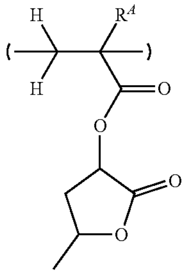

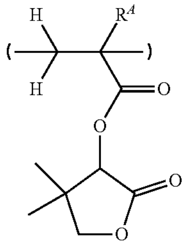

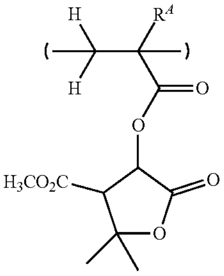

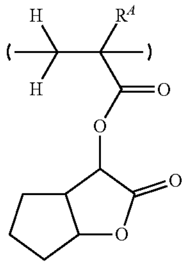

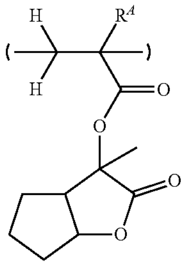

-continued
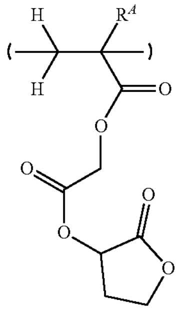
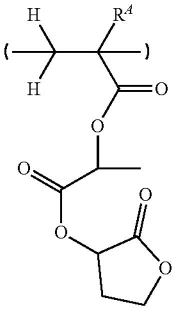
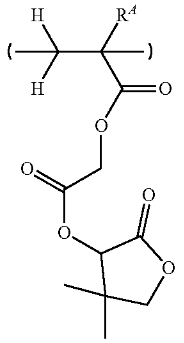
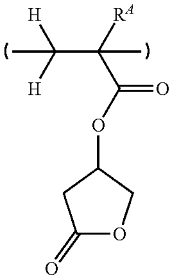
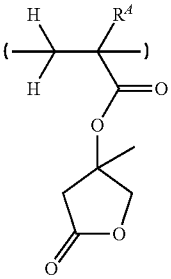
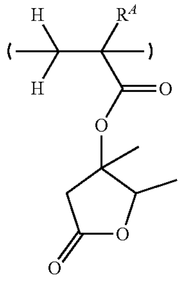
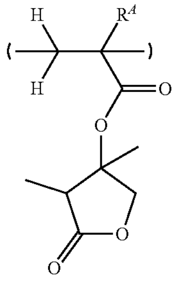
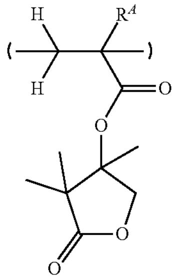
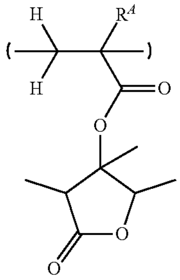
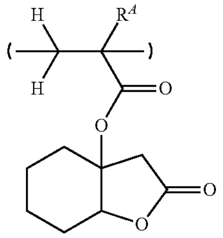
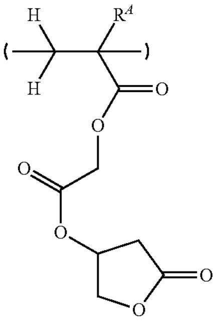
-continued
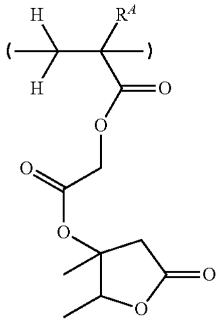
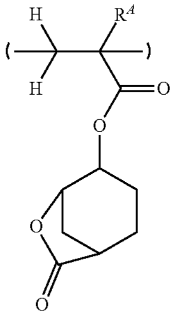
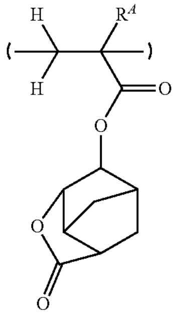
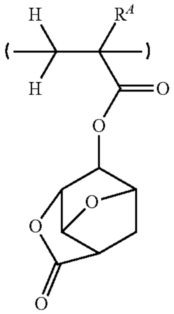
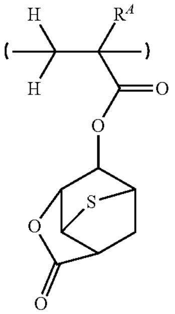
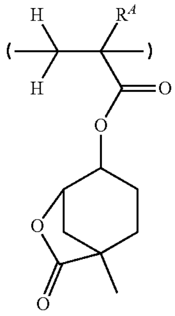
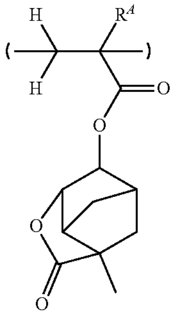
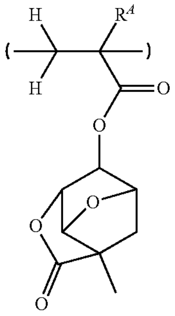
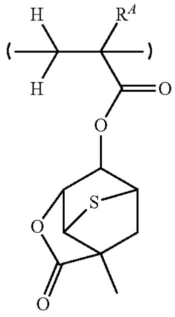
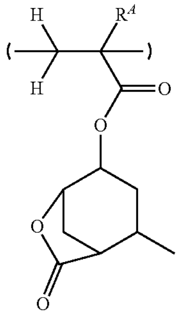
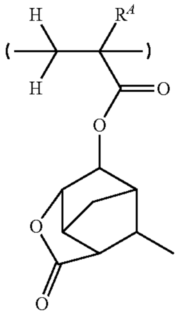

-continued
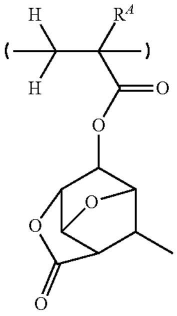
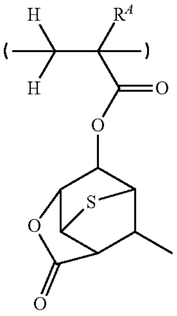
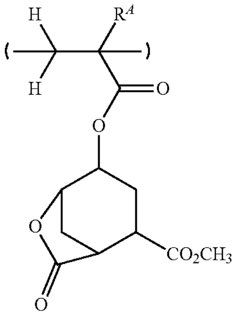
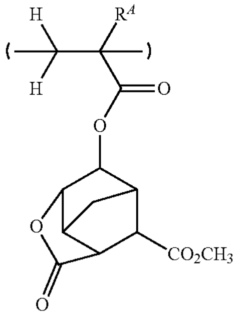
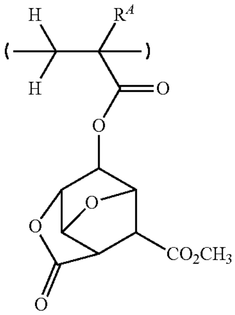
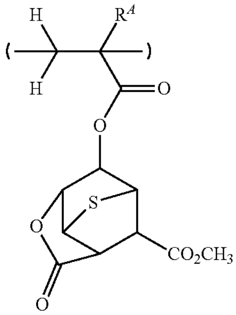
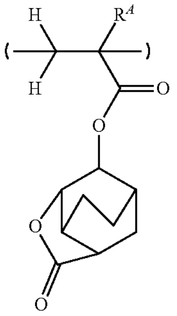
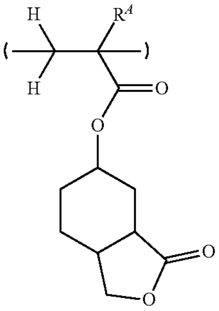
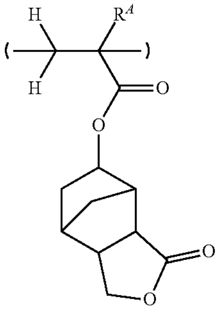
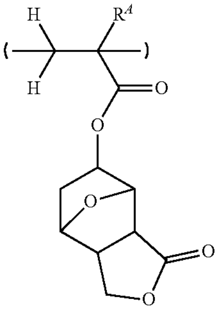
-continued
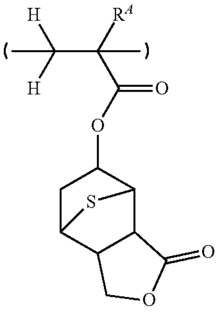
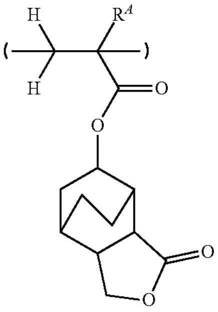
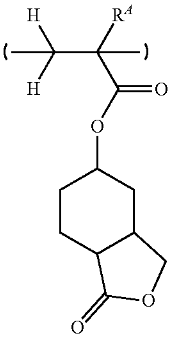
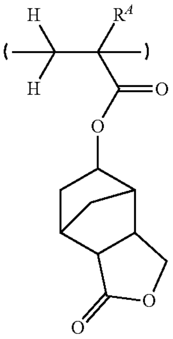
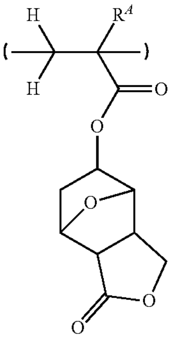
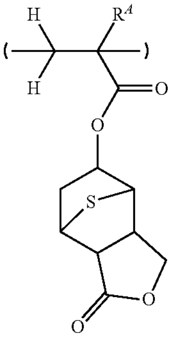
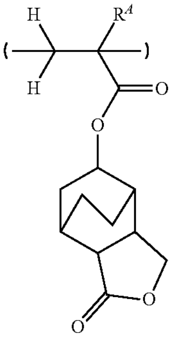
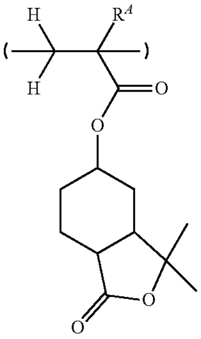
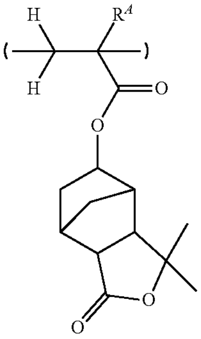
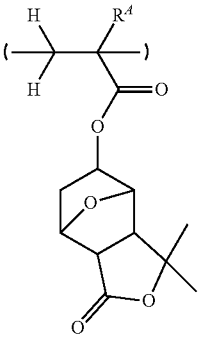
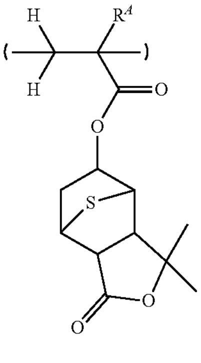

-continued
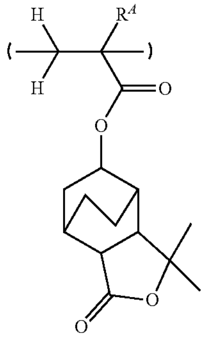
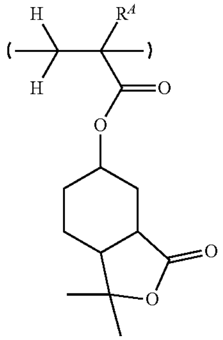
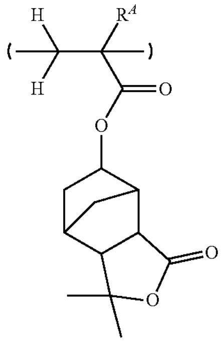
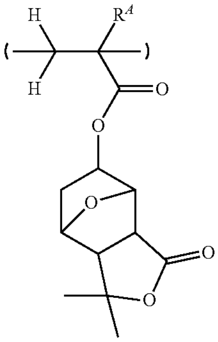
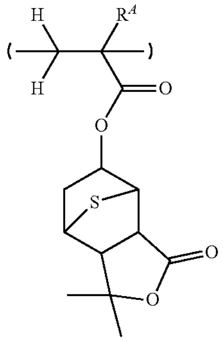
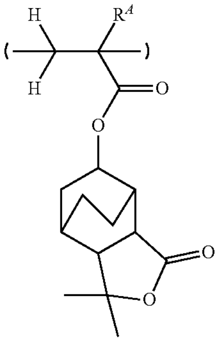
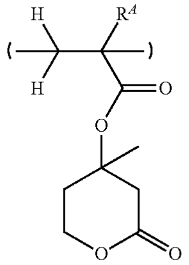
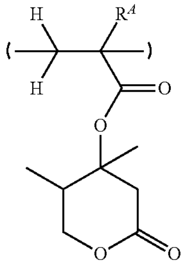
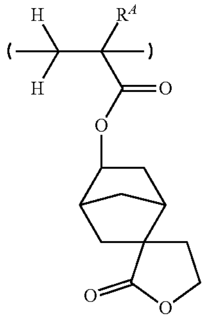
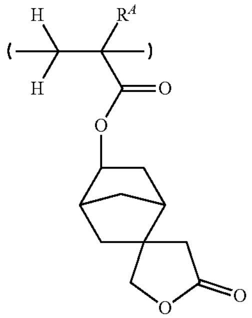
-continued
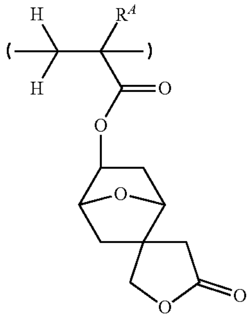
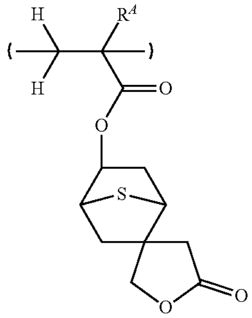
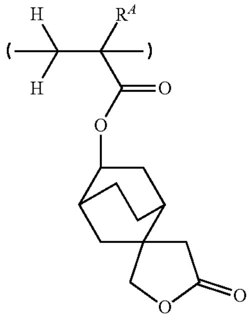
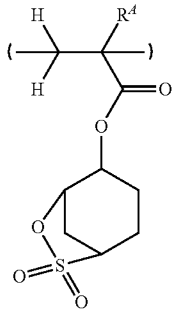
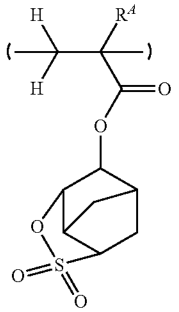
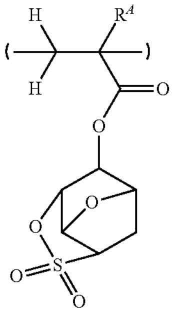
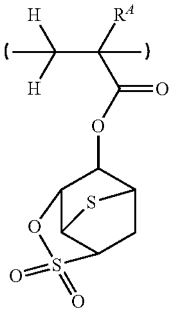
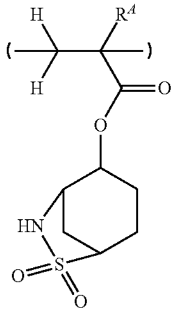
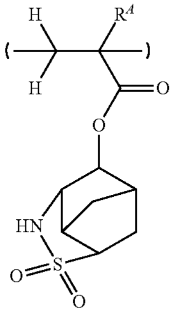
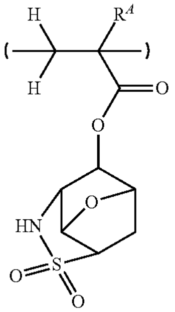
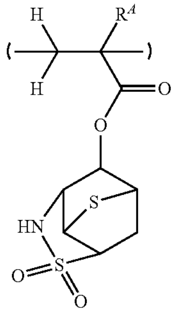
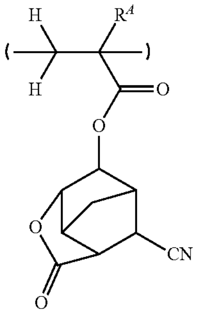

-continued
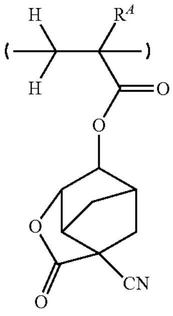
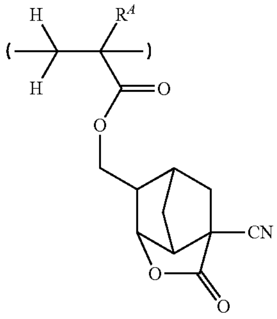
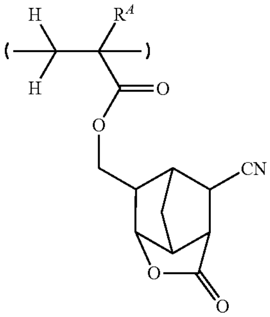
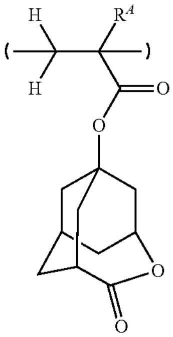
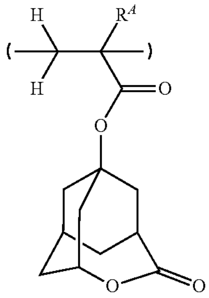
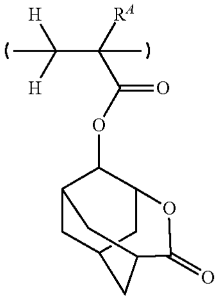
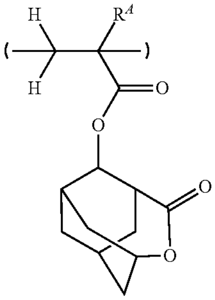
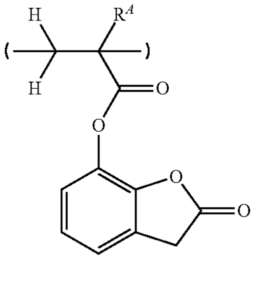
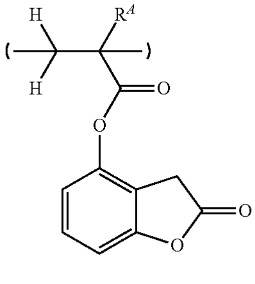
-continued
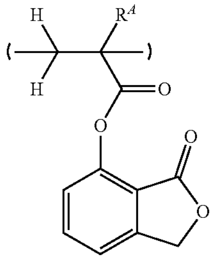
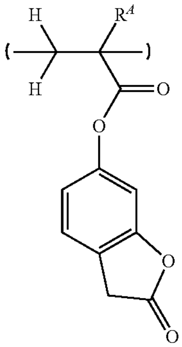
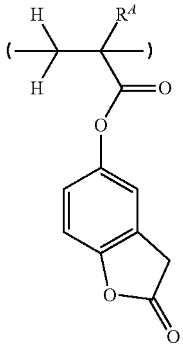
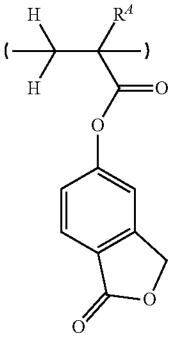
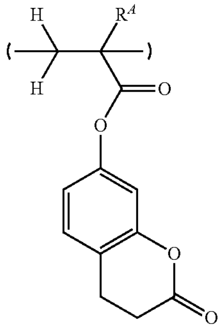
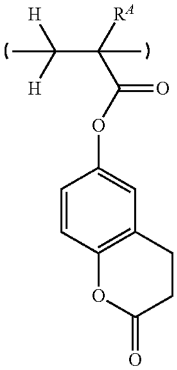
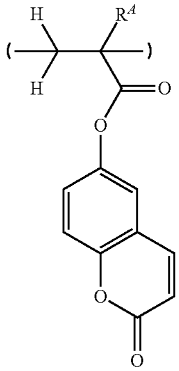
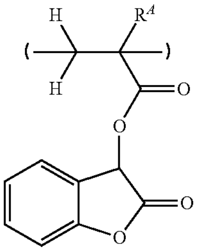
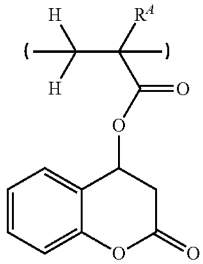
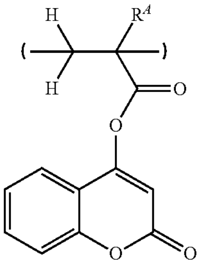

-continued
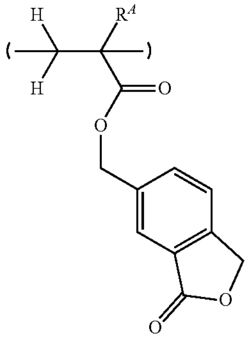
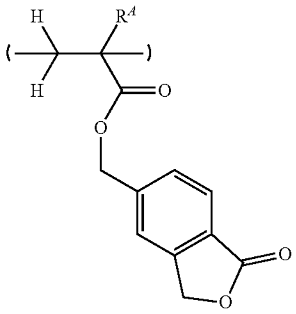
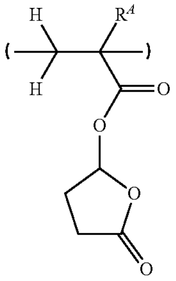
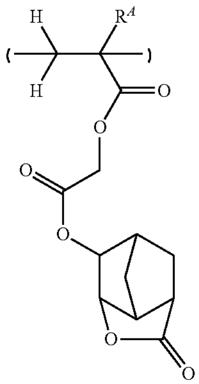
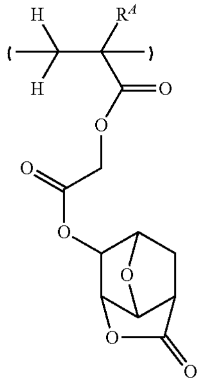
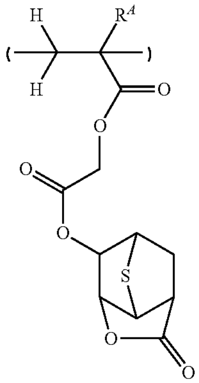
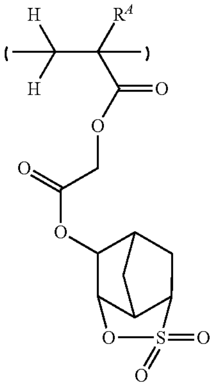
-continued
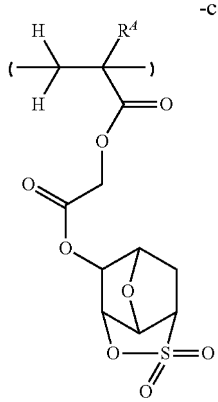
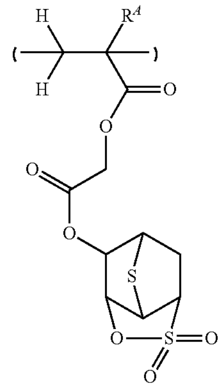
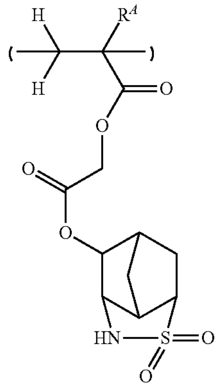
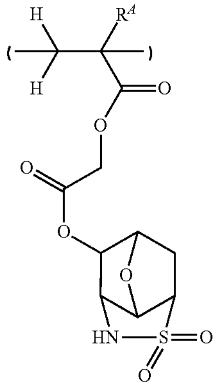
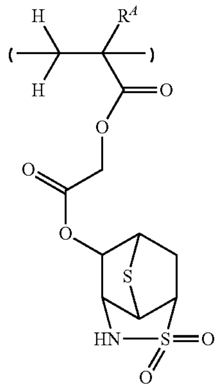
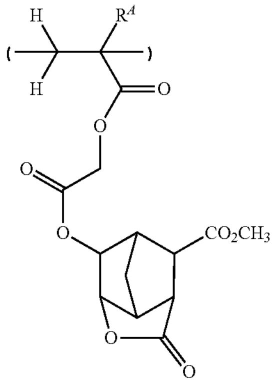
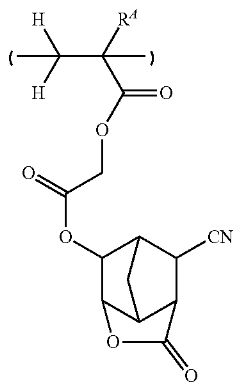
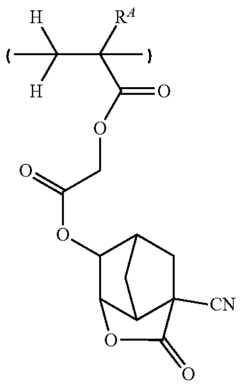

-continued
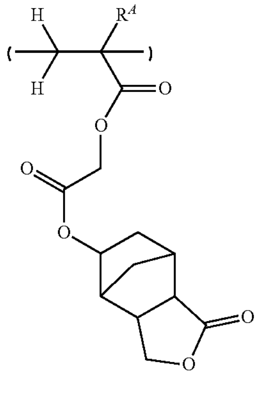
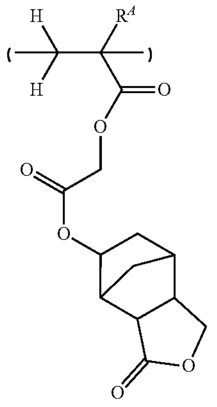
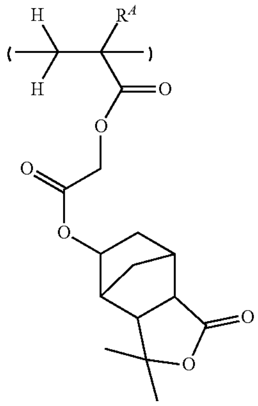
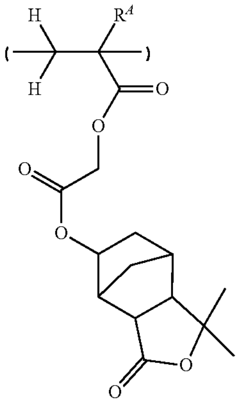
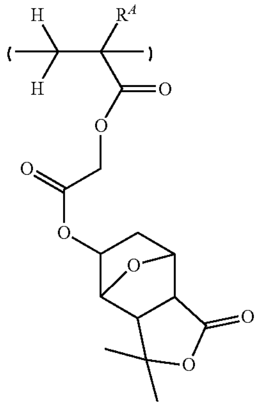
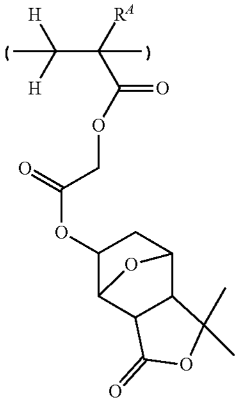
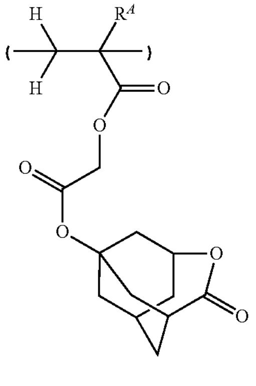
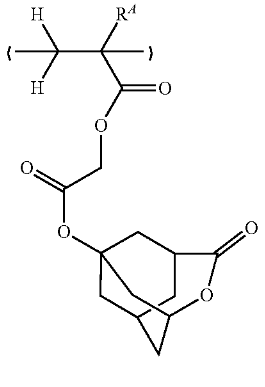
-continued
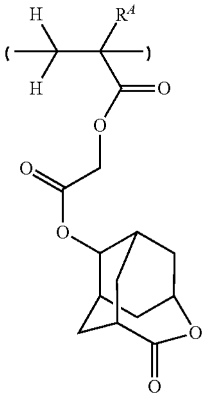
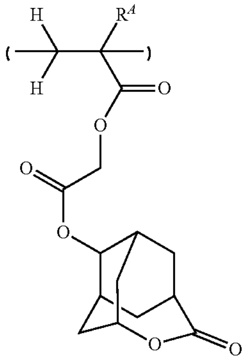
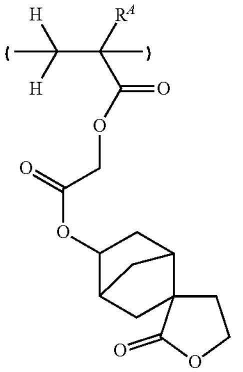
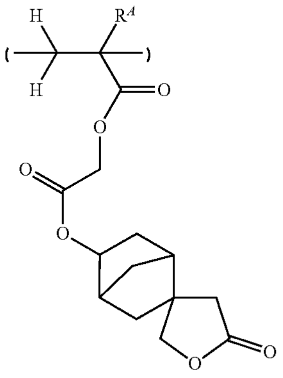
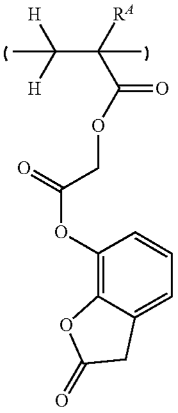
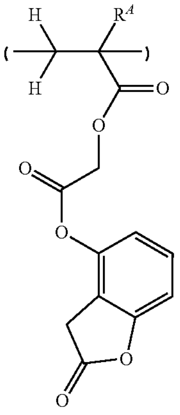
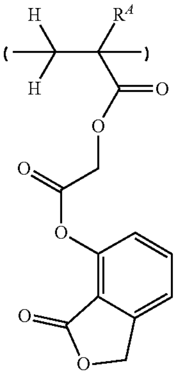
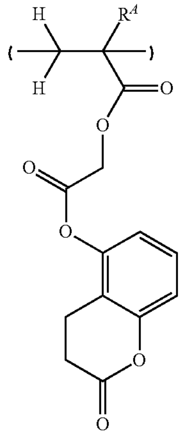

-continued
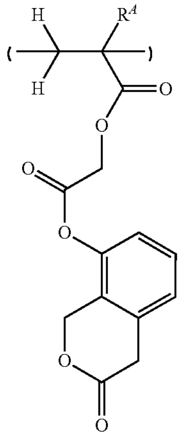
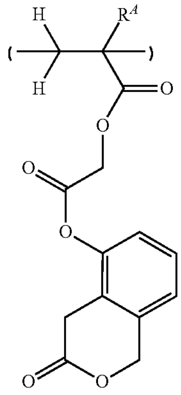
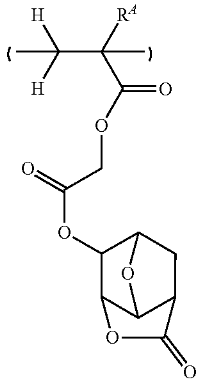
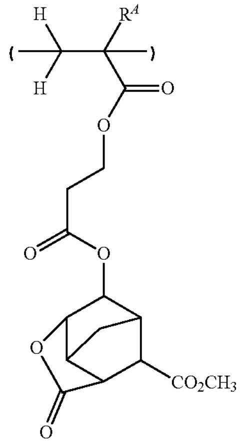
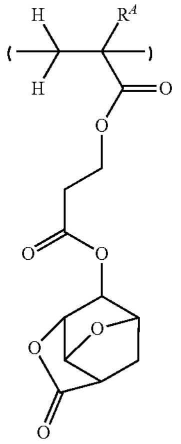
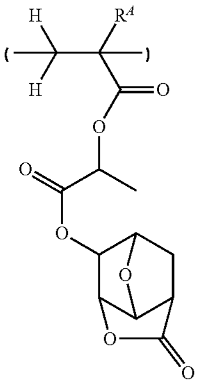
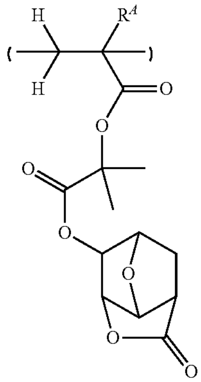
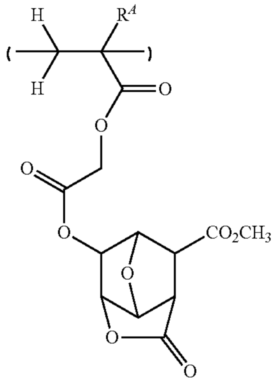
-continued
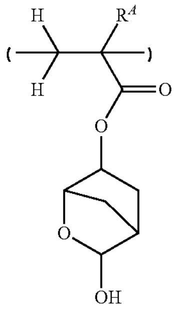
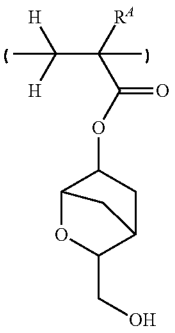
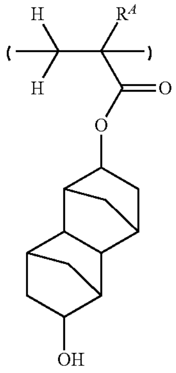
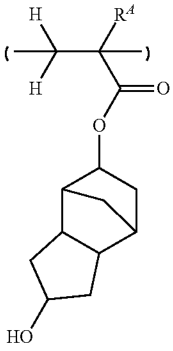
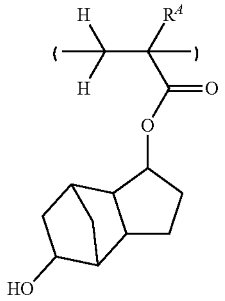
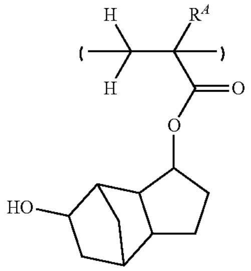
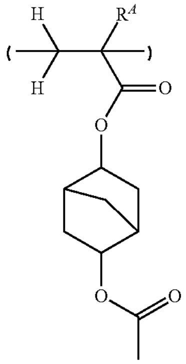
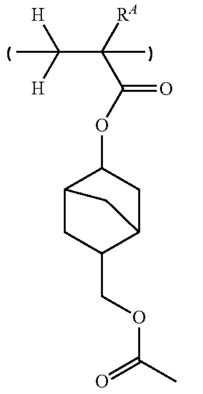

-continued
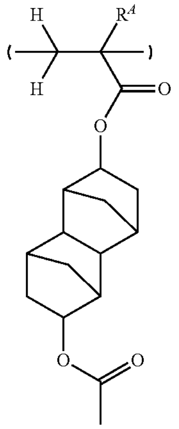
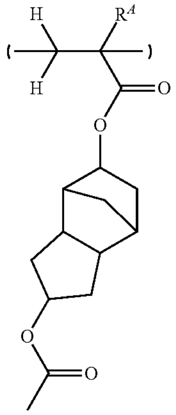
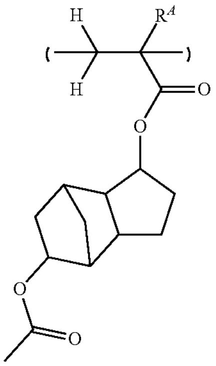
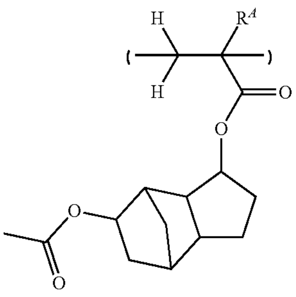
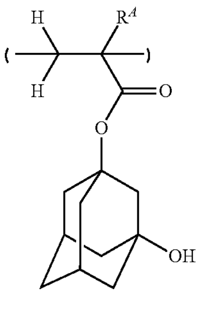
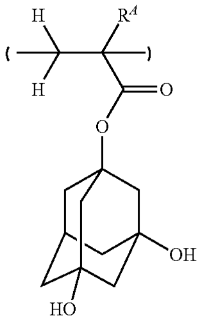
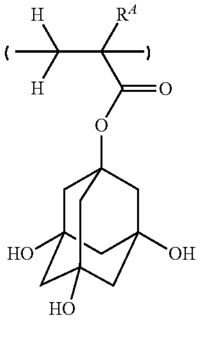
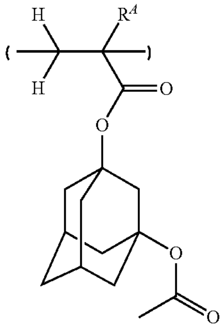
-continued
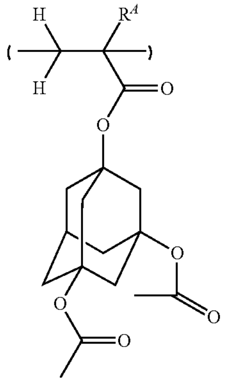
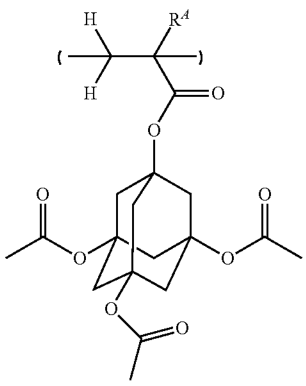
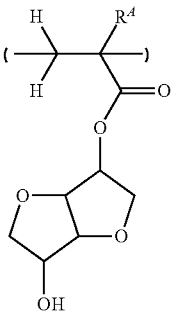
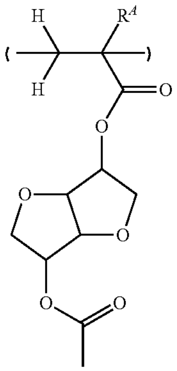
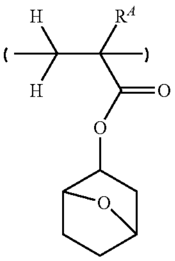
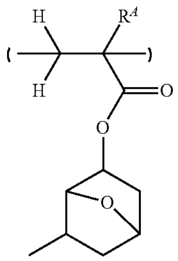
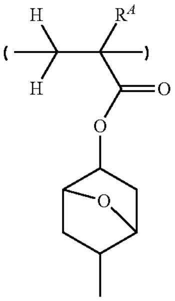
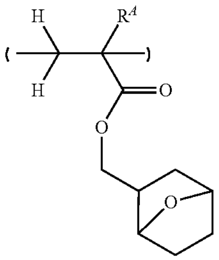
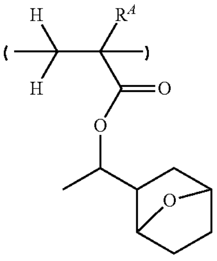
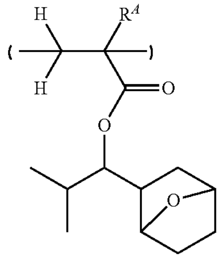

-continued
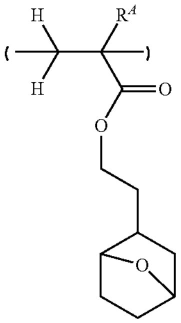
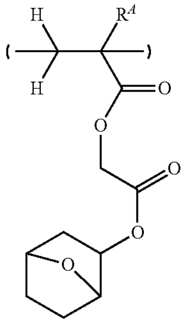
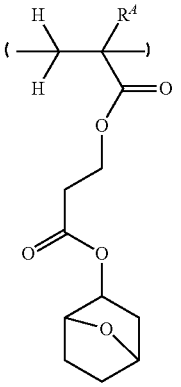
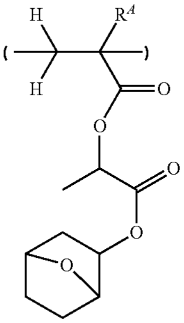
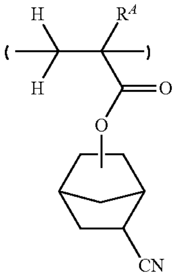
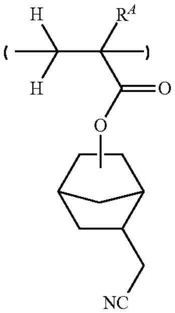
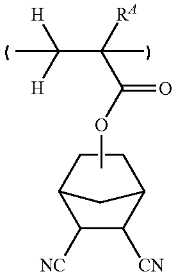
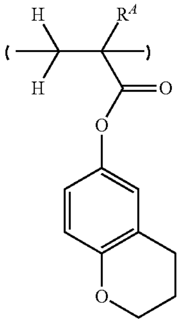
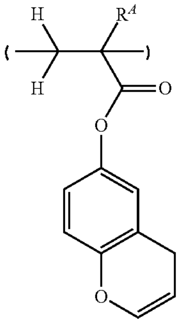
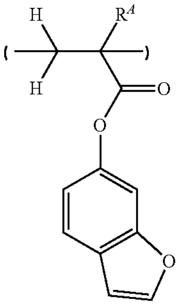
-continued
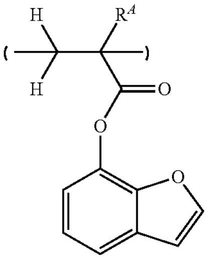
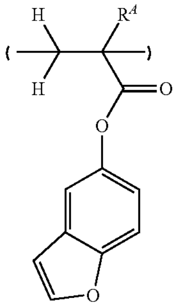
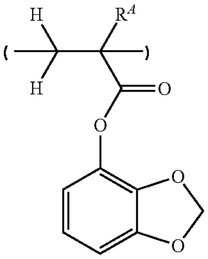
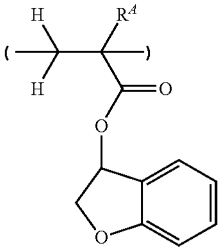
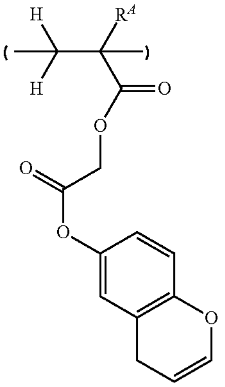
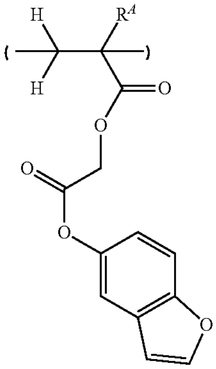
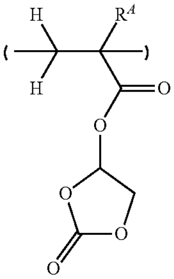
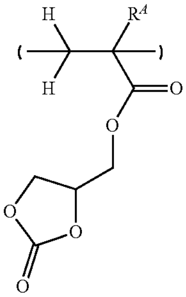
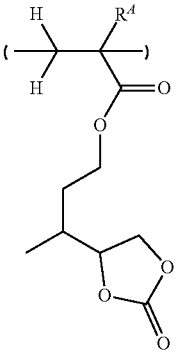
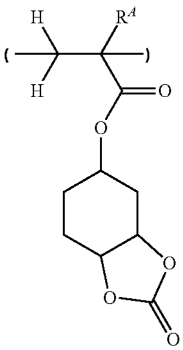

-continued
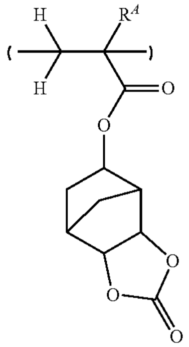
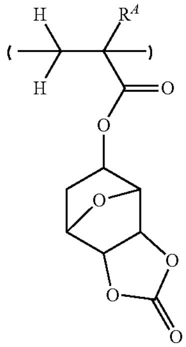
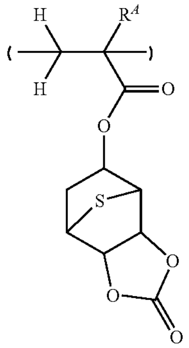
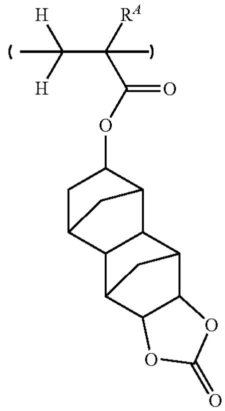
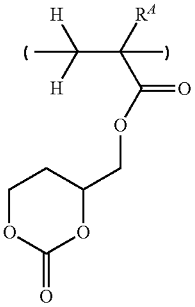
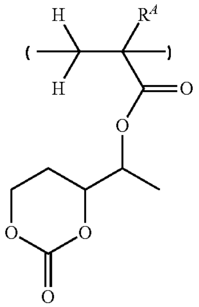
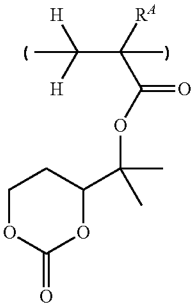
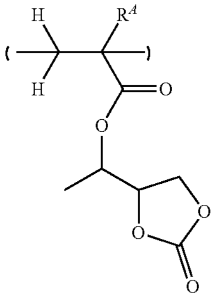
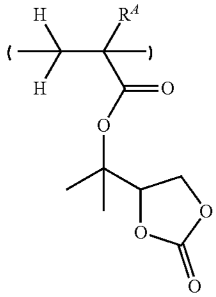
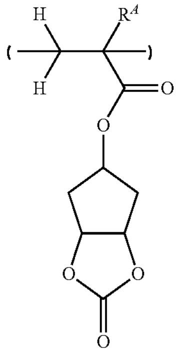
-continued
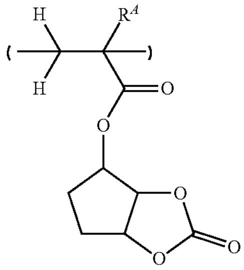
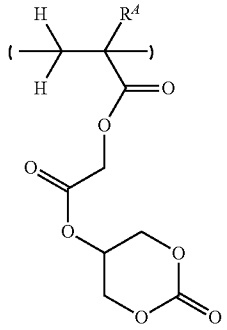
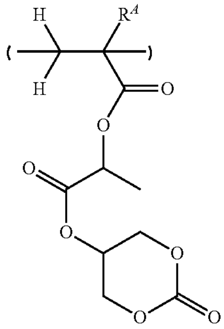
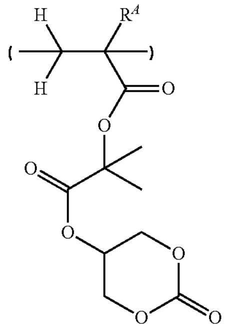
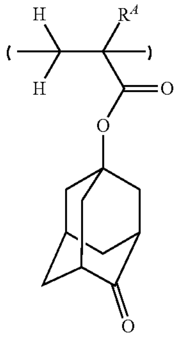
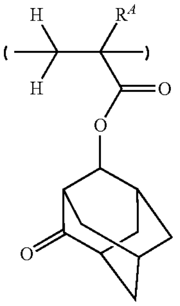
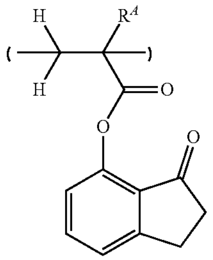
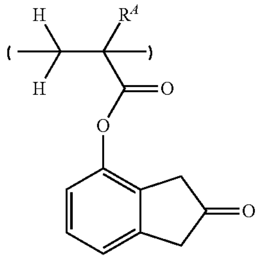
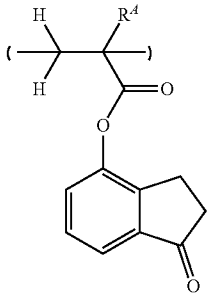
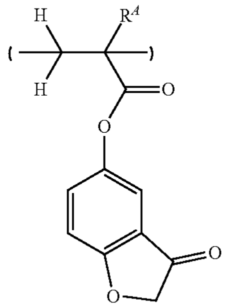

-continued
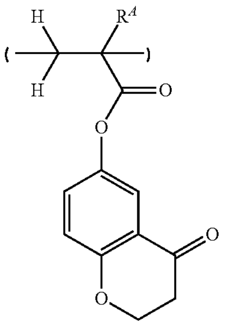
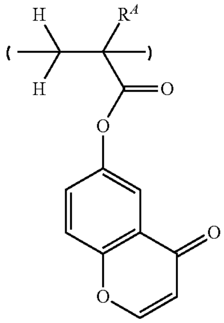
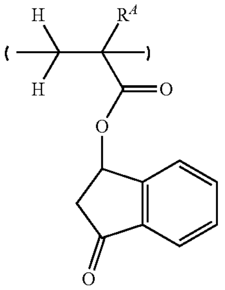
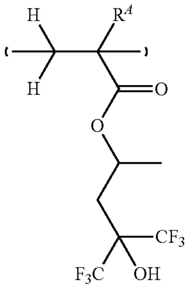
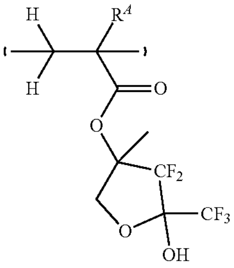
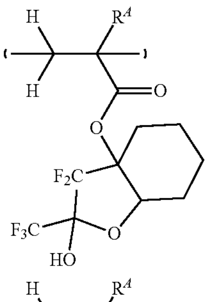
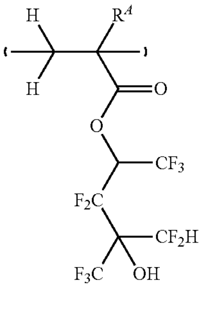
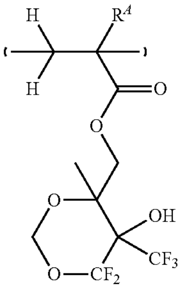
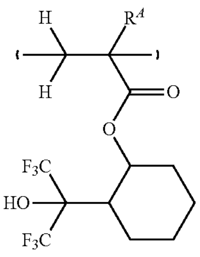
-continued
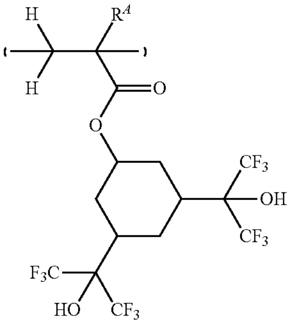
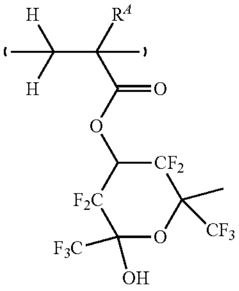
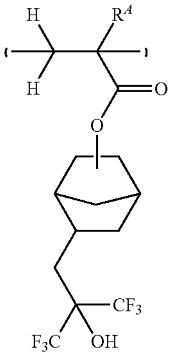
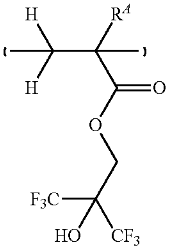
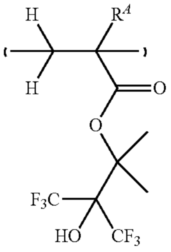
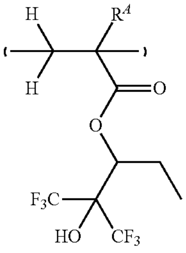
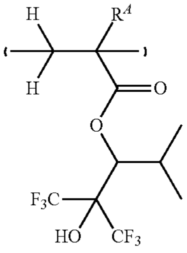
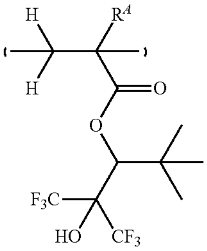
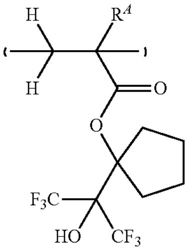
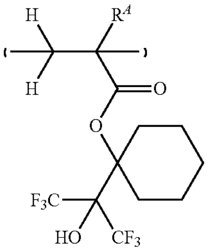
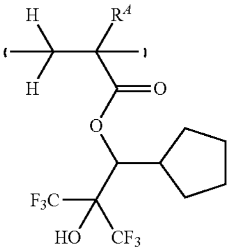

-continued
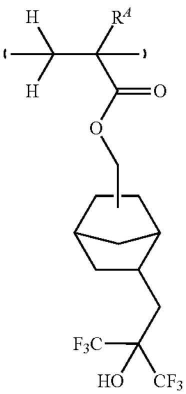
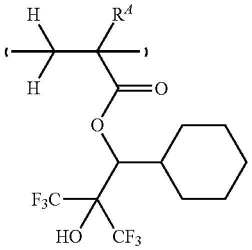
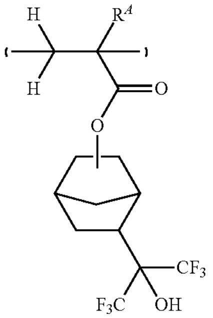
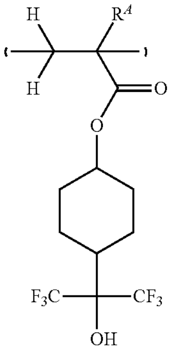
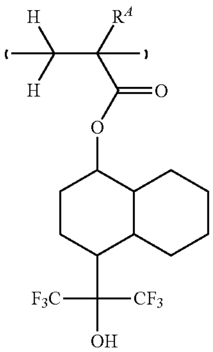
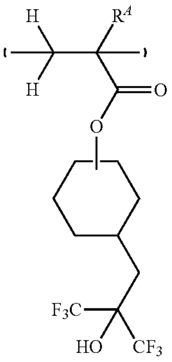
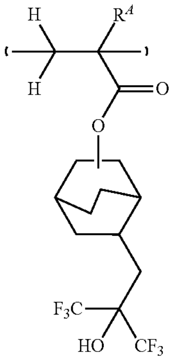
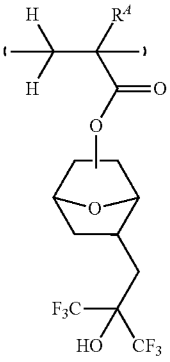
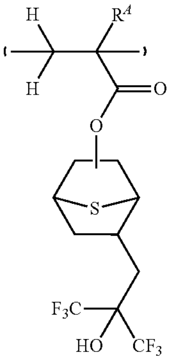
-continued
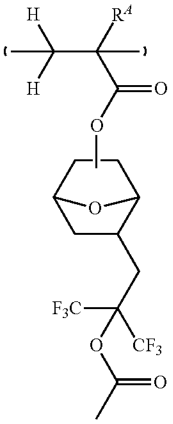
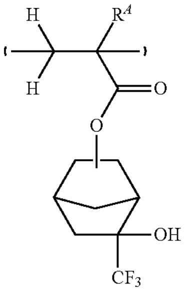
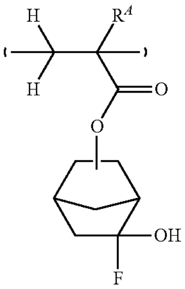
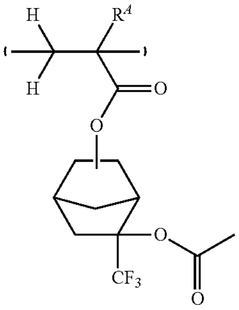
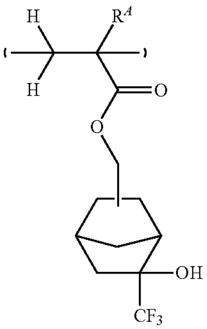
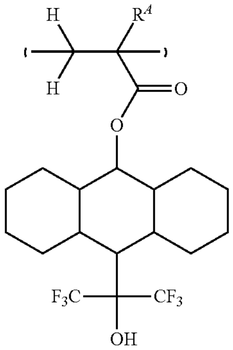
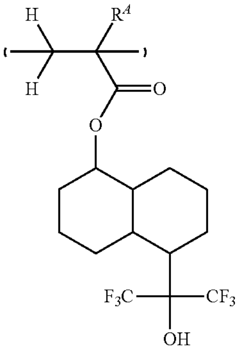
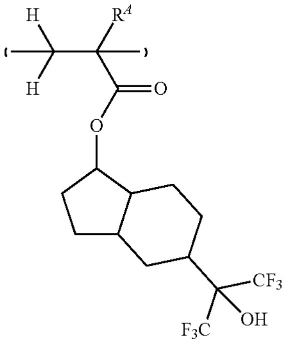
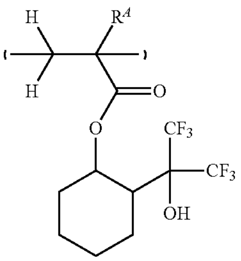
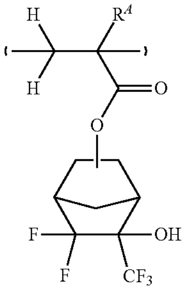

-continued
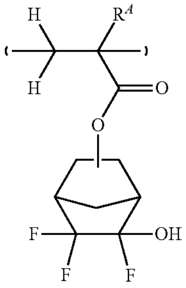
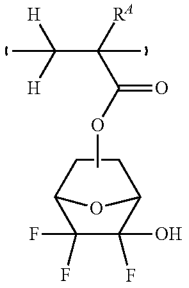
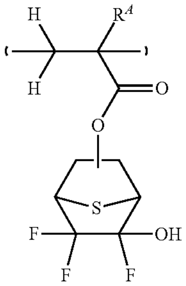
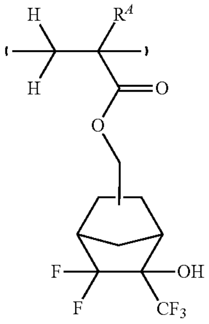
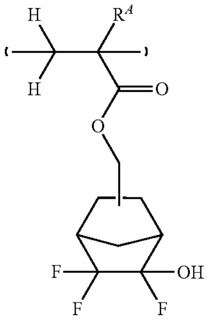
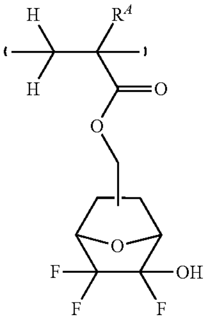
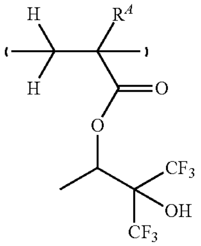
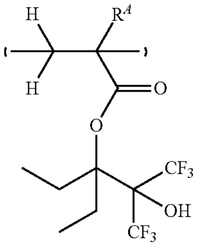
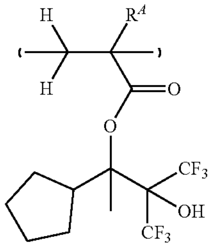
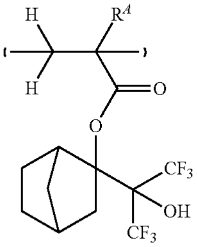
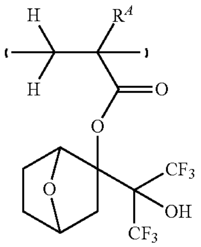
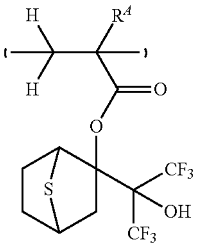
-continued
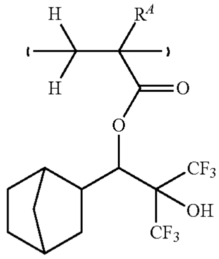
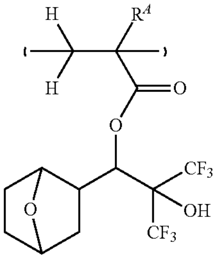
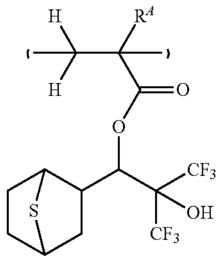
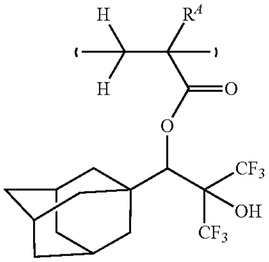
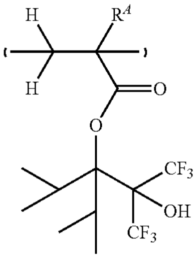
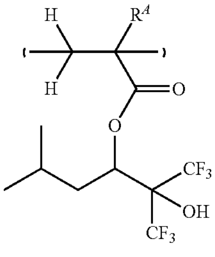
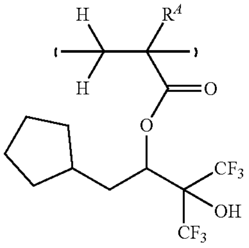
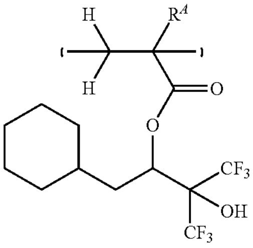
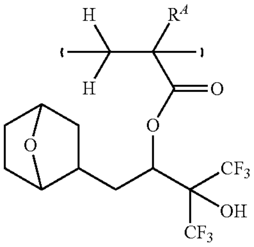
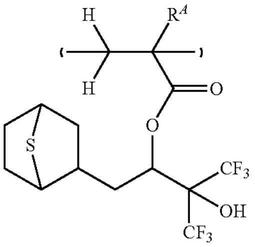
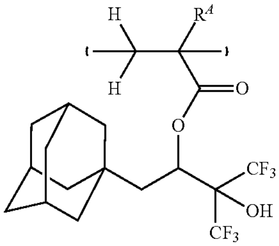

-continued
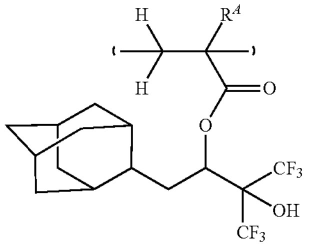
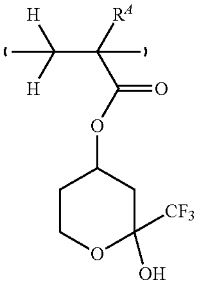
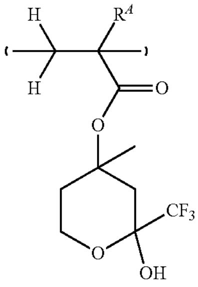
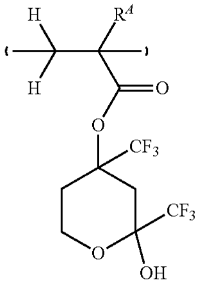
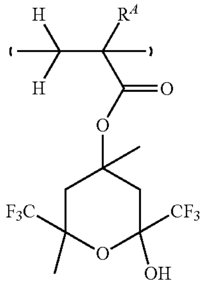
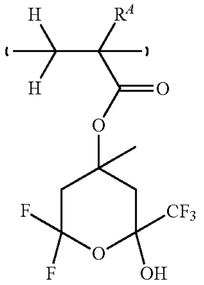
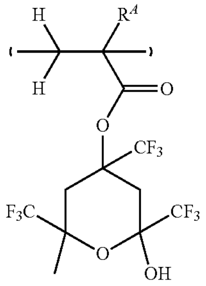
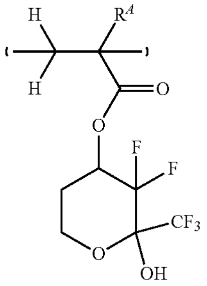
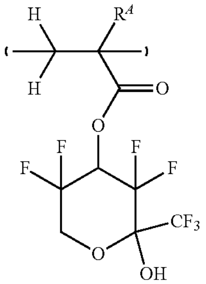
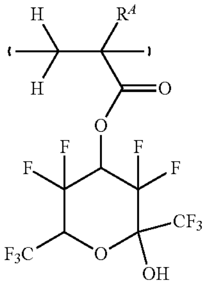
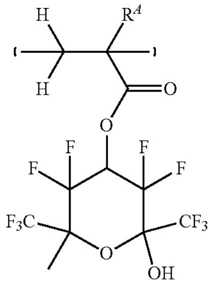
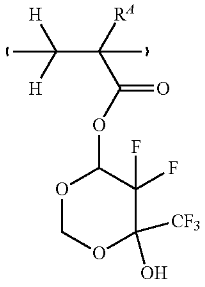
-continued
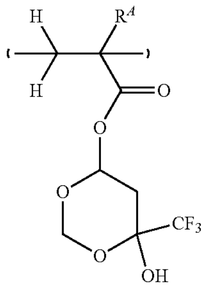
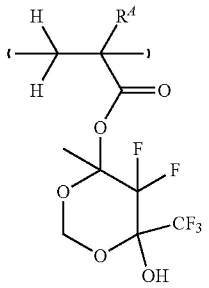
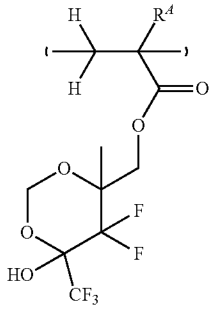
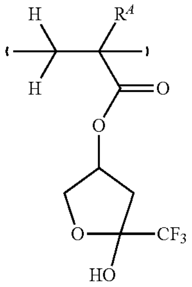
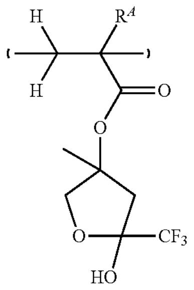
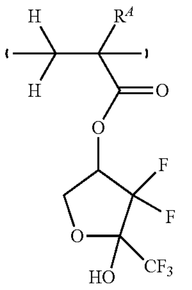
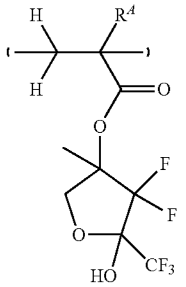
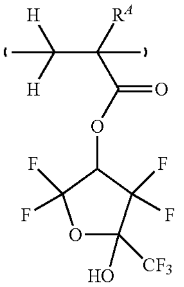
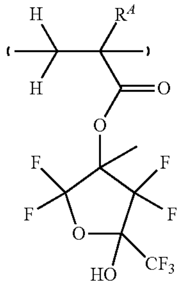
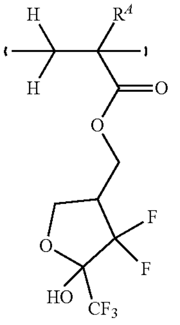
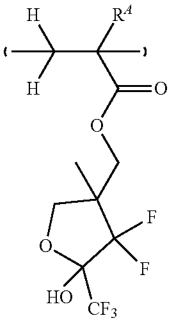

-continued
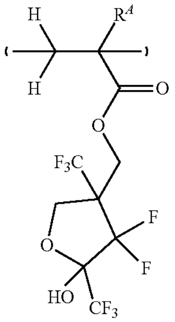
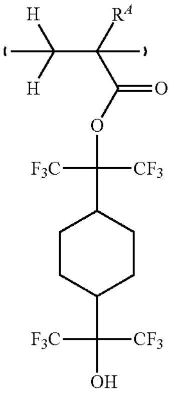
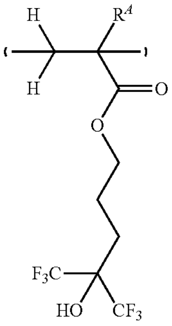
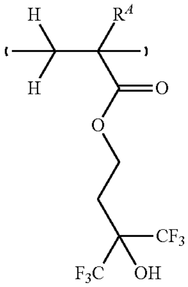
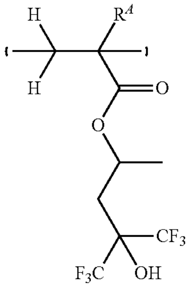
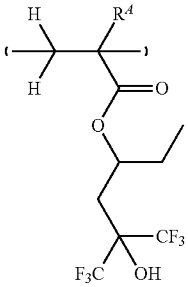
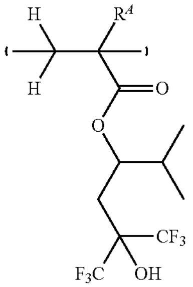
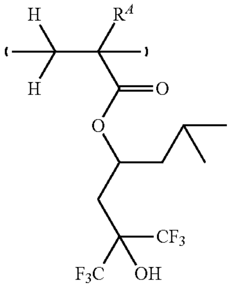
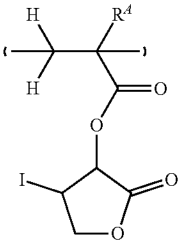
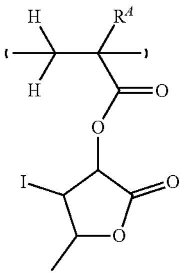
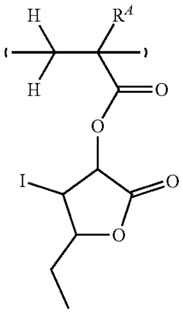
-continued
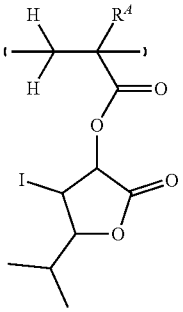
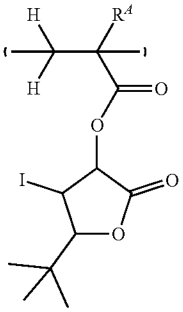
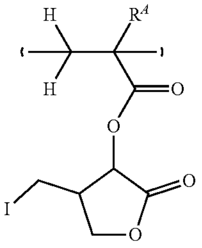
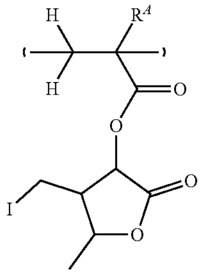
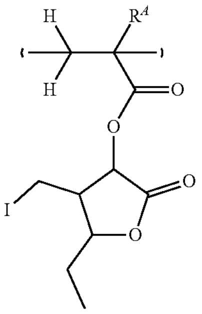
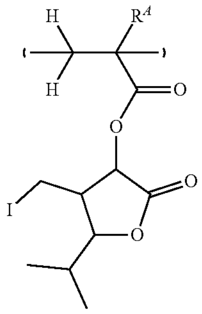
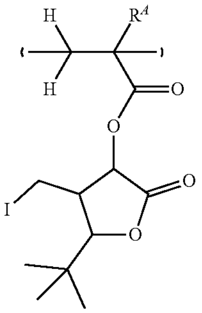
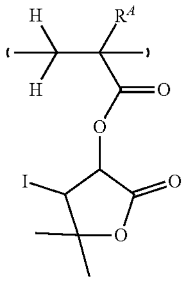
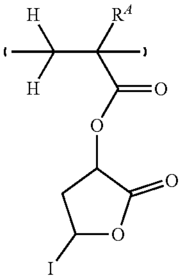
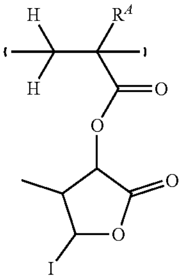

-continued
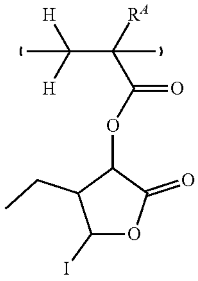
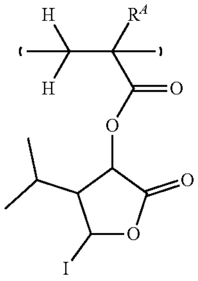
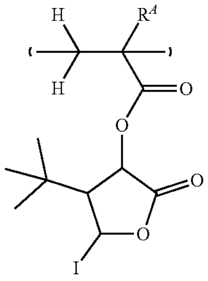
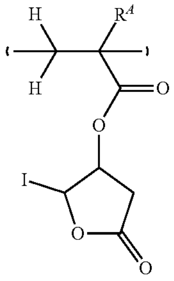
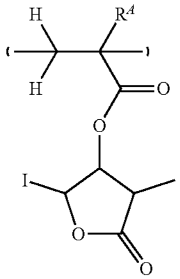
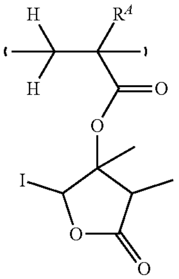
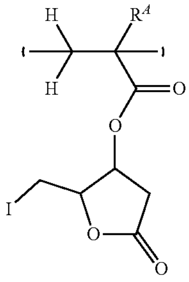
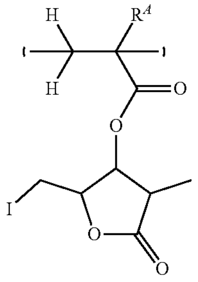
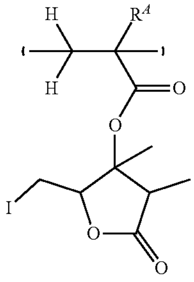
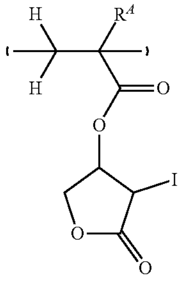
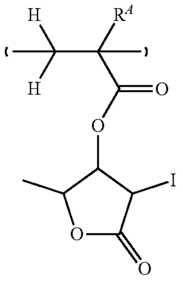
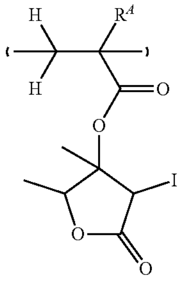
-continued
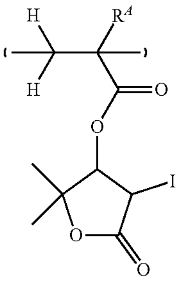
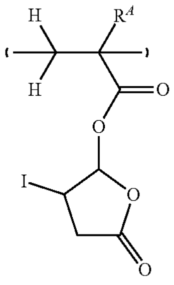
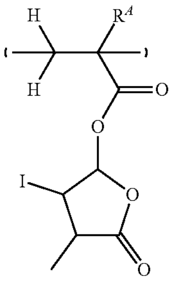
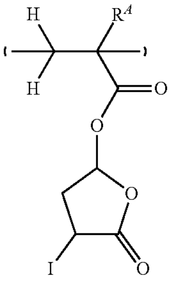
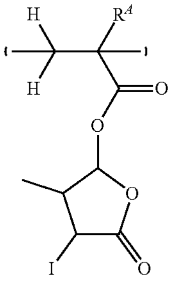
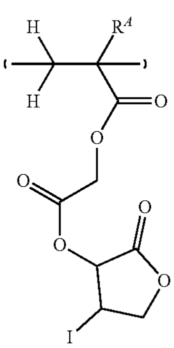
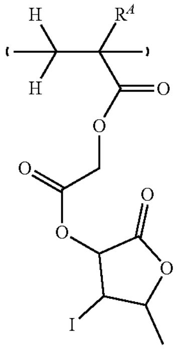
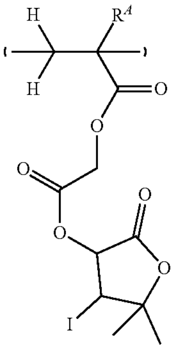
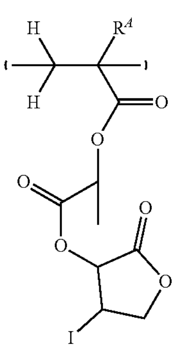
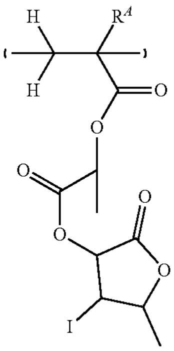
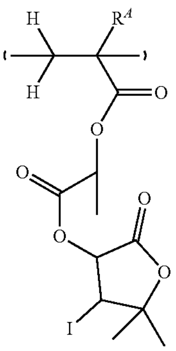

-continued
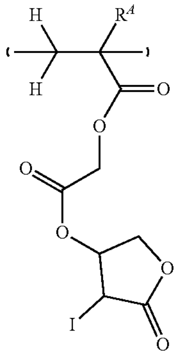
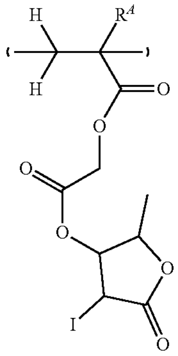
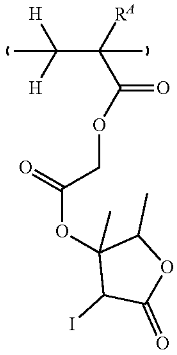
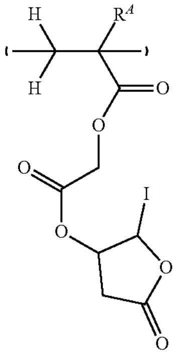
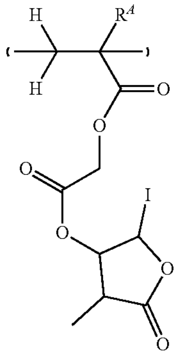
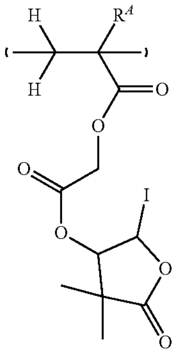
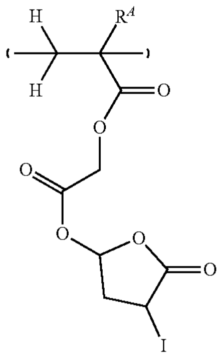
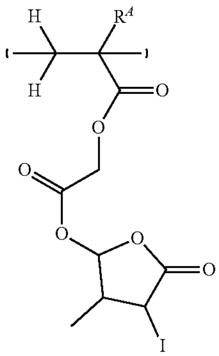
-continued
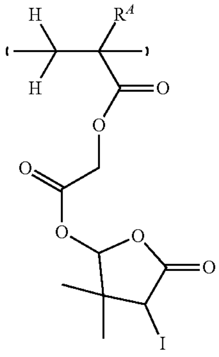
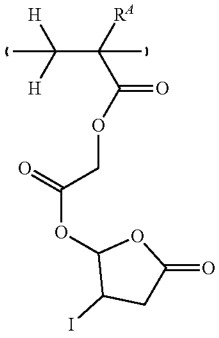
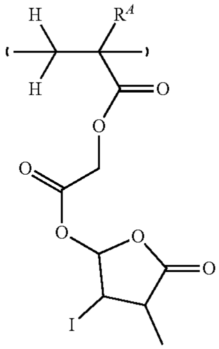
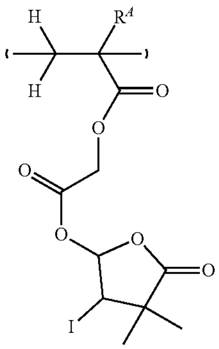
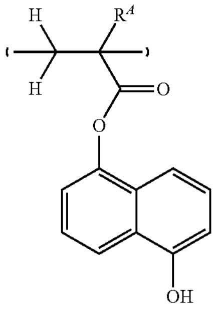
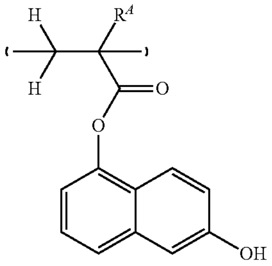
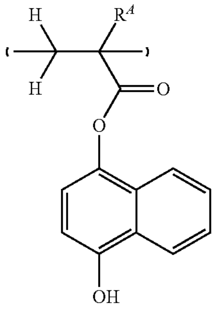
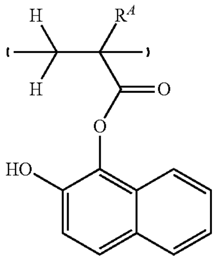
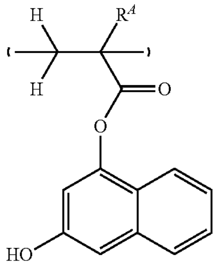
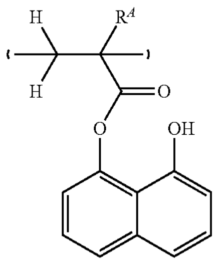

-continued
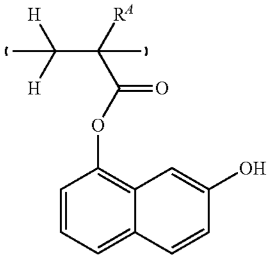
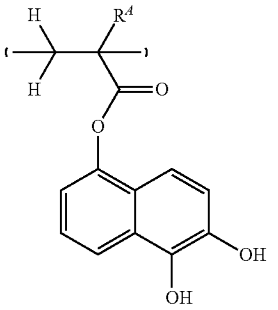
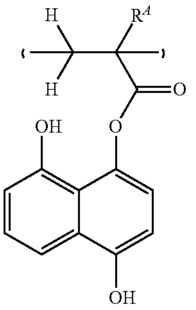
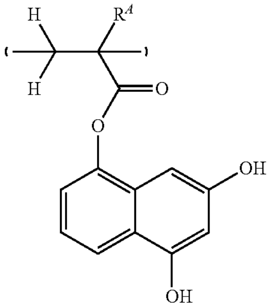
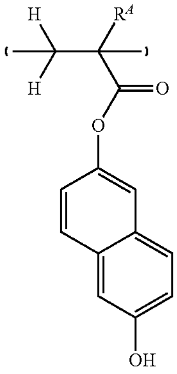
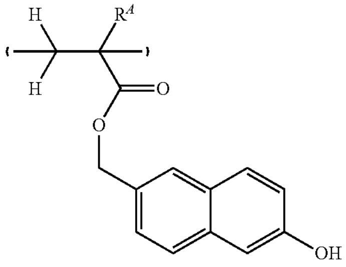
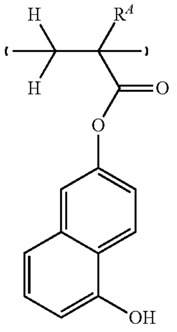
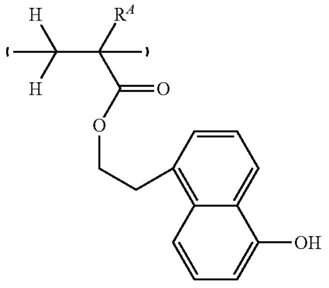
-continued
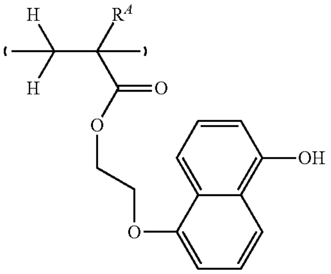
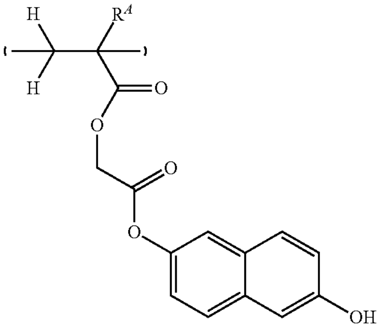
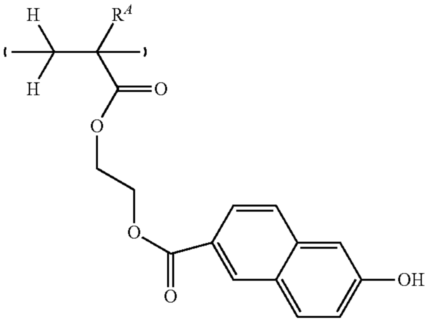
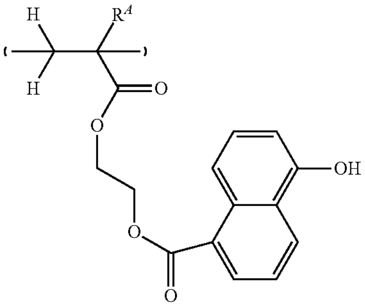
Examples of the repeat unit (b2) are shown below, but not limited thereto. Herein, $R^A$ is as defined above.
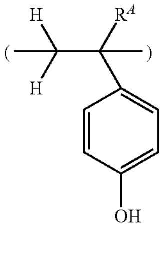
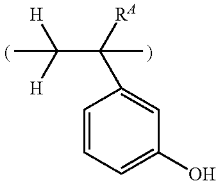

-continued
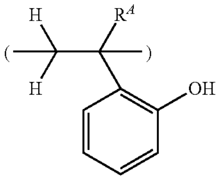
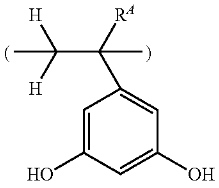
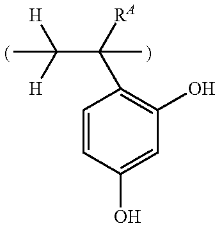
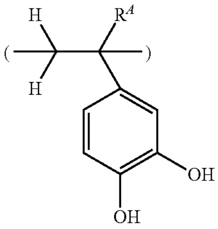
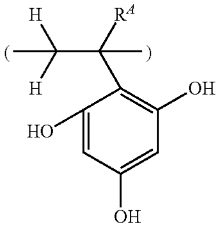
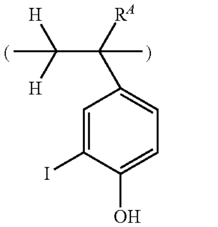
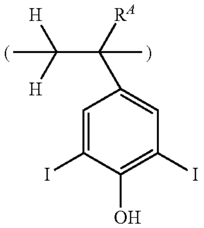
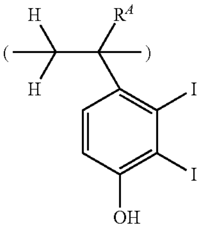
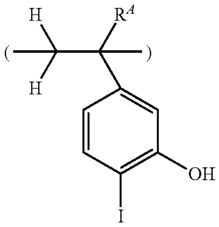
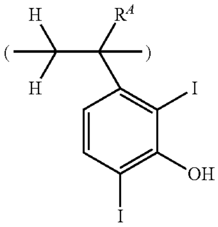
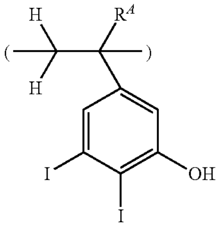
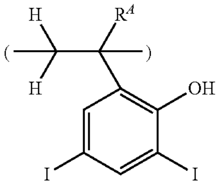
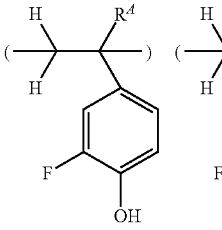
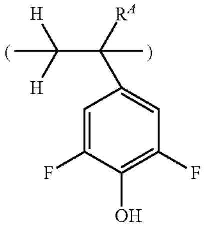
-continued
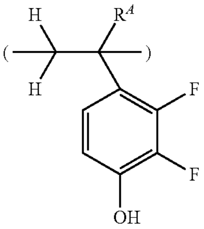
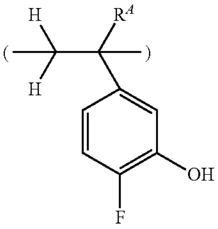
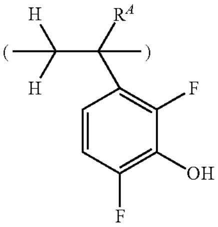
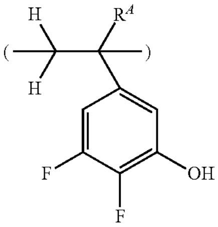
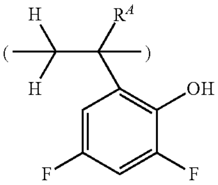
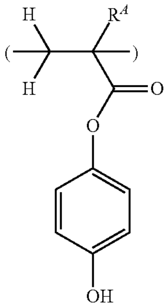
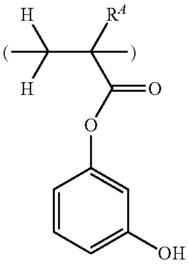
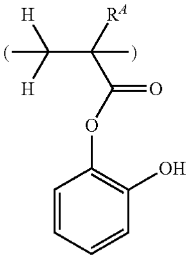
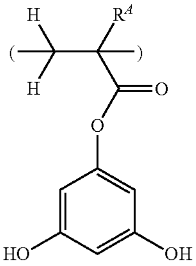
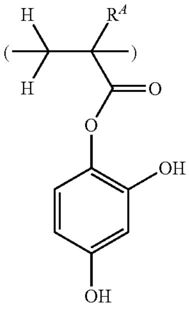
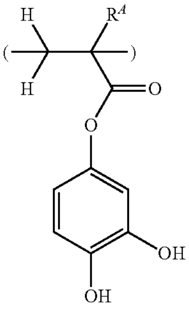
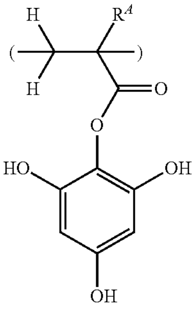

-continued
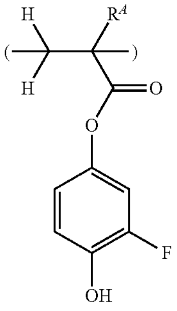
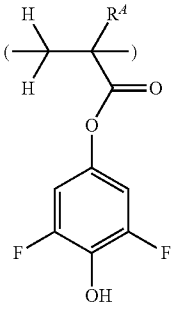
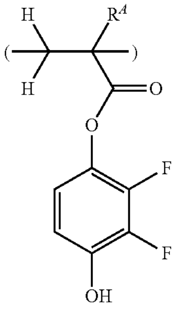
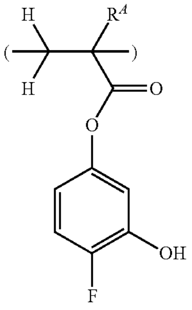
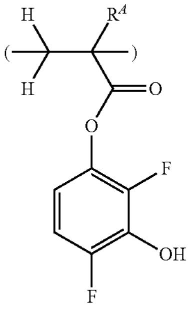
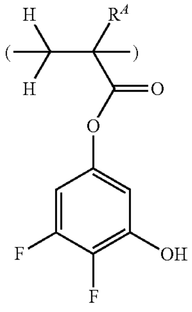
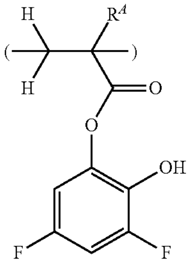
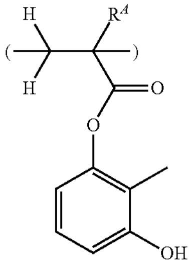
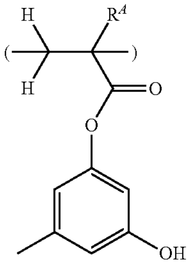
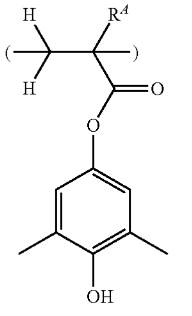
-continued
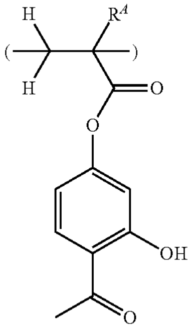
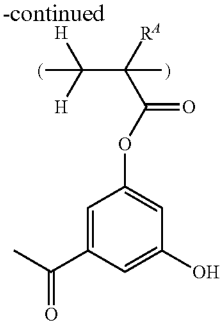
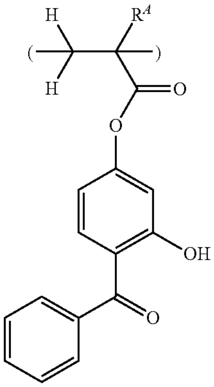
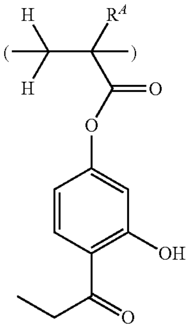
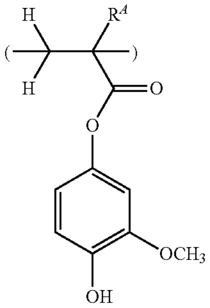
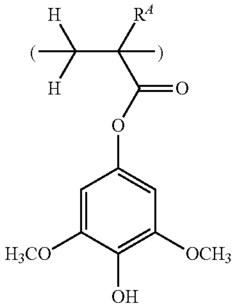
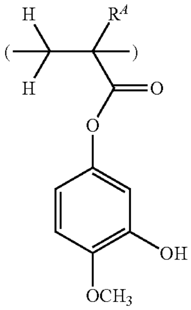
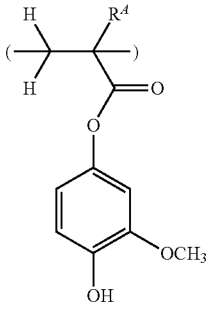
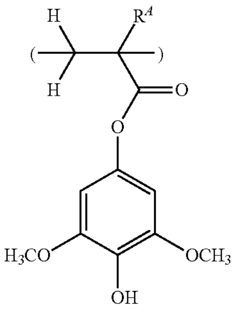
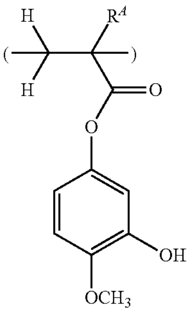
Of the repeat units (b1) and (b2), those units having a lactone ring as the polar group are preferred in the ArF lithography and those units having a phenolic site are preferred in the KrF, EB and EUV lithography.

The base polymer may further comprise repeat units of at least one type selected from repeat units having the formulae (c1) to (c3), which are simply referred to as repeat units (c1) to (c3). Since these units function as a photoacid generator, a photoacid generator to be described later as component (D) may be omitted when a base polymer containing these units is used.

(c1)

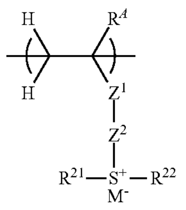

(c2)

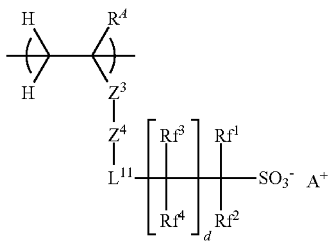

(c3)

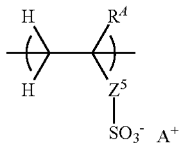

In formulae (c1) to (c3), $R^A$ is as defined above. $Z^1$ is a single bond or phenylene group. $Z^2$ is $*—C(=O)—O—Z^{21}—$, $*—C(=))—NH—Z^{21}—$ or $*—O—Z^{21}—$. $Z^{21}$ is a $C_1$-$C_6$ aliphatic hydrocarbylene group, a phenylene group or a divalent group obtained by combining the foregoing, which may contain a carbonyl moiety, ester bond, ether bond or hydroxy moiety. $Z^3$ is a single bond, phenylene group, naphthylene group or $*—C(=O)—O—Z^{31}—$. $Z^{31}$ is a $C_1$-$C_{10}$ aliphatic hydrocarbylene group which may contain a hydroxy moiety, ether bond, ester bond or lactone ring, or phenylene or naphthylene group. $Z^4$ is a single bond or $**—Z^{41}—C(=O)—O—$. $Z^{41}$ is a $C_1$-$C_{20}$ hydrocarbylene group which may contain a heteroatom. $Z^5$ is a single bond, methylene, ethylene, phenylene, fluorinated phenylene, trifluoromethyl-substituted phenylene group, $*—C(=O)—O—Z^{51}—$, $*—C(=O)—NH—Z^{51}—$, or $*—O—Z^{51}—$. $Z^{51}$ is a $C_1$-$C_6$ aliphatic hydrocarbylene group, phenylene group, fluorinated phenylene group or trifluoromethyl-substituted phenylene group, which may contain a carbonyl moiety, ester bond, ether bond or hydroxy moiety. The asterisk (*) designates a point of attachment to the carbon atom in the backbone, and the double asterisks (**) designates a point of attachment to $Z^3$.

In formula (c1), $R^{21}$ and $R^{22}$ are each independently a $C_1$-$C_{20}$ hydrocarbyl group which may contain a heteroatom.

$R^{21}$ and $R^{22}$ may bond together to form a ring with the sulfur atom to which they are attached.

The hydrocarbyl groups $R^{21}$ and $R^{22}$ may be saturated or unsaturated and straight, branched or cyclic. Examples thereof include $C_1$-$C_{20}$ alkyl groups such as methyl, ethyl, n-propyl, isopropyl, n-butyl, tert-butyl: $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl: $C_2$-$C_{20}$ alkenyl groups such as vinyl, allyl, propenyl, butenyl, hexenyl; $C_3$-$C_{20}$ cyclic unsaturated hydrocarbyl groups such as cyclohexenyl; $C_6$-$C_{20}$ aryl groups such as phenyl and naphthyl; $C_7$-$C_{20}$ aralkyl groups such as benzyl, 1-phenylethyl and 2-phenylethyl, and combinations thereof. Inter alia, aryl groups are preferred. In these hydrocarbyl groups, some or all of the hydrogen atoms may be substituted by a moiety containing a heteroatom such as oxygen, sulfur, nitrogen or halogen, and any constituent $—CH_2—$ may be replaced by a moiety containing a heteroatom such as oxygen, sulfur or nitrogen, so that the group may contain a hydroxy moiety, fluorine, chlorine, bromine, iodine, cyano moiety, carbonyl moiety, ether bond, ester bond, sulfonic ester bond, carbonate bond, lactone ring, sultone ring, carboxylic anhydride ($—C(=O)—O—C(=O)—$) or haloalkyl moiety.

Examples of the cation in the repeat units having formula (c1) are shown below, but not limited thereto. Herein, $R^A$ is as defined above.

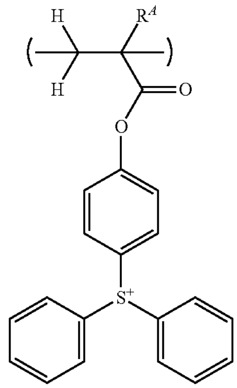

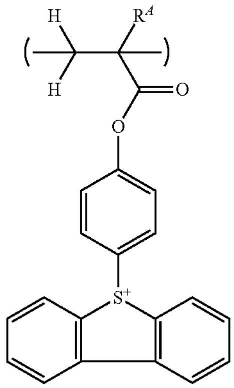

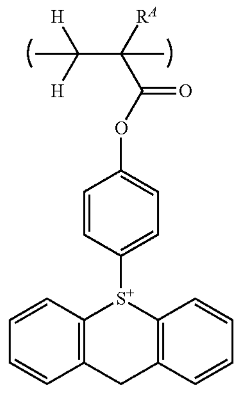

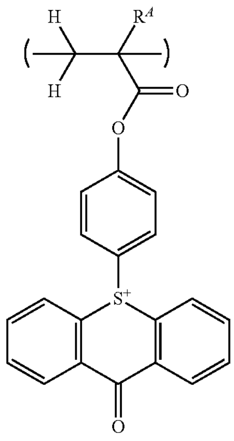

-continued
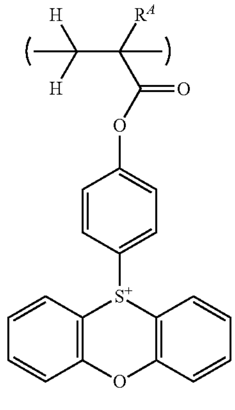
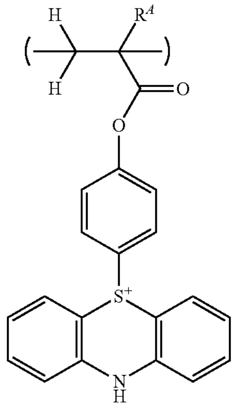
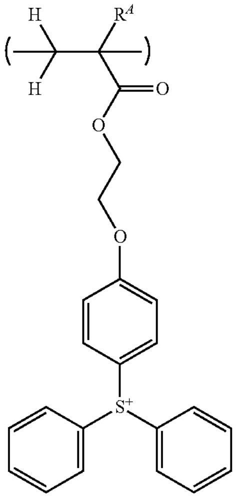
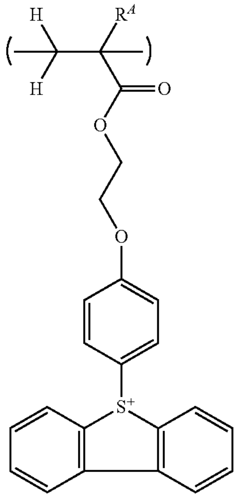
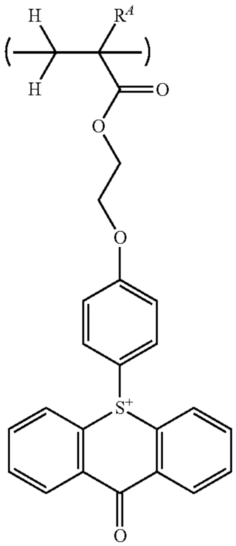
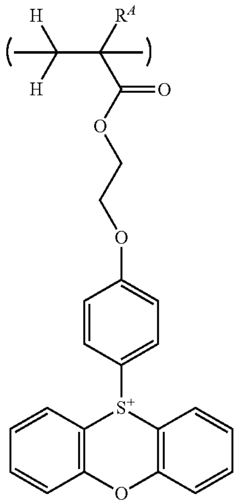
-continued
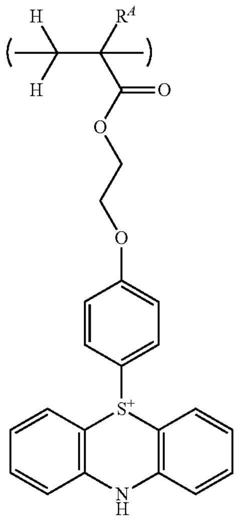
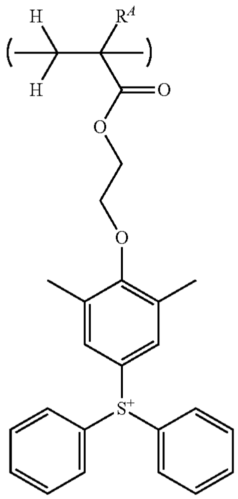
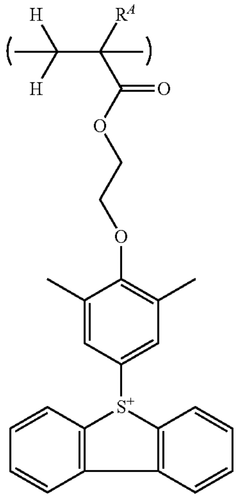
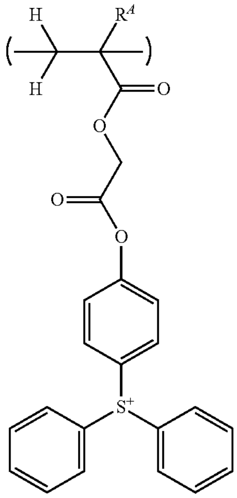
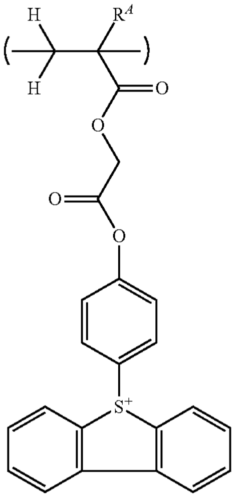
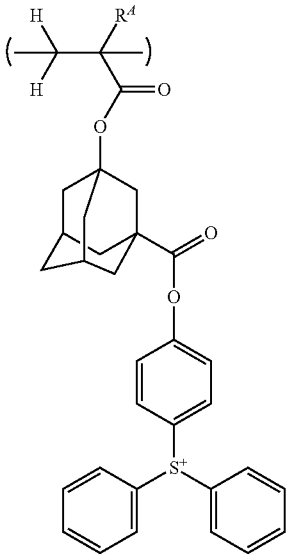

-continued
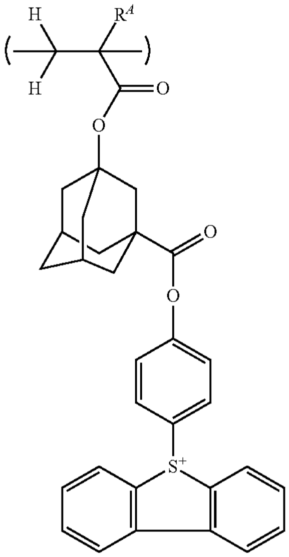
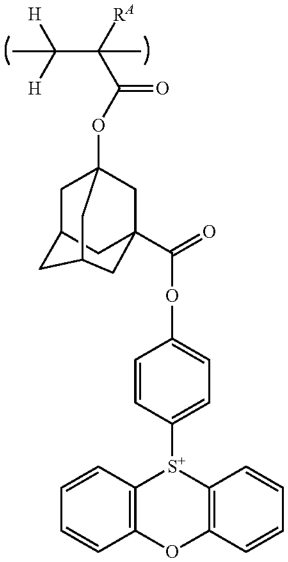
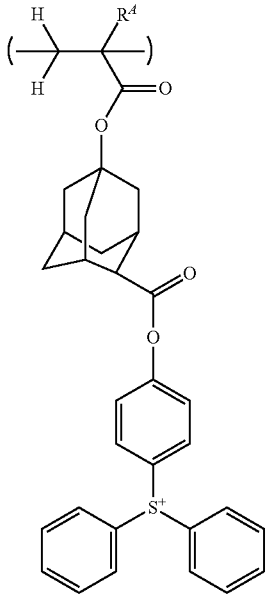
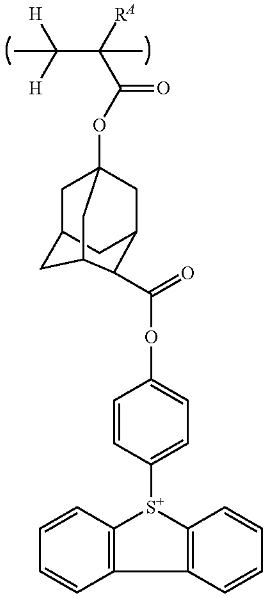
-continued
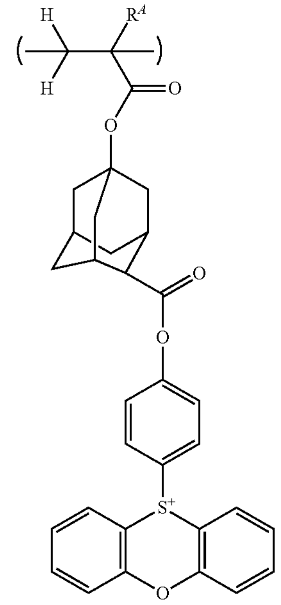
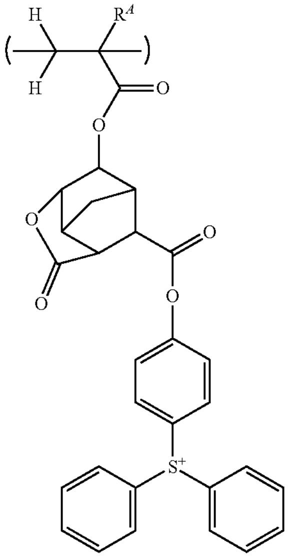
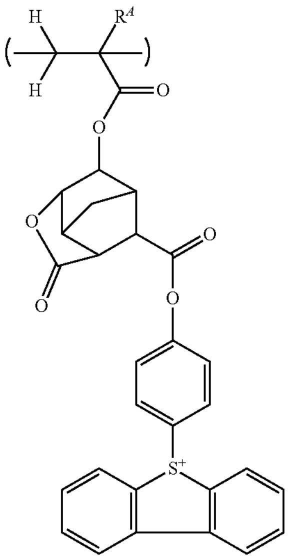
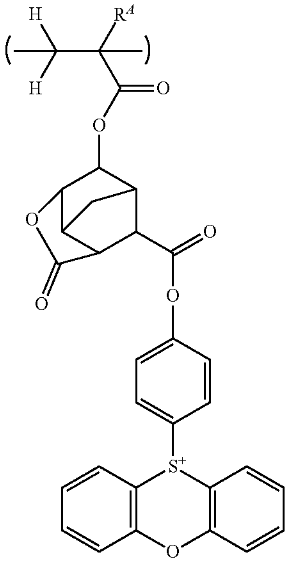
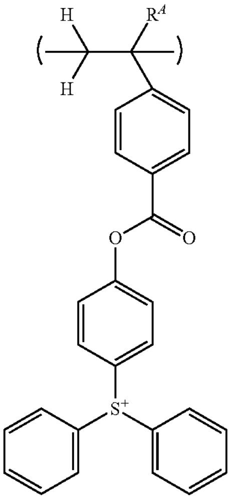
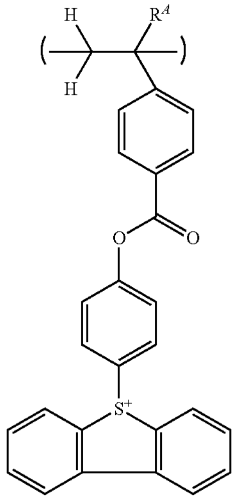

-continued

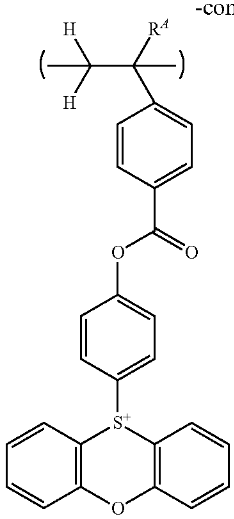

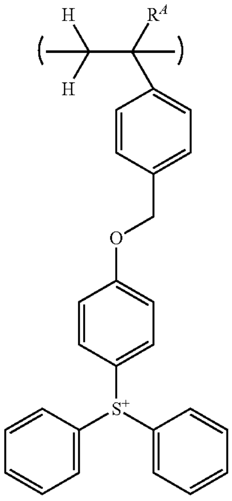

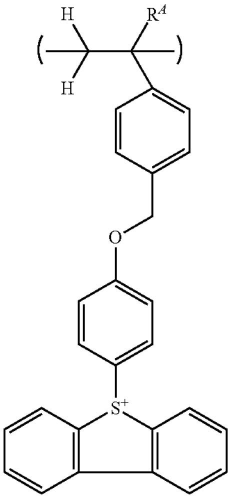

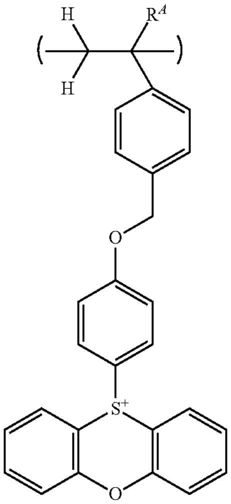

In formula (c1), M is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, beuzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; and methide ions such as tris(trifluoromethylsulfonyl)methide and tris(perfluoroethylsulfonyl)methide.

Also included are a sulfonate anion which is fluorinated at α-position as represented by the formula (c1-1) and a sulfonate anion which is substituted with fluorine at α-position and trifluoromethyl at n-position as represented by the formula (c1-2).

$$R^{23}—CF_2—SO_3^-$$ (c1-1)

(c1-2)

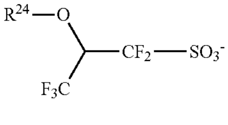

In formula (c1-1), $R^{23}$ is hydrogen or a hydrocarbyl group which may contain an ether bond, ester bond, carbonyl moiety, lactone ring or fluorine atom. The hydrocarbyl group may be saturated or unsaturated and straight, branched or cyclic, and examples thereof are as will be exemplified later for $R^{111}$ in formula (2A').

In formula (c1-2), $R^{24}$ is hydrogen, a $C_1$-$C_{30}$ hydrocarbyl group, or $C_6$-$C_{20}$ hydrocarbylcarbonyl group. The hydrocarbyl group and hydrocarbylcarbonyl group may contain an ether bond, ester bond, carbonyl moiety or lactone ring. The hydrocarbyl group and hydrocarbyl moiety in the hydrocarbylcarbonyl group may be saturated or unsaturated and straight, branched or cyclic, and examples thereof are as will be exemplified later for $R^{111}$ in formula (2A').

Examples of the sulfonate anions which are exemplary of the non-nucleophilic counter ion are shown below, but not limited thereto. Herein $R^{25}$ is hydrogen, fluorine or $C_1$-$C_6$ fluoroalkyl.

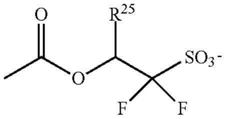

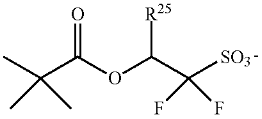

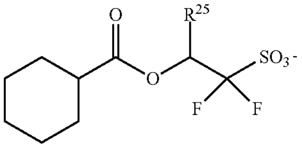

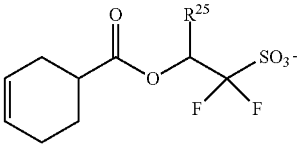

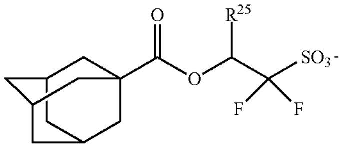

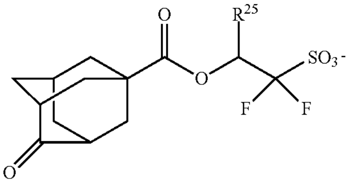

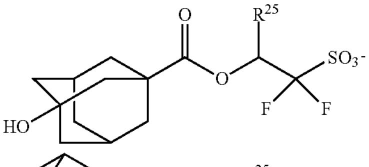

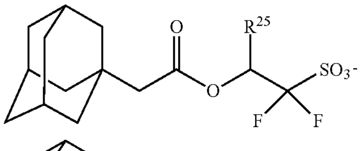

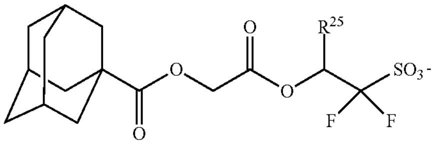

-continued
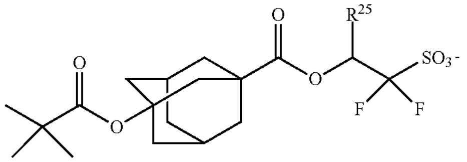
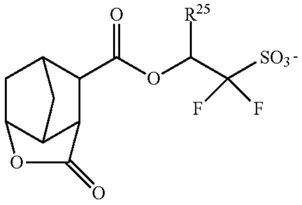
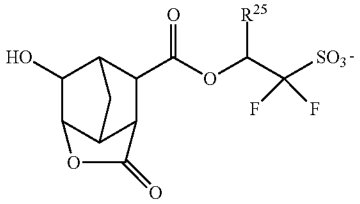
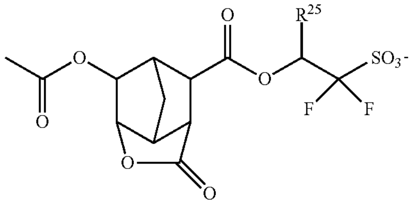
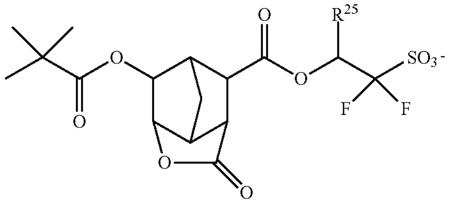
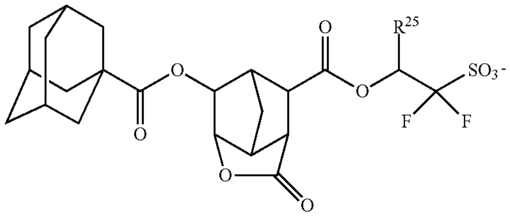
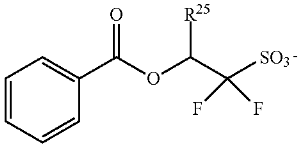
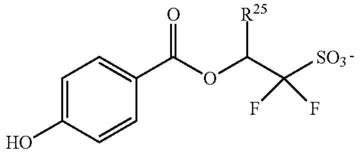
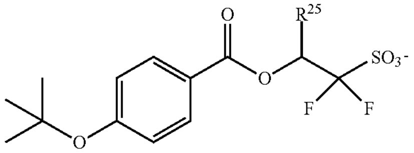
-continued
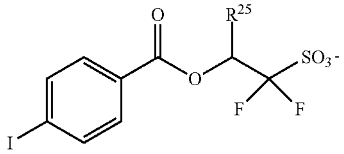
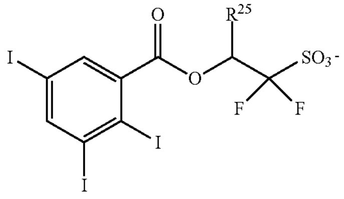
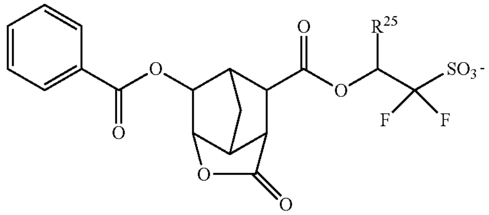
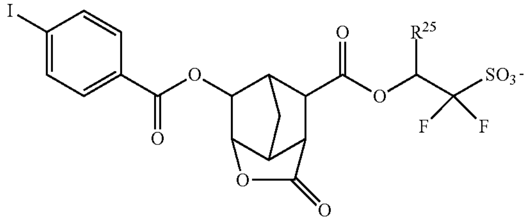
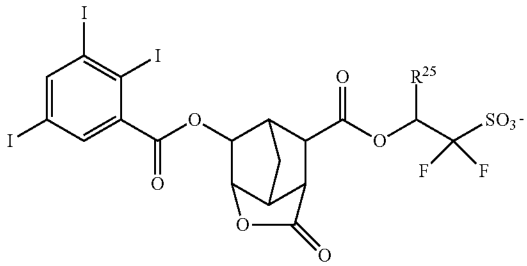
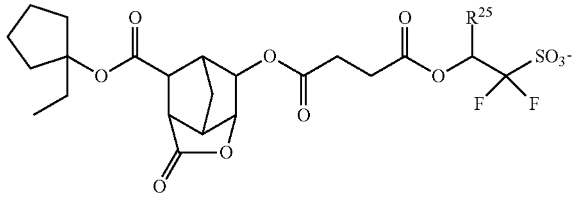
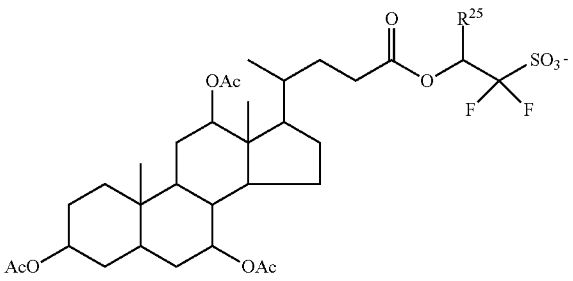

-continued
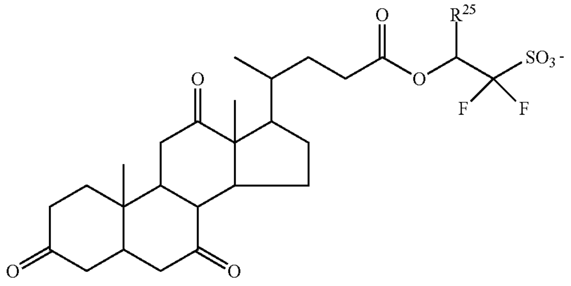
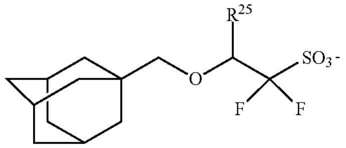
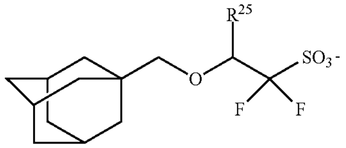
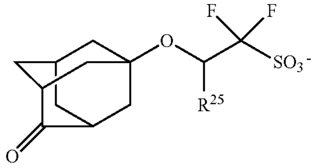
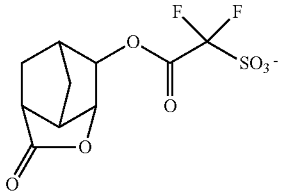
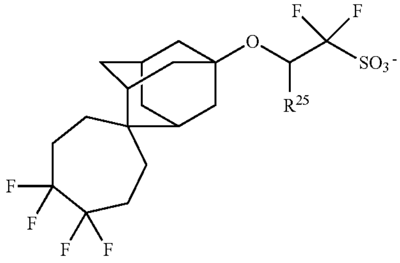
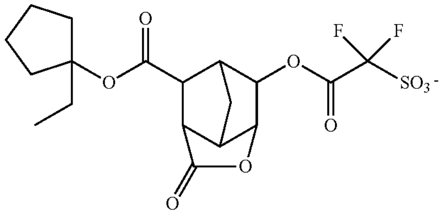
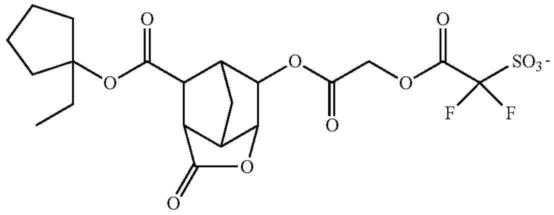
-continued
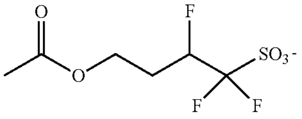
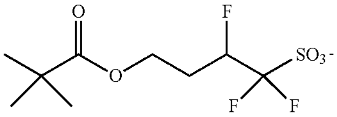
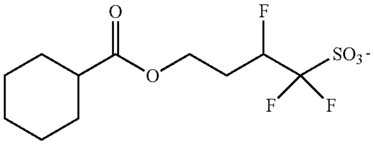
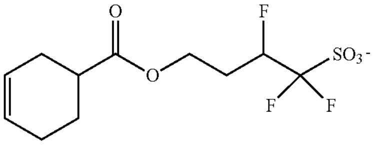
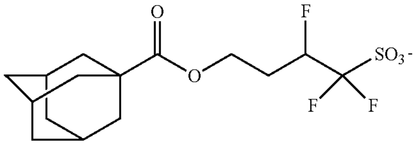
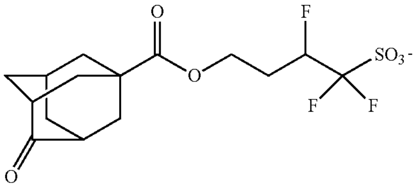
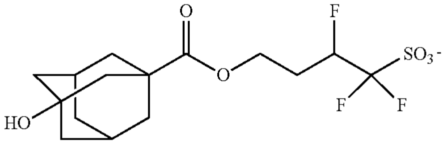
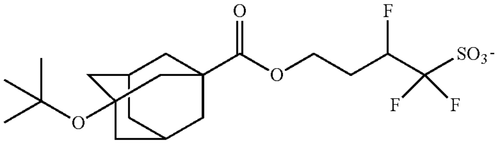
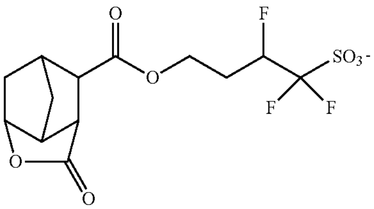
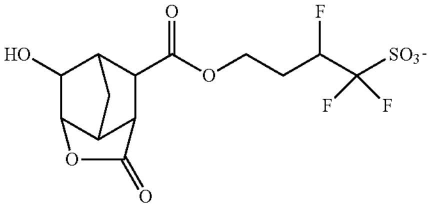

-continued
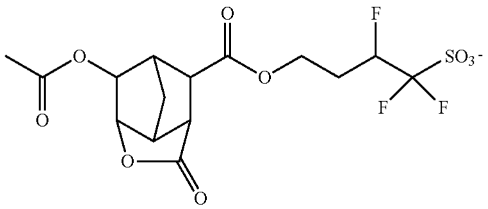
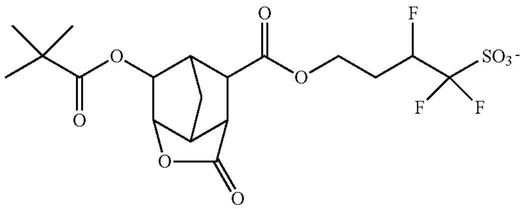
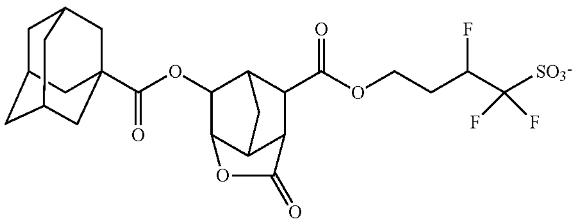
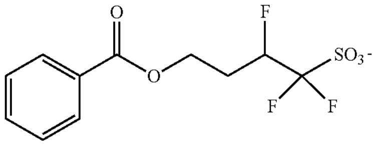
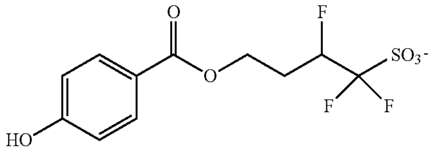
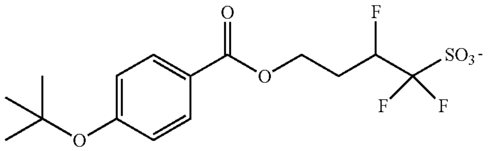
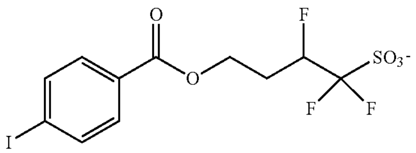
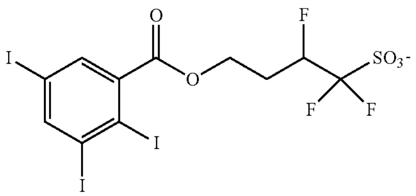
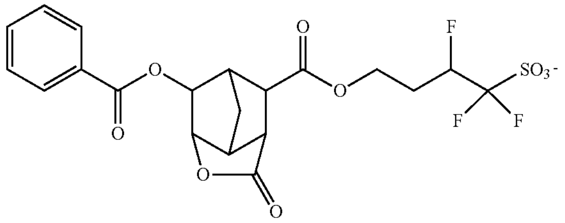
-continued
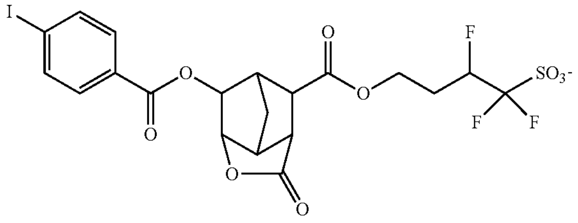
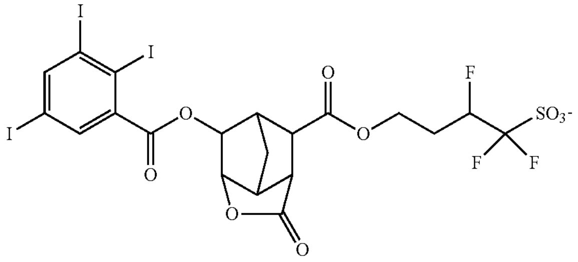
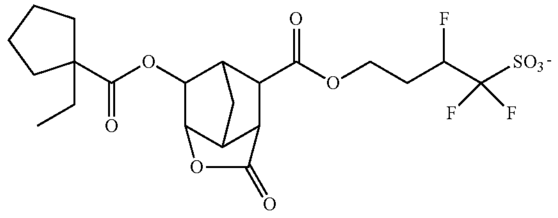
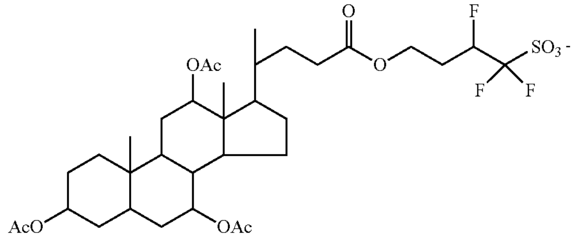
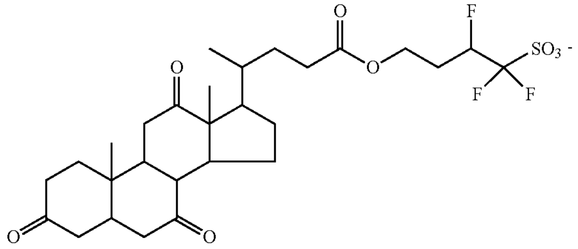
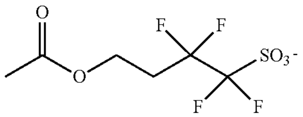
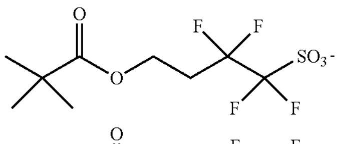
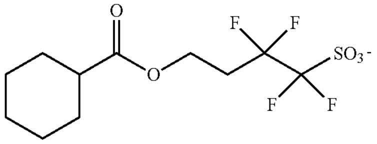
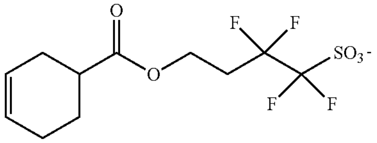

-continued
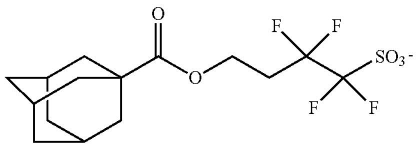
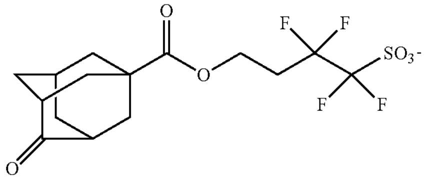
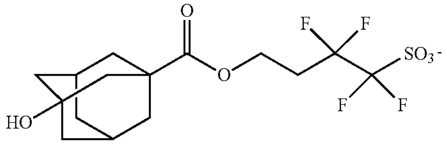
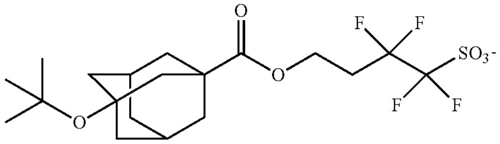
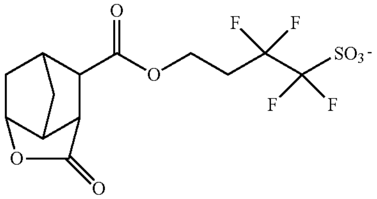
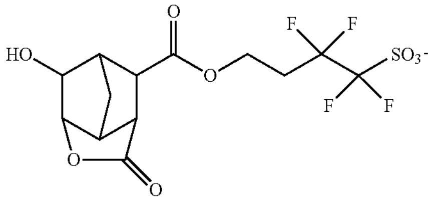
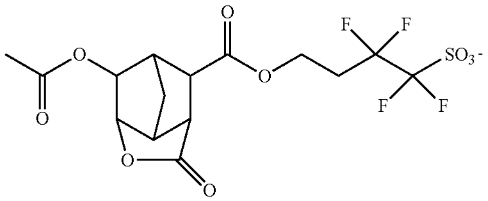
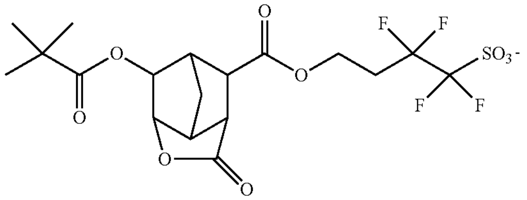
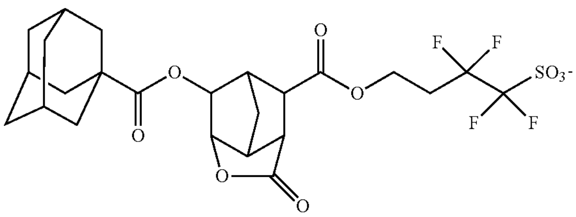
-continued
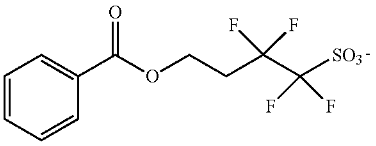
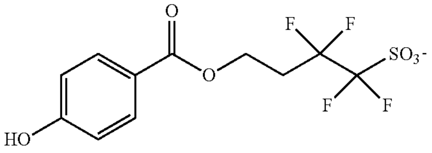
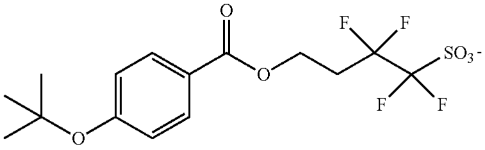
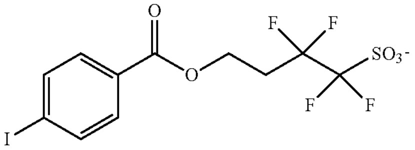
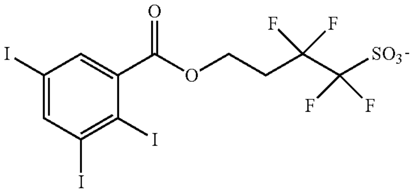
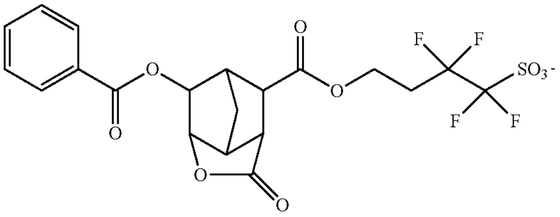
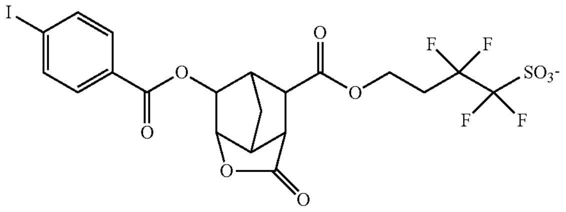
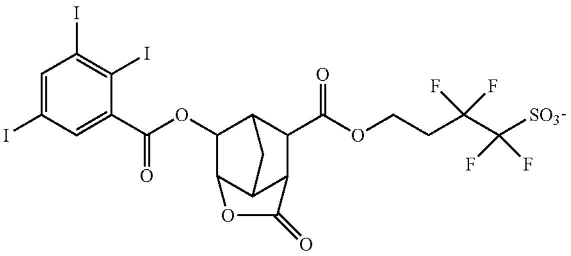
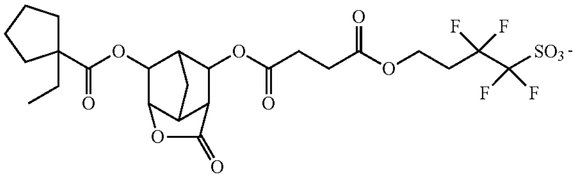

-continued

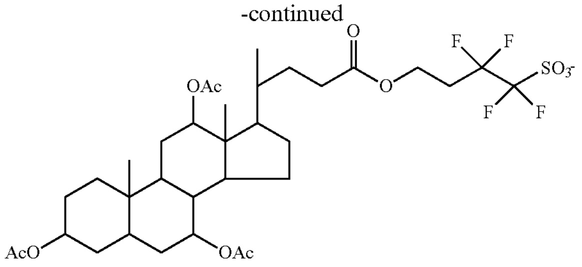

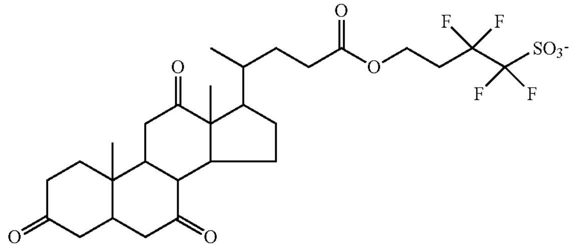

In formula (c2), examples of the optionally heteroatom-containing $C_1$-$C_{20}$ hydrocarbylene group $Z^{41}$ are shown below, but not limited thereto.

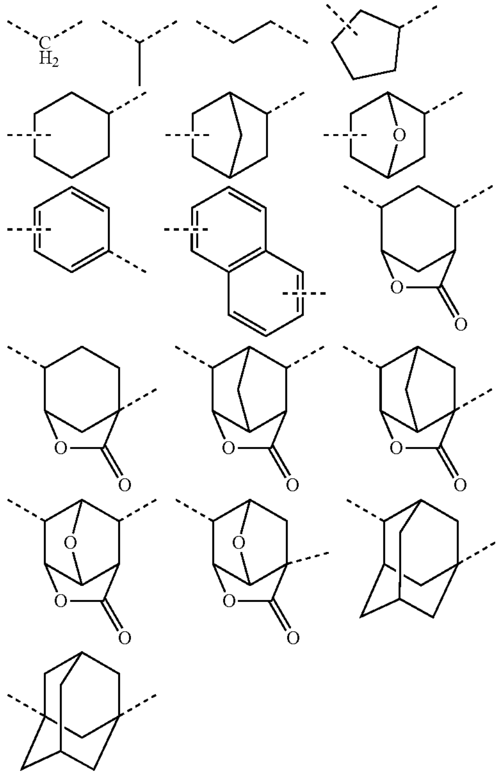

In formula (c2), $L^{11}$ is a single bond, ether bond, ester bond, carbonyl group, sulfonic ester bond, carbonate bond or carbamate bond.

In formula (c2), $Rf^1$ and $Rf^2$ are each independently fluorine or a $C_1$-$C_6$ fluorinated alkyl group. It is preferred for enhancing the acid strength of the generated acid that both $Rf^1$ and $Rf^2$ be fluorine. $Rf^3$ and $Rf^4$ are each independently hydrogen, fluorine or a $C_1$-$C_6$ fluorinated alkyl group. It is preferred for enhancing solvent solubility that at least one of $Rf^3$ and $Rf^4$ be trifluoromethyl. The subscript d is an integer of 0 to 3, preferably 1.

Examples of the anion in repeat unit having formula (c2) are shown below, but not limited thereto. Herein $R^A$ is as defined above.

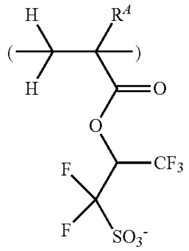

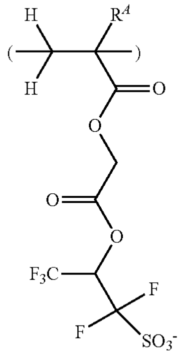

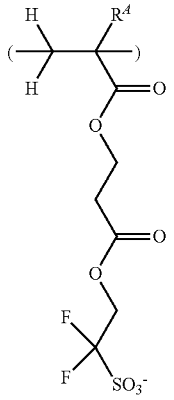

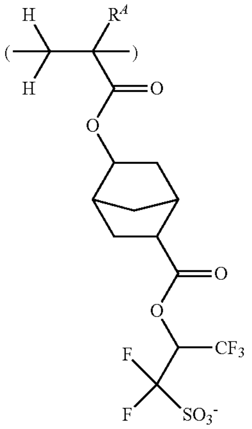

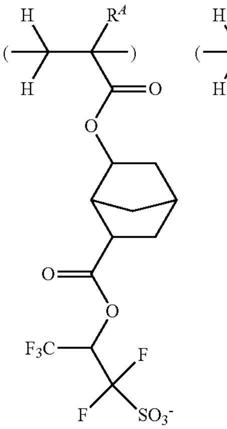

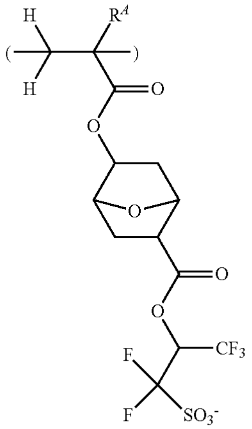

-continued
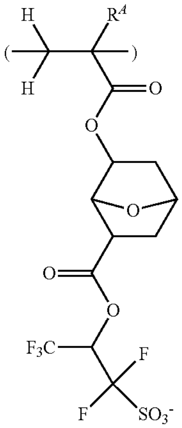
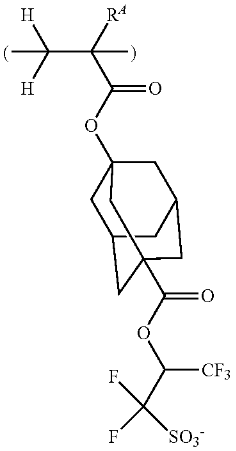
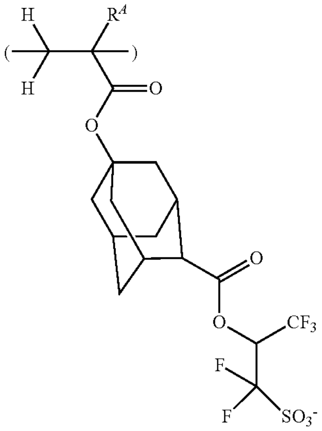
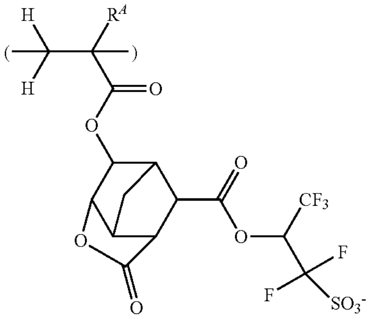
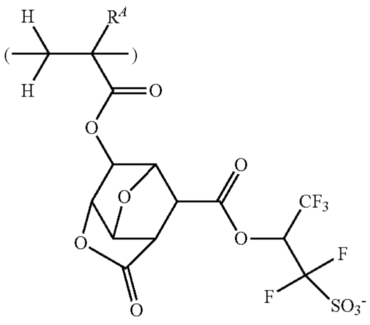
-continued
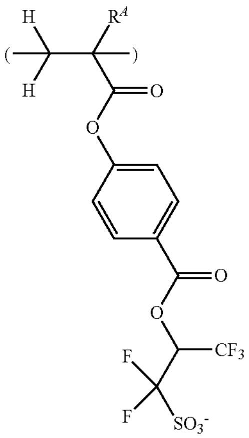
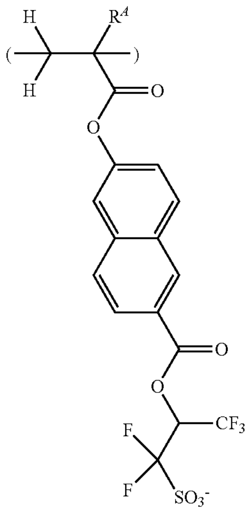
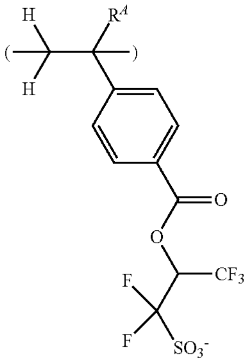
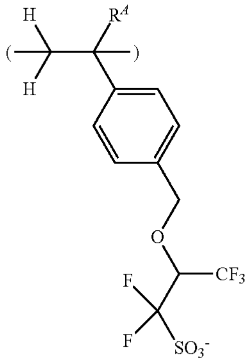
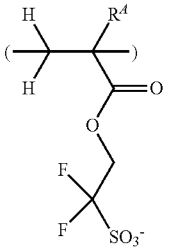
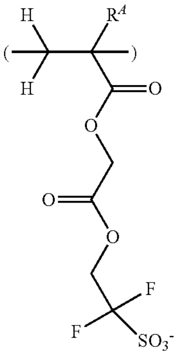
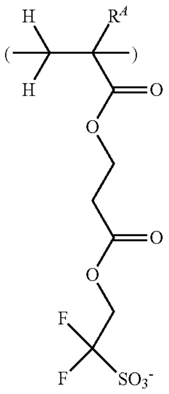
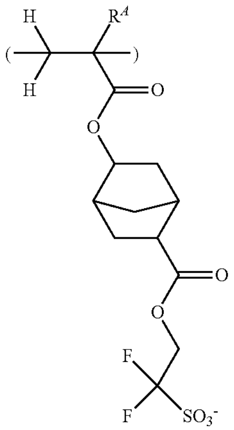

-continued
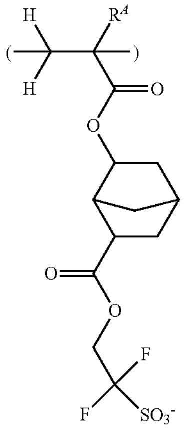
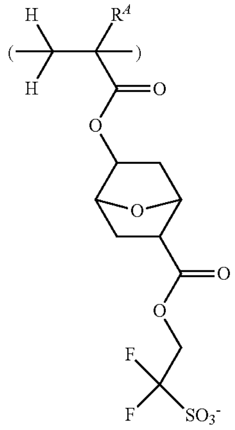
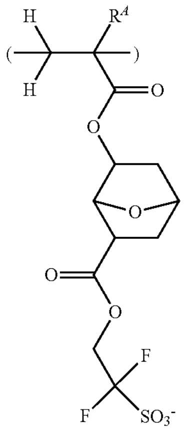
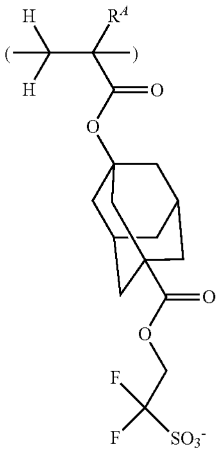
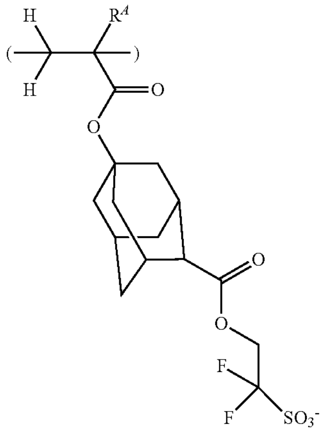
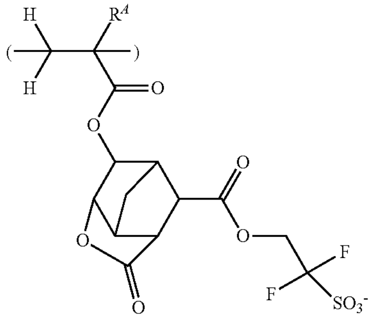
-continued
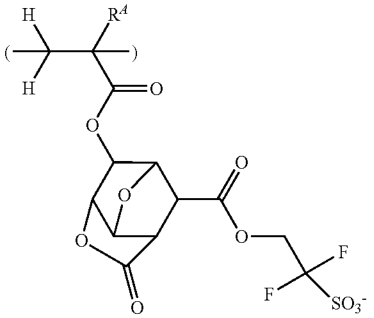
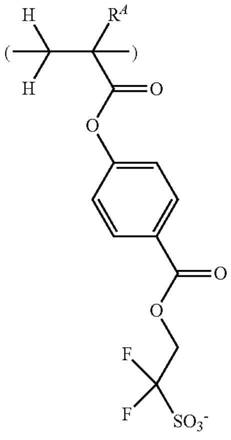
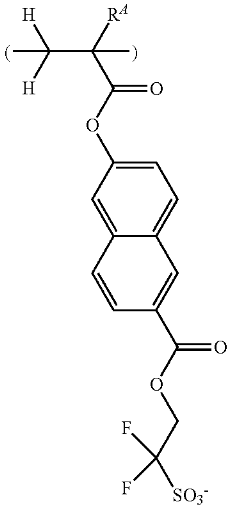
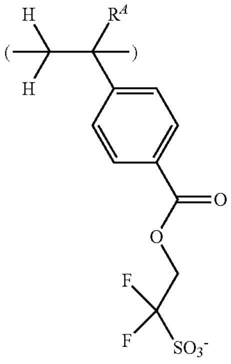
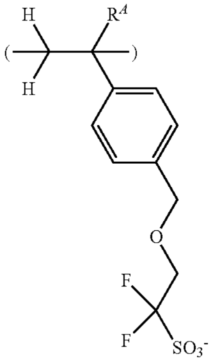
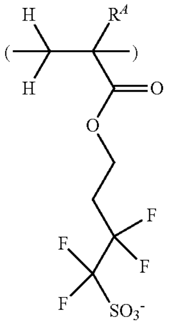
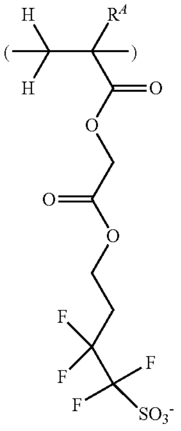

-continued
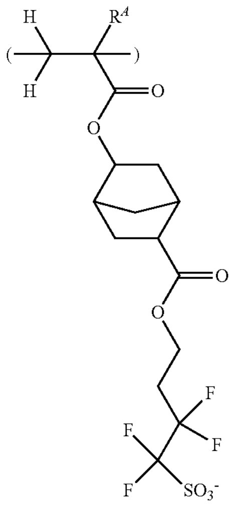
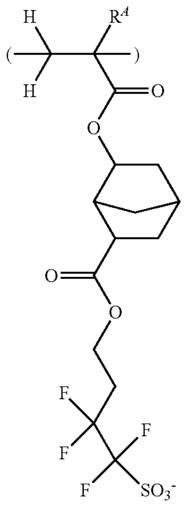
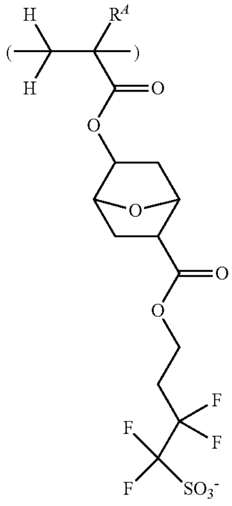
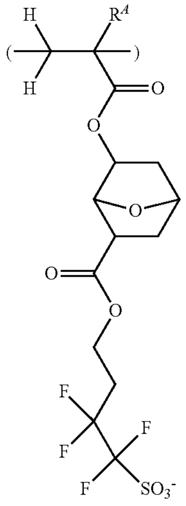
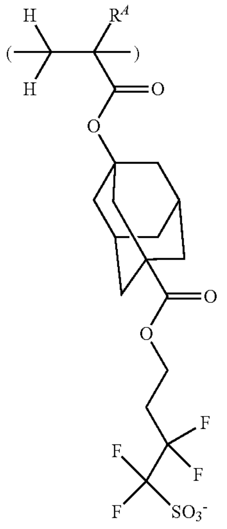
-continued
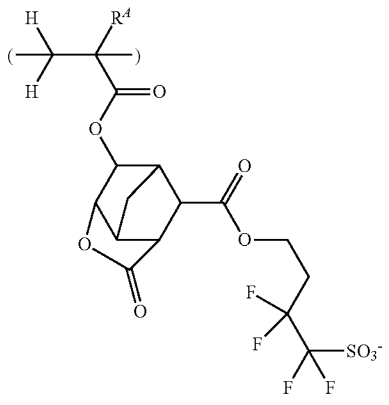
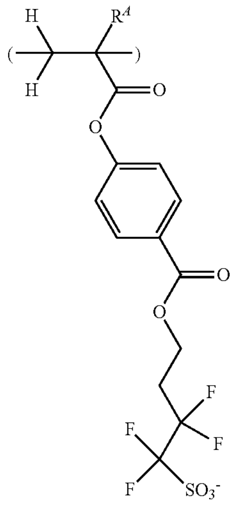
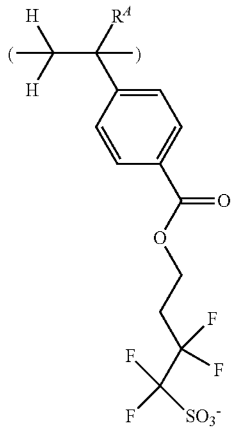
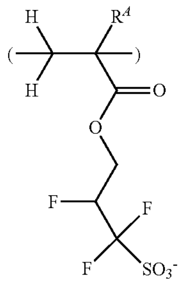
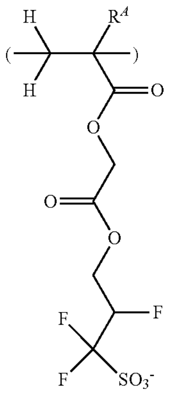

-continued
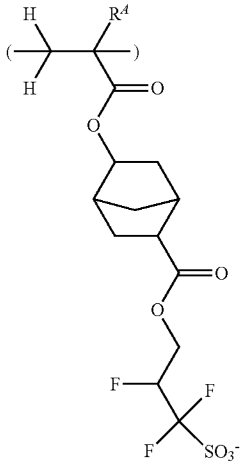
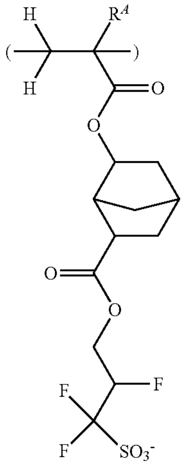
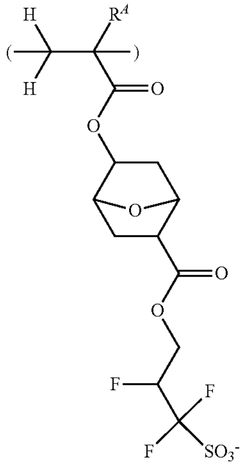
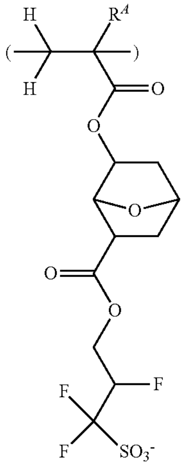
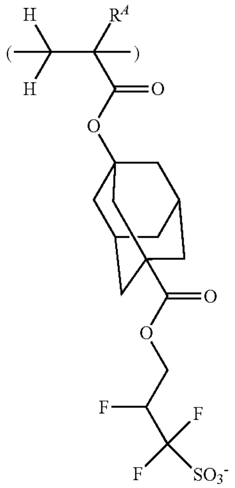
-continued
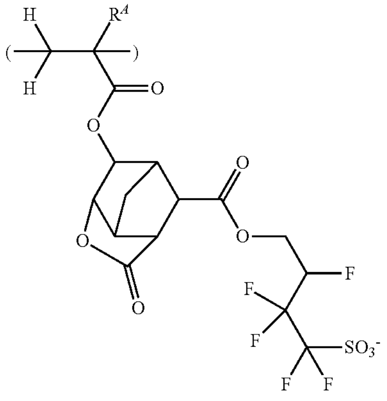
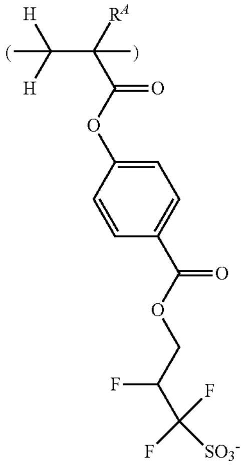
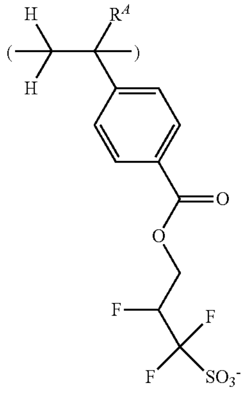
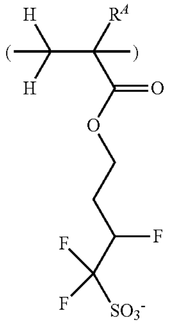
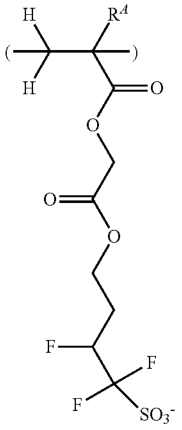

-continued
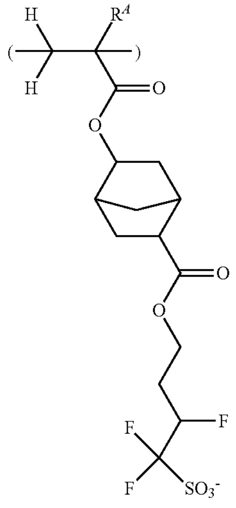
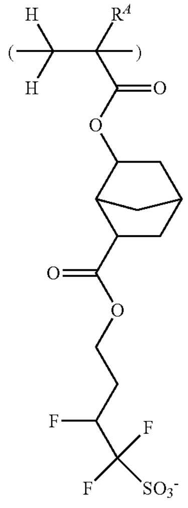
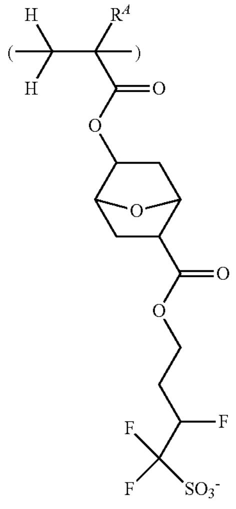
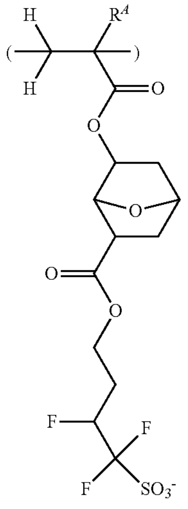
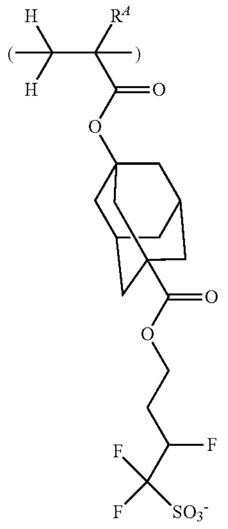
-continued
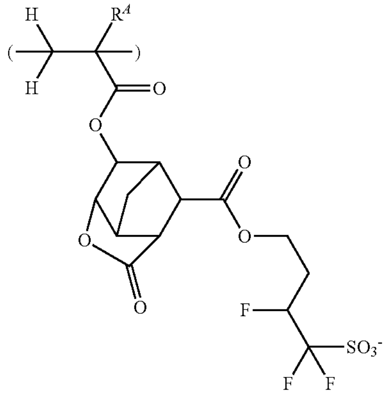
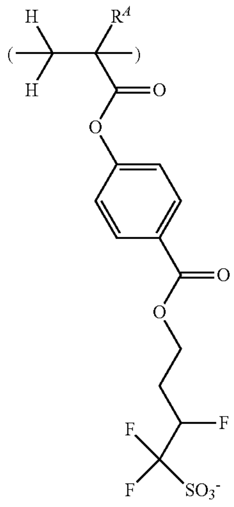
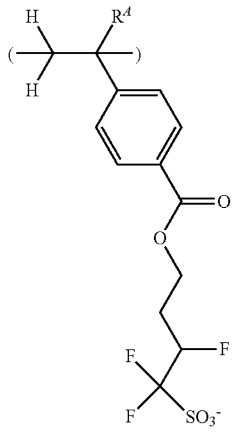
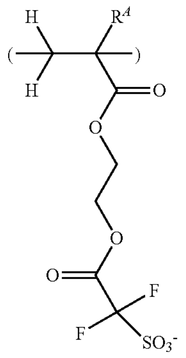
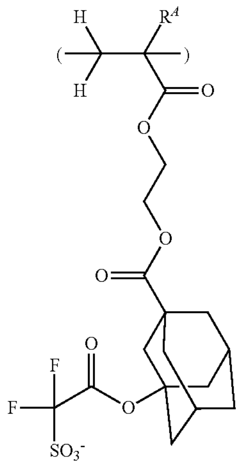

-continued

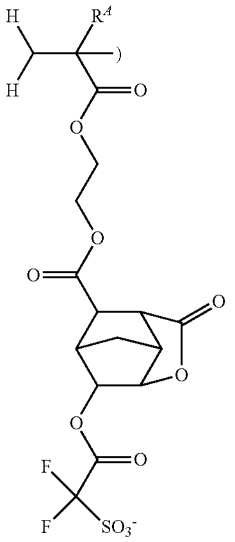

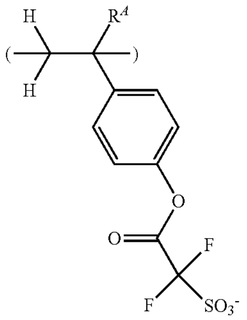

Examples of the anion in repeat unit having formula (c3) are shown below, but not limited thereto. Herein $R^A$ is as defined above.

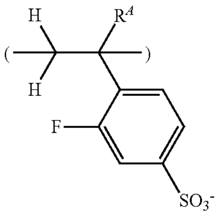

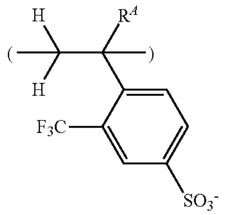

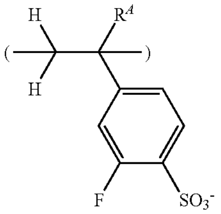

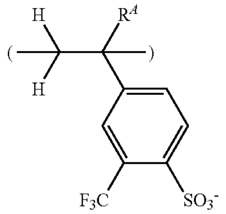

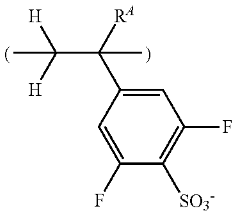

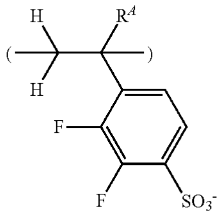

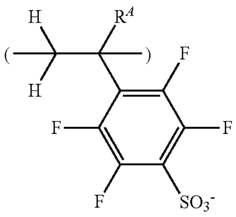

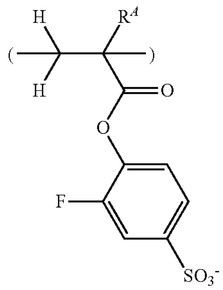

-continued

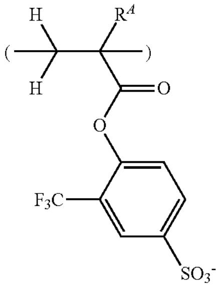

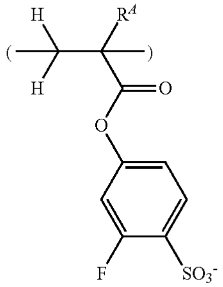

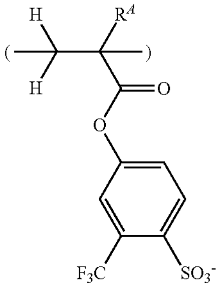

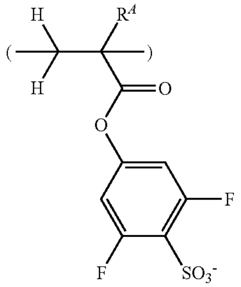

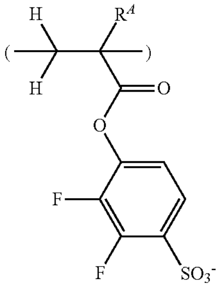

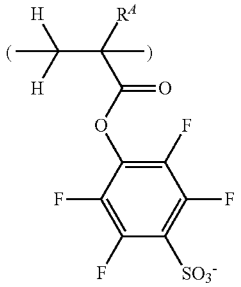

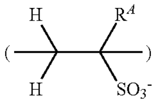

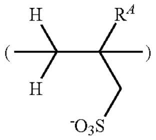

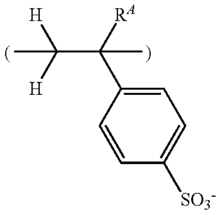

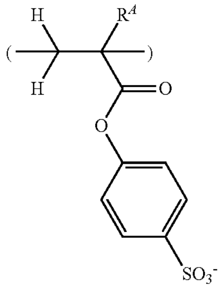

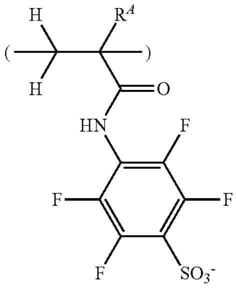

In formulae (c2) and (c3), $A^+$ is an onium cation. Suitable onium cations include sulfonium, iodonium and ammonium cations, with the sulfonium and iodonium cations being preferred. More preferred are sulfonium cations having the formula (c4) and iodonium cations having the formula (c5).

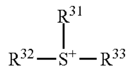

(c4)

$R^{34}-I^{+}-R^{35}$ (c5)

In formulae (c4) and (c5), $R^{31}$ to $R^{35}$ are each independently a $C_1$-$C_{20}$ hydrocarbyl group which may contain a heteroatom. The hydrocarbyl group may be saturated or unsaturated and straight, branched or cyclic. Examples thereof include $C_1$-$C_{20}$ alkyl groups such as methyl, ethyl, n-propyl, isopropyl, n-butyl, and tert-butyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl: $C_2$-$C_{20}$ alkenyl groups such as vinyl, allyl, propenyl, butenyl, and hexenyl; $C_3$-$C_{20}$ cyclic unsaturated hydrocarbyl groups such as cyclohexenyl; $C_6$-$C_{20}$ aryl groups such as phenyl and naphthyl; and $C_1$-$C_{20}$ aralkyl groups such as benzyl, 1-phenylethyl, and 2-phenylethyl, and combinations thereof. Of these, aryl groups are preferred. In the hydrocarbyl group, some or all of the hydrogen atoms may be substituted by a moiety containing a heteroatom such as oxygen, sulfur, nitrogen or halogen, and any constituent $—CH_2—$ may be replaced by a moiety containing a heteroatom such as oxygen, sulfur or nitrogen, so that the group may contain a hydroxy, fluorine, chlorine, bromine, iodine, cyano, carbonyl, ether bond, ester bond, sulfonic ester bond, carbonate bond, lactone ring, sultone ring, carboxylic anhydride (—C(═O)—O—C(═O)—) or haloalkyl moiety.

$R^{31}$ and $R^{32}$ may bond together to form a ring with the sulfur atom to which they are attached. Examples of the sulfonium cation having formula (c4) wherein $R^{31}$ and $R^{32}$ form a ring are shown below.

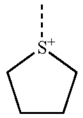
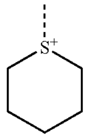
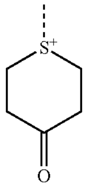
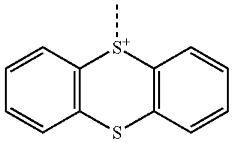
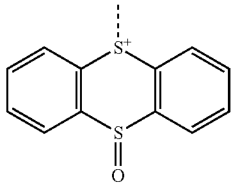
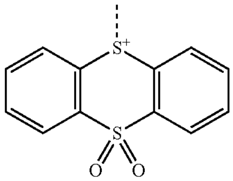
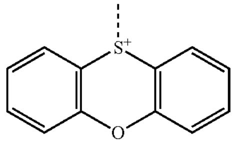
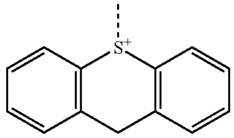
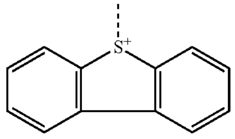
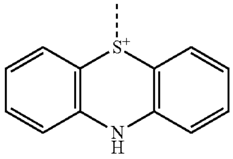

Herein, the broken line designates a point of attachment to $R^{33}$.

Examples of the sulfonium cation having formula (c4) are given below, but not limited thereto.

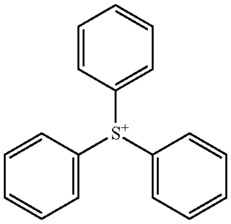
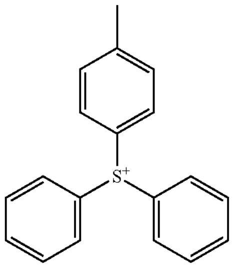
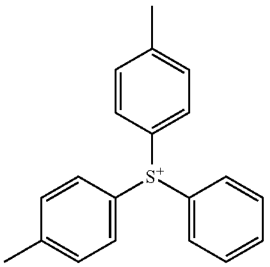
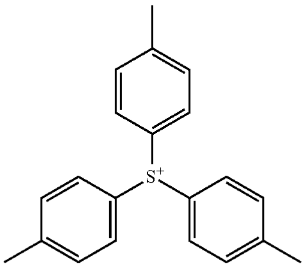
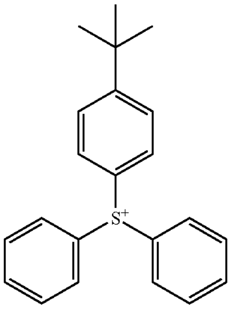
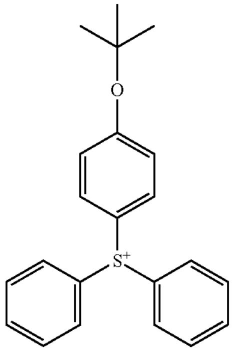
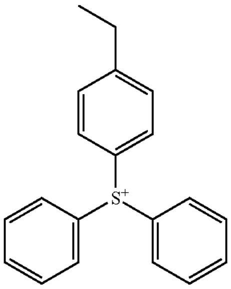
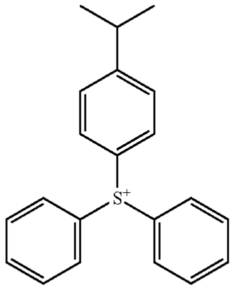

-continued
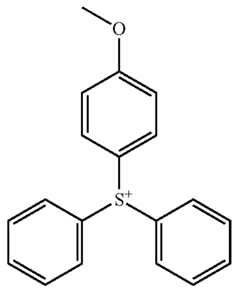
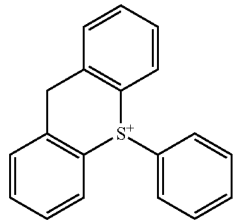
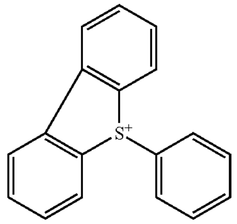
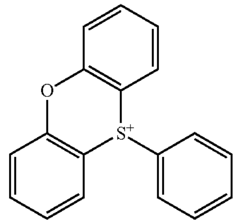
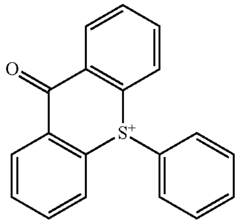
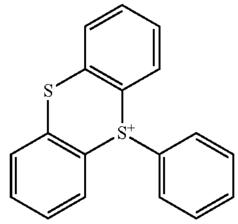
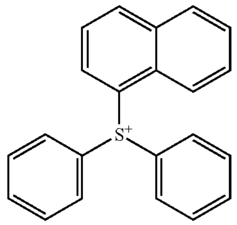
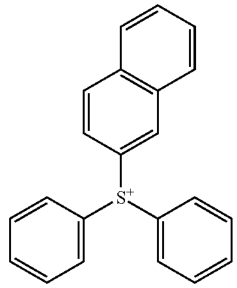
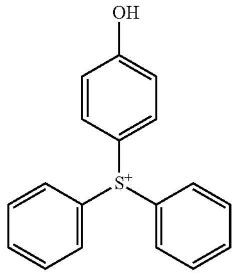
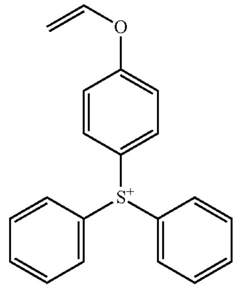
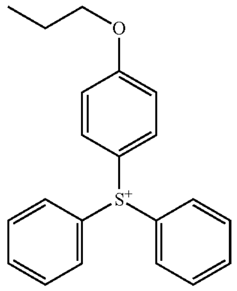
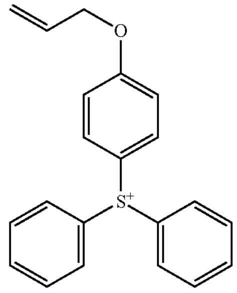
-continued
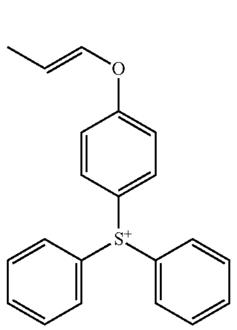
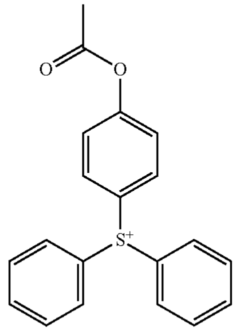
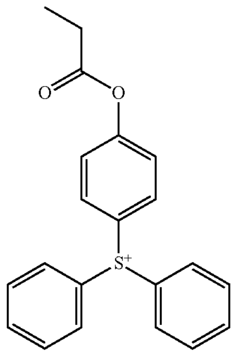
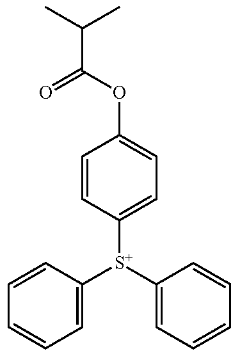
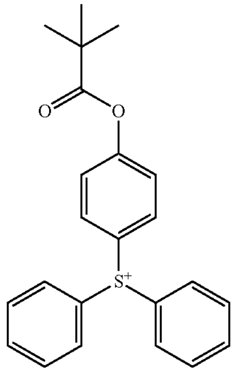
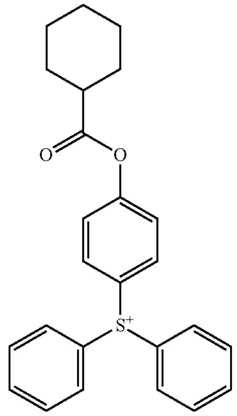
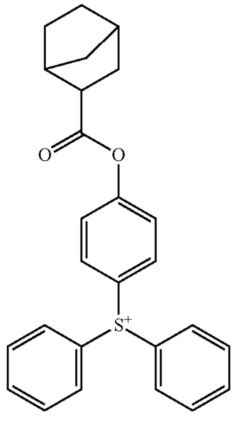
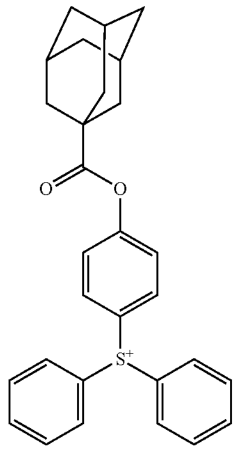

-continued
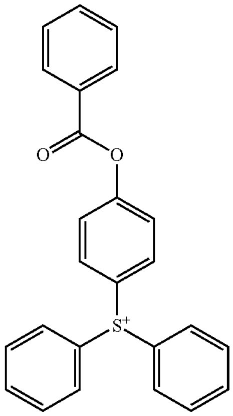
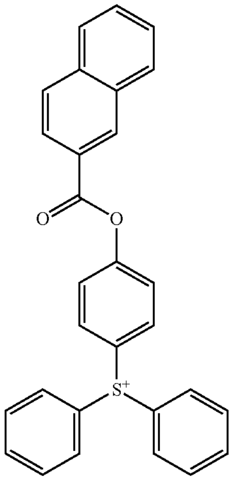
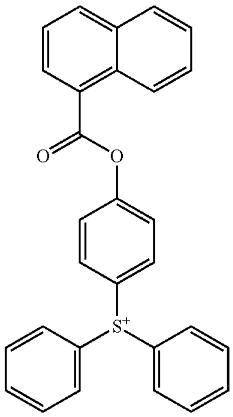
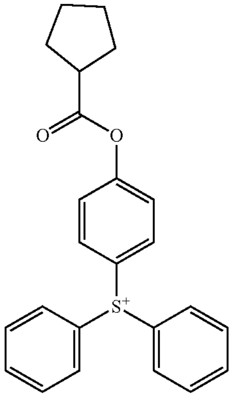
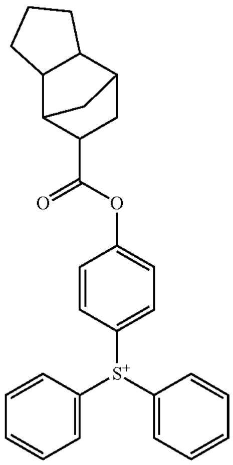
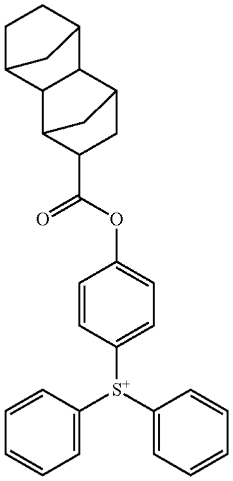
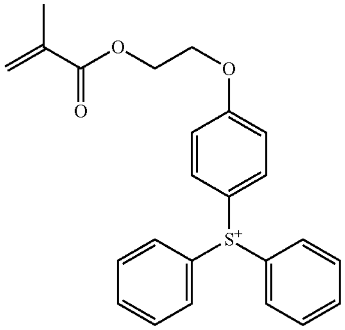
-continued
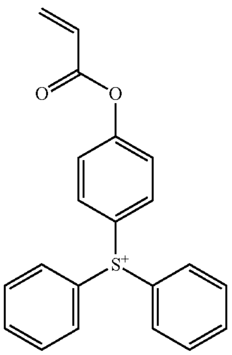
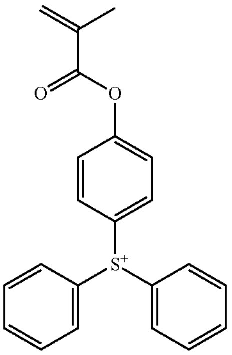
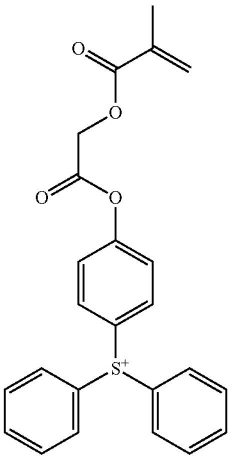
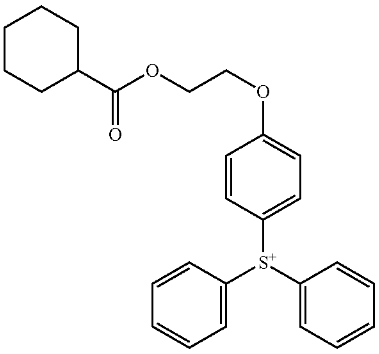
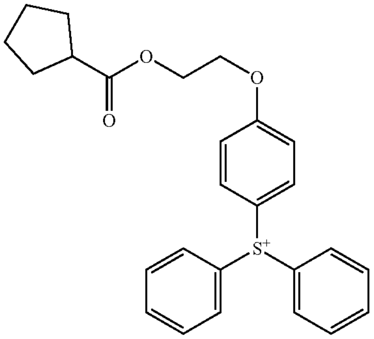

-continued
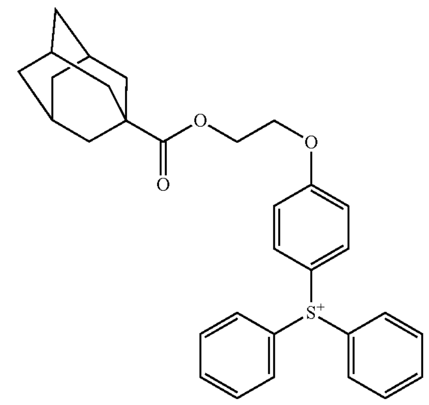
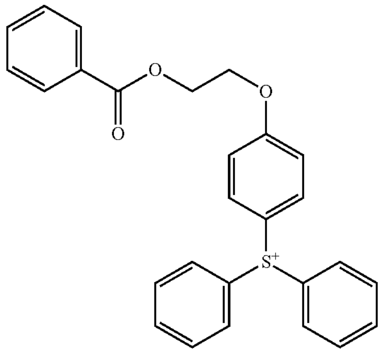
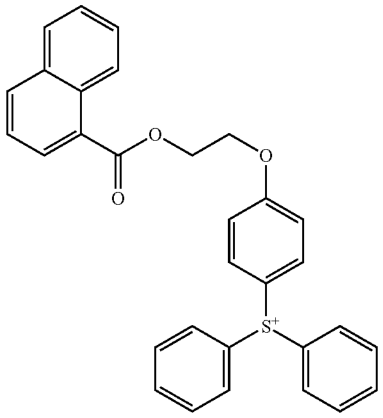
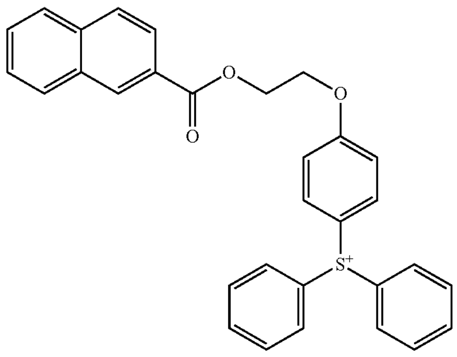
-continued
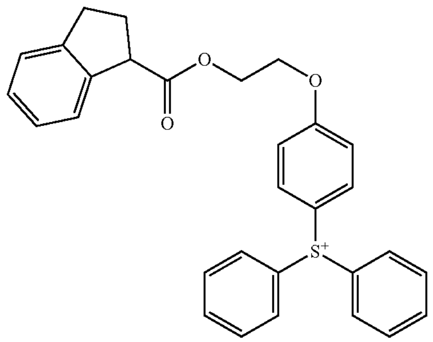
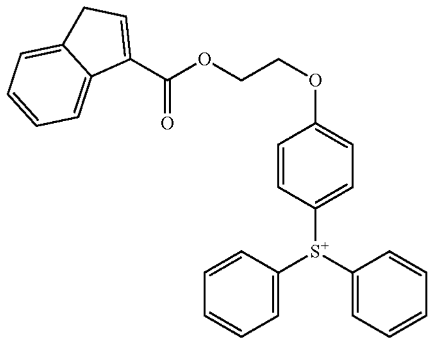
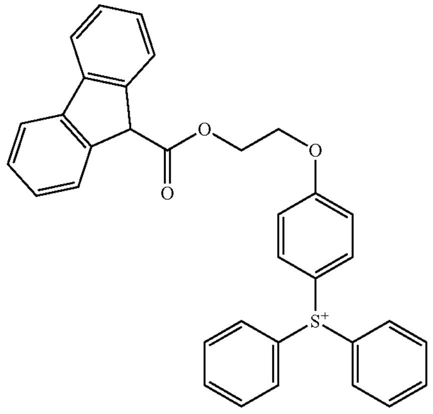
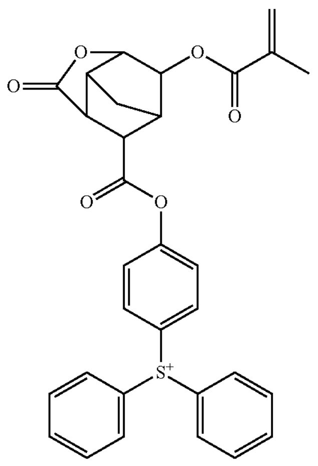

-continued
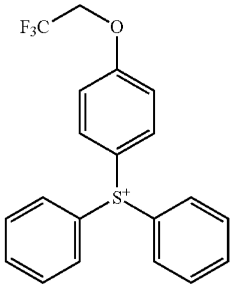
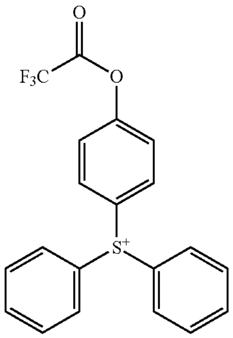
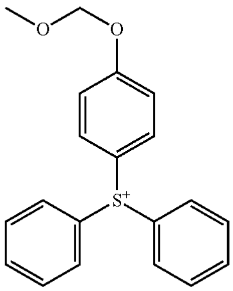
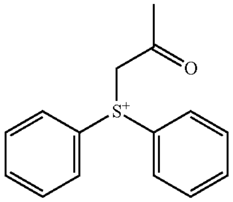
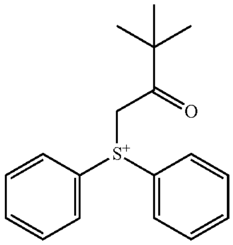
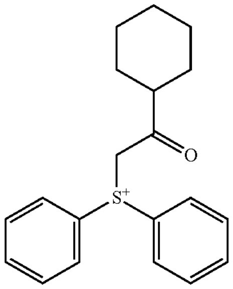
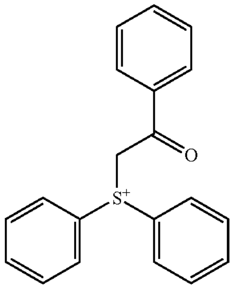
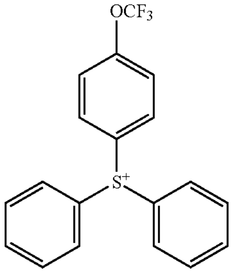
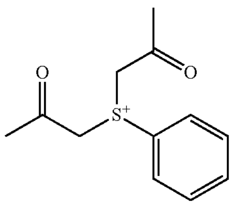
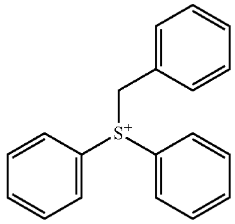
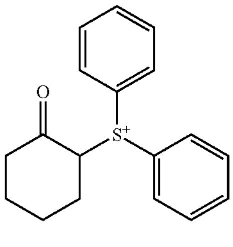
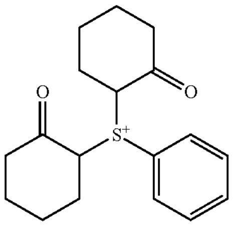
-continued
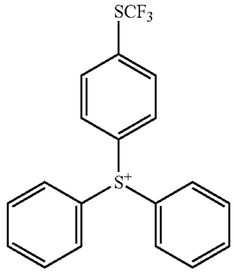
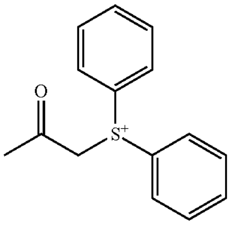
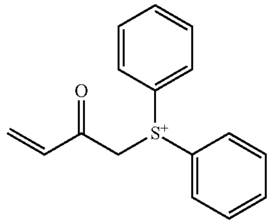
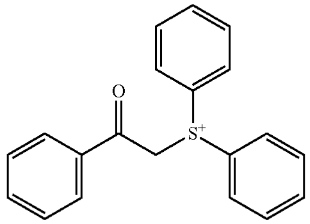
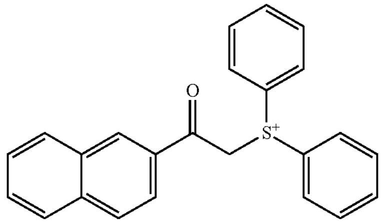
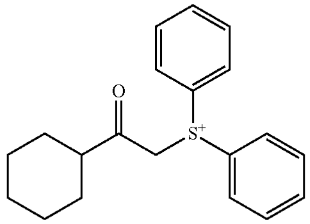
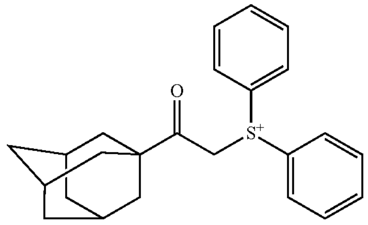
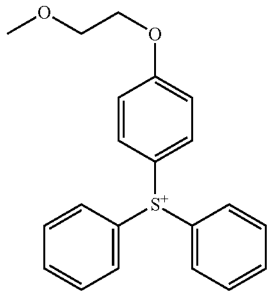

-continued
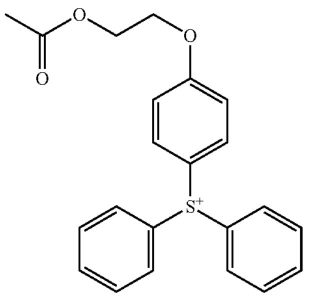
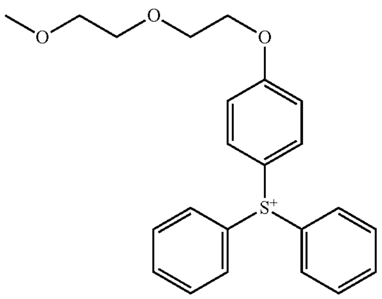
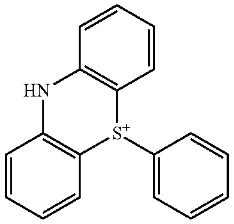
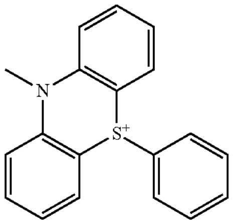
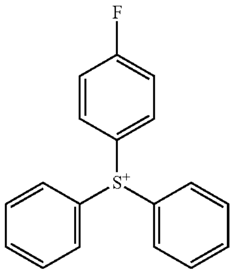
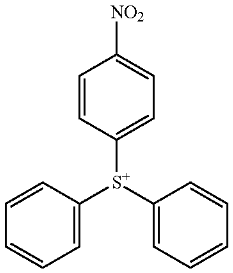
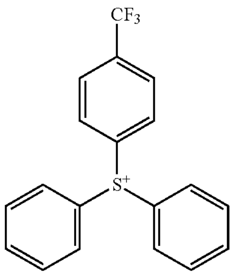
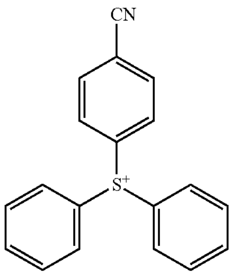
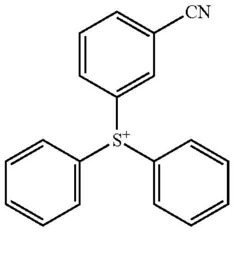
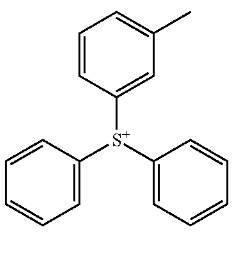
-continued
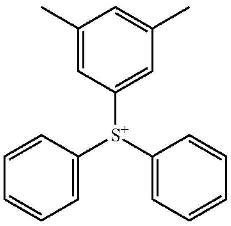
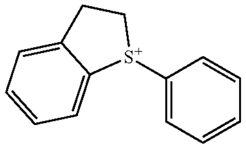
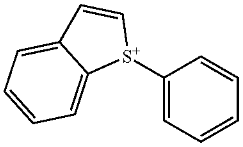
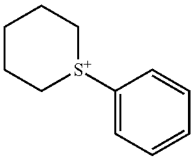
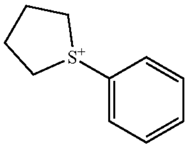
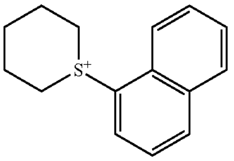
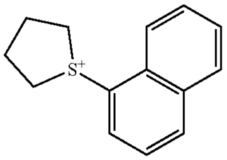
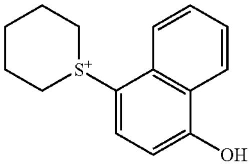
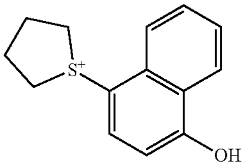
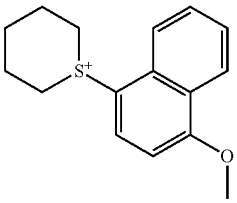
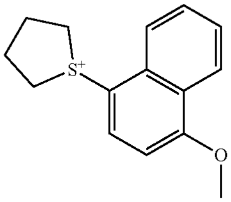
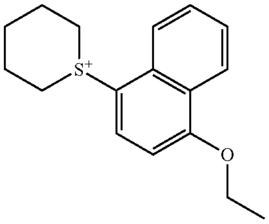
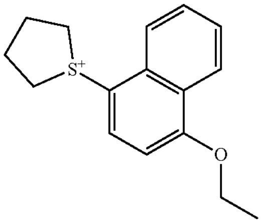
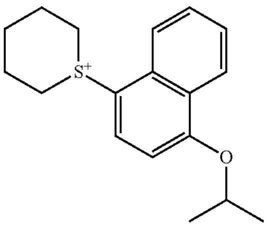

-continued
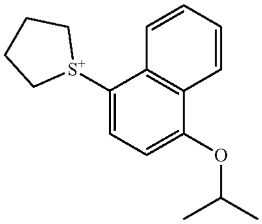
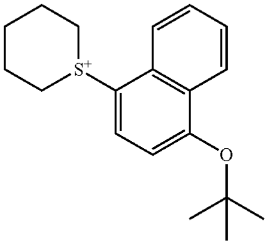
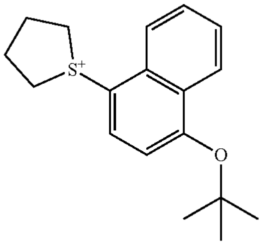
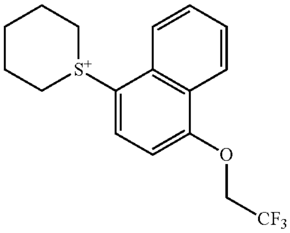
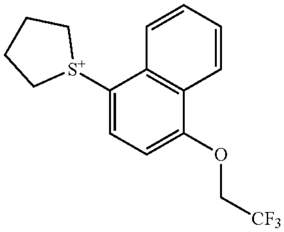
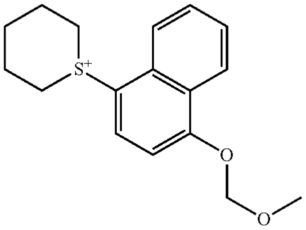
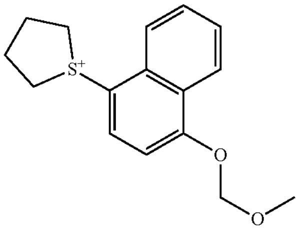
-continued
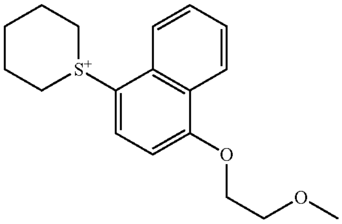
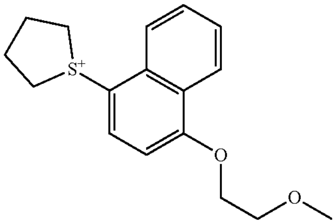
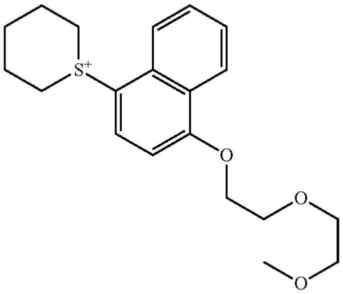
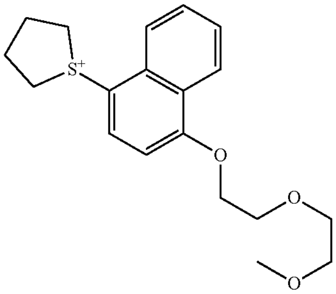
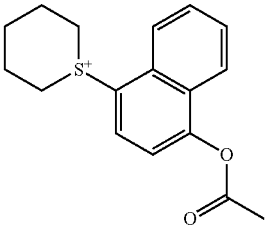
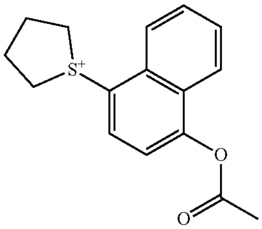
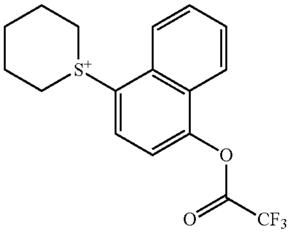

-continued
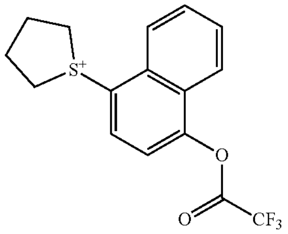
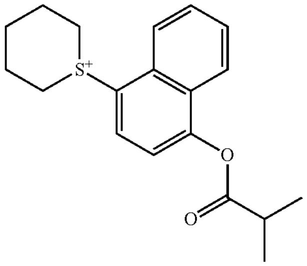
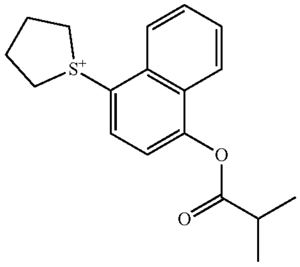
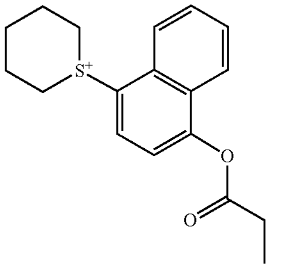
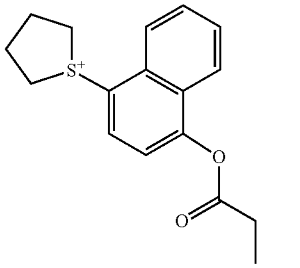
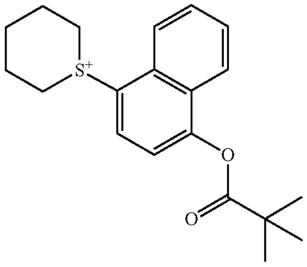
-continued
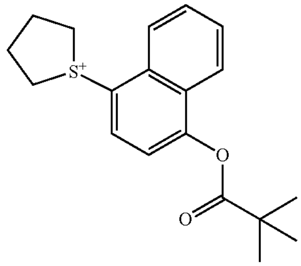
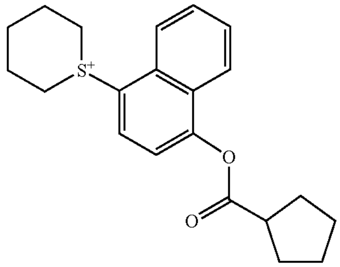
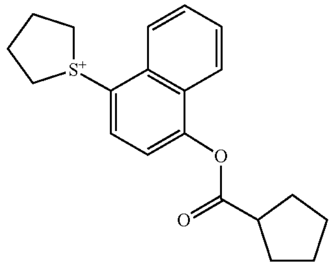
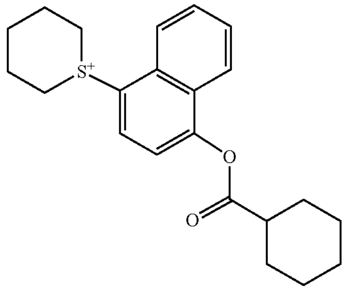
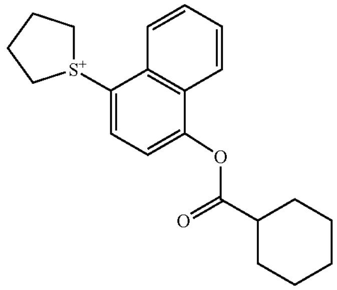
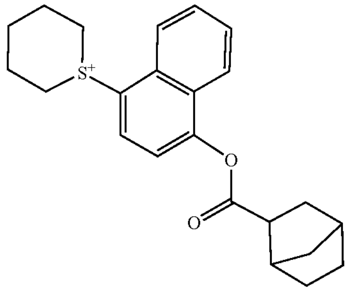

-continued
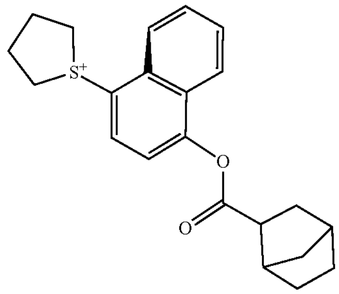
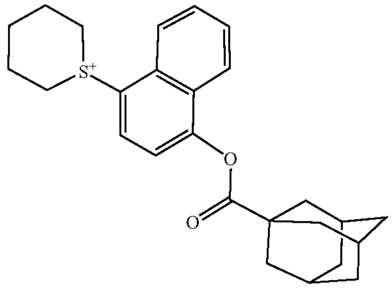
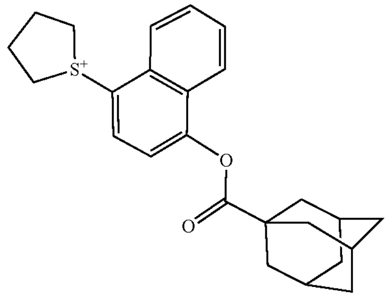
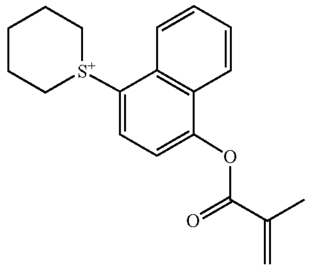
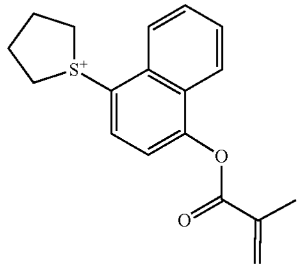
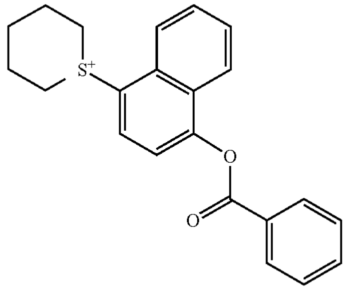
-continued
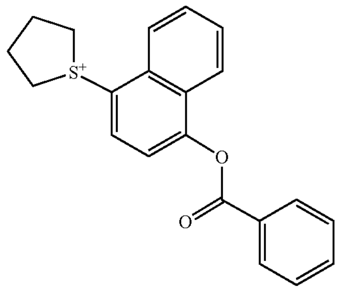
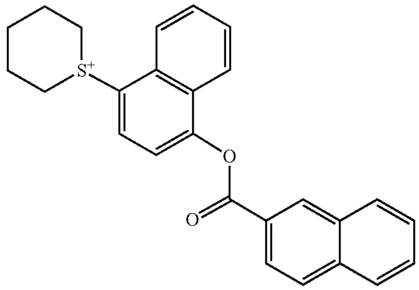
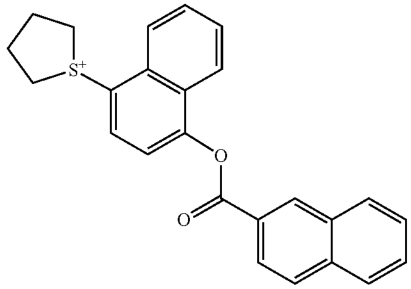
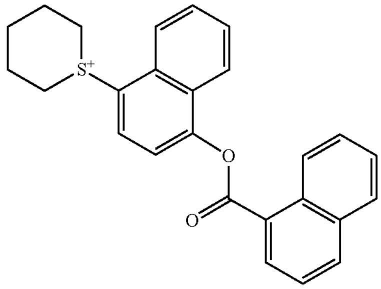
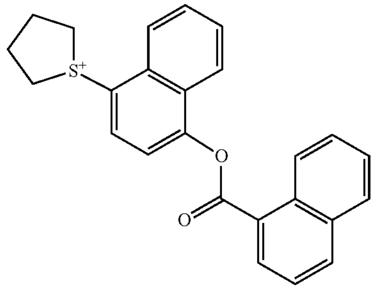

-continued
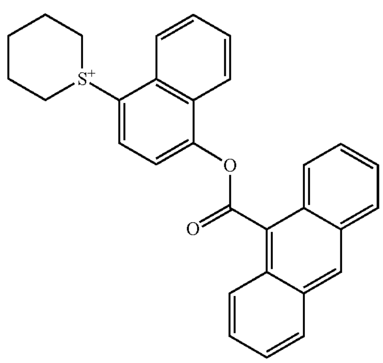
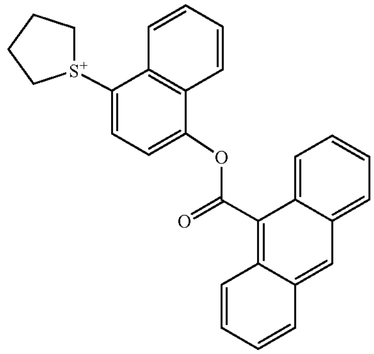
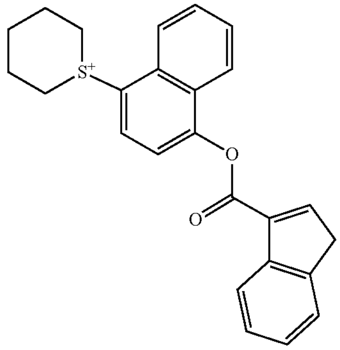
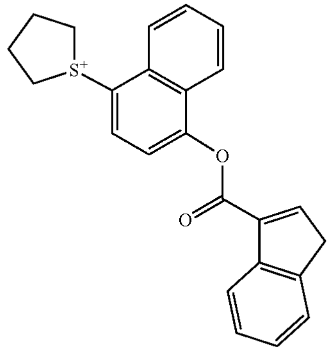
-continued
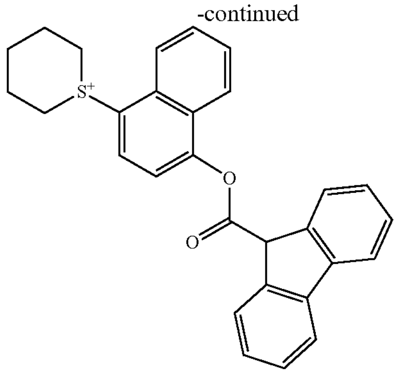
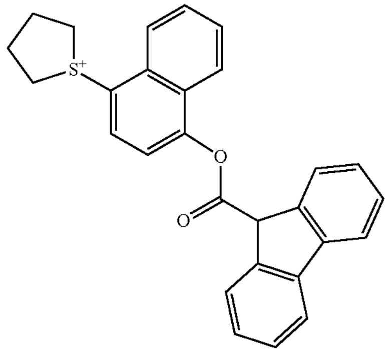
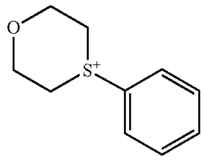
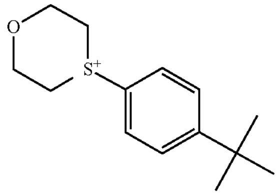
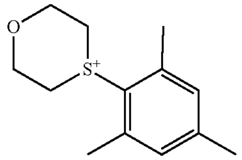
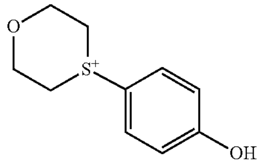
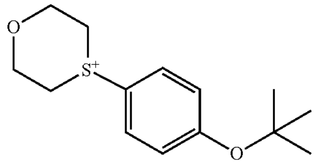
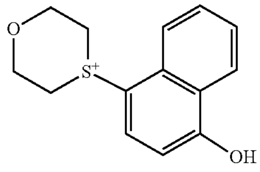

-continued
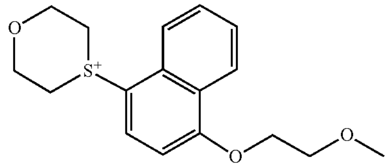
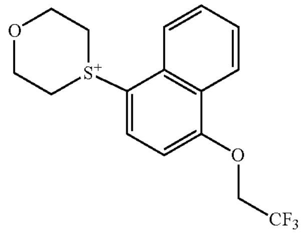
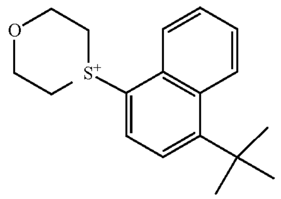
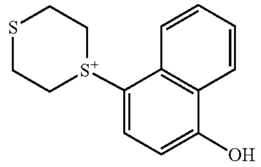
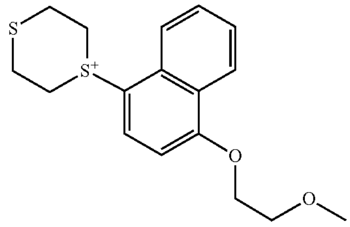
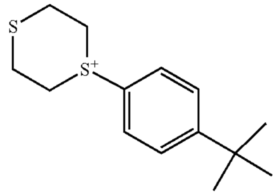
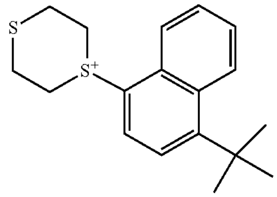
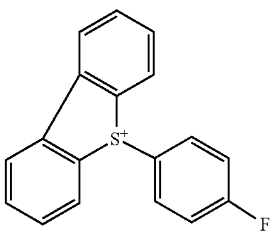
-continued
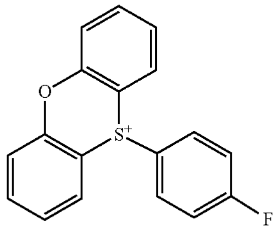
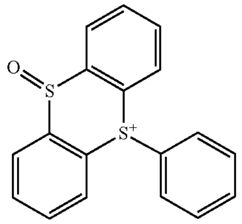
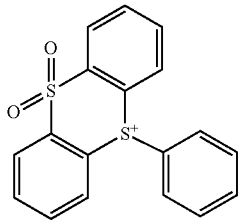
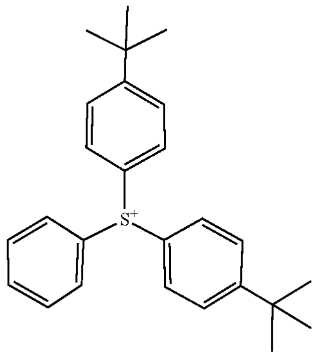
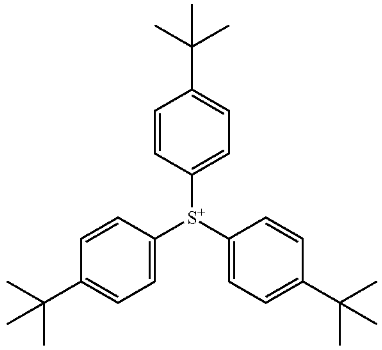
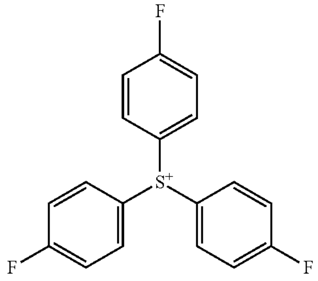

-continued
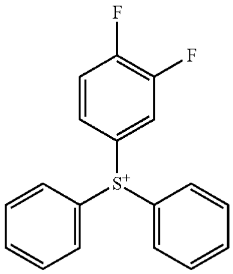
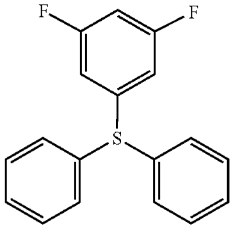
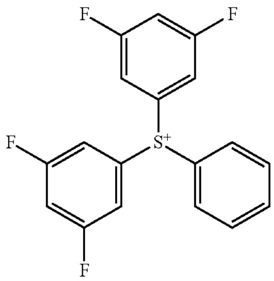
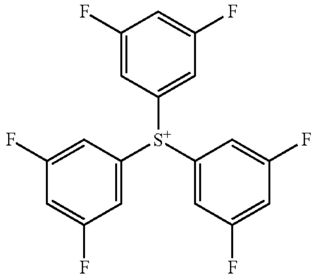
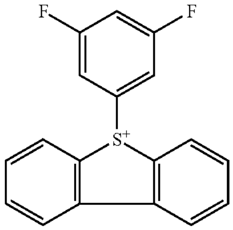
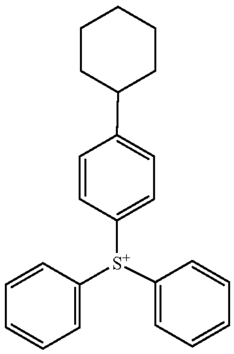
-continued
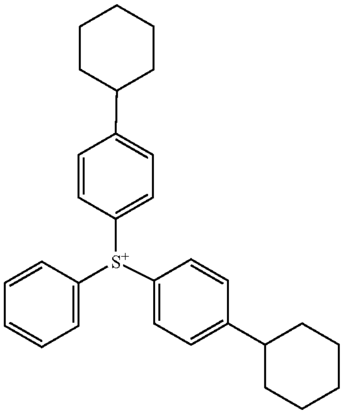
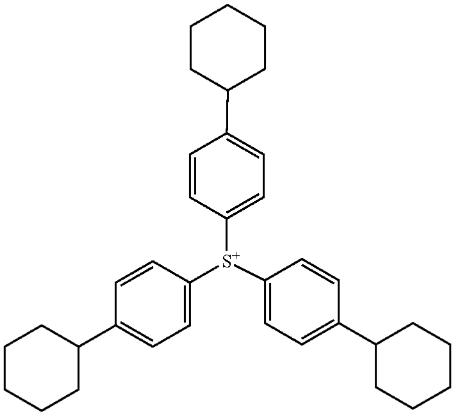
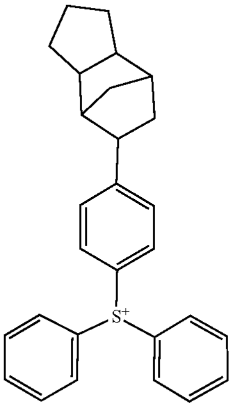

-continued
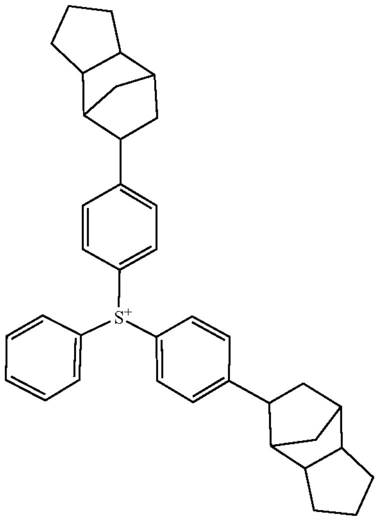
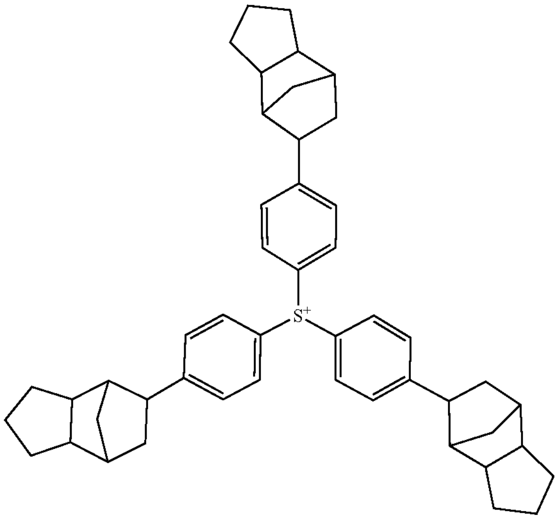
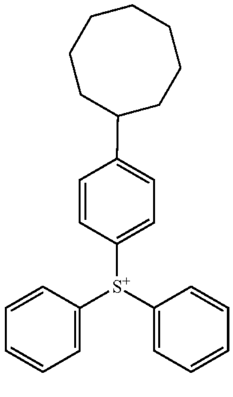
-continued
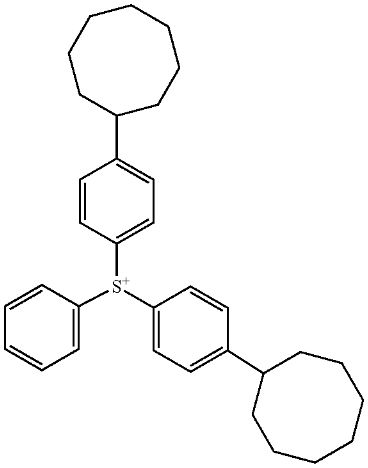
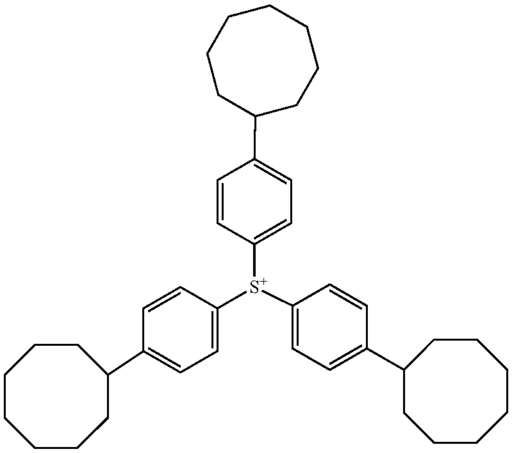
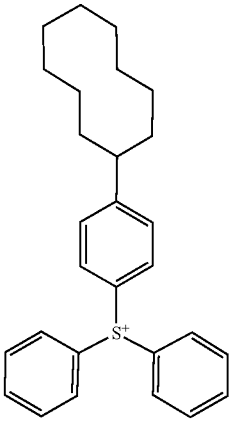

-continued
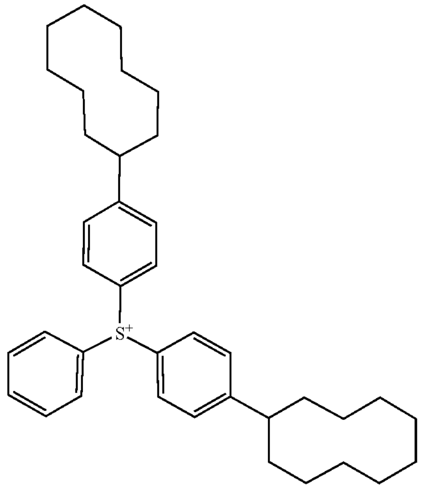
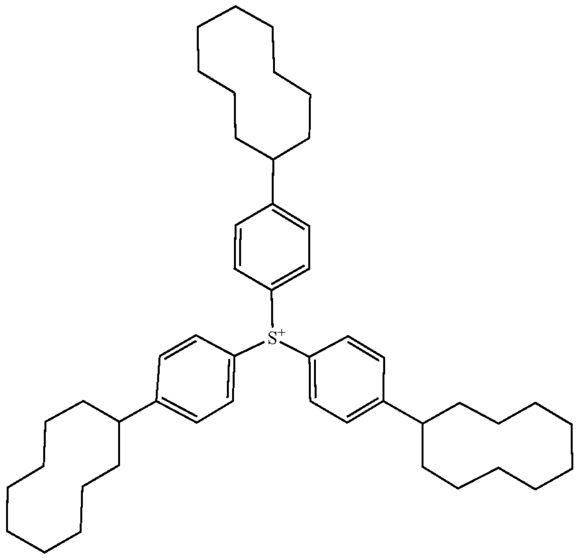
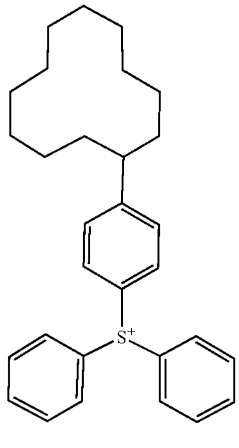
-continued
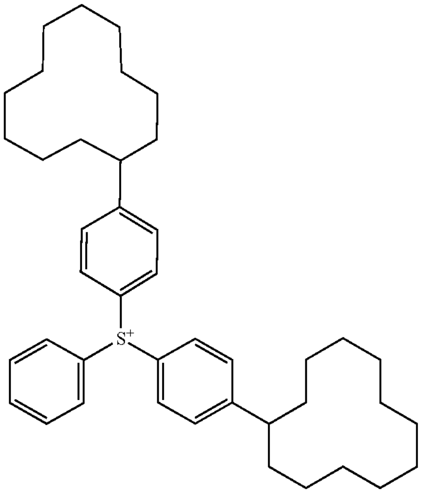
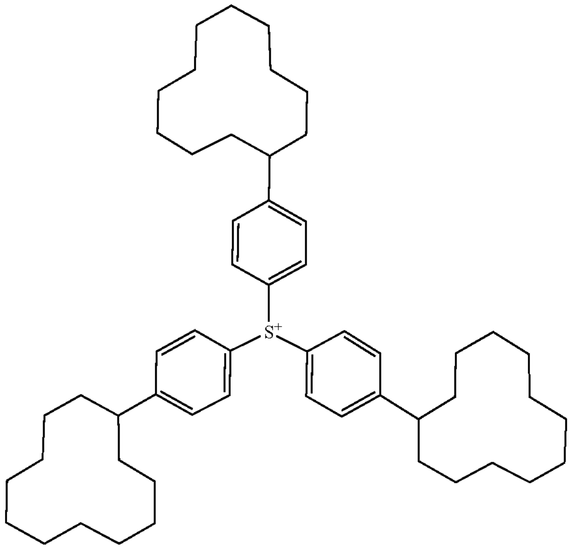
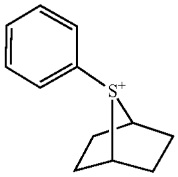
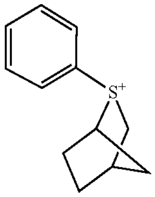
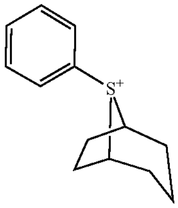

-continued
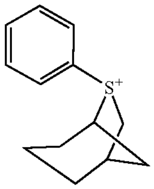
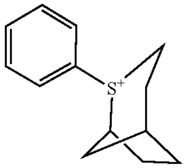
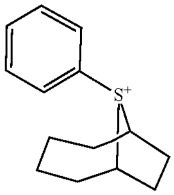
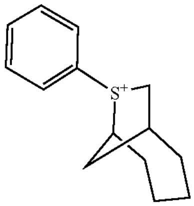
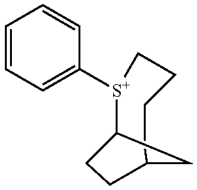
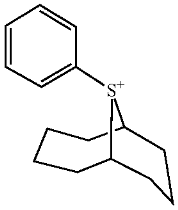
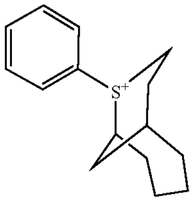
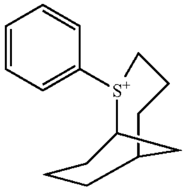
-continued
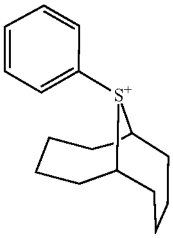
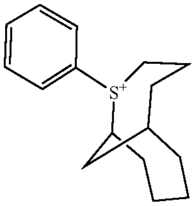
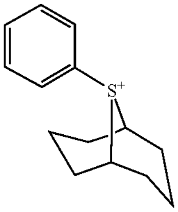
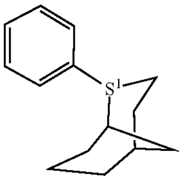
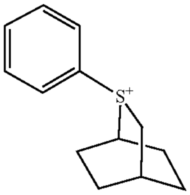
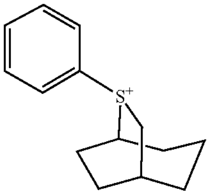
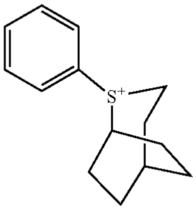
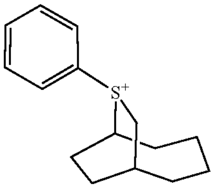

-continued
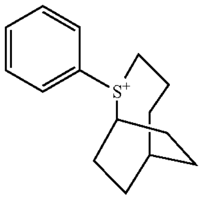
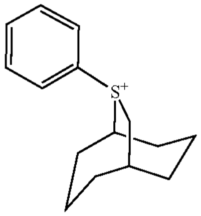
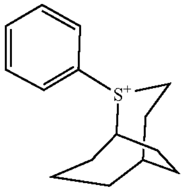
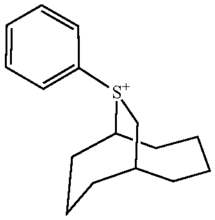
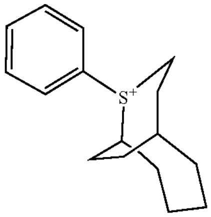
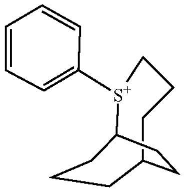
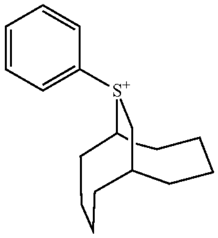
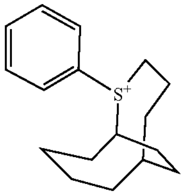
-continued
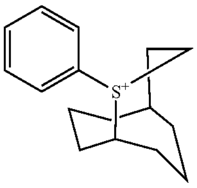
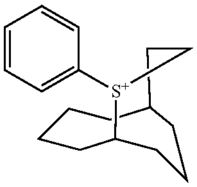
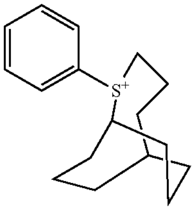
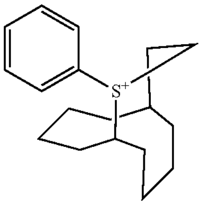
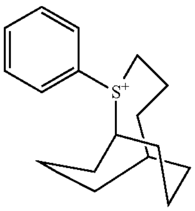
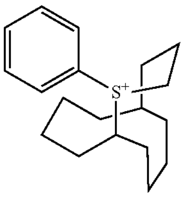
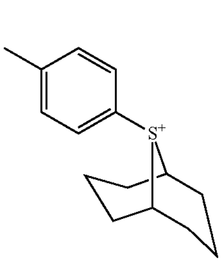
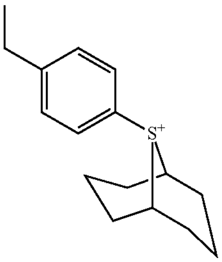

-continued
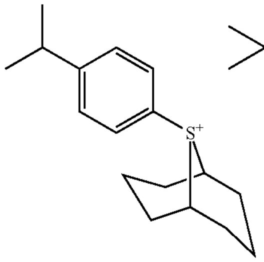
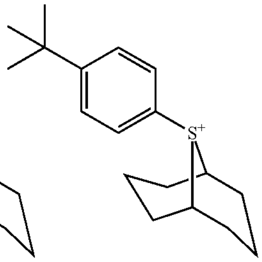
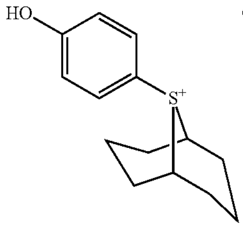
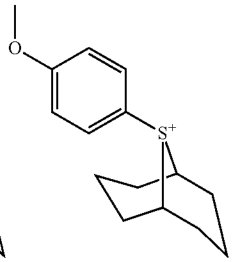
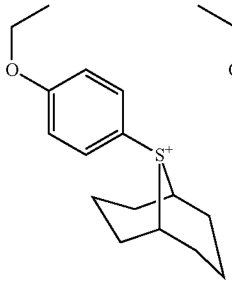
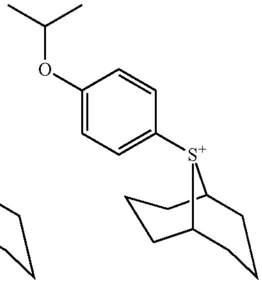
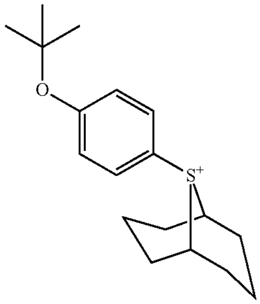
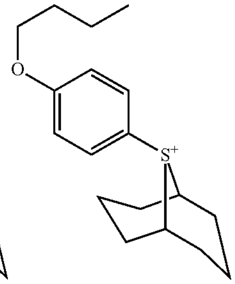
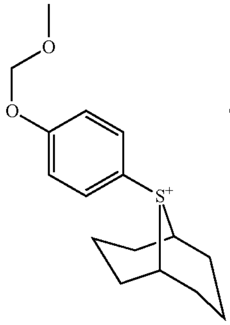
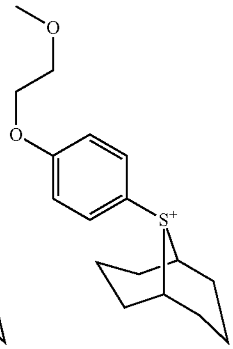
-continued
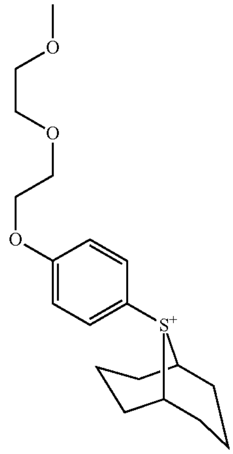
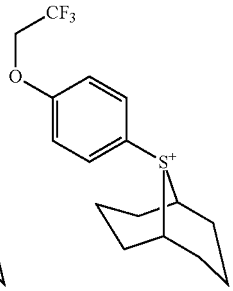
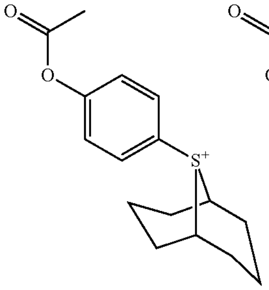
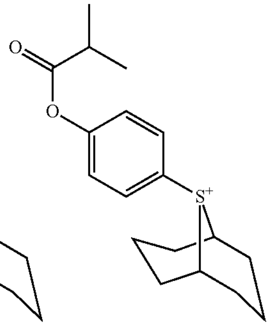
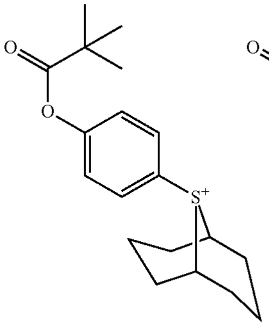
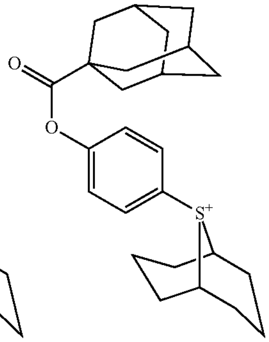
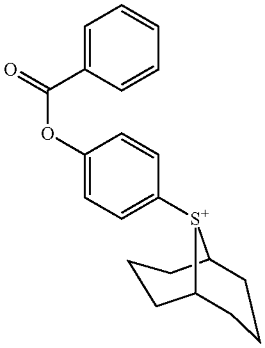
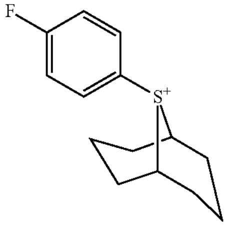
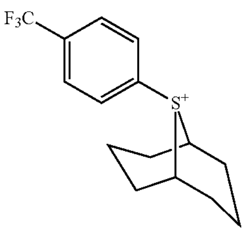
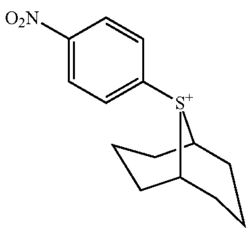

-continued
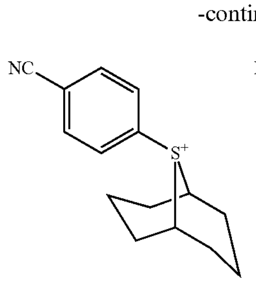
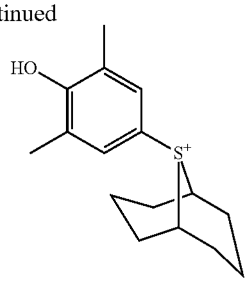
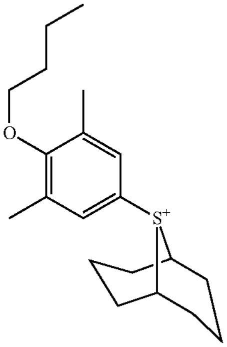
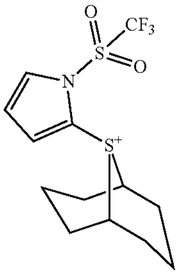
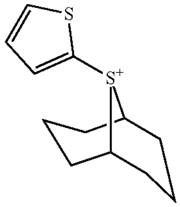
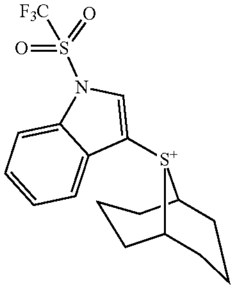
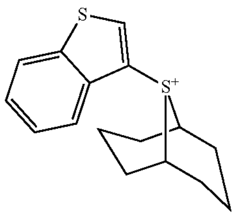
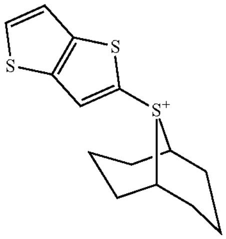
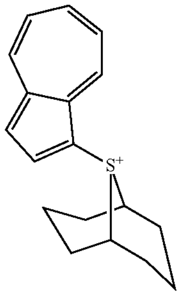
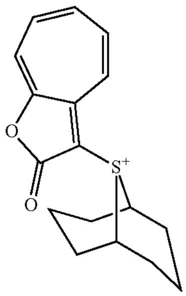
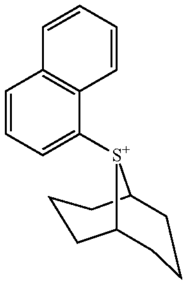
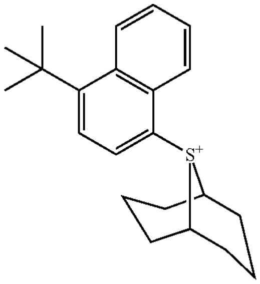
-continued
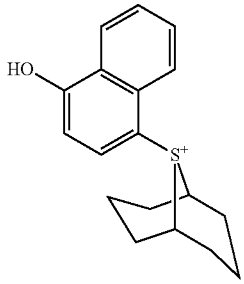
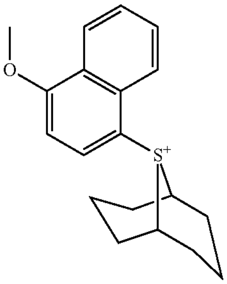
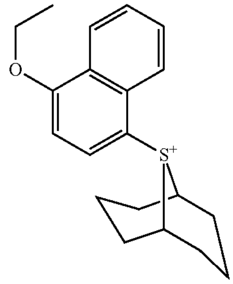
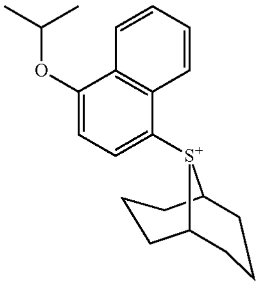
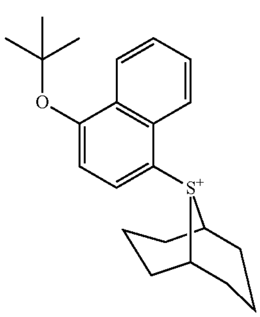
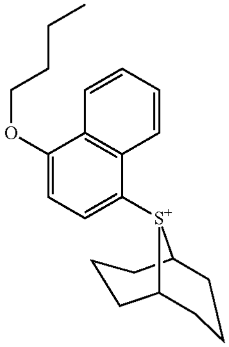
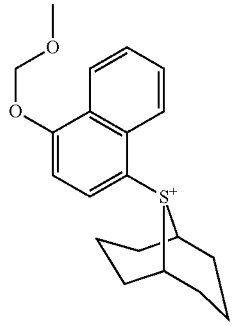
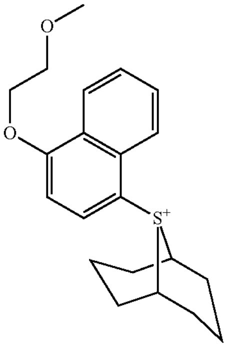
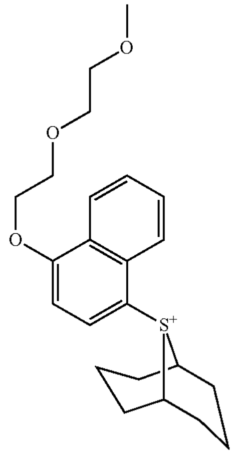
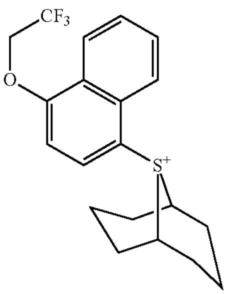

-continued
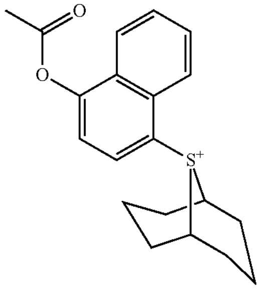
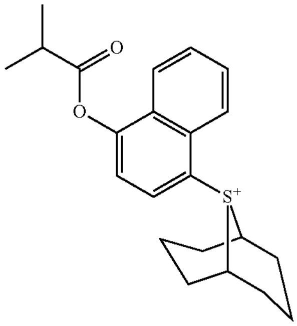
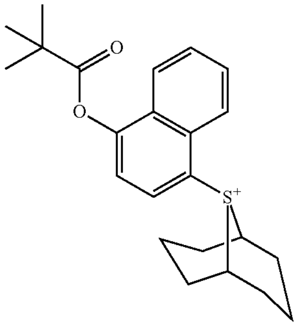
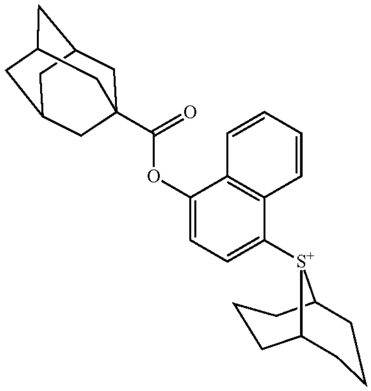
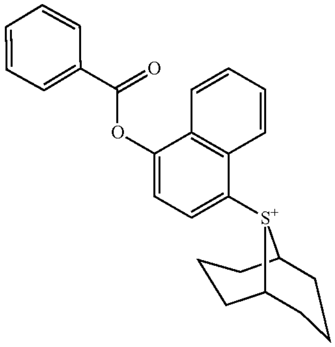
-continued
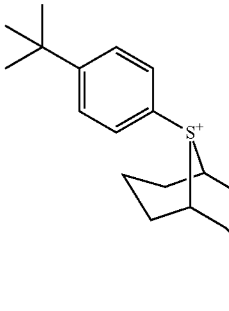
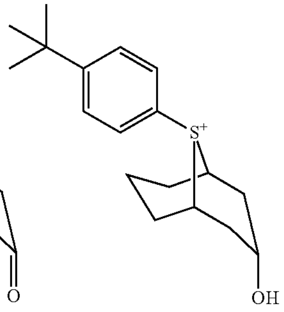
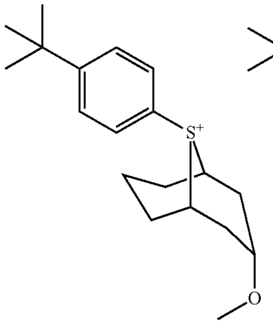
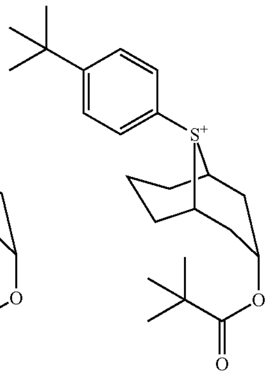
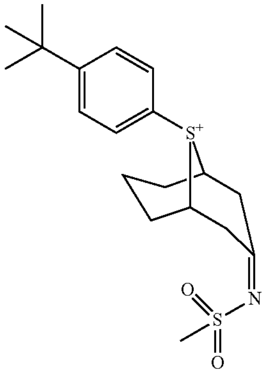
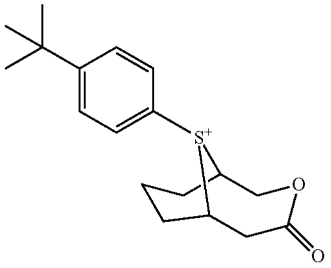
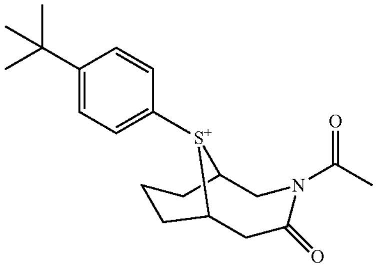

-continued
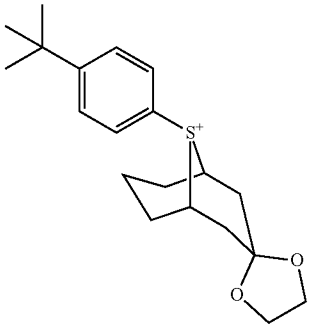
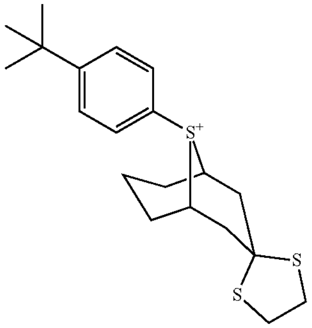
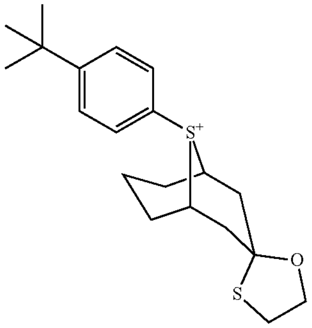
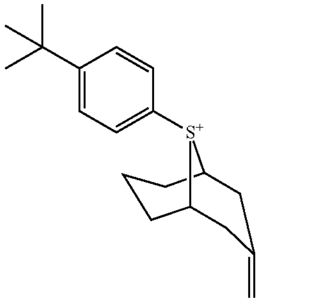
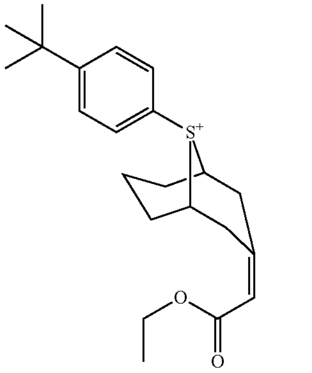
-continued
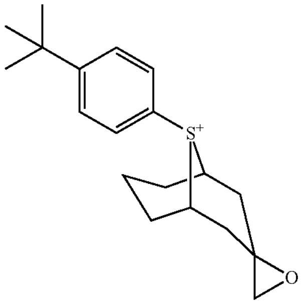
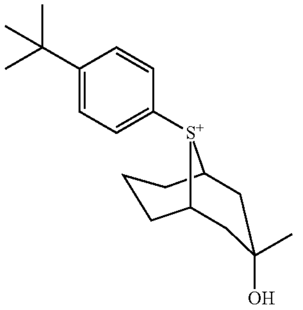
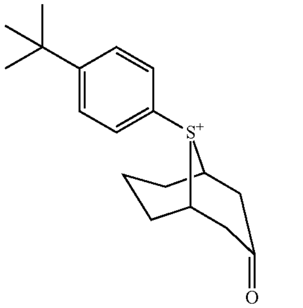
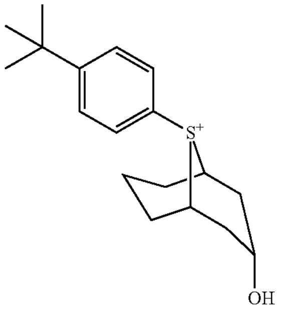
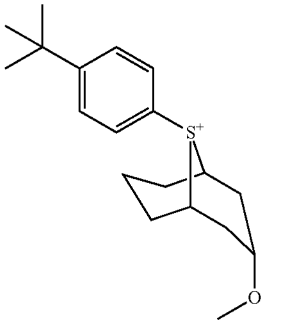

-continued
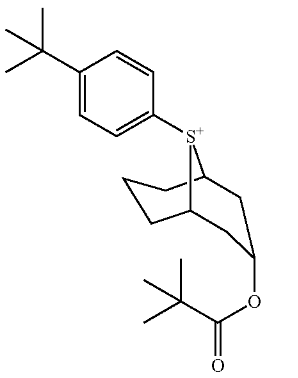
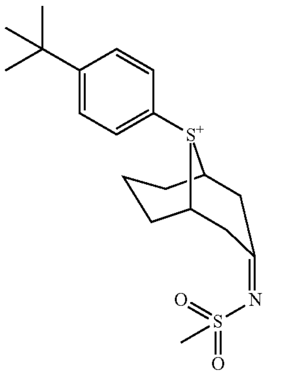
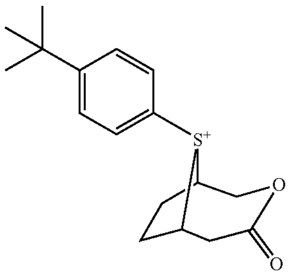
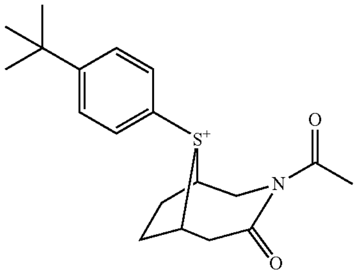
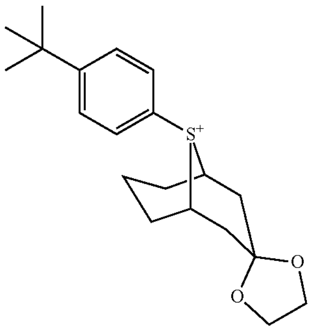
-continued
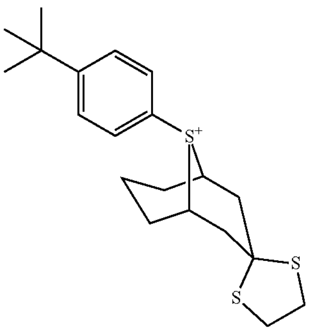
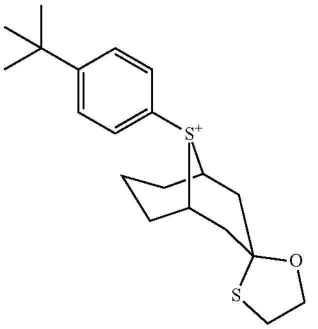
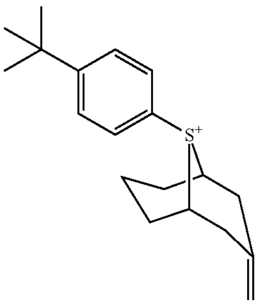
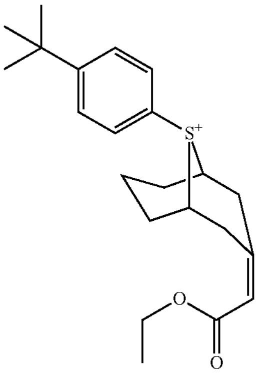
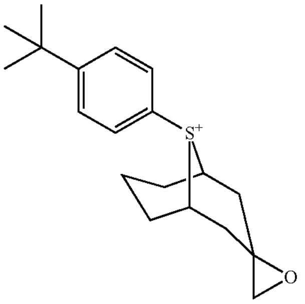

-continued
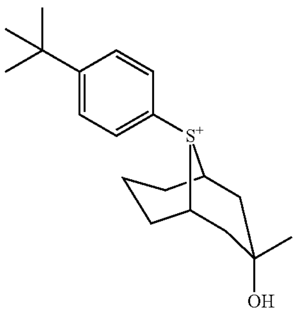
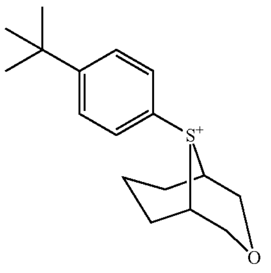
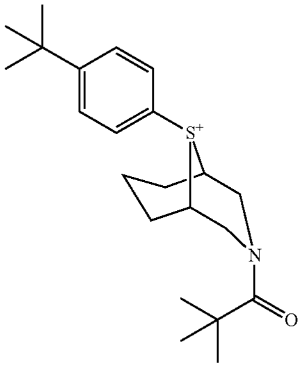
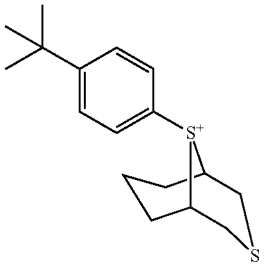
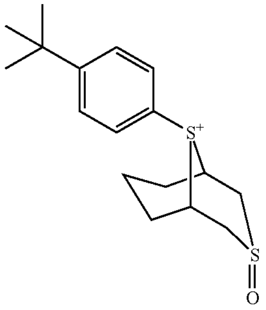
-continued
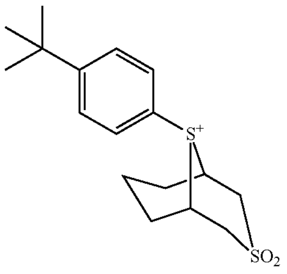
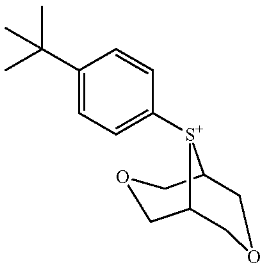
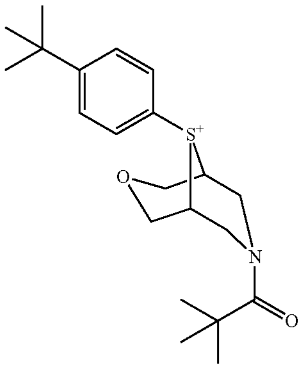
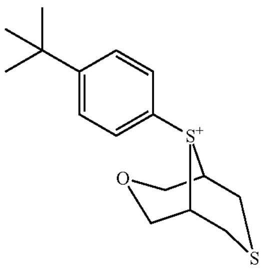
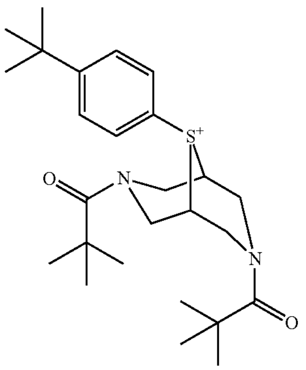

-continued
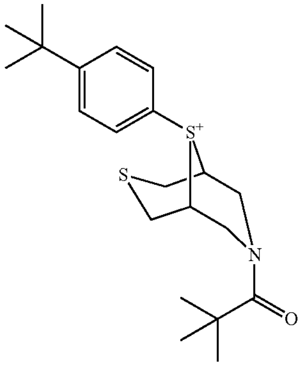
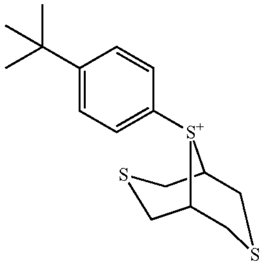
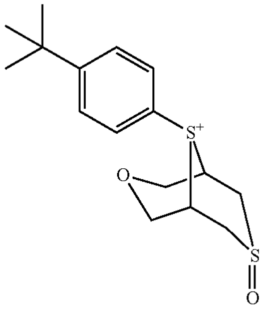
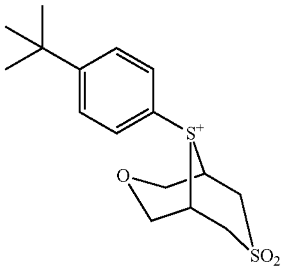
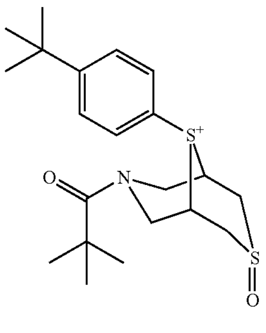
-continued
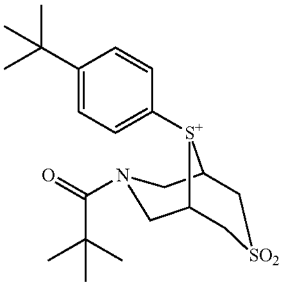
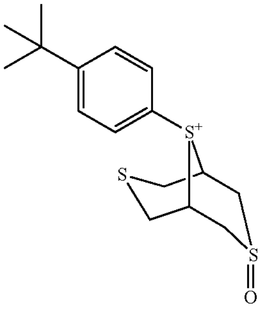
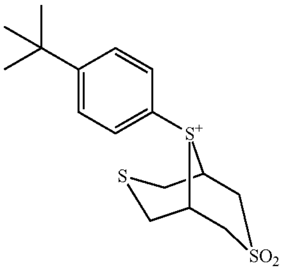
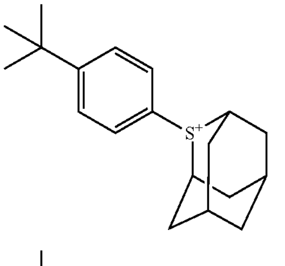
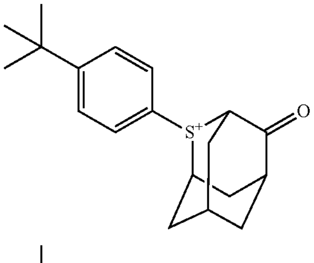
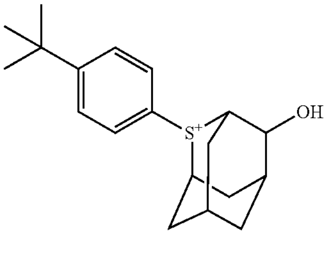

-continued
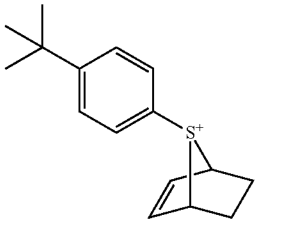
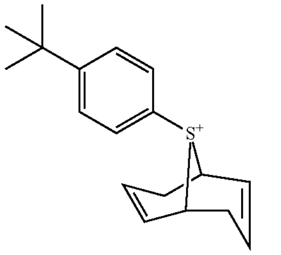
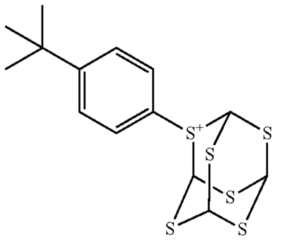
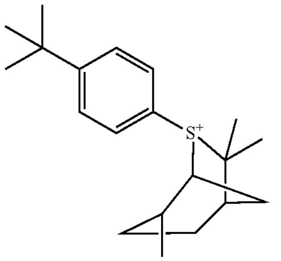
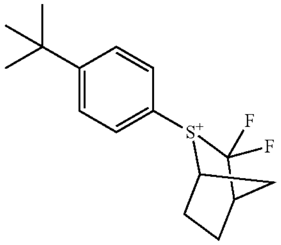
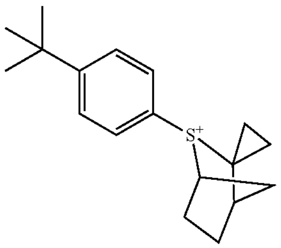
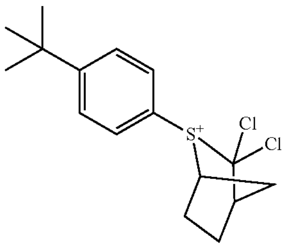
-continued
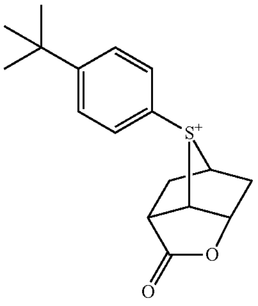
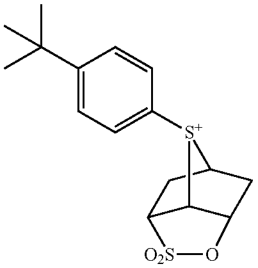
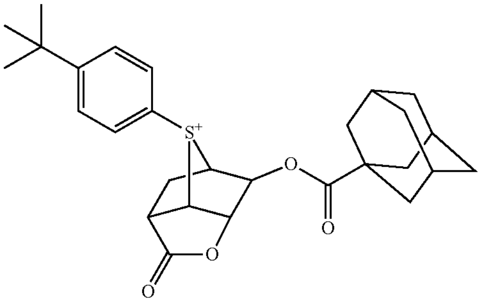
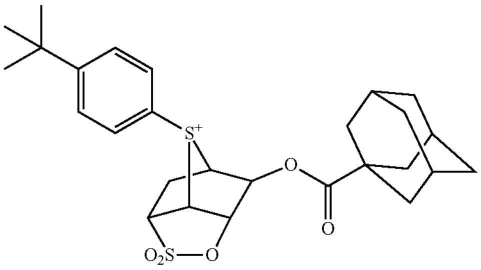
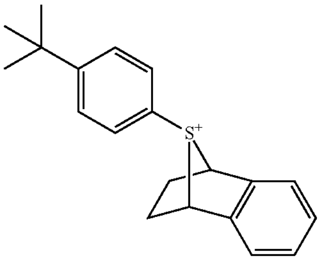
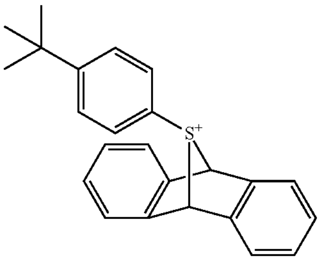

-continued

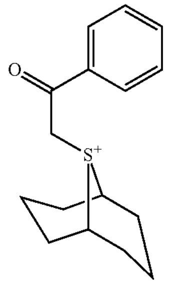

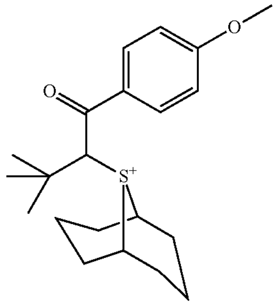

Examples of the iodonium cation having formula (c5) are given below, but not limited thereto.

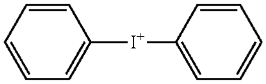

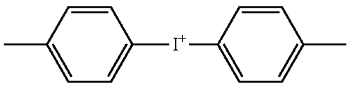

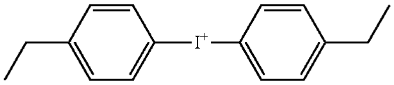

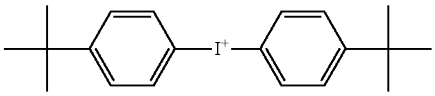

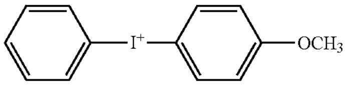

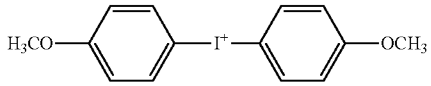

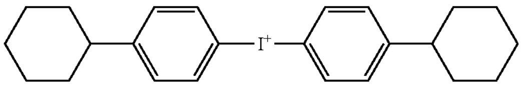

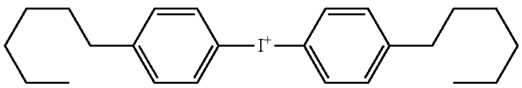

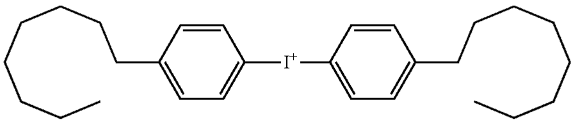

Examples of the repeat units (c1) to (c3) include arbitrary combinations of anions with cations, both as exemplified above.

The base polymer may further comprise repeat units (d) of a structure having a hydroxy group protected with an acid labile group. The repeat unit (d) is not particularly limited as long as the unit includes one or more structures having a hydroxy group protected with a protective group such that the protective group is decomposed to generate the hydroxy group under the action of acid. Repeat units having the formula (d1) are preferred.

(d1)

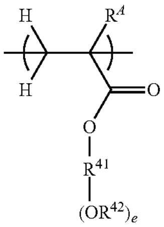

In formula (d1), $R^A$ is as defined above, and e is an integer of 1 to 4. $R^{41}$ is a $C_1$-$C_{30}$ (e+1)-valent hydrocarbon group which may contain a heteroatom. $R^{42}$ is an acid labile group.

In formula (d1), the acid labile group $R^{42}$ is deprotected under the action of acid so that a hydroxy group is generated. The structure of $R^{42}$ is not particularly limited, an acetal structure, ketal structure, alkoxycarbonyl group and alkoxymethyl group having the following formula (d2) are preferred, with the alkoxymethyl group having formula (d2) being more preferred.

(d2)

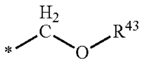

Herein $R^{43}$ is a $C_1$-$C_{15}$ hydrocarbyl group.

Illustrative examples of the acid labile group $R^{42}$, the alkoxymethyl group having formula (d2), and the repeat units (d) are as exemplified for the repeat units (d) in JP-A 2020-111564 (US 20200223796).

In addition to the foregoing units, the base polymer may further comprise repeat units derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo$[6.2.1.1^{3,6}.0^{2,7}]$dodecene derivatives, and unsaturated acid anhydrides such as itaconic anhydride.

The base polymer preferably has a weight average molecular weight (Mw) of 1,000 to 500,000, and more preferably 3,000 to 100,000, as measured versus polystyrene standards by gel permeation chromatography (GPC) using tetrahydrofuran (TI-IF) solvent. The above range of Mw ensures satisfactory etch resistance and eliminates the risk of resolution being reduced due to difficulty to gain a dissolution rate difference before and after exposure.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influence of Mw/Mn becomes stronger as the pattern rale becomes finer. Therefore, the base polymer should preferably have a narrow dispersity (Mw/Mn) of 1.0 to 2.0 in order to provide a resist composition suitable for micropatterning to a small feature size.

The base polymer may be synthesized, for example, by dissolving a monomer or monomers corresponding to the above-mentioned repeat units in an organic solvent, adding a radical polymerization initiator, and heating for polymerization.

One exemplary method of synthesizing the polymer is by dissolving one or more unsaturated bond-bearing monomers in an organic solvent, adding a radical initiator, and heating for polymerization. Examples of the organic solvent which can be used for polymerization include toluene, benzene, THF, diethyl ether, dioxane, cyclohexane, cyclopentane, methyl ethyl ketone (MEK), propylene glycol monomethyl ether acetate (PGMEA), and γ-butyrolactone (GBL). Examples of the polymerization initiator used herein include 2,2'-azobisisobutyronitrile (AIBN), 2,2'-azobis(2,4-dimethylvaleronitrile), dimethyl 2,2-azobis(2-methylpropionate), 1,1'-azobis(1-acetoxy-1-phenylethane), benzoyl peroxide, and lauroyl peroxide. The initiator is preferably added in an amount of 0.01 to 25 mol % based on the total of monomers to be polymerized. The reaction temperature is preferably 50 to 150° C., more preferably 60 to 100° C. The reaction time is preferably 2 to 24 hours, more preferably 2 to 12 hours in view of production efficiency.

The polymerization initiator may be fed to the reactor either by adding the initiator to the monomer solution and feeding the solution to the reactor, or by dissolving the initiator in a solvent to form an initiator solution and feeding the initiator solution and the monomer solution independently to the reactor. Because of a possibility that in the standby duration, the initiator generates a radical which triggers polymerization reaction to form a ultra-high-molecular-weight polymer, it is preferred from the standpoint of quality control to prepare the monomer solution and the initiator solution separately and add them dropwise. The acid labile group that has been incorporated in the monomer may be kept as such, or polymerization may be followed by protection or partial protection. During the polymer synthesis, any known chain transfer agent such as dodecyl mercaptan or 2-mercaptoethanol may be added for molecular weight control purpose. The amount of chain transfer agent added is preferably 0.01 to 20 mol % based on the total of monomers.

When hydroxystyrene or hydroxyvinylnaphthalene is copolymerized, one method is by dissolving hydroxystyrene or hydroxyvinylnaphthalene and other monomers in an organic solvent, adding a radical polymerization initiator thereto, and heating the solution for polymerization. In an alternative method, acetoxystyrene or acetoxyvinylnaphthalene is used instead, and after polymerization, the acetoxy group is deprotected by alkaline hydrolysis, for thereby converting the polymer product to polyhydroxystyrene or polyhydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The amounts of monomers in the monomer solution may be determined appropriate so as to provide the preferred fractions of repeat units.

It is now described how to use the polymer obtained by the above preparation method. The reaction solution resulting from polymerization reaction may be used as the final product. Alternatively, the polymer may be recovered in powder form through a purifying step such as re-precipitation step of adding the polymerization solution to a poor solvent and letting the polymer precipitate as powder, after which the polymer powder is used as the final product. It is preferred from the standpoints of operation efficiency and consistent quality to handle a polymer solution which is obtained by dissolving the powder polymer resulting from the purifying step in a solvent, as the final product. The solvents which can be used herein are described in JP-A 2008-111103, paragraphs [0144]-[0145] (U.S. Pat. No. 7,537,880). Exemplary solvents include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; keto-alcohols such as diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, test-butyl propionate, and propylene glycol mono-tert-butyl ether acetate; lactones such as γ-butyrolactone (GBL); and high-boiling alcohols such as diethylene glycol, propylene glycol, glycerol, 1,4-butanediol, and 1,3-butanediol, which may be used alone or in admixture.

The polymer solution preferably has a polymer concentration of 0.01 to 30% by weight, more preferably 0.1 to 20% by weight.

Prior to use, the reaction solution or polymer solution is preferably filtered through a filter. Filtration is effective for consistent quality because foreign particles and gel which can cause defects are removed.

Suitable materials of which the filter is made include fluorocarbon, cellulose, nylon, polyester, and hydrocarbon base materials. Preferred for the filtration of a resist composition are filters made of fluorocarbons commonly known as Teflon®, hydrocarbons such as polyethylene and polypropylene, and nylon. While the pore size of the filter may be selected appropriate to comply with the desired cleanness, the filter preferably has a pore size of up to 100 nm, more preferably up to 20 nm. A single filter may be used or a plurality of filters may be used in combination. Although the filtering method may be single pass of the solution, preferably the filtering step is repeated by flowing the solution in a circulating manner. In the polymer preparation process, the filtering step may be carried out any times, in any order and in any stage. The reaction solution as polymerized or the polymer solution may be filtered, preferably both are filtered.

The proportion (mol %) of various repeat units in the base polymer is in the following range, but not limited thereto:

(I) preferably 1 to 60 mol %, more preferably 5 to 50 mol %, even more preferably 10 to 50 mol % of repeat units of at least one type selected from repeat units (a1) and (a2):

(II) preferably 40 to 99 mol %, more preferably 50 to 95 mol %, even more preferably 50 to 90 mol % of repeat units of at least one type selected from repeat units (b1) and (b2);

(III) preferably 0 to 30 mol %, more preferably 0 to 20 mol %, even more preferably 0 to 15 mol % of repeat units of at least one type selected from repeat units (c1) to (c3): and (IV) preferably 0 to 80 mol %, more preferably 0 to 70 mol %, even more preferably 0 to 50 mol % of repeat units of at least one type derived from other monomers.

The base polymer (B) may be used alone or as a blend of two or more polymers which differ in compositional ratio, Mw and/or Mw/Mn. Component (B) may also be a blend of the base polymer defined above and a hydrogenated product of ring-opening metathesis polymer (ROMP). For the ROMP, reference is made to JP-A 2003-066612.

(C) Organic Solvent

The resist composition may comprise (C) an organic solvent. The organic solvent used herein is not particularly limited as long as the foregoing and other components are soluble therein. Suitable solvents include ketones such as cyclopentanone, cyclohexanone, and methyl-2-n-pentyl ketone; alcohols such as 3-methoxybutanol, 3-methyl-3-methoxybutanol, 1-methoxy-2-propanol, and 1-ethoxy-2-propanol; keto-alcohols such as diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone (GBL), and mixtures thereof.

Of the foregoing organic solvents, it is recommended to use 1-ethoxy-2-propanol, PGMEA, cyclohexanone, GBL, DAA and mixtures thereof because the base polymer (B) is most soluble therein.

The organic solvent (C) is preferably added in an amount of 200 to 5,000 parts by weight, and more preferably 400 to 3,500 parts by weight per 80 parts by weight of the base polymer (B). The organic solvent may be used alone or in admixture.

(D) Photoacid Generator

The resist composition may comprise (D) a photoacid generator. The PAG is not particularly limited as long as it is capable of generating an acid upon exposure to KrF excimer laser radiation, ArF excimer laser radiation, EB, or EUV, collectively referred to as high-energy radiation. The preferred PAG is a salt having the formula (2-1) or (2-2).

(2-1)

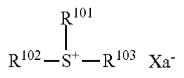

(2-2)

$R^{104}—I^{+}—R^{105}\ Xa^{-}$

In formulae (2-1) and (2-2), $R^{101}$ to $R^{105}$ are each independently a $C_1$-$C_{20}$ hydrocarbyl group which may contain a heteroatom. Any two of $R^{101}$, $R^{102}$ and $R^{103}$ may bond together to form a ring with the sulfur atom to which they are attached. Examples of the hydrocarbyl group are as exemplified above for $R^{31}$ to $R^{35}$ in formulae (c4) and (c5).

Examples of the cation in the sulfonium salt having formula (2-1) are as exemplified above for the sulfonium cation having formula (c4). Examples of the cation in the iodonium salt having formula (2-2) are as exemplified above for the iodonium cation having formula (c5).

In formulae (2-1) and (2-2), Xa- is an anion selected from the formulae (2A) to (2D).

(2A)

$R^{fa}—CF_2—SO_3^{-}$

-continued (2B)

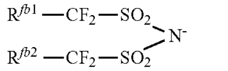

(2C)

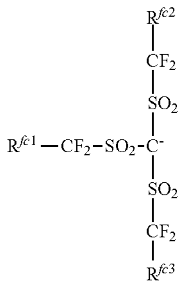

(2D)

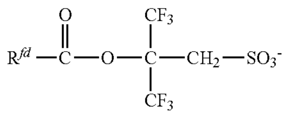

In formula (2A), $R^{fa}$ is fluorine or a $C_1$-$C_{40}$ hydrocarbyl group which may contain a heteroatom. The hydrocarbyl group may be saturated or unsaturated and straight, branched or cyclic. Examples thereof are as will be exemplified later for $R^{111}$ in formula (2A').

Of the anions having formula (2A), anions having the formula (2A') are preferred.

(2A')

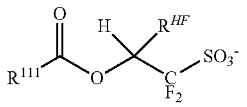

In formula (2A'), $R^{HF}$ is hydrogen or trifluoromethyl, preferably trifluoromethyl.

$R^{111}$ is a $C_1$-$C_{38}$ hydrocarbyl Group which may contain a heteroatom. Of the hydrocarbyl groups, those of 6 to 30 carbon atoms are preferred because a high resolution is available in fine pattern formation. The hydrocarbyl group $R^{111}$ may be saturated or unsaturated and straight, branched or cyclic. Examples thereof include $C_1$-$C_{38}$ alkyl groups such as methyl, ethyl, propyl, isopropyl, butyl, isobutyl, sec-butyl, tert-butyl, pentyl, neopentyl, hexyl, heptyl, octyl, 2-ethylhexyl, nonyl, decyl, undecyl, dodecyl, tridecyl, pentadecyl, heptadecyl, and icosanyl; $C_3$-$C_{38}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl; $C_2$-$C_{38}$ unsaturated aliphatic hydrocarbyl groups such as allyl and 3-cyclohexenyl: $C_6$-$C_{38}$ aryl groups such as phenyl, 1-naphthyl and 2-naphthyl; and $C_7$-$C_{38}$ aralkyl groups such as benzyl and diphenylmethyl.

In the foregoing groups, some or all of the hydrogen atoms may be substituted by a moiety containing a heteroatom such as oxygen, sulfur, nitrogen or halogen, or any constituent —$CH_2$— may be replaced by a moiety containing a heteroatom such as oxygen, sulfur or nitrogen, so that the group may contain a hydroxy, fluorine, chlorine, bromine, iodine, cyano, carbonyl, ether bond, ester bond, sulfonic ester bond, carbonate bond, lactone ring, sultone ring, carboxylic anhydride (—C(═O)—O—C(═O)—) or haloalkyl moiety. Examples of the heteroatom-containing hydrocarbyl group include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, 5-hydroxy-1-adamantyl, 5-tert-butylcarbonyloxy-1-adamantyl, 4-oxatricyclo[4.2.1.$0^{3,7}$]nonan-5-on-2-yl, and 3-oxocyclohexyl.

With respect to the synthesis of the sulfonium salt having an anion of formula (2A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153614.

Examples of the anion having formula (2A) are as exemplified above for the anions having formulae (c1-1) and (c1-2).

In formula (2B), $R^{fb1}$ and $R^{fb2}$ are each independently fluorine or a $C_1$-$C_{40}$ hydrocarbyl group which may contain a heteroatom. The hydrocarbyl group may be saturated or unsaturated and straight, branched or cyclic. Examples thereof are as exemplified above for $R^{111}$ in formula (2A'). Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: —$CF_2$—$SO_2$—$N^-$—$SO_2$—$CF_2$— to which they are attached. It is preferred that a combination of $R^{fb1}$ and $R^{fb2}$ be a fluorinated ethylene or fluorinated propylene group.

In formula (2C), $R^{fc1}$, $R^{fc2}$ and $R^{fc3}$ are each independently fluorine or a $C_1$-$C_{40}$ hydrocarbyl group which may contain a heteroatom. The hydrocarbyl group may be saturated or unsaturated and straight, branched or cyclic. Examples thereof are as exemplified for $R^{111}$. Preferably $R^{fc1}$, $R^{fc2}$ and $R^{fc3}$ are fluorine or $C_1$-$C_4$ straight fluorinated alkyl groups. Also, $R^{fc1}$ and $R^{fc2}$ may bond together to form a ring with the linkage: —$CF_2$—$SO_2$—C—$SO_2$—$CF_2$— to which they are attached. It is preferred that a combination of $R^{fc1}$ and $R^{fc2}$ be a fluorinated ethylene or fluorinated propylene group.

In formula (2D), $R^{fd}$ is a $C_1$-$C_{40}$ hydrocarbyl group which may contain a heteroatom. The hydrocarbyl group may be saturated or unsaturated and straight, branched or cyclic. Examples thereof are as exemplified above for $R^{111}$.

With respect to the synthesis of the sulfonium salt having an anion of formula (2D), reference may be made to JP-A 2010-215608 and JP-A 2014-133723.

Examples of the anion having formula (2D) are as exemplified for the anion having formula (1D) in JP-A 2018-197853.

Notably, the compound having the anion of formula (2D) does not have fluorine at the α-position relative to the sulfo group, but two trifluoromethyl groups at the n-position. For this reason, it has a sufficient acidity to sever the acid labile groups in the base polymer. Thus the compound is an effective PAG.

Also, a compound having the formula (3) is preferred as the PAG (D).

(3)

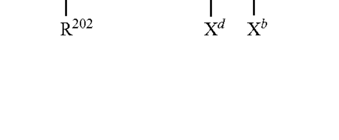

In formula (3), $R^{201}$ and $R^{202}$ are each independently a $C_1$-$C_{30}$ hydrocarbyl group which may contain a heteroatom. $R^{203}$ is a $C_1$-$C_{30}$ hydrocarbylene group which may contain a heteroatom. Any two of $R^{201}$, $R^{202}$ and may bond together to form a ring with the $R^{203}$ sulfur atom to which they are attached.

The hydrocarbyl groups $R^{201}$ and $R^{202}$ may be saturated or unsaturated and straight, branched or cyclic. Examples thereof include $C_1$-$C_{30}$ alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; $C_3$-$C_{30}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.$0^{2,6}$]decanyl, and adamantyl; and $C_6$-$C_{30}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl, and anthracenyl, and combinations thereof. In these hydrocarbyl groups, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain a hydroxy, fluorine, chlorine, bromine, iodine, cyano, carbonyl, ether bond, ester bond, sulfonic ester bond, carbonate bond, lactone ring, sultone ring, carboxylic anhydride (—C(═O)—O—C(═O)—) or haloalkyl moiety.

The hydrocarbylene group $R^{203}$ may be saturated or unsaturated and straight, branched or cyclic. Examples thereof include $C_1$-$C_{30}$ alkanediyl groups such as methanediyl, ethane-1,1-diyl, ethane-1,2-diyl, propane-1,3-diyl, butane-1,4-diyl, pentane-1,5-diyl, hexane-L6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_{30}$ cyclic saturated hydrocarbylene groups such as cyclopentanediyl, cyclohexanediyl, norbomanediyl and adamantanediyl; and $C_6$-$C_{30}$ arylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, sec-butylnaphthylene, and tert-butylnaphthylene, and combinations thereof. In these hydrocarbylene groups, some or all of the hydrogen atoms may be substituted by a moiety containing a heteroatom such as oxygen, sulfur, nitrogen or halogen, or any constituent —$CH_2$— may be replaced by a moiety containing a heteroatom such as oxygen, sulfur or nitrogen, so that the group may contain a hydroxy, fluorine, chlorine, bromine, iodine, cyano, carbonyl, ether bond, ester bond, sulfonic ester bond, carbonate bond, lactone ring, sultone ring, carboxylic anhydride (—C(═O)—O—C(═O)—) or haloalkyl moiety. Of the heteroatoms, oxygen is preferred.

In formula (3), $L^A$ is a single bond, ether bond or a $C_1$-$C_{20}$ hydrocarbylene group which may contain a heteroatom. The hydrocarbylene group may be saturated or unsaturated and straight, branched or cyclic. Examples thereof are as exemplified above for the hydrocarbylene group $R^{203}$.

In formula (3), $X^a$, $X^b$, $X^c$ and $X^d$ are each independently hydrogen, fluorine or trifluoromethyl, with the proviso that at least one of $X^a$, $X^b$, $X^c$ and $X^d$ is fluorine or trifluoromethyl.

Of the PAGs having formula (3), those having formula (3') are preferred.

(3')

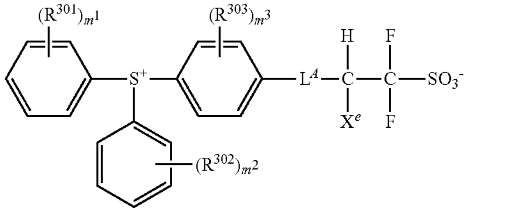

In formula (3'), $L^A$ is as defined above. $X^e$ is hydrogen or trifluoromethyl, preferably trifluoromethyl. $R^{301}$, $R^{302}$ and $R^{303}$ are each independently hydrogen or a $C_1$-$C_{20}$ hydrocarbyl group which may contain a heteroatom. The hydrocarbyl group may be saturated or unsaturated and straight, branched or cyclic. Examples thereof are as exemplified above for $R^{ill}$ in formula (2A'). The subscripts $m^1$ and $m^2$ are each independently an integer of 0 to 5, and $m^3$ is an integer of 0 to 4.

Examples of the PAG having formula (3) include those exemplified for the PAG having formula (2) in JP-A 2017-026980.

Of the foregoing PAGs, those having an anion of formula (2A') or (2D) are especially preferred because of reduced acid diffusion and high solubility in solvents. Also those having formula (3') are especially preferred because of extremely reduced acid diffusion.

When used, the PAG (D) is preferably added in an amount of 0.1 to 40 parts, and more preferably 0.5 to 20 parts by weight per 80 parts by weight of the base polymer (B). As long as the amount of the PAG is in the range, good resolution is achievable and the risk of foreign particles being formed after development or during stripping of resist film is avoided. The PAG may be used alone or in admixture.

(E) Other Quencher

The resist composition may further comprise (E) a quencher other than the amine compound having formula (1). Onium salts having the formulae (4-1) and (4-2) are useful as the other quencher (E).

$$R^{401}—SO_3^-\ \ Mq^+ \quad (4\text{-}1)$$

$$R^{402}—CO_2^-\ \ Mq^+ \quad (4\text{-}2)$$

In formula (4-1), $R^{401}$ is hydrogen or a $C_1$-$C_{40}$ hydrocarbyl group which may contain a heteroatom, exclusive of the hydrocarbyl group in which the hydrogen atom bonded to the carbon atom at α-position of the sulfo group is substituted by fluorine or fluoroalkyl.

The hydrocarbyl group $R^{401}$ may be saturated or unsaturated and straight, branched or cyclic. Examples thereof include $C_1$-$C_{40}$ alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; $C_3$-$C_{40}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; $C_6$-$C_{40}$ aryl groups such as phenyl, naphthyl and anthracenyl, and combinations thereof. In these hydrocarbyl groups, some or all hydrogen atoms may be substituted by a moiety containing a heteroatom such as oxygen, sulfur, nitrogen or halogen, or any constituent $—CH_2—$ may be replaced by a moiety containing a heteroatom such as oxygen, sulfur or nitrogen, so that the group may contain a hydroxy, fluorine, chlorine, bromine, iodine, cyano, carbonyl, ether bond, ester bond, sulfonic ester bond, carbonate bond, lactone ring, sultone ring, carboxylic anhydride ($—C(=O)—O—C(=O)—$) or haloalkyl moiety.

In formula (4-2), $R^{402}$ is hydrogen or a $C_1$-$C_{40}$ hydrocarbyl group which may contain a heteroatom. Examples of the hydrocarbyl group $R^{402}$ include those exemplified above for $R^{401}$ and fluoroalkyl groups such as trifluoromethyl and trifluoroethyl, and fluorinated aryl groups such as pentafluorophenyl and 4-trifluoromethylphenyl.

Examples of the anion in the onium salt having formula (4-1) are shown below, but not limited thereto.

$CH_3SO_3^-$ $CH_3CH_2SO_3^-$

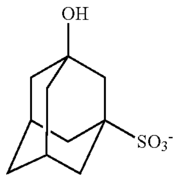

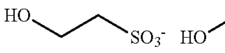

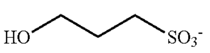

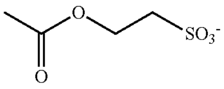

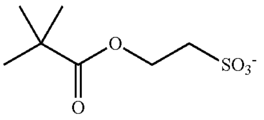

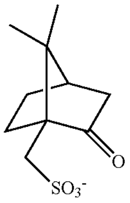

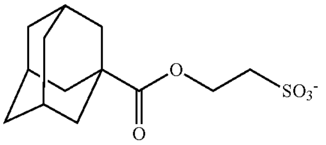

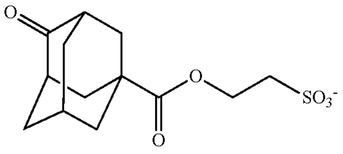

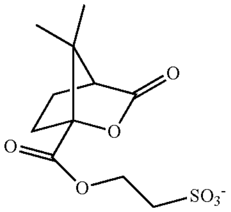

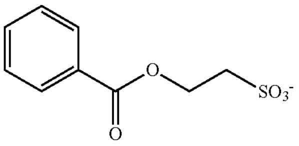

-continued
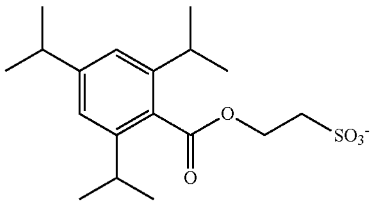
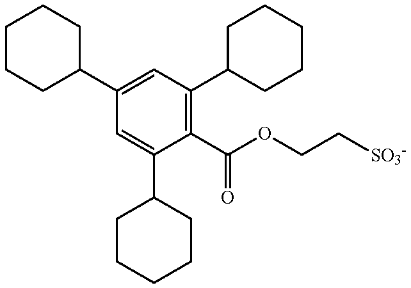
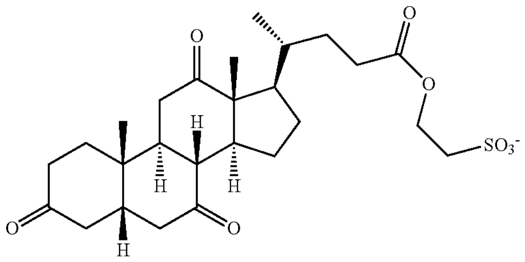
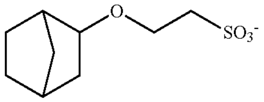
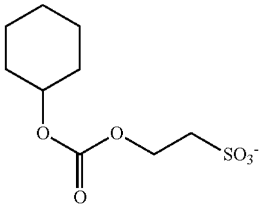
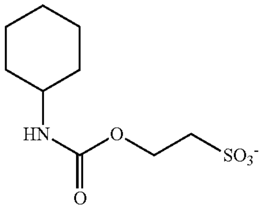
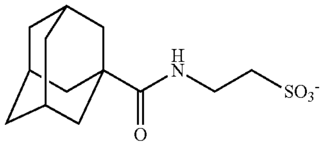
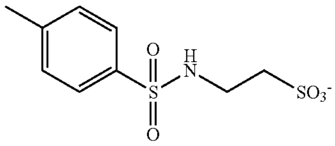
-continued
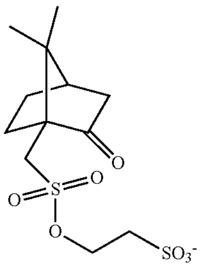
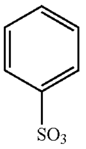
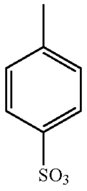
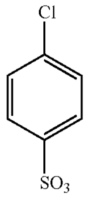
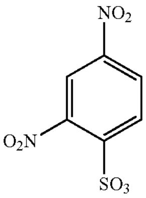
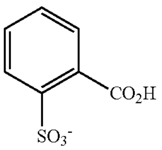
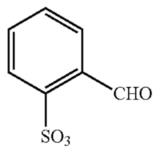
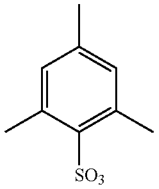
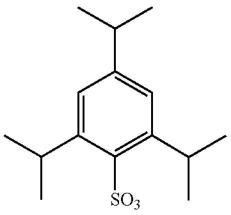
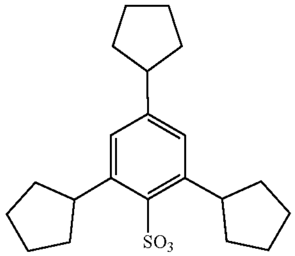
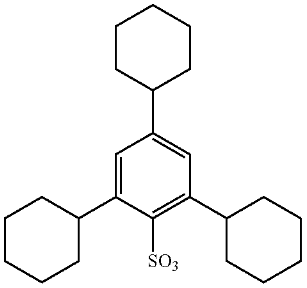
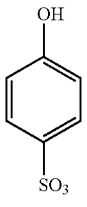
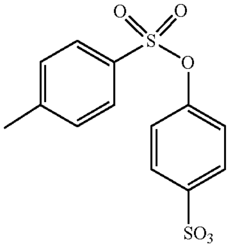
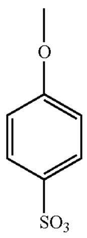
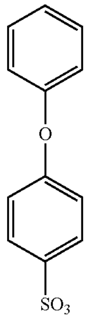

-continued
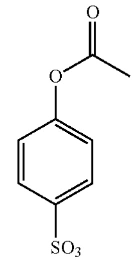 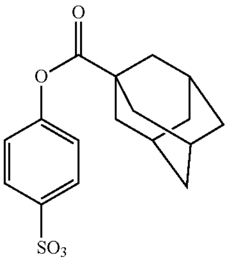
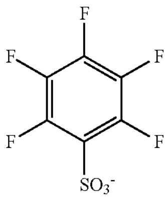 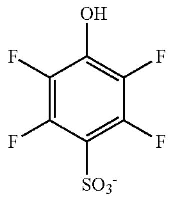 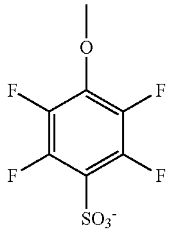
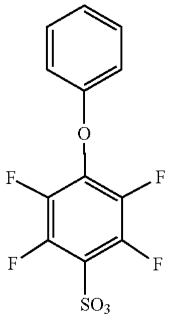 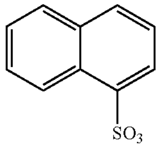
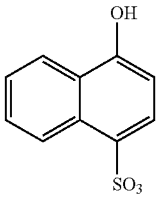 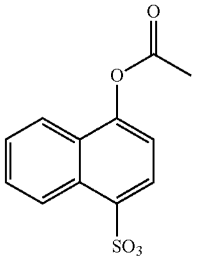 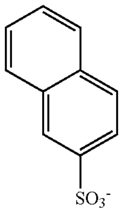
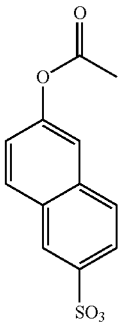 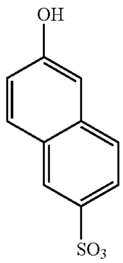 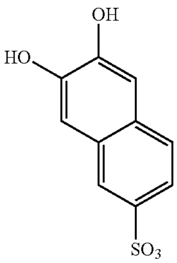
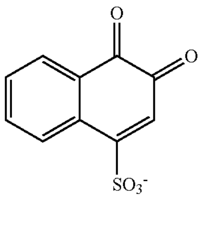 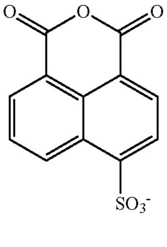
-continued
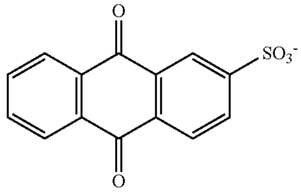
Examples of the anion in the onium salt having formula (4-2) are shown below, but not limited thereto.
$CH_3CO_2^-$ $CH_3CH_2CO_2^-$ $CH_3CH(CH_3)CO_2^-$ 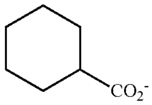
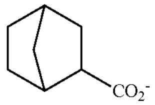 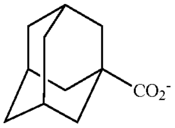 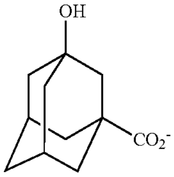
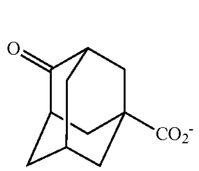 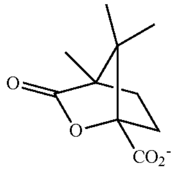
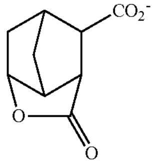 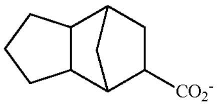
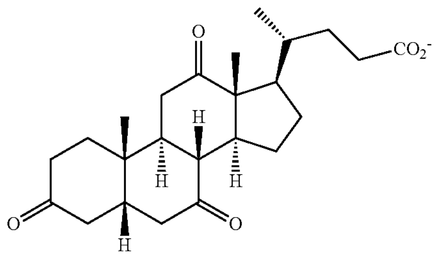
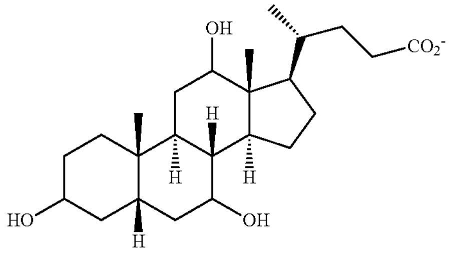

-continued
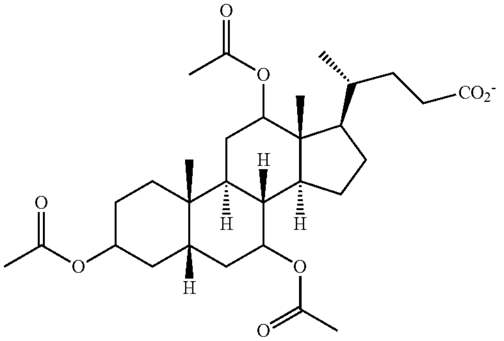
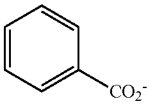
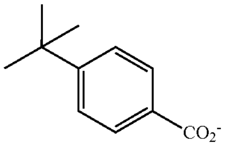
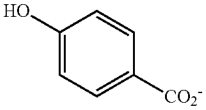
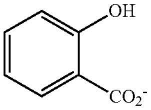
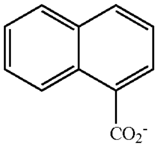
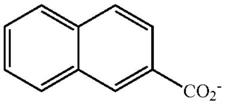
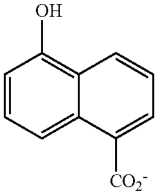
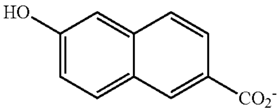
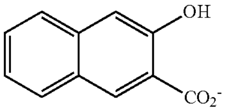
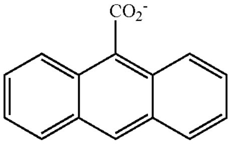
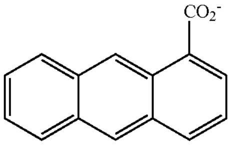
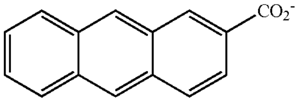
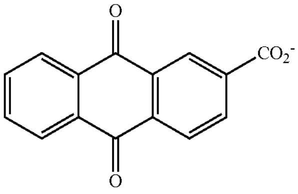
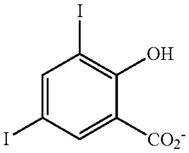
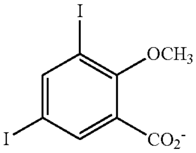
-continued
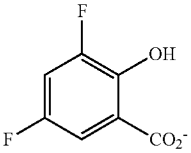
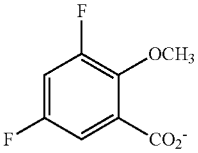
$CF_3CO_2^-$ $CF_3CH_2CO_2^-$ $CF_3CF_2CO_2^-$ $CF_3C(CH_3)(OH)CO_2^-$
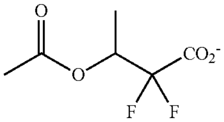
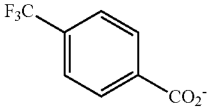
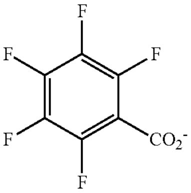
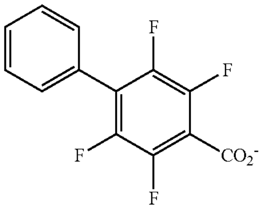
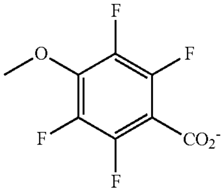
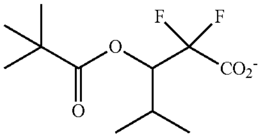
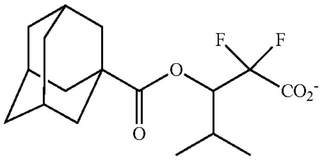
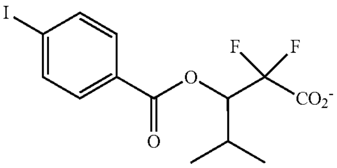
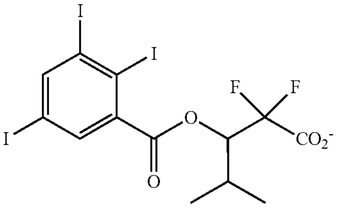
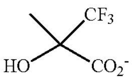
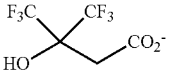
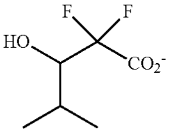
In formulae (4-1) and (4-2), $Mq^+$ is an onium cation, which is preferably selected from cations having the formulae (4A), (4B) and (4C).
(4a)
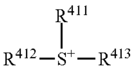
(4b)
$R^{414}—I^+—R^{415}$ -continued (4c)

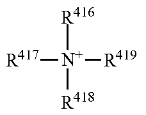

In formulae (4A) to (4C), $R^{411}$ to $R^{419}$ are each independently a $C_1$-$C_{40}$ hydrocarbyl group which may contain a heteroatom. A pair of $R^{411}$ and $R^{412}$ may bond together to form a ring with the sulfur atom to which they are attached. A pair of $R^{416}$ and $R^{417}$ may bond together to form a ring with the nitrogen atom to which they are attached. Examples of the hydrocarbyl group are as exemplified above for $R^{401}$ in formula (4-1).

Examples of the onium cation represented by $Mq^+$ are shown below, but not limited thereto.

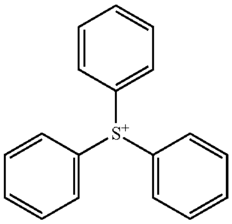
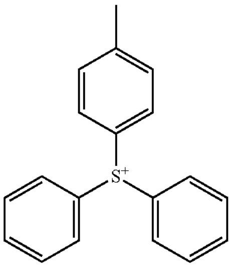
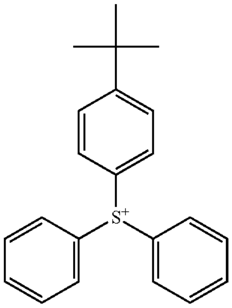
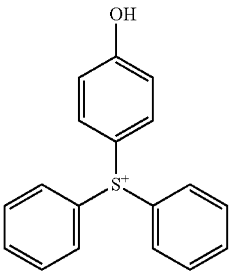
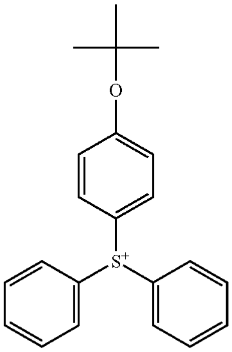
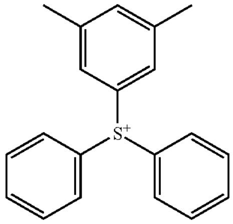
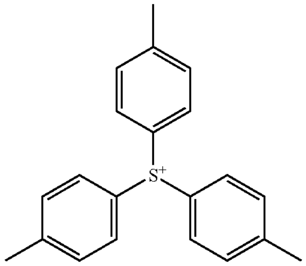

-continued

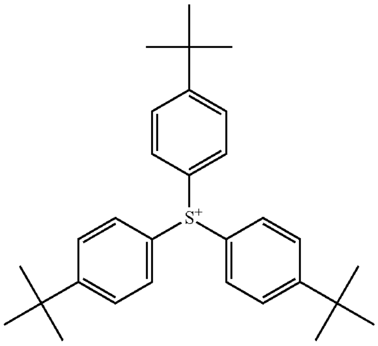
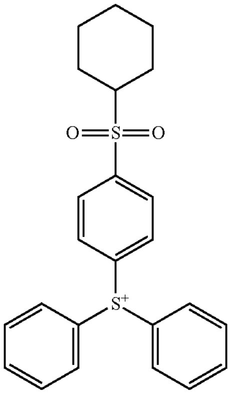
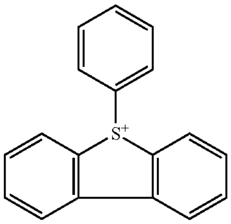
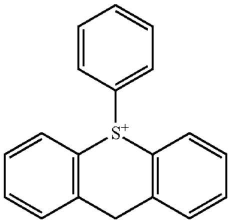
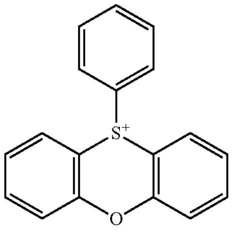
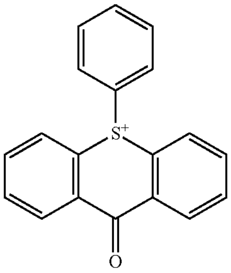
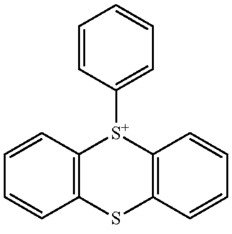
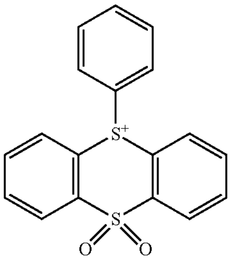
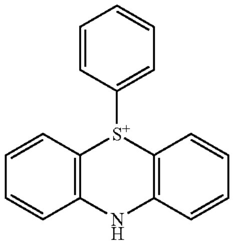

-continued
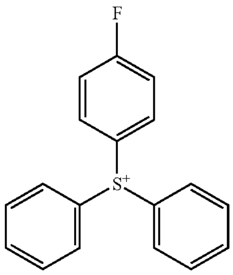
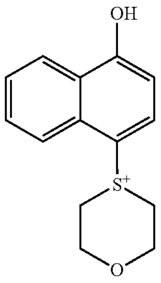
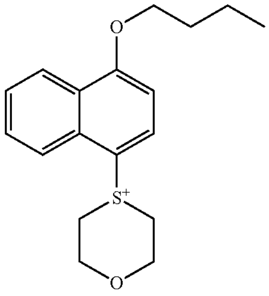
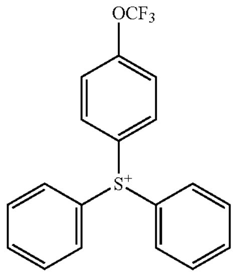
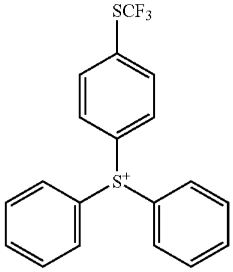
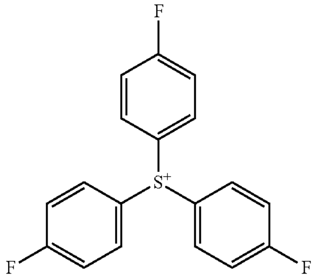
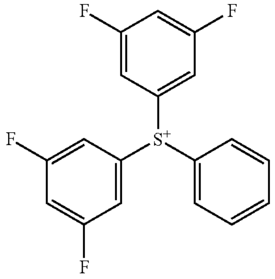
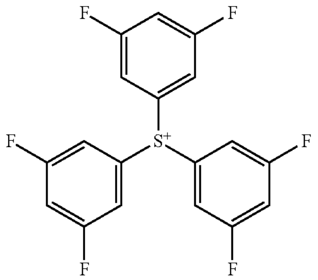
-continued
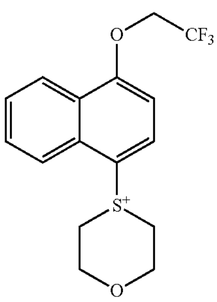
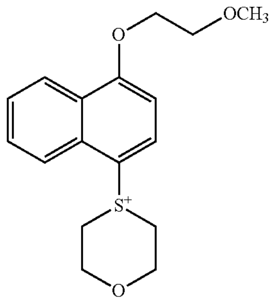
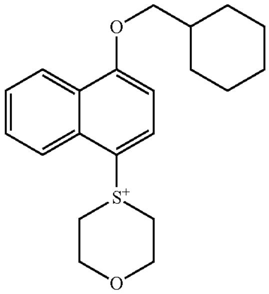
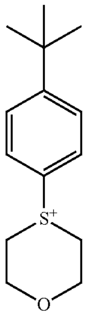
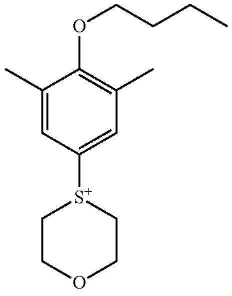
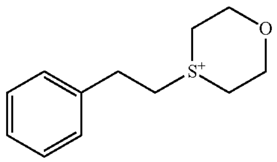
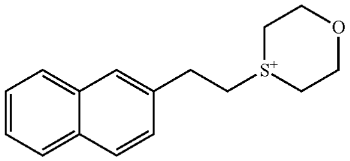
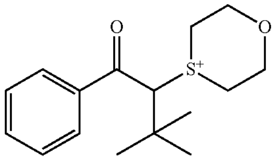
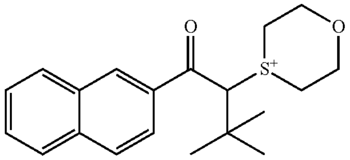
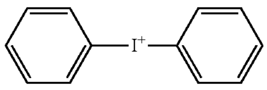
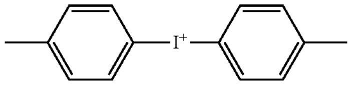
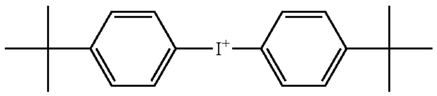

-continued

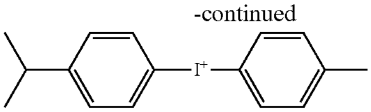
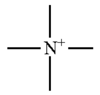
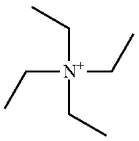
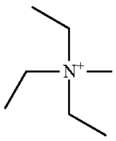
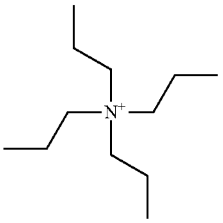
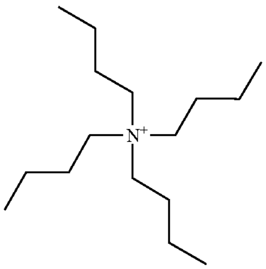
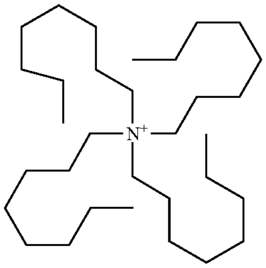
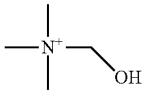
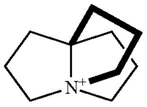
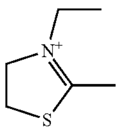
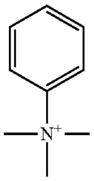
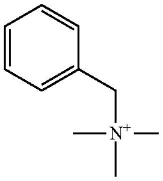
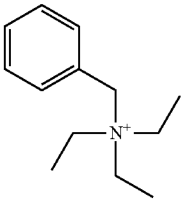
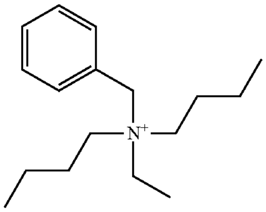

Examples of the onium salt having formula (4-1) or (4-2) include arbitrary combinations of anions with cations, both as exemplified above. These onium salts may be readily prepared by ion exchange reaction using any well-known organic chemistry technique. For the ion exchange reaction, reference may be made to JP-A 2007-145797, for example.

The onium salt having formula (4-1) or (4-2) functions as a quencher in the chemically amplified resist composition because the counter anion of the onium salt is a conjugated base of a weak acid. As used herein, the weak acid indicates an acidity insufficient to deprotect an acid labile group from an acid labile group-containing unit in the base polymer. The onium salt having formula (4-1) or (4-2) functions as a quencher when used in combination with an onium salt type PAG having a conjugated base of a strong acid (typically a sulfonic acid which is fluorinated at α-position) as the counter anion. In a system using a mixture of an onium salt capable of generating a strong acid (e.g., α-position fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If a PAG capable of generating a strong acid is an onium salt, an exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

When the onium salt having formula (4-1) or (4-2) is used as the other quencher (E), the amount of the onium salt used is preferably 0.1 to 10 parts by weight, more preferably 0.1 to 5 parts by weight per 80 parts by weight of the base polymer (B). As long as the amount of component (E) is in the range, a satisfactory resolution is available without a substantial lowering of sensitivity. The onium salt having formula (4-1) or (4-2) may be used alone or in admixture.

Also, nitrogen-containing compounds other than component (A) may be used as the other quencher (E). Suitable nitrogen-containing compounds include primary, secondary and tertiary amine compounds, specifically amine compounds having a hydroxy group, ether bond, ester bond, lactone ring, cyano group or sulfonic ester bond, as described in JP-A 2008-111103, paragraphs [0146]-[0164] (U.S. Pat. No. 7,537,880), and primary or secondary amine compounds protected with a carbamate group, as described in JP 3790649.

A sulfonic acid sulfonium salt having a nitrogen-containing substituent may also be used as the nitrogen-containing compound. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595 and JP-A 2012-046501, for example.

When the nitrogen-containing compound is used as the other quencher (E), the amount of the nitrogen-containing compound used is preferably 0.001 to 12 parts by weight, more preferably 0.01 to 8 parts by weight per 80 parts by weight of the base polymer (B). The nitrogen-containing compound may be used alone or in admixture.

(F) Surfactant

The resist composition may further include (F) a surfactant which is insoluble or substantially insoluble in water and soluble in alkaline developer, and/or a surfactant which is insoluble or substantially insoluble in water and alkaline developer. For the surfactant, reference should be made to those compounds described in JP-A 2010-215608 and JP-A 2011-016746.

While many examples of the surfactant which is insoluble or substantially insoluble in water and alkaline developer are described in the patent documents cited herein, preferred examples are surfactants FC-4430 (3M), Olfine® E1004 (Nissin Chemical Co., Ltd.), Stuflon® S-381, KH-20 and KH-30 (AGC Seimi Chemical Co., Ltd.). Partially fluorinated oxetane ring-opened polymers having the formula (surf-1) are also useful.

(surf-1)

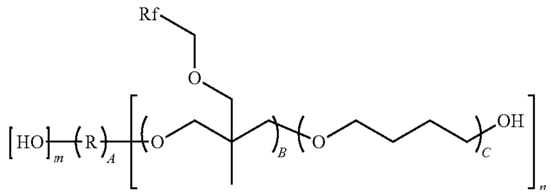

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent aliphatic groups include ethylene, 1,4-butylene, 1,2-propylene, 2,2-dimethyl-1,3-propylene and 1,5-pentylene. Exemplary tri- and tetra-valent groups are shown below.

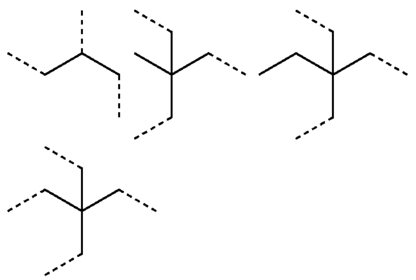

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of in and n, which represents the valence of R, is an integer of 2 to 4. "A" is equal to 1, B is an integer of 2 to 25, and C is au integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water sliding.

Suitable polymeric surfactants include those containing repeat units of at least one type selected from the formulae (5A) to (5E).

(5A)

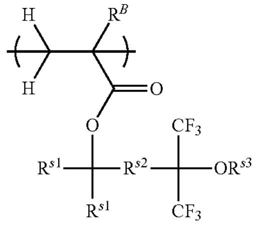

(5B)

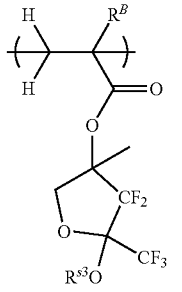

(5C)

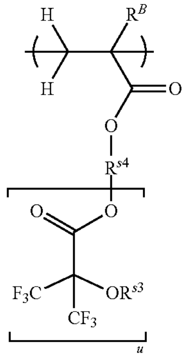

(5D)

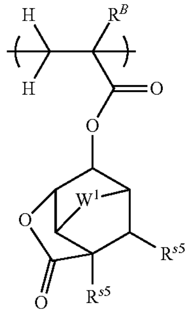

-continued

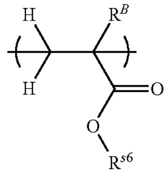

(5E)

Herein, $R^B$ is hydrogen, fluorine, methyl or trifluoromethyl. W' is —$CH_2$—, —$CH_2CH_2$— or —O—, or two separate —H. $R^{s1}$ is each independently hydrogen or a $C_1$-$C_{10}$ hydrocarbyl group. $R^{s2}$ is a single bond or a $C_1$-$C_5$ straight or branched hydrocarbylene group. $R^{s3}$ is each independently hydrogen, a $C_1$-$C_{15}$ hydrocarbyl or fluorinated hydrocarbyl group, or an acid labile group. When $R^{s3}$ is a hydrocarbyl or fluorinated hydrocarbyl group, an ether bond or carbonyl moiety may intervene in a carbon-carbon bond. $R^{s4}$ is a $C_1$-$C_{20}$ (u+1)-valent hydrocarbon or fluorinated hydrocarbon group, and u is an integer of 1 to 3. $R^{s5}$ is each independently hydrogen or a group: —C(═O)—O—$R^{s7}$ wherein $R^{s7}$ is a $C_1$-$C_{20}$ fluorinated hydrocarbyl group. $R^{s6}$ is a $C_1$-$C_{15}$ hydrocarbyl or fluorinated hydrocarbyl group in which an ether bond or carbonyl moiety may intervene in a carbon-carbon bond.

The hydrocarbyl group represented by $R^{s1}$ may be straight, branched or cyclic. Examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbornyl. Inter glia, $C_1$-$C_6$ hydrocarbyl groups are preferred.

The hydrocarbylene group represented by $R^{s2}$ may be straight, branched or cyclic. Examples thereof include methylene, ethylene, propylene, butylene and pentylene.

The hydrocarbyl group represented by $R^{s3}$ or $R^{s6}$ may be straight, branched or cyclic. Examples thereof include alkyl, alkenyl and alkynyl groups, with the alkyl groups being preferred. Suitable alkyl groups include those exemplified for the hydrocarbyl group represented by $R^{s1}$ as well as n-undecyl, n-dodecyl, tridecyl, tetradecyl, and pentadecyl. Examples of the fluorinated hydrocarbyl group represented by $R^{s3}$ or $R^{s6}$ include the foregoing hydrocarbyl groups in which some or all carbon-bonded hydrogen atoms are substituted by fluorine atoms. In these groups, an ether bond or carbonyl moiety may intervene in a carbon-carbon bond as mentioned above.

Examples of the acid labile group represented by $R^{s3}$ include groups of the above formulae (L1) to (L4), $C_4$-$C_{20}$, preferably $C_4$-$C_{15}$ tertiary hydrocarbyl groups, trialkylsilyl groups in which each alkyl moiety has 1 to 6 carbon atoms, and $C_4$-$C_{20}$ oxoalkyl groups.

The (u+1)-valent hydrocarbon or fluorinated hydrocarbon group represented by $R^{s4}$ may be straight, branched or cyclic and examples thereof include the foregoing hydrocarbyl or fluorinated hydrocarbyl groups from which the number (u) of hydrogen atoms are eliminated.

The fluorinated hydrocarbyl group represented by $R^{s7}$ may be straight, branched or cyclic. Examples thereof include the foregoing hydrocarbyl groups in which some or all hydrogen atoms are substituted by fluorine atoms. Illustrative examples include trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, 2-(perfluorooctyl)ethyl, and 2-(perfluorodecyl)ethyl.

Examples of the repeat units having formulae (5A) to (5E) are shown below, but not limited thereto. Herein $R^B$ is as defined above.

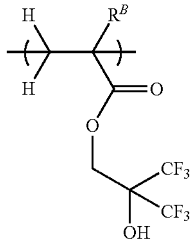
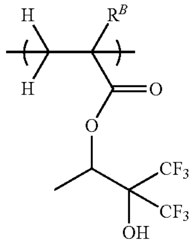
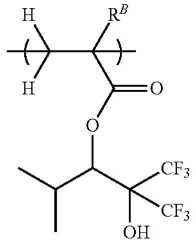
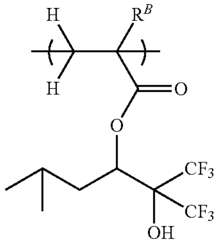
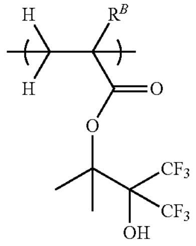
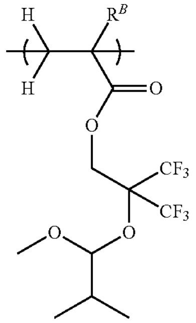
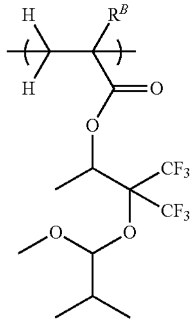
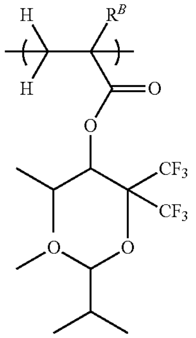
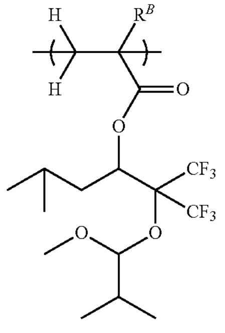
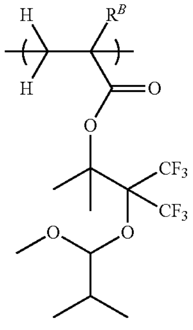

-continued
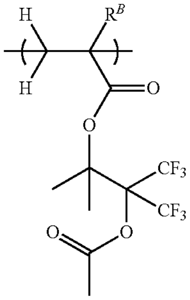
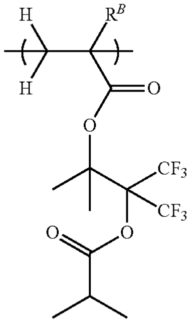
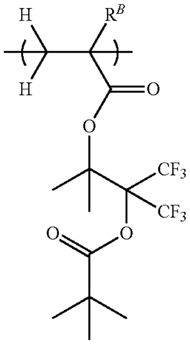
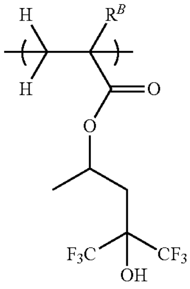
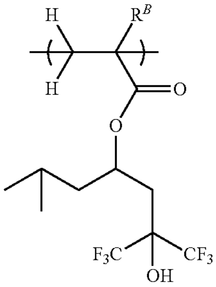
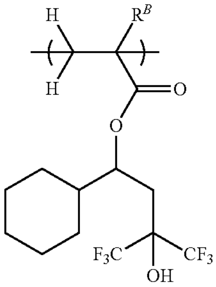
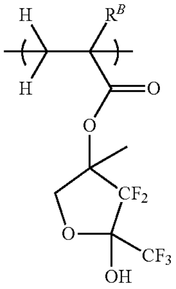
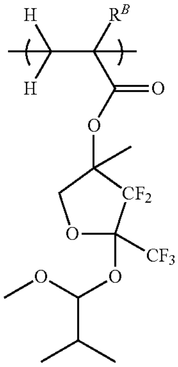
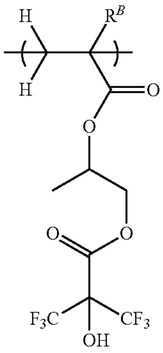
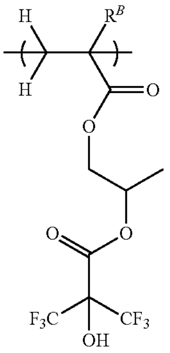
-continued
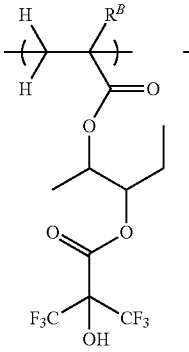
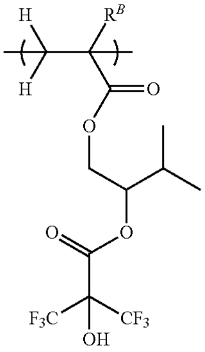
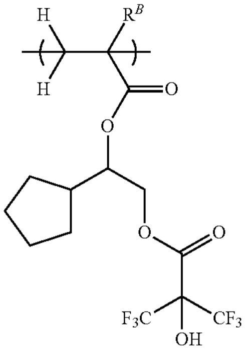
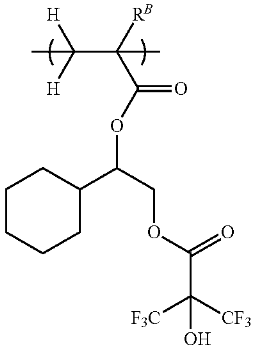
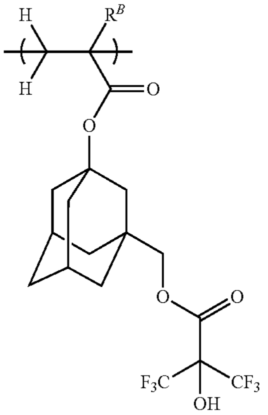
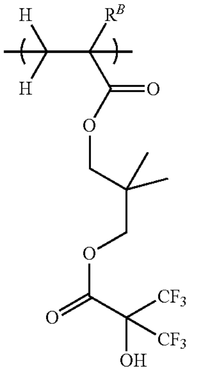
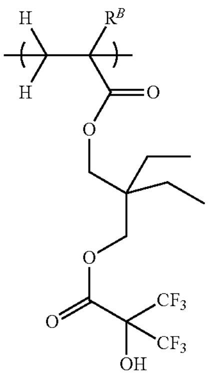
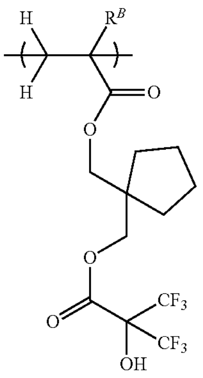

-continued
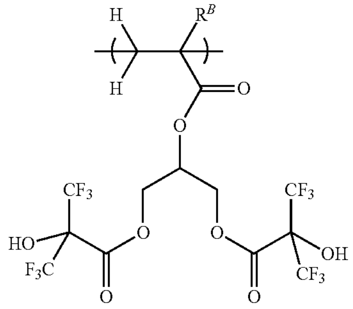
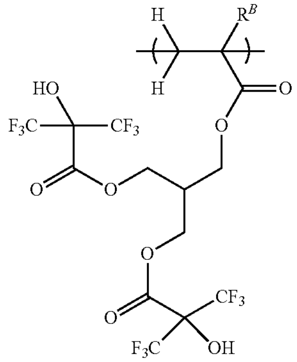
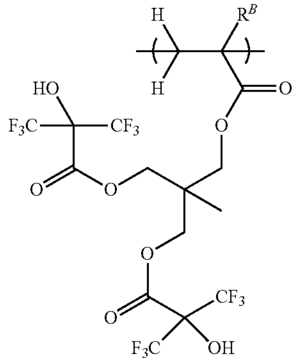
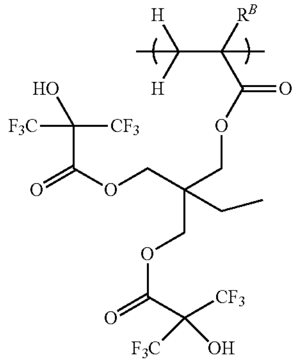
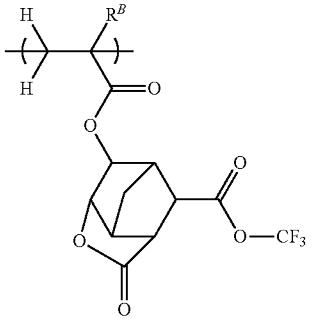
-continued
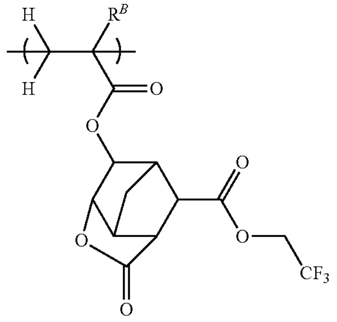
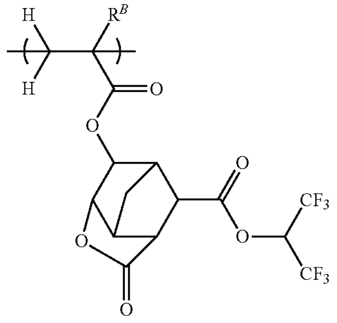
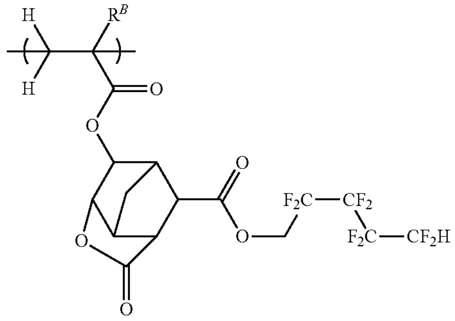
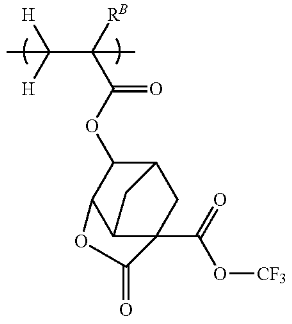
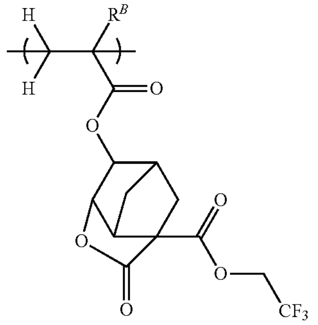

-continued
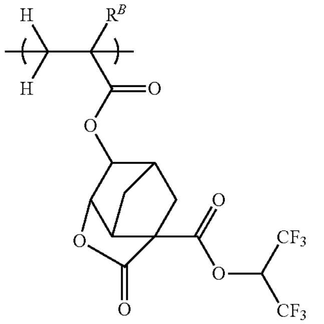
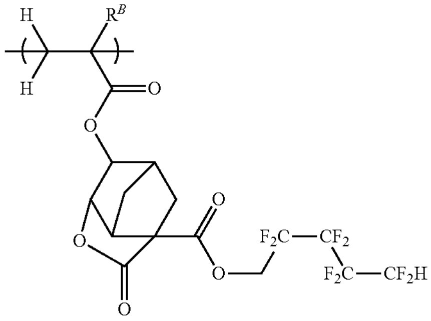
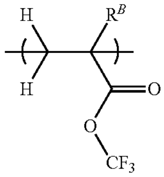
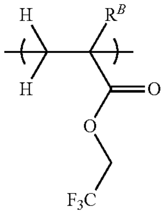
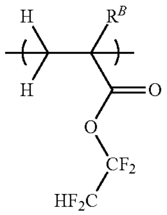
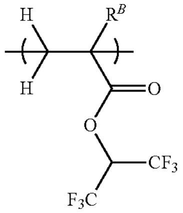
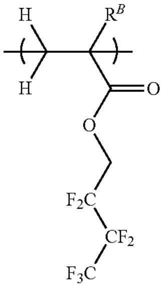
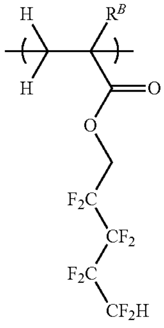
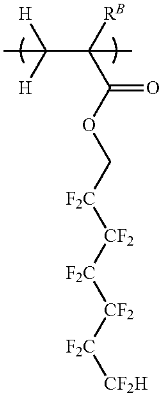
-continued
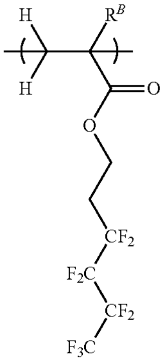
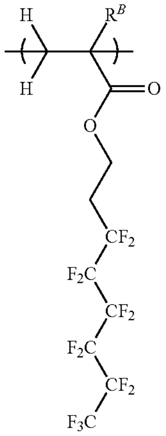
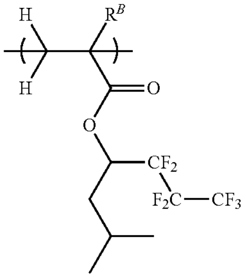
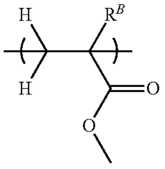
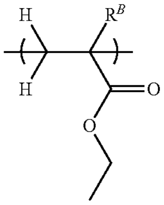
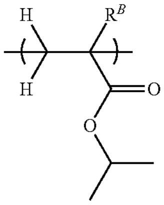
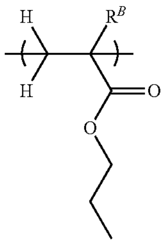
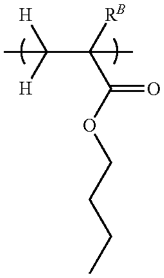
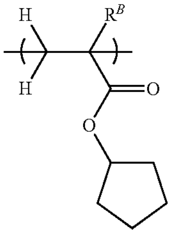
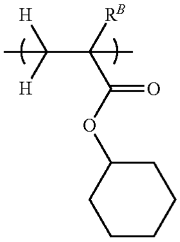
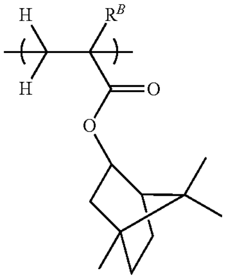

-continued

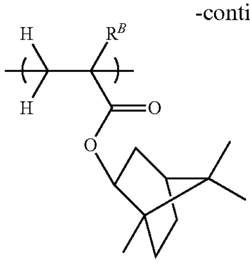

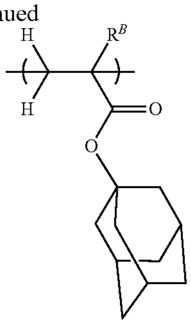

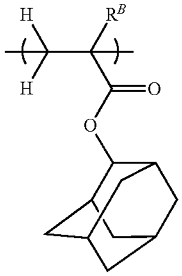

The polymeric surfactant may further contain repeat units other than the repeat units having formulae (5A) to (5E). Typical other repeat units are those derived from methacrylic acid and α-trifluoromethylacrylic acid derivatives. In the polymeric surfactant, the content of the repeat units having formulae (5A) to (5E) is preferably at least 20 mol %, more preferably at least 60 mol %, most preferably 100 mol % of the overall repeat units.

The polymeric surfactant preferably has a Mw of 1,000 to 500,000, more preferably 3,000 to 100,000 and a Mw/Mn of 1.0 to 2.0, more preferably 1.0 to 1.6.

The polymeric surfactant may be synthesized by any desired method, for example, by dissolving an unsaturated bond-containing monomer or monomers providing repeat units having formula (5A) to (5E) and optionally other repeat units in an organic solvent, adding a radical initiator, and heating for polymerization. Suitable organic solvents used herein include toluene, benzene, THF, diethyl ether, and dioxane. Examples of the polymerization initiator used herein include AIBN, 2,2'-azobis(2,4-dimethylvaleronitrile), dimethyl 2,2-azobis(2-methylpropionate), benzoyl peroxide, and lauroyl peroxide. Preferably the reaction temperature is 50 to 100° C. and the reaction time is 4 to 24 hours. The acid labile group that has been incorporated in the monomer may be kept as such, or the polymer may be protected or partially protected therewith at the end of polymerization.

During the synthesis of polymeric surfactant, any known chain transfer agent such as dodecyl mercaptan or 2-mercaptoethanol may be added for molecular weight control purpose. The amount of chain transfer agent added is preferably 0.01 to 10 mol % based on the total moles of monomers to be polymerized.

When the resist composition contains a surfactant (F), the amount thereof is preferably 0.1 to 50 parts by weight, and more preferably 0.5 to 10 parts by weight per 80 parts by weight of the base polymer (B). At least 0.1 part of the surfactant is effective in improving the receding contact angle with water of the resist film at its surface. Up to 50 parts of the surfactant is effective in forming a resist film having a low rate of dissolution in a developer and capable of maintaining the height of a fine pattern formed therein.

Other Components

The resist composition may further comprise another component, for example, a compound which is decomposed with an acid to generate another acid (i.e., acid amplifier compound), an organic acid derivative, a fluorinated alcohol, and a compound having a Mw of up to 3,000 which changes its solubility in developer under the action of an acid (i.e., dissolution inhibitor). Specifically, the acid amplifier compound is described in JP-A 2009-269953 and JP-A 2010-215608 and preferably used in an amount of 0 to 5 parts, more preferably 0 to 3 parts by weight per 80 parts by weight of the base polymer (B). An extra amount of the acid amplifier compound can make the acid diffusion control difficult and cause degradations to resolution and pattern profile. With respect to the remaining additives, reference should be made to JP-A 2009-269953 and JP-A 2010-215608.

Process

A further embodiment of the invention is a process of forming a pattern from the resist composition defined above by lithography. The preferred process includes the steps of applying the resist composition to form a resist film on a substrate, exposing the resist film to KrF excimer laser, ArF excimer laser, EB or EUV, and developing the exposed resist film in a developer. Any desired steps may be added to the process if necessary.

The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc.

The resist composition is applied onto a substrate by a suitable coating technique such as spin coating. The coating is prebaked on a hot plate preferably at a temperature of 60 to 150° C. for 1 to 10 minutes, more preferably at 80 to 140° C. for 1 to 5 minutes. The resulting resist film preferably has a thickness of 0.05 to 2 μm.

Then the resist film is exposed patternwise to KrF or ArF excimer laser, EUV or EB. On use of KrF excimer laser, ArF excimer laser or EUV of wavelength 13.5 nm, the resist film is exposed through a mask having a desired pattern, preferably in a dose of 1 to 200 $mJ/cm^2$, more preferably 10 to 100 $mJ/cm^2$. On use of EB, a pattern may be written directly or through a mask having the desired pattern, preferably in a dose of 1 to 300 $\mu C/cm^2$, more preferably 10 to 200 $\mu C/cm^2$.

The exposure may be performed by conventional lithography whereas the immersion lithography of holding a liquid having a refractive index of at least 1.0 between the resist film and the projection lens may be employed if desired. The liquid is typically water, and in this case, a protective film which is insoluble in water may be formed on the resist film.

While the water-insoluble protective film serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In the development step, the exposed region of resist film is dissolved away, and a desired resist pattern is formed on the substrate.

Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning process may be used for pattern formation. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, negative tone development may also be used. That is, an organic solvent may be used instead of the aqueous alkaline solution as the developer for developing and dissolving away the unexposed region of the resist film.

The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLES

Synthesis Examples, Examples and Comparative Examples are given below by way of illustration and not by way of limitation. The abbreviation "pbw" is parts by weight. For all polymers, Mw and Mn are determined by GPC versus polystyrene standards using THF solvent. THF stands for tetrahydrofuran, and PGMEA for propylene glycol monomethyl ether acetate. Analysis is made by IR and $^{1}$H-NMR spectroscopy using analytic instruments as shown below.

IR: NICOLET 6700 by Thermo Fisher Scientific Inc.

$^{1}$H-NMR: ECA-500 by JEOL Ltd.

[1] Synthesis of Amine Compounds

Example 1-1

Synthesis of AQ-1

(1) Synthesis of Intermediate In-1

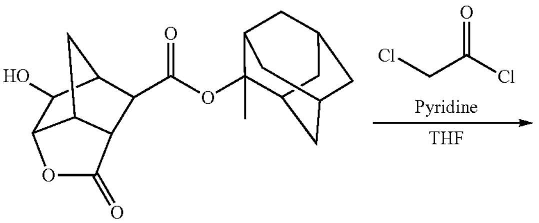

M-1

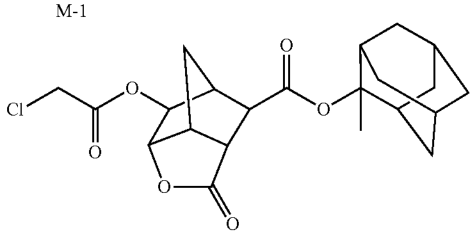

In-1

In a reactor under nitrogen atmosphere, 17.3 g of reactant M-1 and 6.8 g of chloroacetyl chloride were dissolved in 90 g of THF. The reactor was cooled below 10° C., to which a solution of 4.6 g of pyridine in 10 g of THF was added dropwise. At the end of addition, the reaction system was aged at an internal temperature of 20° C. for 4 hours. At the end of aging, the reaction system was cooled, after which 20 g of saturated sodium bicarbonate aqueous solution was added dropwise to quench the reaction. The desired compound was extracted with a solvent mixture consisting of 35 g of ethyl acetate and 35 g of THF, followed by separatory operation. The organic layer was taken out by washing twice with 20 g of saturated sodium bicarbonate aqueous solution and twice with 20 g of saturated brine. The organic layer thus separated was added dropwise to a solvent mixture of 390 g of water and 195 g of methanol, whereupon the desired compound crystallized out. The crystals were collected by filtration and dried in vacuum, obtaining Intermediate In-1 as white crystals (amount 21.1 g, yield 99%).

(2) Synthesis of AQ-1

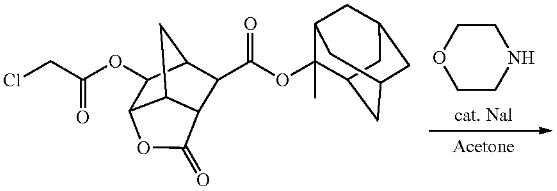

In-1

-continued

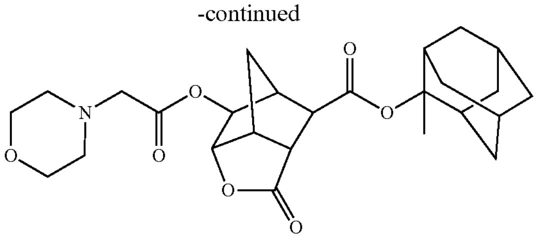

AQ-1

In nitrogen atmosphere, a reactor was charged with 20.8 g of Intermediate In-1, 0.7 g of sodium iodide, and 70 g of acetone. At room temperature, 5.2 g of morpholine was added dropwise thereto. At the end of addition, the reaction system was aged for 24 hours while heating under reflux. After the disappearance of Intermediate In-1 was confirmed by TLC, the reaction solution was cooled down to room temperature, to which 35 g of saturated sodium bicarbonate aqueous solution was added to quench the reaction. Using an evaporator, the acetone was distilled off After distillation, 105 g of methylene chloride was added for extracting the desired compound, followed by separatory operation. The organic layer was washed 4 times with 35 g of water and once with 35 g of saturated brine. The organic layer was separated and concentrated. The residue was purified through a silica gel column, obtaining AQ-1 as oily matter (amount 21.9 g, yield 85%).

AQ-1 was analyzed by IR spectroscopy, with the data shown below. FIG. 1 is the $^1$H-NMR/DMSO-$d_6$ spectrum of AQ-1.

IR (D-ATR): ν=3562, 2914, 2859, 1788, 1756, 1723, 1452, 1423, 1374, 1359, 1295, 1257, 1208, 1158, 1115, 1103, 1094, 1069, 1043, 1020, 955, 931, 902, 886, 867, 849, 819, 781, 750, 725, 530 $cm^{-1}$

Example 1-2

Synthesis of AQ-2

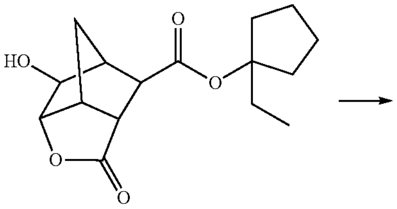

M-2

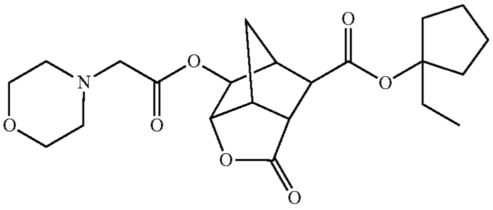

AQ-2

AQ-2 was synthesized by the same procedure as in Example 1-1 aside from using reactant M-2 instead of reactant M-1. (amount 23.3 g, yield 90%).

Figure 2:
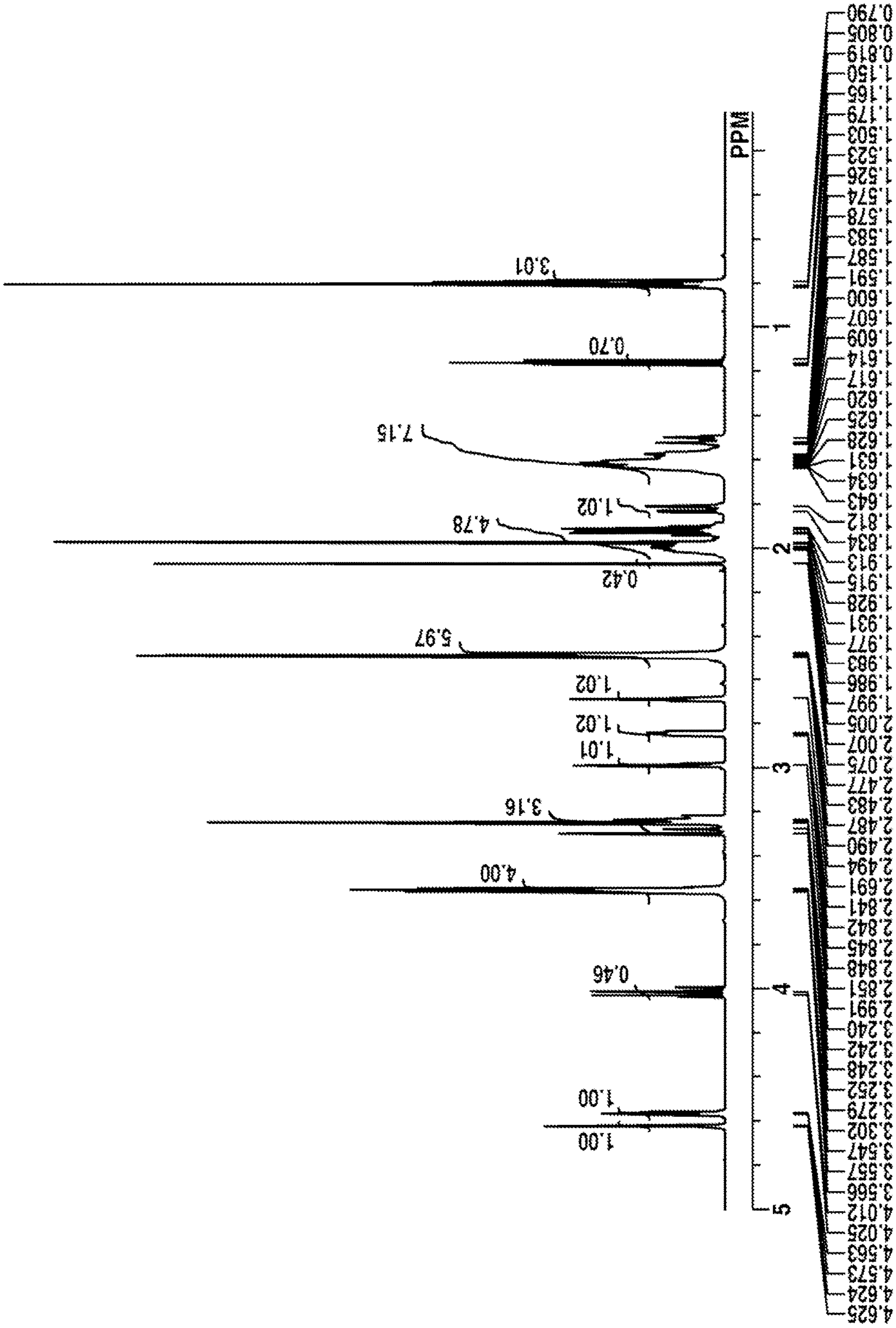
FIG. 2 is a $^{1}$H-NMR spectrum of Compound AQ-2 synthesized in Example 1-2.

AQ-2 was analyzed by IR spectroscopy, with the data shown below. FIG. 2 is the $^1$H-NMR/DMSO-$d_6$ spectrum of AQ-2.

IR (D-ATR): ν=3629, 2967, 2858, 1788, 1756, 1724, 1454, 1355, 1295, 1258, 1212, 1174, 1159, 1115, 1069, 1038, 1020, 939, 902, 867, 810, 751, 495, 441 $cm^{-1}$

Example 1-3

Synthesis of AQ-3

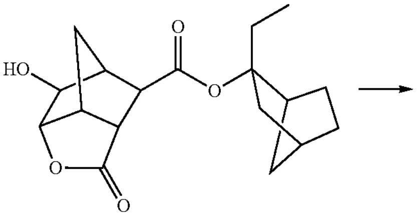

M-3

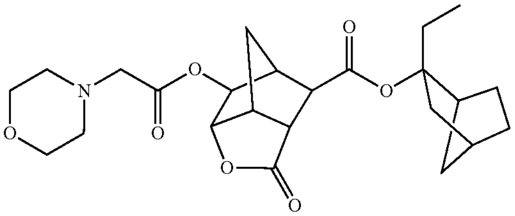

AQ-3

AQ-3 was synthesized by the same procedure as in Example 1-1 aside from using reactant M-3 instead of reactant M-1. (amount 13.7 g, yield 88%).

Figure 3:
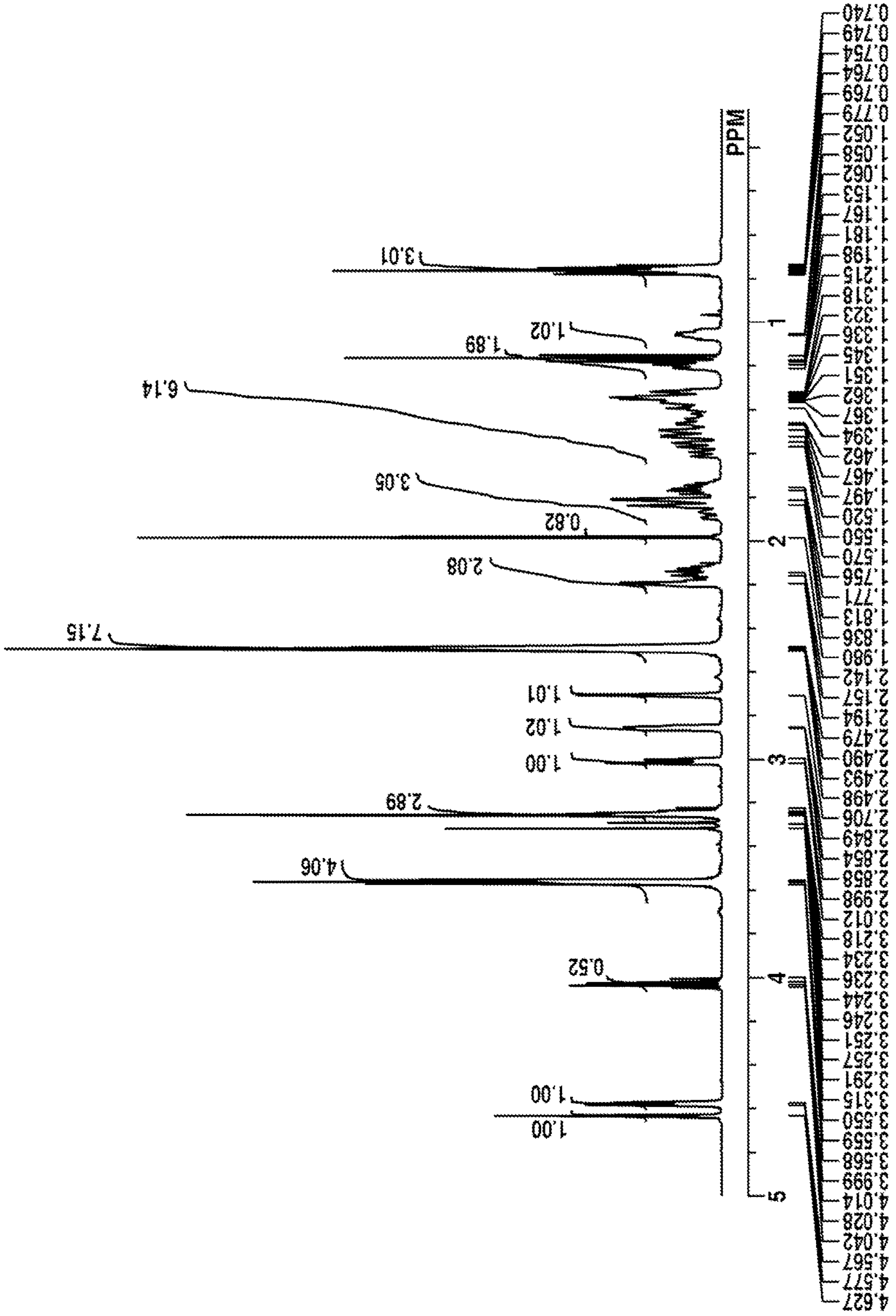
FIG. 3 is a $^{1}$H-NMR spectrum of Compound AQ-3 synthesized in Example 1-3.

AQ-3 was analyzed by IR spectroscopy, with the data shown below. FIG. 3 is the $^1$H-NMR/DMSO-$d_6$ spectrum of AQ-3.

IR (D-ATR): ν=3559, 2965, 2878, 1789, 1756, 1723, 1455, 1356, 1295, 1260, 1207, 1173, 1158, 1134, 1115, 1070, 1041, 1020, 947, 933, 902, 867, 849, 810, 764, 747, 724, 636, 492, 440 $cm^{-1}$

Example 1-4

Synthesis of AQ-4

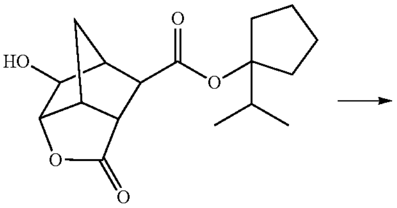

M-4

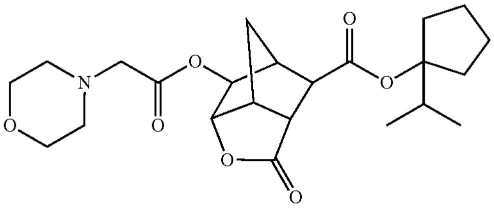

AQ-4

AQ-4 was synthesized by the same procedure as in Example 1-1 aside from using reactant M-4 instead of reactant M-1. (amount 42.5 g, yield 90%).

Figure 4:
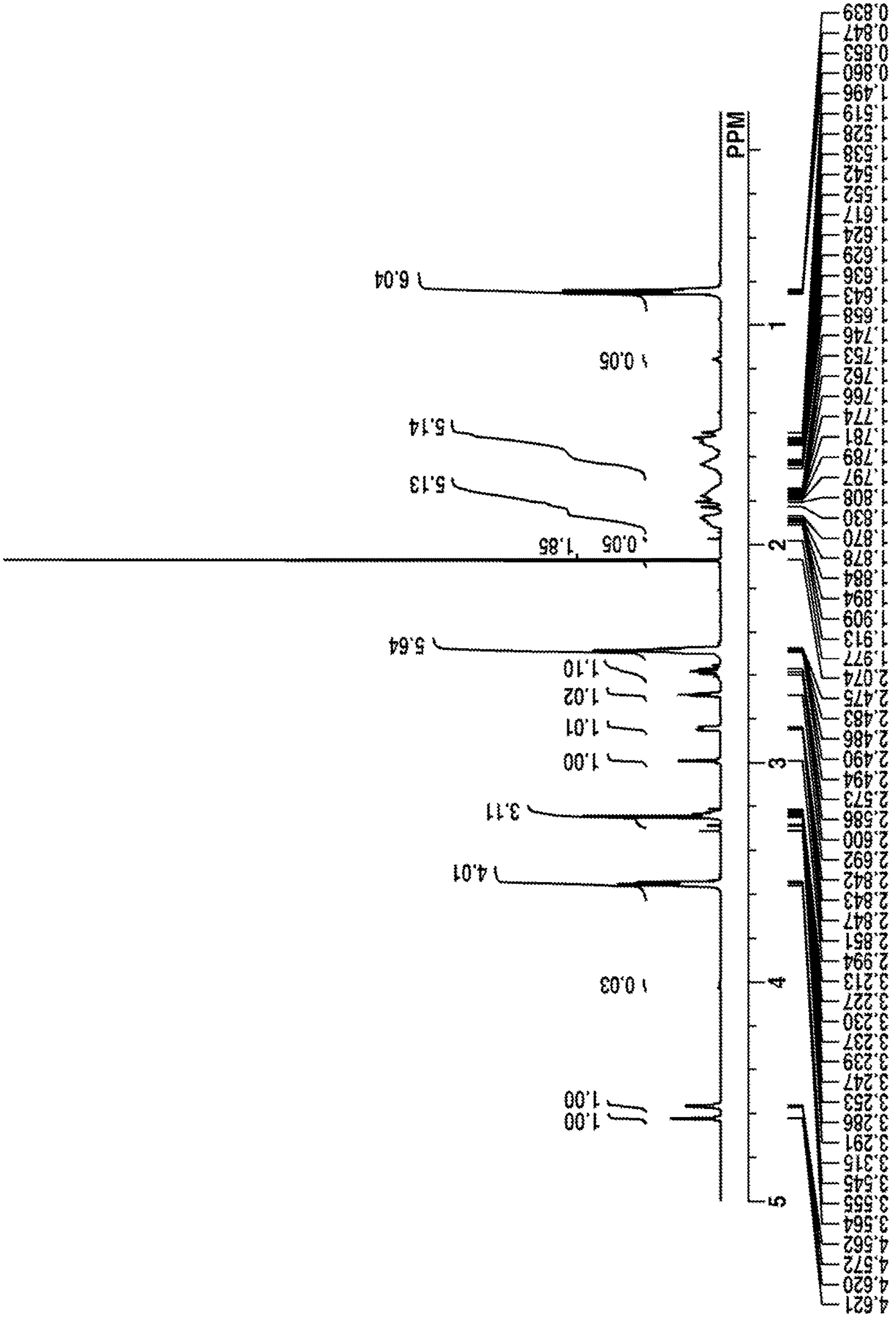
FIG. 4 is a $^{1}$M-NMR spectrum of Compound AQ-4 synthesized in Example 1-4.

AQ-4 was analyzed by IR spectroscopy, with the data shown below. FIG. 4 is the $^1$H-NMR/DMSO-$d_6$ spectrum of AQ-4.

ER (D-ATR): ν=2966, 2874, 1788, 1757, 1722, 1454, 1388, 1370, 1356, 1295, 1259, 1212, 1157, 1115, 1070, 1038, 1020, 941, 902, 867, 810, 750, 530, 495, 422 $cm^{-1}$

Example 1-5

Synthesis of AQ-5

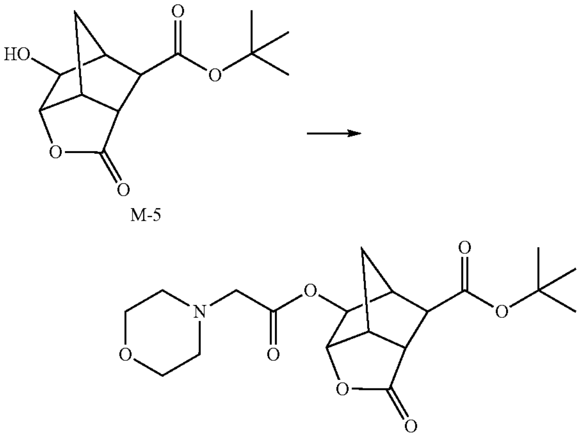
M-5

AQ-5

AQ-5 was synthesized by the same procedure as in Example 1-1 aside from using reactant M-5 instead of reactant M-1. (amount 15.7 g, yield 59%).

Figure 5:
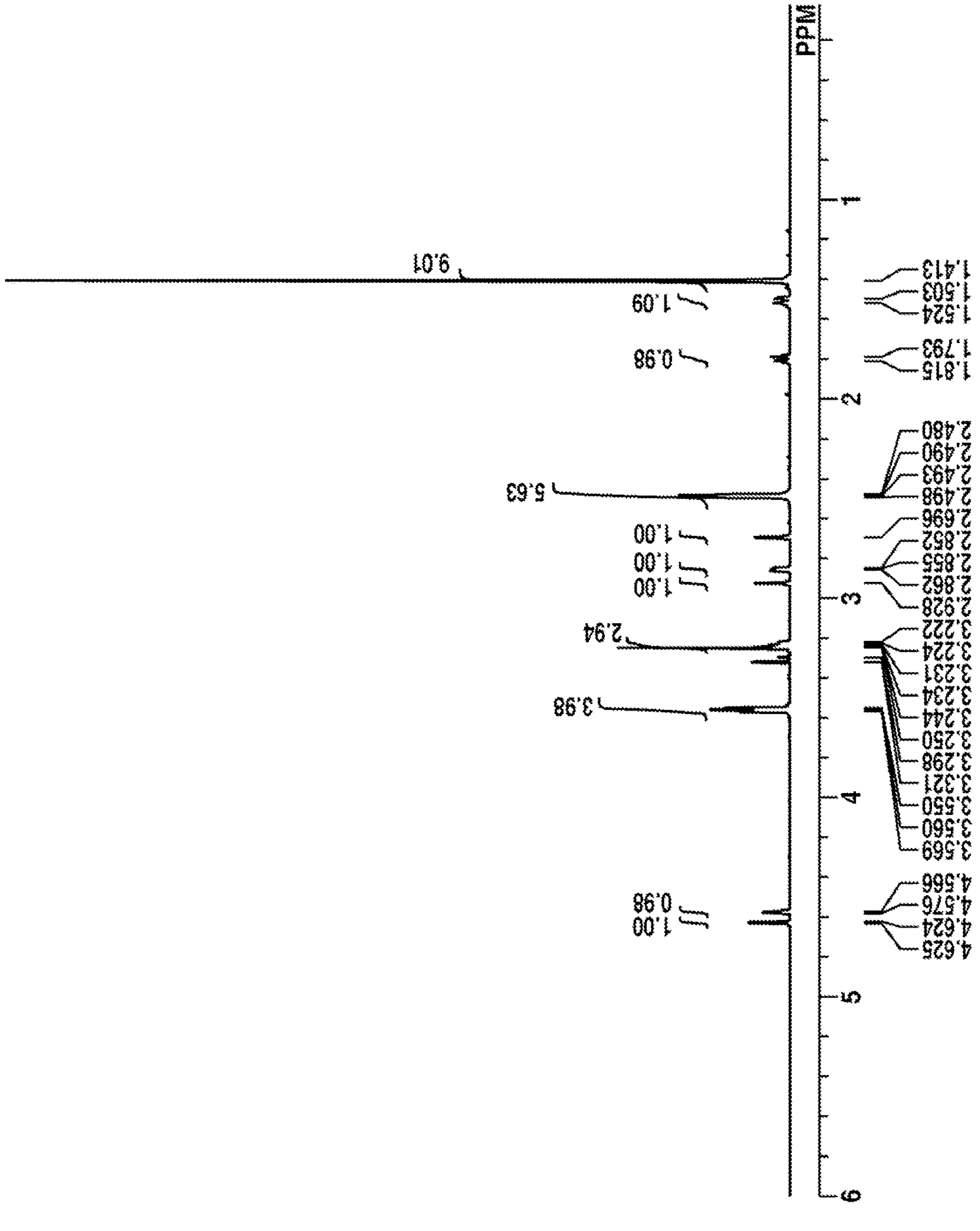
FIG. 5 is a $^{1}$H-NMR spectrum of Compound AQ-5 synthesized in Example 1-5.

AQ-5 was analyzed by IR spectroscopy, with the data shown below. FIG. 5 is the $^1$H-NMR/DMSO-$d_6$ spectrum of AQ-5.

IR (D-ATR): ν=2967, 2937, 2873, 2810, 1788, 1755, 1748, 1720, 1452, 1422, 1405, 1394, 1366, 1346, 1297, 1283, 1267, 1256, 1226, 1215, 1192, 1169, 1160, 1115, 1078, 1057, 1041, 1025, 1013, 945, 926, 908, 890, 869, 851, 837, 813, 788, 751, 733, 719, 705, 639, 497, 442 $cm^{-1}$

Examples 1-6 to 1-11

Synthesis of AQ-6 to AQ-11

Amine compounds AQ-6 to AQ-11 were synthesized by any organic chemistry methods. These compounds have the following structures.

AQ-6

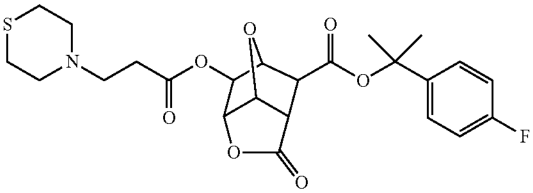

-continued

AQ-7

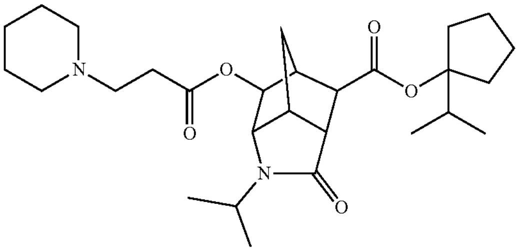

AQ-8

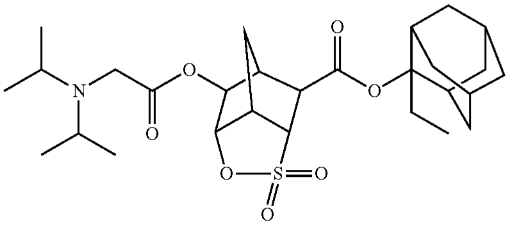

AQ-9

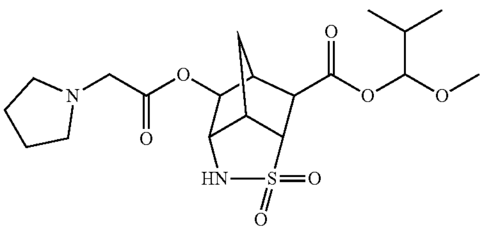

AQ-10

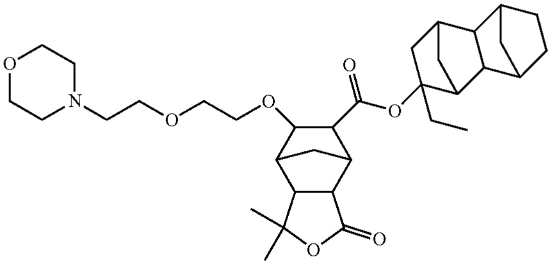

AQ-11

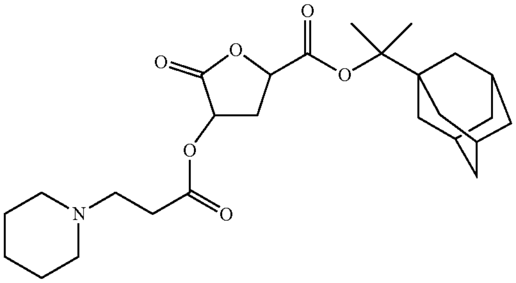

[2] Synthesis of Base Polymers

Base polymers used in chemically amplified resist compositions were synthesized by the following procedure.

Synthesis Example 1

Synthesis of Polymer P-1

In a flask under nitrogen atmosphere, 5.0 g of 3-hydroxy-1-adamantyl methacrylate, 14.4 g of α-methacryloxy-γ-butyrolactone, 20.8 g of 1-isopropylcyclopentyl methacrylate, 0.49 g of dimethyl 2,2'-azobis(2-methylpropionate) (V-601 by Fuji Film Wako Pure Chemical Industries, Ltd.), 0.41 g of 2-mercaptoethanol, and 56 g of PGMEA were combined to form a monomer/initiator solution. Another flask in nitrogen atmosphere was charged with 19 g of PGMEA, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining Polymer P-1 in white powder form (amount 35.3 g, yield 88%). On GPC analysis, Polymer P-1 had a Mw of 8,500 and a Mw/Mn of 1.58.

P-1

Mw = 8,500
Mw/Mn = 1.58

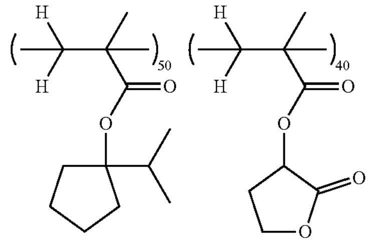

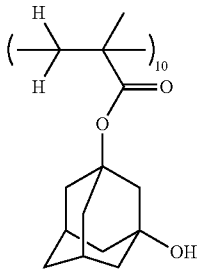

Synthesis Examples 2 to 7

Synthesis of Polymers P-2 to P-7

Polymers P-2 to P-7 were synthesized by the same procedure as in Synthesis Example 1 aside from changing the type and amount of monomers. Table 1 tabulates the type and molar ratio (mol %) of repeat units in Polymers P-1 to P-7.

The repeat units in Table 1 are shown below.

a1-1

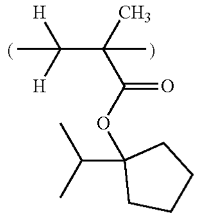

a1-2

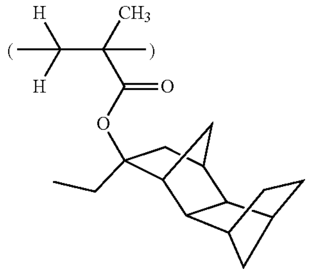

a1-3

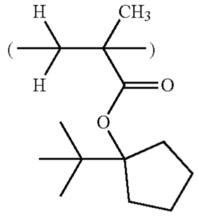

a1-4

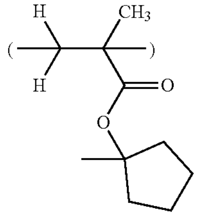

a2-1

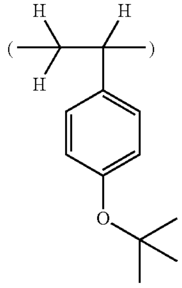

TABLE 1

| Polymer | Unit 1 | Ratio (mol %) | Unit 2 | Ratio (mol %) | Unit 3 | Ratio (mol %) | Unit 4 | Ratio (mol %) | Unit 5 | Ratio (mol %) | Mw | Mw/Mn |
|---|---|---|---|---|---|---|---|---|---|---|---|---|
| P-1 | a1-1 | 50 | b1-1 | 40 | b1-4 | 10 | — | — | — | — | 8,500 | 1.58 |
| P-2 | a1-2 | 40 | a1-1 | 10 | b1-1 | 20 | b1-2 | 20 | b1-4 | 10 | 8,100 | 1.73 |
| P-3 | a1-2 | 35 | a1-1 | 15 | b1-1 | 40 | b1-4 | 10 | — | — | 8,300 | 1.67 |
| P-4 | a1-2 | 10 | a1-3 | 40 | b1-1 | 10 | b1-3 | 25 | b1-4 | 15 | 9,400 | 1.71 |
| P-5 | a1-4 | 55 | b2-2 | 30 | c2-1 | 15 | — | — | — | — | 10,600 | 2.05 |
| P-6 | a1-2 | 10 | a2-1 | 30 | b1-2 | 30 | b2-1 | 20 | c2-2 | 10 | 11,200 | 2.08 |
| P-7 | a1-4 | 50 | b2-2 | 50 | — | — | — | — | — | — | 85,00 | 1.67 |

-continued b1-1

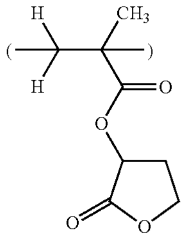

b1-2

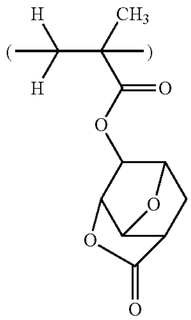

b1-3

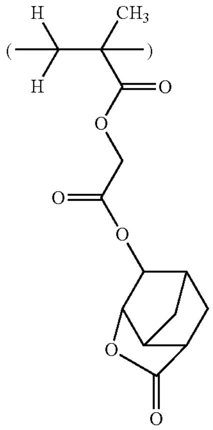

b1-4

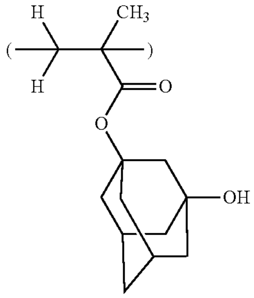

b2-1

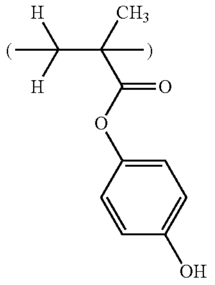

-continued b2-2

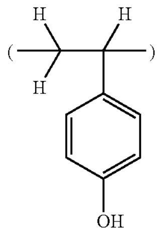

c2-1

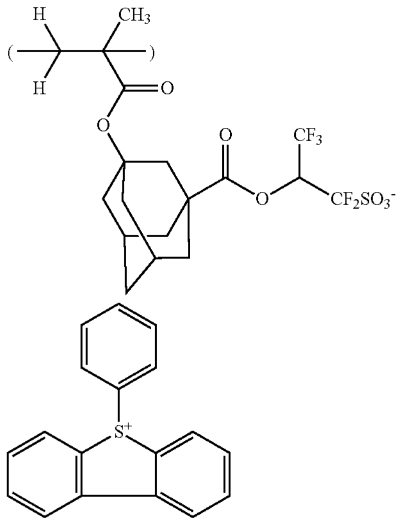

c2-2

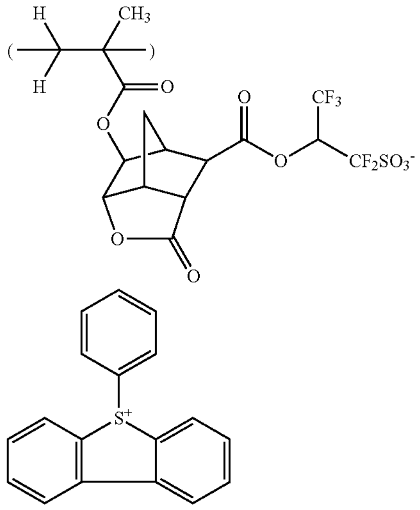

[3] Preparation of Chemically Amplified Resist Compositions

Examples 2-1 to 2-26 and Comparative Examples 1-1 to 1-14

Chemically amplified resist compositions (R-1 to R-26, CR-1 to CR-14) in solution form were prepared by dissolving an amine compound (AQ-1 to AQ-11), comparative amine quencher (AQ-A to AQ-F), base polymer (Polymers P-1 to P-7), photoacid generator (PAG-1 to PAG-3), quencher (Q-1, Q-2), and alkali-soluble surfactant (SF-1) in a solvent containing 0.01 wt % of surfactant A in accordance with the formulation shown in Tables 2 and 3, and filtering through a Teflon® filter with a pore size of 0.2 μm.

TABLE 2

| | | Resist composition | Amine compound (pbw) | Base polymer (pbw) | Photoacid generator (pbw) | Quencher (pbw) | Surfactant (pbw) | Solvent 1 (pbw) | Solvent 2 (pbw) |
|---|---|---|---|---|---|---|---|---|---|
| Example | 2-1 | R-1 | AQ-1 (3.0) | P-1 (80) | PAG-1 (12.0) | Q-1 (5.0) | SF-1 (3.0) | PGMEA (1,400) | GBL (400) |
| | 2-2 | R-2 | AQ-2 (3.0) | P-1 (80) | PAG-1 (12.0) | Q-1 (5.0) | SF-1 (3.0) | PGMEA (1,400) | GBL (400) |
| | 2-3 | R-3 | AQ-3 (3.0) | P-1 (80) | PAG-1 (12.0) | Q-1 (5.0) | SF-1 (3.0) | PGMEA (1,400) | GBL (400) |
| | 2-4 | R-4 | AQ-4 (3.0) | P-1 (80) | PAG-1 (12.0) | Q-1 (5.0) | SF-1 (3.0) | PGMEA (1,400) | GBL (400) |
| | 2-5 | R-5 | AQ-5 (3.0) | P-1 (80) | PAG-1 (12.0) | Q-1 (5.0) | SF-1 (3.0) | PGMEA (1,400) | GBL (400) |
| | 2-6 | R-6 | AQ-6 (3.0) | P-1 (80) | PAG-1 (12.0) | Q-1 (5.0) | SF-1 (3.0) | PGMEA (1,400) | GBL (400) |
| | 2-7 | R-7 | AQ-7 (3.0) | P-1 (80) | PAG-1 (12.0) | Q-1 (5.0) | SF-1 (3.0) | PGMEA (1,400) | GBL (400) |
| | 2-8 | R-8 | AQ-8 (3.0) | P-1 (80) | PAG-1 (12.0) | Q-1 (5.0) | SF-1 (3.0) | PGMEA (1,400) | GBL (400) |
| | 2-9 | R-9 | AQ-9 (3.0) | P-1 (80) | PAG-1 (12.0) | Q-1 (5.0) | SF-1 (3.0) | PGMEA (1,400) | GBL (400) |
| | 2-10 | R-10 | AQ-10 (3.0) | P-1 (80) | PAG-1 (12.0) | Q-1 (5.0) | SF-1 (3.0) | PGMEA (1,400) | GBL (400) |
| | 2-11 | R-11 | AQ-11 (3.0) | P-1 (80) | PAG-1 (12.0) | Q-1 (5.0) | SF-1 (3.0) | PGMEA (1,400) | GBL (400) |
| | 2-12 | R-12 | AQ-1 (5.0) | P-2 (80) | PAG-2 (10.0) | Q-1 (2.0) | SF-1 (3.0) | PGMEA (1,400) | GBL (400) |
| | 2-13 | R-13 | AQ-1 (5.0) | P-3 (80) | PAG-1 (12.0) | Q-1 (2.0) | SF-1 (3.0) | PGMEA (1,400) | GBL (400) |
| | 2-14 | R-14 | AQ-2 (5.0) | P-3 (80) | PAG-1 (12.0) | Q-1 (2.0) | SF-1 (3.0) | PGMEA (1,400) | GBL (400) |
| | 2-15 | R-15 | AQ-4 (3.0) | P-4 (80) | PAG-2 (10.0) | Q-1 (2.0) | SF-1 (3.0) | PGMEA (1,400) | GBL (400) |
| | 2-16 | R-16 | AQ-2 (3.0) | P-4 (80) | PAG-2 (10.0) | Q-1 (2.0) | SF-1 (3.0) | PGMEA (1,400) | GBL (400) |
| | 2-17 | R-17 | AQ-10 (3.0) | P-4 (80) | PAG-2 (10.0) | Q-1 (2.0) | SF-1 (3.0) | PGMEA (1,400) | GBL (400) |
| | 2-18 | R-18 | AQ-1 (5.0) | P-5 (80) | — | 0.2 (7.0) | — | PGMEA (2,200) | DAA (900) |
| | 2-19 | R-19 | AQ-2 (5.0) | P-5 (80) | — | Q-2 (7.0) | — | PGMEA (2,200) | DAA (900) |
| | 2-20 | R-20 | AQ-2 (5.0) | P-5 (80) | PAG-3 (8.0) | Q-2 (7.0) | — | PGMEA (2,200) | DAA (900) |
| | 2-21 | R-21 | AQ-8 (5.0) | P-5 (80) | — | Q-2 (7.0) | — | PGMEA (2,200) | DAA (900) |
| | 2-22 | R-22 | AQ-3 (5.0) | P-6 (80) | — | Q-2 (7.0) | — | PGMEA (2,200) | DAA (900) |
| | 2-23 | R-23 | AQ-2 (5.0) | P-6 (80) | — | Q-2 (7.0) | — | PGMEA (2,200) | DAA (900) |
| | 2-24 | R-24 | AQ-1 (5.0) | P-7 (80) | PAG-3 (20.0) | Q-2 (7.0) | — | PGMEA (2,200) | DAA (900) |
| | 2-25 | R-25 | AQ-2 (5.0) | P-7 (80) | PAG-3 (20.0) | — | — | PGMEA (2,200) | DAA (900) |
| | 2-26 | R-26 | AQ-7 (5.0) | P-7 (80) | PAG-3 (20.0) | — | — | PGMEA (2,200) | DAA (900) |

TABLE 3

| | | Resist composition | Amine compound (pbw) | Base polymer (pbw) | Photoacid generator (pbw) | Quencher (pbw) | Surfactant (pbw) | Solvent 1 (pbw) | Solvent 2 (pbw) |
|---|---|---|---|---|---|---|---|---|---|
| Comparative Example | 1-1 | CR-1 | AQ-A (3.0) | P-1 (80) | PAG-1 (12.0) | Q-1 (5.0) | SF-1 (3.0) | PGMEA (1,400) | GBL (400) |
| | 1-2 | CR-2 | AQ-B (3.0) | P-1 (80) | PAG-1 (12.0) | Q-1 (5.0) | SF-1 (3.0) | PGMEA (1,400) | GBL (400) |
| | 1-3 | CR-3 | AQ-C (3.0) | P-1 (80) | PAG-1 (12.0) | Q-1 (5.0) | SF-1 (3.0) | PGMEA (1,400) | GBL (400) |
| | 1-4 | CR-4 | AQ-D (3.0) | P-1 (80) | PAG-1 (12.0) | Q-1 (5.0) | SF-1 (3.0) | PGMEA (1,400) | GBL (400) |
| | 1-5 | CR-5 | AQ-E (3.0) | P-1 (80) | PAG-1 (12.0) | Q-1 (5.0) | SF-1 (3.0) | PGMEA (1,400) | GBL (400) |
| | 1-6 | CR-6 | AQ-F (3.0) | P-1 (80) | PAG-1 (12.0) | Q-1 (5.0) | SF-1 (3.0) | PGMEA (1,400) | GBL (400) |

TABLE 3-continued

| | Resist composition | Amine compound (pbw) | Base polymer (pbw) | Photoacid generator (pbw) | Quencher (pbw) | Surfactant (pbw) | Solvent 1 (pbw) | Solvent 2 (pbw) |
|---|---|---|---|---|---|---|---|---|
| 1-7 | CR-7 | AQ-A (3.0) | P-3 (80) | PAG-1 (12.0) | Q-1 (2.0) | SF-1 (3.0) | PGMEA (1,400) | GBL (400) |
| 1-8 | CR-8 | AQ-C (3.0) | P-4 (80) | PAG-2 (10.0) | Q-1 (2.0) | SF-1 (3.0) | PGMEA (1,400) | GBL (400) |
| 1-9 | CR-9 | AQ-A (5.0) | P-5 (80) | — | Q-2 (7.0) | — | PGMEA (2,200) | DAA (900) |
| 1-10 | CR-10 | AQ-C (5.0) | P-5 (80) | — | Q-2 (7.0) | — | PGMEA (1,400) | DAA (900) |
| 1-11 | CR-11 | AQ-E (5.0) | P-5 (80) | — | Q-2 (7.0) | — | PGMEA (1,400) | DAA (900) |
| 1-12 | CR-12 | AQ-B (5.0) | P-6 (80) | — | Q-2 (7.0) | — | PGMEA (1,400) | DAA (900) |
| 1-13 | CR-13 | AQ-D (5.0) | P-6 (80) | — | Q-2 (7.0) | — | PGMEA (1,400) | DAA (900) |
| 1-14 | CR-14 | AQ-A (5.0) | P-7 (80) | PAG-3 (20.0) | Q-2 (7.0) | — | PGMEA (1,400) | DAA (900) |

The solvents, alkali-soluble surfactant SF-1, photoacid generators PAG-1 to PAG-3, and quenchers Q-1 and Q-2 in Tables 2 and 3 are identified below.

Solvent:

PGMEA (propylene glycol monomethyl ether acetate)

GBL (γ-butyrolactone)

DAA (diacetone alcohol)

Alkali-soluble surfactant SF-1:

poly(2,2,3,3,4,4,4-heptafluoro-1-isobutyl-1-butyl methacrylate/9-(2,2,2-trifluoro-1-trifluoroethyloxycarbonyl)-4-oxatricyclo[4.2.1.$0^{3,7}$]nonan-5-on-2-yl methacrylate)

SF-1

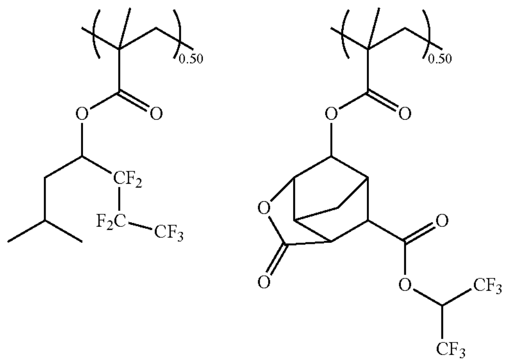

Mw = 7,700, Mw/Mn = 1.82

Photoacid generator: PAG-1 to PAG-3

PAG-1

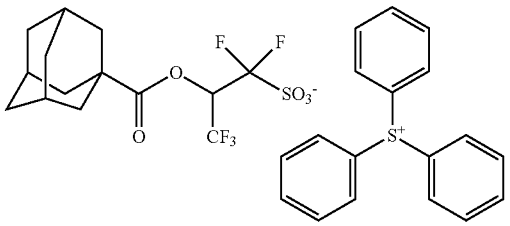

-continued
PAG-2
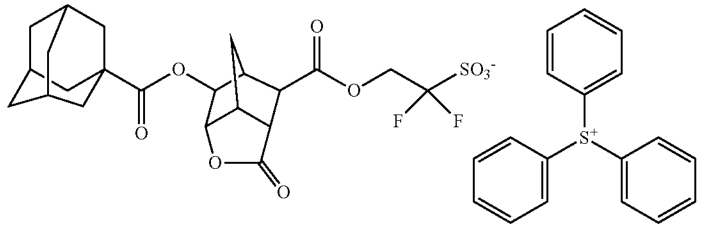
PAG-3
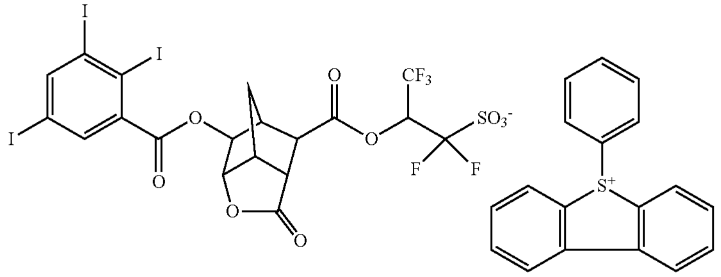
Quencher: Q-1 and Q-2
Q-1
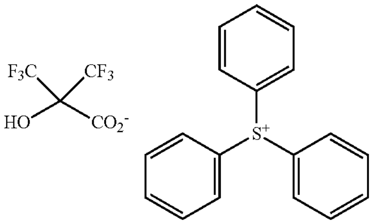
Q-2
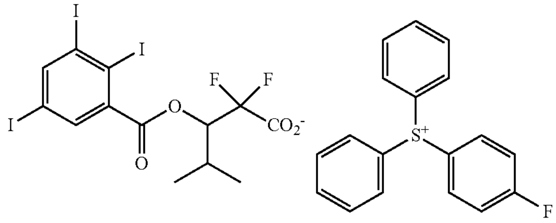
Comparative amine quenchers: AQ-A to AQ-F
AQ-A
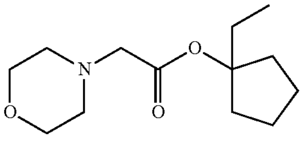
AQ-B
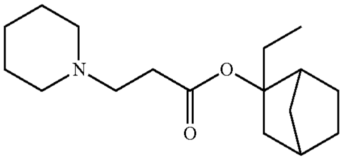
-continued
AQ-C
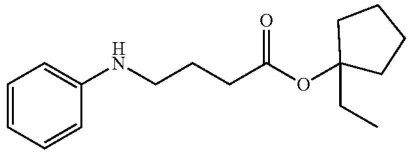
AQ-D
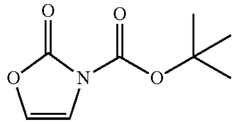
AQ-E
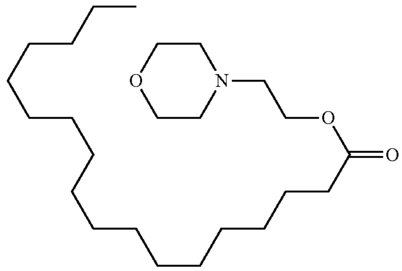
AQ-F
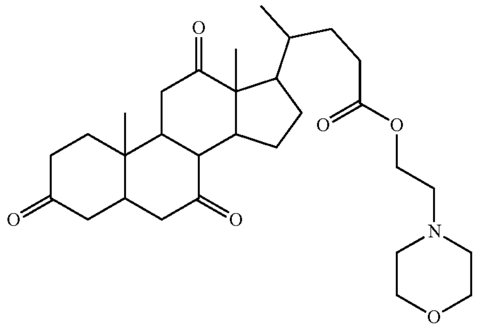
Surfactant A:
3-methyl-3-(2,2,2-trifluoroethoxymethyl)oxetane/tetrahydrofuran/2,2-dimethyl-1,3-propane diol copolymer (Onmova Solutions, Inc.)

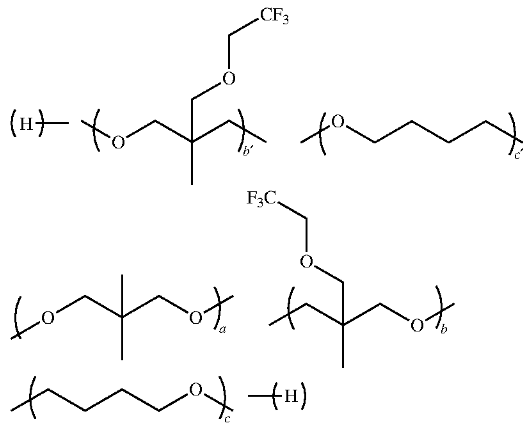

a:(b+b'):(c+c')=1:4-7:0.01-1 (molar ratio)

Mw=1,500

[4] Evaluation of Resist Composition: ArF Lithography Patterning Test 1

Examples 3-1 to 3-12 and Comparative Examples 2-1 to 2-6

On a silicon substrate, an antireflective coating solution (ARC29A, Nissan Chemical Corp.) was coated and baked at 200° C. for 60 seconds to form an ARC of 100 nm thick. Each of the resist compositions (R-1 to R-12, CR-1 to CR-6) was spin coated on the ARC and prebaked on a hotplate at 100° C. for 60 seconds to form a resist film of 90 nm thick on the ARC. The wafer was exposed on an ArF excimer laser immersion lithography scanner (NSR-S610C by Nikon Corp., NA 1.30, dipole illumination) through a Cr mask having a line-and-space (LS) pattern with a line width of 40 mu and a pitch of 80 nm (on-wafer size), while varying the exposure dose and focus at a dose pitch of 1 mJ/cm$^2$ and a focus pitch of 0.025 μm. The immersion liquid used herein was water. After exposure, the resist film was baked (PEB) at the temperature shown in Table 4 for 60 seconds. The resist film was puddle developed in a 2.38 wt % tetramethylammonium hydroxide (TMAH) aqueous solution for 30 seconds, rinsed with deionized water and spin dried, forming a positive pattern. The LS pattern after development was observed under CD-SEM (CG4000 by Hitachi High-Technologies Corp.), whereupon sensitivity, EL, MEF, and LWR were evaluated by the following methods. The results are shown in Table 4.

Evaluation of Sensitivity

The optimum exposure dose Eop (mJ/cm$^2$) which provided a LS pattern having a line width of 40 nm and a pitch of 80 nm was determined as an index of sensitivity. A smaller dose value indicates a higher sensitivity.

Evaluation of Exposure Latitude (EL)

The exposure dose which provided a LS pattern with a space width of 40 nm±10% (i.e., 36 nm to 44 run) was determined. EL (%) is calculated from the exposure doses according to the following equation:

$$EL\,(\%) = (|E_1 - E_2|/Eop) \times 100$$

wherein $E_1$ is an optimum exposure dose which provides a LS pattern with a line width of 36 nm and a pitch of 80 nm, $E_2$ is an optimum exposure dose which provides a LS pattern with a line width of 44 nm and a pitch of 80 run, and Eop is an optimum exposure dose which provides a LS pattern with a line width of 40 mu and a pitch of 80 urn. A larger value indicates better performance.

Evaluation of Mask Error Factor (MEF)

A LS pattern was formed by exposure in the optimum dose Eop through the mask with the pitch fixed and the line width varied. MEF was calculated from the mask line width and a variation of the pattern line width according to the following equation:

$$MEF = (\text{pattern line width})/(\text{mask line width}) - b$$

wherein b is a constant. A value closer to unity (1) indicates better performance.

Evaluation of Line Width Roughness (LWR)

A LS pattern was formed by exposure in the optimum dose Eop. The line width was measured at longitudinally spaced apart 10 points, from which a 3-fold value (3σ) of standard deviation (σ) was determined and reported as LWR. A smaller value of 3σ indicates a pattern having a lower roughness and more uniform line width.

TABLE 4

| | | Resist composition | PEB temp. (° C.) | Eop (mJ/cm$^2$) | EL (%) | MEF | LWR (nm) |
|---|---|---|---|---|---|---|---|
| Example | 3-1 | R-1 | 95 | 46 | 15 | 2 | 2.2 |
| | 3-2 | R-2 | 95 | 45 | 14 | 1.8 | 1.9 |
| | 3-3 | R-3 | 90 | 45 | 18 | 1.9 | 2.1 |
| | 3-4 | R-4 | 90 | 46 | 15 | 2 | 2.2 |
| | 3-5 | R-5 | 100 | 49 | 16 | 2.1 | 2.3 |
| | 3-6 | R-6 | 95 | 47 | 15 | 2.3 | 2.1 |
| | 3-7 | R-7 | 90 | 48 | 19 | 2.3 | 2.2 |
| | 3-8 | R-8 | 95 | 44 | 15 | 2.2 | 2.1 |
| | 3-9 | R-9 | 95 | 44 | 14 | 2.1 | 2.2 |
| | 3-10 | R-10 | 90 | 46 | 15 | 2 | 2.1 |
| | 3-11 | R-11 | 95 | 45 | 14 | 2.2 | 2.3 |
| | 3-12 | R-12 | 100 | 46 | 15 | 1.9 | 2.3 |
| Comparative Example | 2-1 | CR-1 | 95 | 45 | 10 | 2.8 | 2.7 |
| | 2-2 | CR-2 | 90 | 50 | 10 | 3.2 | 2.8 |
| | 2-3 | CR-3 | 95 | 52 | 11 | 2.7 | 3 |
| | 2-4 | CR-4 | 95 | 55 | 10 | 2.5 | 3.2 |
| | 2-5 | CR-5 | 90 | 54 | 9 | 3.3 | 2.8 |
| | 2-6 | CR-6 | 100 | 58 | 10 | 3.1 | 3 |

As is evident from Table 4, the chemically amplified resist compositions containing amine compounds within the scope of the invention exhibit a satisfactory sensitivity, improved values of EL, MEF and LWR. The resist compositions are useful as the ArF immersion lithography material.

[5] Evaluation of Resist Composition: ArF Lithography Patterning Test 2

Examples 4-1 to 4-5 and Comparative Examples 3-1 to 3-2

On a substrate, a spin-on carbon film ODL-180 (Shin-Etsu Chemical Co., Ltd.) having a carbon content of 80 wt % was deposited to a thickness of 180 mu and a silicon-containing spin-on hard mask SHB-A941 having a silicon content of 43 wt % was deposited thereon to a thickness of 35 nm. On this substrate for trilayer process, each of the resist compositions (R-13 to R-17, CR-7, CR-8) was spin coated, then baked on a hot plate at 100° C. for 60 seconds to form a resist film of 100 mu thick.

Using an ArF excimer laser immersion lithography scanner NSR-S610C (Nikon Corp., NA 1.30. σ 0.90/0.72, cross-pole opening 35 deg., cross-pole illumination, azimuthally polarized illumination), exposure was performed through a 6% halftone phase shift mask bearing a contact hole (CH) pattern with a hole size of 45 nm and a pitch of 110 nm (on-wafer size) while varying the dose and focus (dose pitch: 1 mJ/cm$^2$, focus pitch: 0.025 μm). The immersion liquid used herein was water. After the exposure, the wafer was baked (PEB) at the temperature shown in Table 5 for 60 seconds. Thereafter, the resist film was puddle developed in n-butyl acetate for 30 seconds, rinsed with 4-methyl-2-pentanol, and spin dried, obtaining a negative pattern. The CH pattern after development was observed under CD-SEM CG4000 (Hitachi High Technologies Corp.) whereupon sensitivity, MEF, CDU, and DOF were evaluated by the following methods. The results are shown in Table 5.

Evaluation of Sensitivity

The optimum dose Eop (mJ/cm$^2$) which provided a CH pattern with a hole size of 45 mu and a pitch of 110 μm was determined as an index of sensitivity. A smaller dose value indicates a higher sensitivity.

Evaluation of MEF

A CH pattern was formed by exposure at the optimum dose Eop by ArF lithography patterning test 2 with the pitch fixed and the mask size varied. MEF was calculated from the mask size and a variation of the CH pattern size according to the following equation:

$$MEF=(\text{pattern size})/(\text{mask size})-b$$

wherein b is a constant. A value closer to unity (1) indicates better performance.

Evaluation of Critical Dimension Uniformity (CDU)

For the CH pattern formed by exposure at the optimum dose Eop, the hole size was measured at 10 areas subject to an identical dose of shot (9 contact holes per area), from which a 3-fold value (3σ) of standard deviation (α) was determined and reported as CDU. A smaller value of 3σ indicates a CH pattern having improved CDU.

Evaluation of Depth of Focus (DOF)

As an index of DOF, a range of focus which provided a CH pattern with a size of 45 nm±10% (i.e., 40.5 to 49.5 nm) was determined. A greater value indicates a wider DOF.

TABLE 5

| | | Resist composition | PEB temp. (° C.) | Eop (mJ/cm$^2$) | MEF | CDU (nm) | DOF (nm) |
|---|---|---|---|---|---|---|---|
| Example | 4-1 | R-13 | 85 | 40 | 2.3 | 2 | 120 |
| | 4-2 | R-14 | 80 | 42 | 2.4 | 2.1 | 120 |
| | 4-3 | R-15 | 85 | 41 | 2.5 | 1.9 | 120 |
| | 4-4 | R-16 | 85 | 42 | 2.2 | 1.8 | 120 |
| | 4-5 | R-17 | 80 | 41 | 2.4 | 1.9 | 120 |
| Comparative | 3-1 | CR-7 | 80 | 55 | 3 | 2.3 | 80 |
| Example | 3-2 | CR-8 | 85 | 54 | 3.1 | 2.5 | 80 |

As is evident from Table 5, the chemically amplified resist compositions containing amine compounds within the scope of the invention exhibit a satisfactory sensitivity and improved values of MEF, CDU and DOF. The resist compositions are useful in the ArF immersion lithography process.

[6] EUV Lithography Test

Examples 5-1 to 5-9 and Comparative Examples 4-1 to 4-6

Each of the chemically amplified resist compositions (R-18 to R-26, CR-9 to CR-14) was spin coated on a silicon substrate having a 20-nm coating of silicon-containing spin-on hard mask SHB-A940 (Shin-Etsu Chemical Co., Ltd., silicon content 43 wt %) and prebaked on a hotplate at 100° C. for 60 seconds to form a resist film of 50 nm thick. Using an EUV scanner NXE3300 (ASML, NA 0.33, σ 0.9/0.6, dipole illumination), the resist film was exposed to EUV through a mask bearing a LS pattern having a size of 18 nm and a pitch of 36 nm (on-wafer size) while varying the dose and focus (dose pitch: 1 mJ/cm$^2$, focus pitch: 0.020 μm). The resist film was baked (PEB) on a hotplate at the temperature shown in Table 6 for 60 seconds and puddle developed in a 2.38 wt % TMAH aqueous solution for 30 seconds, rinsed with a rinse fluid containing surfactant, and spin dried to form a positive pattern.

The LS pattern as developed was observed under CD-SEM (CG6300, Hitachi High-Technologies Corp.) whereupon sensitivity, EL, LWR, and DOF were evaluated by the following methods. The results are shown in Table 6.

Evaluation of Sensitivity

The optimum dose Eop (mJ/cm$^2$) which provided a LS pattern with a line width of 18 nm and a pitch of 36 nm was determined as an index of sensitivity.

Evaluation of EL

The exposure dose which provided a LS pattern with a space width of 18 nm±10% (i.e., 16.2 to 19.8 mu) was determined. EL (%) is calculated from the exposure doses according to the following equation:

$$EL\ (\%) = (|E_1 - E_2|/Eop) \times 100$$

wherein $E_1$ is an optimum exposure dose which provides a LS pattern with a line width of 16.2 nm and a pitch of 36 nm, $E_2$ is an optimum exposure dose which provides a LS pattern with a line width of 19.8 mu and a pitch of 36 nm, and Eop is an optimum exposure dose which provides a LS pattern with a line width of 18 mu and a pitch of 36 nm. A larger value indicates better performance.

Evaluation of LWR

For the LS pattern formed by exposure at the optimum dose Eop, the line width was measured at 10 longitudinally spaced apart points, from which a 3-fold value (3σ) of standard deviation (σ) was determined and reported as LWR. A smaller value of 3σ indicates a pattern having small roughness and uniform line width.

Evaluation of DOF

As an index of DOF, a range of focus which provided a LS pattern with a size of 18 nm±10% (i.e., 16.2 to 19.8 mu) was determined. A greater value indicates a wider DOF.

TABLE 6

| | | Resist composition | PEB temp. (° C.) | Eop (mJ/cm$^2$) | EL (%) | LWR (nm) | DOF (nm) |
|---|---|---|---|---|---|---|---|
| Example | 5-1 | R-18 | 95 | 43 | 18 | 3 | 100 |
| | 5-2 | R-19 | 95 | 45 | 17 | 2.9 | 100 |
| | 5-3 | R-20 | 95 | 41 | 19 | 2.8 | 100 |
| | 5-4 | R-21 | 95 | 44 | 15 | 2.9 | 100 |
| | 5-5 | R-22 | 95 | 43 | 16 | 2.7 | 100 |
| | 5-6 | R-23 | 85 | 45 | 15 | 3.2 | 120 |
| | 5-7 | R-24 | 85 | 50 | 17 | 3.3 | 120 |
| | 5-8 | R-25 | 90 | 49 | 16 | 3.4 | 120 |
| | 5-9 | R-26 | 90 | 49 | 17 | 3.5 | 110 |
| Comparative | 4-1 | CR-9 | 95 | 48 | 8 | 3.8 | 80 |
| Example | 4-2 | CR-10 | 95 | 47 | 12 | 3.9 | 80 |
| | 4-3 | CR-11 | 95 | 49 | 10 | 3.8 | 80 |

TABLE 6-continued

| | Resist composition | PEB temp. (° C.) | Eop ($mJ/cm^2$) | EL (%) | LWR (nm) | DOF (nm) |
|---|---|---|---|---|---|---|
| 4-4 | CR-12 | 95 | 50 | 11 | 3.8 | 80 |
| 4-5 | CR-13 | 95 | 48 | 9 | 3.9 | 60 |
| 4-6 | CR-14 | 85 | 55 | 10 | 3.9 | 80 |

It is demonstrated in Table 6 that chemically amplified resist compositions comprising amine compounds within the scope of the invention exhibit a high sensitivity and improved values of EL, LWR and DOF. The resist compositions are useful in the EUV lithography process.

Japanese Patent Application No. 2021-155395 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An amine compound having the formula (1):

(1)

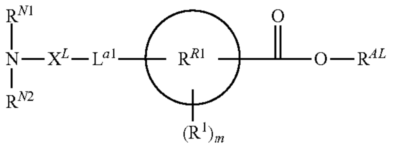

wherein m is an integer of 0 to 10, $R^{N1}$ and $R^{N2}$ are each independently hydrogen or a $C_1$-$C_{20}$ hydrocarbyl group in which some or all of the hydrogen atoms may be substituted by halogen and any constituent —$CH_2$— may be replaced by —O— or —C(═O)—, $R^{N1}$ and $R^{N2}$ may bond together to form a ring with the nitrogen atom to which they are attached, the ring optionally containing —O— or —S—, with the proviso that $R^{N1}$ and $R^{N2}$ are not hydrogen at the same time, $X^L$ is a $C_1$-$C_{40}$ hydrocarbylene group which may contain a heteroatom, $L^{a1}$ is an ether bond, ester bond, sulfonic ester bond, carbonate bond or carbamate bond, the ring $R^{R1}$ is a $C_2$-$C_{20}$ (m+2)-valent heterocyclic group having a lactone, lactam, sultone or sultam structure, $R^1$ is a $C_1$-$C_{20}$ hydrocarbyl group which may contain a heteroatom, and when m is 2 or more, a plurality of $R^1$ may be the same or different, a plurality of $R^1$ may bond together to form a ring with the atoms on $R^{R1}$ to which they are attached, and $R^{AL}$ is an acid labile group.

2. The amine compound of claim 1 having the formula (1A):

(1A)

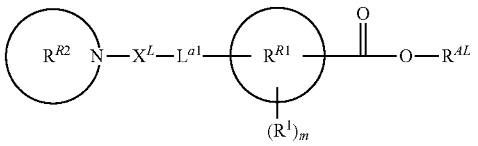

wherein m, $X^L$, $L^{a1}$, $R^{R1}$, $R^1$, and $R^{AL}$ are as defined above, a $C_3$-$C_{20}$ alicyclic hydrocarbon group forms the ring $R^{R2}$ with the nitrogen atom, any constituent —$CH_2$— in the ring may be replaced by —O— or —S—.

3. The amine compound of claim 2 having the formula (1B):

(1B)

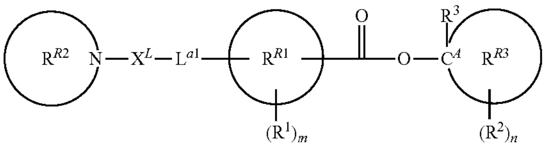

wherein m, $X^L$, $L^{a1}$, $R^{R1}$, $R^{R2}$, and $R^1$ are as defined above, n is an integer of 0 to 20, a $C_3$-$C_{20}$ alicyclic hydrocarbon group forms the ring $R^{R3}$ with the carbon atom CA, any constituent —$CH_2$— in the ring may be replaced by a heteroatom-containing moiety, $R^2$ is a $C_1$-$C_{20}$ hydrocarbyl group which may contain a heteroatom, and when n is 2 or more, a plurality of $R^2$ may be the same or different, a plurality of $R^2$ may bond together to form a ring structure, and $R^3$ is a $C_1$-$C_{20}$ hydrocarbyl group which may contain a heteroatom.

4. A chemically amplified resist composition comprising (A) a quencher in the form of the amine compound of claim 1.

5. The resist composition of claim 4, further comprising (B) a base polymer comprising repeat units having the formula (a1) or (a2):

(a1)

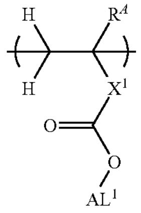

(a2)

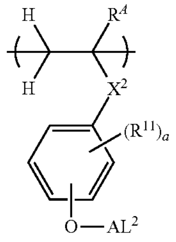

wherein $R^A$ is each independently hydrogen, fluorine, methyl or trifluoromethyl, $X^1$ is a single bond, phenylene, naphthylene, or *—C(═O)—O—$X^{11}$—, $X^{11}$ is a $C_1$-$C_{10}$ alkanediyl group which may contain a hydroxy moiety, ether bond, ester bond or lactone ring, or phenylene group or naphthylene group, $X^2$ is a single bond or *—C(═O)—O—, the asterisk (*) designates a point of attachment to the carbon atom in the backbone, $A^{L1}$ and $A^{L2}$ are each independently an acid labile group, $R^{11}$ is a $C_1$-$C_{20}$ hydrocarbyl group which may contain a heteroatom, and a is an integer of 0 to 4.

6. The resist composition of claim 4 wherein the base polymer further comprises repeat units having the formula (b1) or (b2):

(b1)

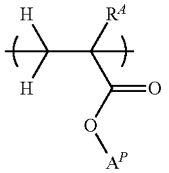

(b2)

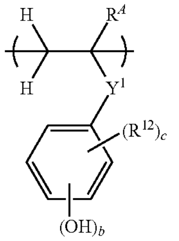

wherein $R^A$ is each independently hydrogen, fluorine, methyl or trifluoromethyl, $A^P$ is hydrogen, or a polar group containing at least one structure selected from a hydroxy moiety, cyano moiety, carbonyl moiety, carboxy moiety, ether bond, ester bond, sulfonic ester bond, carbonate bond, lactone ring, sultone ring, and carboxylic anhydride (—C(═O)—O—C(═O)—), $Y^1$ is a single bond or *—C(═O)—O—, the asterisk (*) designates a point of attachment to the carbon atom in the backbone, $R^{12}$ is halogen, cyano group, or a $C_1$-$C_{20}$ hydrocarbyl group which may contain a heteroatom, $C_1$-$C_{20}$ hydrocarbyloxy group which may contain a heteroatom, or $C_2$-$C_{20}$ hydrocarbylcarbonyl group which may contain a heteroatom, b is an integer of 1 to 4, c is an integer of 0 to 4, and $1 \le b+c \le 5$.

7. The resist composition of claim 4 wherein the base polymer further comprises repeat units of at least one type selected from the formulae (c1) to (c3):

(c1)

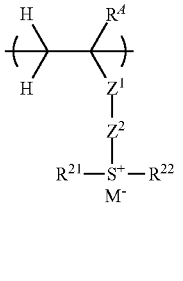

-continued (c2)

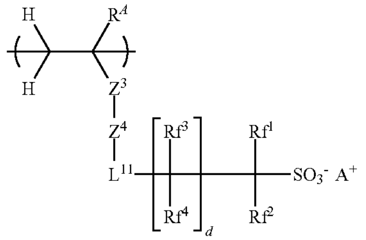

(c3)

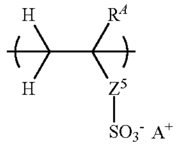

wherein $R^A$ is each independently hydrogen, fluorine, methyl or trifluoromethyl, $Z^1$ is a single bond or phenylene group, $Z^2$ is *—C(═O)—O—$Z^{21}$—, *—C(═O)—NH—$Z^{21}$— or *—O—$Z^{21}$—, $Z^{21}$ is a $C_1$-$C_6$ aliphatic hydrocarbylene group, phenylene group or a divalent group obtained by combining the foregoing, which may contain a carbonyl moiety, ester bond, ether bond or hydroxy moiety, $Z^3$ is a single bond, phenylene group, naphthylene group or *—C(═O)—O—$Z^{31}$—, $Z^{31}$ is a $C_1$-$C_{10}$ aliphatic hydrocarbylene group which may contain a hydroxy moiety, ether bond, ester bond or lactone ring, or phenylene group or naphthylene group, $Z^4$ is a single bond or *—$Z^{41}$—C(═O)—O—, $Z^{41}$ is a $C_1$-$C_{20}$ hydrocarbylene group which may contain a heteroatom, $Z^5$ is a single bond, methylene group, ethylene group, phenylene group, fluorinated phenylene group, trifluoromethyl-substituted phenylene group, *—C(═O)—O—$Z^{51}$—, *—C(═O)—NH—$Z^{51}$— or —O—$Z^{51}$—, $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety, the asterisk (*) designates a point of attachment to the carbon atom in the backbone, $R^{21}$ and $R^{22}$ are each independently a $C_1$-$C_{20}$ hydrocarbyl group which may contain a heteroatom, $R^{21}$ and $R^{22}$ may bond together to form a ring with the sulfur atom to which they are attached, $L^{11}$ is a single bond, ether bond, ester bond, carbonyl group, sulfonic ester bond, carbonate bond or carbamate bond, $Rf^1$ and $Rf^2$ are each independently fluorine or a $C_1$-$C_6$ fluorinated alkyl group, $Rf^3$ and $Rf^4$ are each independently hydrogen, fluorine or a $C_1$-$C_6$ fluorinated alkyl group, $M^-$ is a non-nucleophilic counter ion, $A^-$ is an onium cation, and d is an integer of 0 to 3.

8. The resist composition of claim 4, further comprising (C) an organic solvent.

9. The resist composition of claim 4, further comprising (D) a photoacid generator.

10. The resist composition of claim 4, further comprising (E) a quencher other than the amine compound having formula (1).

11. The resist composition of claim 4, further comprising (F) a surfactant.

12. A pattern forming process comprising the steps of applying the chemically amplified resist composition of claim 4 onto a substrate to form a resist film thereon, exposing a selected region of the resist film to KrF excimer laser radiation, ArF excimer laser radiation, EB or EUV, and developing the exposed resist film in a developer.

13. The process of claim 12 wherein the developing step uses an aqueous alkaline solution as the developer to form a positive tone pattern wherein the exposed region of resist film is dissolved away and the unexposed region of resist film is not dissolved.

14. The process of claim 12 wherein the developing step uses an organic solvent as the developer to form a negative tone pattern wherein the unexposed region of resist film is dissolved away and the exposed region of resist film is not dissolved.

15. The process of claim 12 wherein the exposing step is carried out by the immersion lithography while a liquid having a refractive index of at least 1.0 is held between the resist film and a projection lens.

16. The process of claim 15, further comprising the step of forming a protective film on the resist film prior to the exposure step, wherein the immersion lithography is carried out while the liquid is held between the protective film and the projection lens.

* * * * *